United States Patent
Tanaka et al.

(10) Patent No.: US 11,344,029 B2
(45) Date of Patent: May 31, 2022

(54) HETEROCYCLIC COMPOUND AND COMPOSITION CONTAINING SAME

(71) Applicant: Sumitomo Chemical Company, Limited, Tokyo (JP)

(72) Inventors: Ayaka Tanaka, Tokyo (JP); Naoya Sugimoto, Takarazuka (JP); Takeshi Tsuruda, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 39 days.

(21) Appl. No.: 16/617,211

(22) PCT Filed: Jun. 1, 2018

(86) PCT No.: PCT/JP2018/021157
§ 371 (c)(1),
(2) Date: Nov. 26, 2019

(87) PCT Pub. No.: WO2018/221720
PCT Pub. Date: Dec. 6, 2018

(65) Prior Publication Data
US 2020/0085051 A1    Mar. 19, 2020

(30) Foreign Application Priority Data

Jun. 1, 2017  (JP) .............................. JP2017-108998
Dec. 22, 2017  (JP) .............................. JP2017-245956
Apr. 2, 2018  (JP) .............................. JP2018-070879

(51) Int. Cl.
| | | |
|---|---|---|
| A01N 43/40 | (2006.01) | |
| A01N 43/54 | (2006.01) | |
| A01N 43/58 | (2006.01) | |
| A01N 43/653 | (2006.01) | |
| C07D 213/70 | (2006.01) | |
| C07D 213/71 | (2006.01) | |
| C07D 239/52 | (2006.01) | |
| C07D 401/04 | (2006.01) | |
| C07D 401/14 | (2006.01) | |

(52) U.S. Cl.
CPC ............ *A01N 43/40* (2013.01); *A01N 43/54* (2013.01); *A01N 43/58* (2013.01); *A01N 43/653* (2013.01); *C07D 213/70* (2013.01); *C07D 213/71* (2013.01); *C07D 239/52* (2013.01); *C07D 401/04* (2013.01); *C07D 401/14* (2013.01)

(58) Field of Classification Search
CPC combination set(s) only.
See application file for complete search history.

(56) References Cited

U.S. PATENT DOCUMENTS

| | | |
|---|---|---|
| 2016/0316751 A1 | 11/2016 | Kohler et al. |
| 2017/0305896 A1 | 10/2017 | Tanabe et al. |
| 2018/0297978 A1 | 10/2018 | Orimoto et al. |

FOREIGN PATENT DOCUMENTS

| | | |
|---|---|---|
| GB | 2130214 A | 5/1984 |
| JP | S59106472 A | 6/1984 |
| JP | H08104677 A | 4/1996 |
| JP | 2011511080 A | 4/2011 |
| JP | 2017503008 A | 1/2017 |
| WO | 2009099929 A1 | 8/2009 |
| WO | 2013018928 A1 | 2/2013 |
| WO | WO 2014154829 * | 10/2014 |
| WO | 2016052247 A1 | 4/2016 |
| WO | 2017065228 A1 | 4/2017 |

OTHER PUBLICATIONS

Extended European Search Report dated Feb. 19, 2021 in EP Application No. 18810584.5.
English Translation of International Preliminary Report on Patentability dated Dec. 3, 2019 in International Application No. PCT/JP2018/021157.
English Translation of International Search Report dated Jul. 3, 2018 in International Application No. PCT/JP2018/021157.
Examination Report dated Jun. 24, 2021 in IN Application No. 201947053380.
Office Action dated Sep. 29, 2021 in IL Application No. 270962.
Office Action dated Jan. 31, 2022 in IL Application No. 270962.

* cited by examiner

*Primary Examiner* — Kathrien A Cruz
(74) *Attorney, Agent, or Firm* — Panitch Schwarze Belisario & Nadel LLP

(57) ABSTRACT

A heterocyclic compound is represented by formula (I):

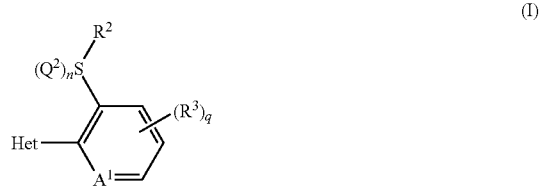

in which $R^2$ represents a C1-C6 alkyl group optionally having one or more halogen atoms, n is 0, $R^3$ represents a C1-C6 chain hydrocarbon group optionally having one or more substituents selected from Group B, q is 0, Het represents a group represented by the formulae Het 1 or Het 2, $A^1$ represents a nitrogen atom, and $Q^2$ represents an oxygen atom. The compound has excellent efficacy for controlling harmful arthropods. A composition is provided which contains the compound of formula (I) and one or more additional ingredients.

20 Claims, No Drawings

HETEROCYCLIC COMPOUND AND COMPOSITION CONTAINING SAME

CROSS-REFERENCE TO RELATED APPLICATIONS

This application is a Section 371 of International Application No. PCT/JP2018/021157, filed Jun. 1, 2018, which was published in the Japanese language on Dec. 6, 2018 under International Publication No. WO 2018/221720 A1, which claims priority under 35 U.S.C. § 119(b) to Japanese Application No. 2017-108998, filed on Jun. 1, 2017, Japanese Application No. 2017-245956, filed on Dec. 22, 2017, and Japanese Application No. 2018-070879, filed on Apr. 2, 2018, the disclosures of which are incorporated herein by reference in their entireties.

TECHNICAL FIELD

The present invention is related to a certain class of heterocyclic compound, an intermediate compound thereof, and an agent for controlling harmful arthropods comprising the same.

BACKGROUND ART

To date, in order to control harmful arthropods, some compounds have been studied and come into practical use.

Also, a certain class of compound has been known to have an effect on controlling pests (see Patent Document 1).

CITATION LIST

Patent Document

Patent Document 1: WO 2013/018928 pamphlet

SUMMARY OF THE INVENTION

Problems to be Solved by Invention

An object of the present invention is to provide a compound having an excellent efficacy for controlling harmful arthropods.

Means to Solve Problems

The present invention includes the followings.
[1] A compound represented by formula (I):

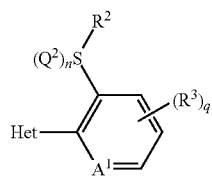

wherein, $R^2$ represents a C1-C6 alkyl group optionally having one or more halogen atoms, a cyclopropyl group or a cyclopropylmethyl group, n is 0, 1 or 2, $R^3$ represents a C1-C6 chain hydrocarbon group optionally having one or more substituents selected from Group B, a C3-C7 cycloalkyl group optionally having one or more substituents selected from group E, a C3-C7 cycloalkenyl group optionally having one or more substituents selected from Group J, a phenyl group optionally having one or more substituents selected from Group H, a five or six membered aromatic heterocyclic group optionally having one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{15}R^{16}$, $NR^{24}NR^{11}C(O)NR^{15}R^{16}$, $N=CHNR^{15}R^{16}$, $N=S(O)_xR^{15}R^{16}$, $C(O)R^{17}$, $C(O)OR^{17}$, $C(O)NR^{15}R^{16}$, $CR^{24}=NOR^{17}$, $NR^{11}CR^{24}=NOR^{17}$, a cyano group, a nitro group, or a halogen atom, q is 0, 1, 2 or 3, and when q is 2 or 3, a plurality of $R^3$ may be identical to or different from each other, When two $R^3$ are adjacent to each other, said two $R^3$ may combined together with a carbon atom to which they are attached to form benzene ring, pyrrole ring, furan ring, thiophene ring, pyrazole ring, imidazole ring, triazole ring, oxazole ring, isoxazole ring, thiazole ring, oxadiazole ring, thiadiazole ring, pyridine ring, pyridazine ring, pyrimidine ring, or pyrazine ring {the benzene ring, the pyrrole ring, the furan ring, the thiophene ring, the pyrazole ring, the imidazole ring, the triazole ring, the oxazole ring, the isoxazole ring, the thiazole ring, the pyridine ring, the pyridazine ring, the pyrimidine ring, and the pyrazine ring each independently may optionally have one or more substituents selected from Group H}, Het represents a group represented by the following formula Het 1 or a group represented by the following formula Het 2:

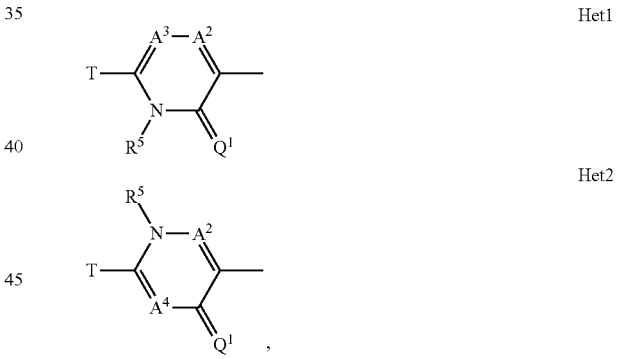

$A^1$ represents a nitrogen atom or $CR^6$,
$A^2$ represents a nitrogen atom or $CR^{4a}$,
$A^3$ represents a nitrogen atom or $CR^{4b}$,
$A^4$ represents a nitrogen atom or $CR^{4c}$,
$Q^1$ represents an oxygen atom or a sulfur atom,
$Q^2$ represents an oxygen atom, N—CN, N—$NO_2$, $NR^{20}$, N—$C(O)R^{20}$, or N—$C(O)OR^{15}$, and when n is 2, two $Q^2$ may be identical to or different from each other, $R^{20}$ represents a C1-C6 alkyl group optionally having one or more halogen atoms, or a hydrogen atom, $R^5$ represents a C1-C6 chain hydrocarbon group optionally having one or more substituents selected from group F, a C3-C6 cycloalkyl group optionally having one or more substituents selected from Group J, a phenyl group optionally having one or more substituents selected from Group H, or a five or six membered aromatic heterocyclic group optionally having one or more substituents selected from Group H, $R^{4a}$, $R^{4b}$ and $R^{4c}$ are identical to or different from each other and each represents independently a C1-C6 chain hydrocarbon group optionally having one or more halogen atoms, a nitro group, $OR^{18}$, $NR^{18}R^{19}$, a cyano group, an amino group, a halogen atom, or a hydrogen atom, $R^6$ represents a hydrogen atom or a halogen atom, T represents a C1-C10 chain hydrocarbon group, a (C1-C5 alkoxy)C2-C5 alkyl group, a (C1-C5 alkylsulfanyl)C2-C5 alkyl group, a (C1-C5 alkylsulfinyl)C2-C5 alkyl group, a (C1-C5 alkylsulfonyl)C2-C5 alkyl group {the C1-C10 chain hydrocarbon group, the (C1-C5 alkoxy)C2-C5 alkyl group, the (C1-C5 alkylsulfanyl)C2-C5 alkyl group, the (C1-C5 alkylsulfinyl)C2-C5 alkyl group, and the (C1-C5 alkylsulfonyl)C2-C5 alkyl group each independently have one or more substituents selected from the group consisting of a cyano group and a halogen atom}, a (C3-C7 cycloalkyl)C1-C3 alkyl group, a C3-C7 cycloalkyl group {the (C3-C7 cycloalkyl)C1-C3 alkyl group and the C3-C7 cycloalkyl group each independently have one or more substituents selected from the group consisting of a cyano group, a halogen atom and a C1-C6 haloalkyl group}, $OR^1$, $S(O)_vR^1$, $OS(O)_2R^1$, $CH_2OR^1$, $NR^1R^{29}$, $C(O)R^1$, $C(O)NR^1R^{29}$, $NR^{29}C(O)R^1$, $N{=}CR^1R^{30}$, a group represented by formula T-1, a group represented by formula T-2, a group represented by formula T-3, a group represented by formula T-4, a group represented by formula T-5, a group represented by formula T-6, a group represented by formula T-7, a group represented by formula T-8, a group represented by formula T-9, a group represented by formula T-10, a group represented by formula T-11, or a group represented by formula T-12:

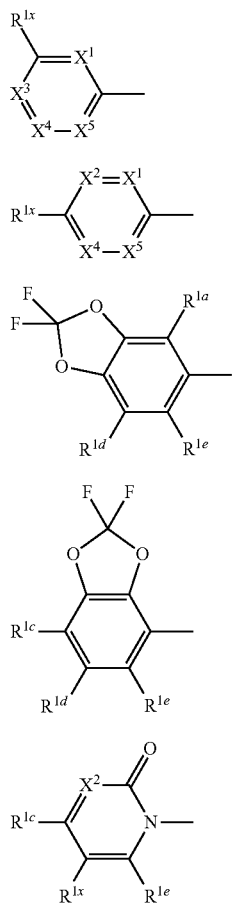

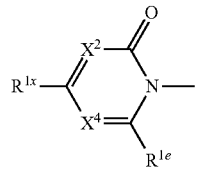

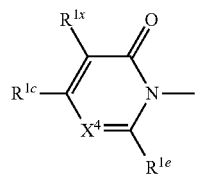

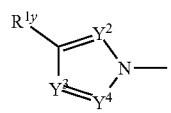

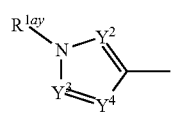

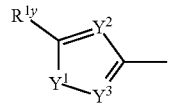

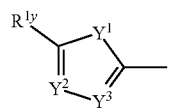

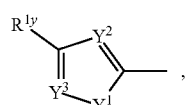

$X^1$ represents a nitrogen atom or $CR^{1a}$,
$X^2$ represents a nitrogen atom or $CR^{1b}$,
$X^3$ represents a nitrogen atom or $CR^{1c}$,
$X^4$ represents a nitrogen atom or $CR^{1d}$,
$X^5$ represents a nitrogen atom or $CR^{1e}$, $R^{1x}$ represents a C1-C5 chain hydrocarbon group having one or more halogen atoms, $OR^7$, $OS(O)_2R^7$, $S(O)_mR^7$, $NR^8S(O)_2R^7$, or a halogen atom, $R^{1a}$, $R^{1b}$, $R^{1c}$, $R^{1d}$, and $R^{1e}$ are identical to or different from each other and each represents independently a C1-C6 chain hydrocarbon group optionally having one or more halogen atoms, a C3-C6 cycloalkyl group optionally having one or more halogen atoms, a halogen atom, or a hydrogen atom, $Y^2$ represents $NR^{25}$, an oxygen atom or a sulfur atom,
$Y^2$ represents a nitrogen atom or $CR^{26}$,
$Y^3$ represents a nitrogen atom or $CR^{27}$,
$Y^4$ represents a nitrogen atom or $CR^{28}$, $R^{25}$, $R^{26}$, $R^{27}$ and $R^{28}$ are identical to or different from each other and each represents independently a C1-C6 chain hydrocarbon group optionally having one or more halogen atoms, a C3-C6 cycloalkyl group optionally having one or more halogen atoms, a halogen atom or a hydrogen atom, $R^{1y}$ represents a C1-C5 chain hydrocarbon group having one or more halogen atoms, $OR^7$, $OS(O)_2R^7$, $S(O)_mR^7$, $NR^8S(O)_2R^7$, a cyano group, or a halogen atom, $R^{1ay}$ and $R^7$ are identical to or different from each other and each represents independently a C1-C6 chain hydrocarbon group having one or more halogen atoms, m and v are identical to or different from each other and each is 0, 1 or 2, $R^1$ represents a C1-C10 chain hydrocarbon group, a (C1-C5 alkoxy)C2-C5 alkyl group, a (C1-C5 alkylsulfanyl)C2-C5 alkyl group, a (C1-C5 alkylsulfinyl)C2-C5 alkyl group, a (C1-C5 alkylsulfonyl)C2-C5 alkyl group {the C1-C10 chain hydrocarbon group, the (C1-C5 alkoxy)C2-C5 alkyl group, the (C1-C5 alkylsulfanyl)C2-C5 alkyl group, the (C1-C5 alkylsulfinyl)C2-C5 alkyl group, and the (C1-C5 alkylsulfonyl)C2-C5 alkyl group each independently have one or more substituents selected from the group consisting of a cyano group and a halogen atom}, a (C3-C7 cycloalkyl)C1-C3 alkyl group, or a C3-C7 cycloalkyl group {the (C3-C7 cycloalkyl)C1-C3 alkyl group and the C3-C7 cycloalkyl group each independently have one or more substituents selected from the group consisting of a cyano group, a halogen atom and a C1-C6 haloalkyl group}, $R^{30}$ represents a C1-C6 chain hydrocarbon group optionally having one or more halogen atoms, a halogen atom, $OR^{35}$, $NR^{36}R^{37}$, or a hydrogen atom, $R^{18}$ and $R^{35}$ are identical to or different from each other and each represents independently a C1-C6 chain hydrocarbon group optionally having one or more halogen atoms, $R^{17}$ represents a C1-C6 chain hydrocarbon group optionally having one or more halogen atoms, a phenyl group optionally having one or more substituents selected from Group D, or a hydrogen atom, $R^8$, $R^{11}$, $R^{19}$, $R^{24}$, $R^{29}$, $R^{36}$, and $R^{37}$ are identical to or different from each other and each represents independently a C1-C6 chain hydrocarbon group optionally having one or more halogen atoms, or a hydrogen atom, $R^{12}$ represents a C1-C6 chain hydrocarbon group optionally having one or more substituents selected from Group F, a C3-C7 cycloalkyl group optionally having one or more substituents selected from. Group J, a C3-C7 cycloalkenyl group optionally having one or more substituents selected from Group J, a phenyl group, a six membered heterocyclic group {the phenyl group, and the six membered heterocyclic group each independently may optionally have one or more substituents selected from Group D}, a hydrogen atom, or a $S(O)_2R^{23}$, $R^{23}$ represents a C1-C6 chain hydrocarbon group optionally having one or more halogen atoms, or a phenyl group optionally having one or more substituents selected from Group D, $R^{11a}$ and $R^{12a}$ combine together with the nitrogen atom to which they are attached to form a three to seven membered nonaromatic heterocyclic group optionally having one or more substituents selected from group E, $R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D, $R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {the phenyl moiety in the phenyl C1-C3 alkyl group may optionally have one or more substituents selected from Group D}, $R^{15}$ represents a C1-C6 alkyl group optionally having one or more halogen atoms, or a hydrogen atom, $R^{16}$ represents a C1-C6 chain hydrocarbon group optionally having one or more substituents selected from Group F, a C3-C7 cycloalkyl group optionally having one or more substituents selected from Group J, $S(O)_2R^{23}$ or a hydrogen atom, x is 0 or 1, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom, Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NR^9R^{10}$, $C(O)R^{10}$, $OC(O)R^9$, $C(O)OR^9$, a cyano group, a nitro group, and a halogen atom, $R^9$ represents a C1-C6 alkyl group optionally having one or more halogen atoms, or a C3-C6 cycloalkyl group optionally having one or more halogen atoms, $R^{10}$ represents a C1-C6 alkyl group optionally having one or more halogen atoms, a C3-C6 cycloalkyl group optionally having one or more halogen atoms, or a hydrogen atom, Group E; a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C3-C6 cycloalkyl group optionally having one or more halogen atoms, a phenyl group or a six membered aromatic heterocyclic group {the phenyl group and the six membered aromatic heterocyclic group each independently may optionally have one or more substituents selected from Group D}, $OR^{10}$, an amino group, $NR^9R^{10}$, a halogen atom, a nitro group, and a cyano group;

Group H: a group consisting of a five or six membered aromatic heterocyclic group, a C1-C6 alkyl group optionally having one or more halogen atoms, a C3-C6 cycloalkyl group optionally having one or more halogen atoms, $OR^{10}$, an amino group, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, and a cyano group;

Group J; a group consisting of a C1-C6 alkyl group optionally having one or more halogen atoms, a halogen atom, a cyano group, a triazolyl group, and $NR^{10}C(O)R^9$. (hereinafter, referred to as "Present compound Z" or "Compound Z of the present invention").

[2] The compound according to [1] wherein

T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_vR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by formula T-1, a group represented by formula T-2, a group represented by formula T-3, a group represented by formula T-4, a group represented by formula T-5, a group represented by formula T-6, a group represented by formula T-7, a group represented by formula T-8, a group represented by formula T-9, a group represented by formula T-10, a group represented by formula T-11, or a group represented by formula T-12, and $R^1$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G.

(hereinafter, referred to as "Present compound" or "Compound of the present invention").

[3] The compound according to [1] or [2] wherein $A^1$ represents CH.

[4] The compound according to [1] or [2] wherein $A^1$ represents a nitrogen atom.

[5] The compound according to any one of [1] to [4] wherein Het represents Het 1.

[6] The compound according to any one of [1] to [4] wherein Het represents Het 2.

[7] The compound according to any one of [1] to [4] wherein Het represents Het 1, $A^2$ represents $CR^{4a}$, and $A^3$ represents $CR^{4b}$.

[8] The compound according to any one of [1] to [4] wherein Het represents Het 2, $A^2$ represents $CR^{4a}$, and $A^4$ represents $CR^{4c}$.

[9] The compound according to any one of [1] to [8] wherein $Q^1$ represents an oxygen atom, T represents a C1-C10 chain hydrocarbon group having one or more halogen atoms, $OR^1$, $S(O)_vR^1$, $OS(O)_2R^1$, $NR^1R^{29}$, a group represented by formula T-1, a group represented by formula T-2, a group represented by formula T-3, a group represented by formula T-4, or a group represented by formula T-8.

[10] The compound according to any one of [1] to [8] wherein $Q^1$ represents an oxygen atom, T represents a C1-C5 chain hydrocarbon group having one or more halogen atoms, $OR^1$, $S(O)_vR^1$, $OS(O)_2R^1$, $NR^1R^{29}$, a group represented by formula T-1, a group represented by formula T-2, a group represented by formula T-3, a group represented by formula T-4, or a group represented by formula T-8, $R^1$, $R^{1x}$ and $R^{1y}$ are identical to or different from each other and each represents independently a C1-C5 chain hydrocarbon group having one or more halogen atoms, and q is 0 or 1.

[11] The compound according to any one of [1] to [8] wherein $Q^1$ represents an oxygen atom, T represents a C1-C5 chain hydrocarbon group having one or more halogen atoms, or $OR^1$, $R^1$ represents a C1-C5 chain hydrocarbon group having one or more halogen atoms, and q is 0 or 1.

[12] The compound according to any one of [1] to [11] wherein $R^3$ represents a C1-C6 alkyl group optionally having one or more substituents selected from Group B, a C3-C7 cycloalkyl group optionally having one or more substituents selected from Group E, a phenyl group, a five aromatic heterocyclic group containing one to four nitrogen atoms, a six aromatic heterocyclic group {the phenyl group, the five aromatic heterocyclic group containing one to four nitrogen atoms, and the six aromatic heterocyclic group each independently may optionally have one or more substituents selected from Group J}, $NR^{11}R^{12}$, $NR^{11}C(O)OR^{14}$, $OR^{12}$, or a halogen atom.

[13] The compound according to any one of [1] to [12] wherein $R^2$ represents an ethyl group.

[14] The compound according to any one of [1] to [13] wherein $Q^2$ represents an oxygen atom.

[15] A composition for controlling harmful arthropod comprising the compound according to any one of [1] to [14] and an inert carrier.

[16] A method for controlling harmful arthropod which comprises applying an effective amount of the compound according to any one of [1] to [14] to a harmful arthropod or a habitat where a harmful arthropod lives.

[17] A method for controlling harmful arthropod which comprises applying an effective amount of the compound according to any one of [1] to [14] to a plant or a soil where a plant grows.

[18] A method for controlling harmful arthropod which comprises applying an effective amount of the compound according to any one of [1] to [14] to a seed or a bulb.

[19] A composition comprising one or more ingredients selected from the group consisting of the following Group (a), Group (b), Group (c), Group (d) and Group (e), and the compound according to any one of [1] to [14] (hereinafter, referred to as "Present composition" or "Composition of the present invention"), Group (a): one or more ingredients selected from the group consisting of insecticidal ingredients, miticidal ingredients, and nematicidal ingredients;

Group (b): fungicidal ingredients;

Group (c): plant growth modulating ingredients;

Group (d): phytotoxicity-reducing ingredients; and

Group (e): synergist ingredients.

[20] A composition for controlling pest comprising the composition according to [19] and an inert carrier.

[21] A method for controlling pest which comprises applying an effective amount of the composition according to [19] to a pest or a habitat where a pest lives.

[22] A method for controlling pest which comprises applying an effective amount of the composition according to [19] to a plant or a soil where a plant grows. [23] A method for controlling pest which comprises applying an effective amount of the compound according to [19] to a seed or a bulb.

[24] A seed or bulb carrying an effective amount of the compound according to any one of [1] to [14] or an effective amount of the composition according to [19].

[25] A compound represented by formula (II):

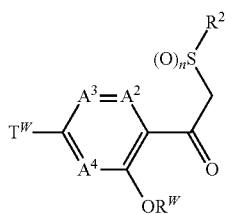
(II)

[wherein,

R² represents a C1-C6 alkyl group optionally having one or more halogen atoms, a cyclopropyl group or a cyclopropylmethyl group, n is 0, 1 or 2, $A^2$ represents a nitrogen atom or $CR^{4a}$, a combination of $A^3$ and $A^4$ represents a combination where $A^3$ represents a nitrogen atom, $A^4$ represents a nitrogen atom or $CR^{4c}$, or a combination where $A^3$ represents $CR^{4b}$, and $A^4$ represents a nitrogen atom, $R^{4a}$, $R^{4b}$ and $R^{4c}$ are identical to or different from each other and each represents independently a C1-C6 chain hydrocarbon group optionally having one or more halogen atoms, a nitro group, $OR^{18}$, $NR^{18}R^{19}$, a cyano group, an amino group, a halogen atom, or a hydrogen atom, $R^{19}$ represents a C1-C6 chain hydrocarbon group optionally having one or more halogen atoms, or a hydrogen atom, $R^w$ represents a C1-C6 chain hydrocarbon group optionally having one or more halogen atoms, a benzyl group optionally having one or more substituents selected from Group A, a C2-C7 alkylcarbonyl group, a (C1-C3 alkoxy)methyl group, or a hydrogen atom, $T^w$ represents a C1-C10 chain hydrocarbon group, a (C1-C5 alkoxy)C2-C5 alkyl group, a (C1-C5 alkylsulfanyl)C2-C5 alkyl group, a (C1-C5 alkylsulfinyl)C2-C5 alkyl group, a (C1-C5 alkylsulfonyl)C2-C5 alkyl group {the C1-C10 chain hydrocarbon group, the (C1-C5 alkoxy)C2-C5 alkyl group, the (C1-C5 alkylsulfanyl)C2-C5 alkyl group, the (C1-C5 alkylsulfinyl)C2-C5 alkyl group, and the (C1-C5 alkylsulfonyl)C2-C5 alkyl group each independently have one or more substituents selected from the group consisting of a cyano group and a halogen atom}, a (C3-C7 cycloalkyl)C1-C3 alkyl group or a C3-C7 cycloalkyl group {the (C3-C7 cycloalkyl)C1-C3 alkyl group and the C3-C7 cycloalkyl group each independently have one or more substituents selected from the group consisting of a cyano group, a halogen atom and a C1-C6 haloalkyl group}, $OR^1$, $S(O)_vR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by formula T-1, a group represented by formula T-2, a group represented by formula T-3, a group represented by formula T-4, a group represented by formula T-5, a group represented by formula T-6, a group represented by formula T-7, a group represented by formula T-8, a group represented by formula T-9, a group represented by formula T-10, a group represented by formula T-11, or a group represented by formula T-12, a halogen atom, a C1-C6 alkylsulfanyl group, a C1-C6 alkylsulfinyl group, a C1-C6 alkylsulfonyl group {the C1-C6 alkylsulfanyl group, the C1-C6 alkylsulfinyl group, and the C1-C6 alkylsulfonyl group each may optionally have a C3-C6 cycloalkyl group}, a C3-C6 cycloalkylsulfanyl group, a C3-C6 cycloalkylsulfinyl group, a C3-C6 cycloalkylsulfonyl group, a benzyloxy group optionally having one or more substituents selected from Group A, a C2-C7 alkylcarbonyloxy group optionally having one or more halogen atoms, a (C1-C3 alkoxy)methoxy group, or a hydroxy group,

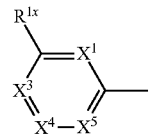
T-1

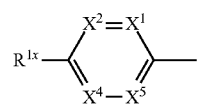
T-2

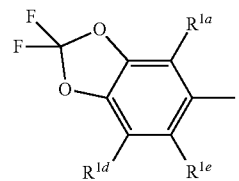
T-3

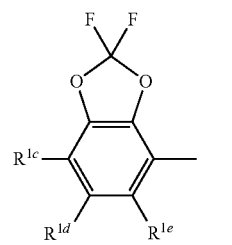
T-4

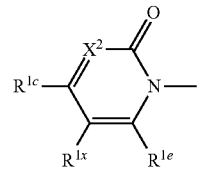
T-5

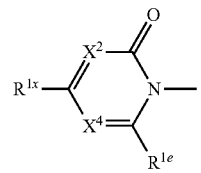
T-6

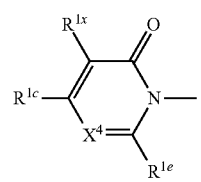
T-7

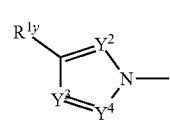
T-8

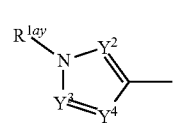
T-9

-continued

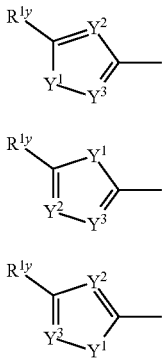

T-10

T-11

T-12

$X^1$ represents a nitrogen atom or $CR^{1a}$,
$X^2$ represents a nitrogen atom or $CR^{1b}$,
$X^3$ represents a nitrogen atom or $CR^{1c}$,
$X^4$ represents a nitrogen atom or $CR^{1d}$,
$X^5$ represents a nitrogen atom or $CR^{1e}$,
$R^{1x}$ represents a C1-C5 chain hydrocarbon group having one or more halogen atoms, $OR^7$, $OS(O)_2R^7$, $S(O)_mR^7$, $NR^8S(O)_2R^7$, or a halogen atom,
$R^{1a}$, $R^{1b}$, $R^{1c}$, $R^{1d}$, and $R^{1e}$ are identical to or different from each other and each represents independently a C1-C6 chain hydrocarbon group optionally having one or more halogen atoms, a C3-C6 cycloalkyl group optionally having one or more halogen atoms, a halogen atom, or a hydrogen atom,
$Y^1$ represents $NR^{25}$, an oxygen atom or a sulfur atom,
$Y^2$ represents a nitrogen atom or $CR^{26}$,
$Y^3$ represents a nitrogen atom or $CR^{27}$,
$Y^4$ represents a nitrogen atom or $CR^{28}$,
$R^{25}$, $R^{26}$, $R^{27}$ and $R^{29}$ are identical to or different from each other and each represents independently a C1-C6 chain hydrocarbon group optionally having one or more halogen atoms, a C3-C6 cycloalkyl group optionally having one or more halogen atoms, a halogen atom or a hydrogen atom,
$R^{1y}$ represents a C1-C5 chain hydrocarbon group having one or more halogen atoms, $OR^7$, $OS(O)_2R^7$, $S(O)_mR^7$, $NR^8S(O)_2R^7$, a cyano group, or a halogen atoms,
$R^{1ay}$ and $R^7$ are identical to or different from each other and each represents a C1-C6 chain hydrocarbon group having one or more halogen atoms,
m and v are identical to or different from each other and each is 0, 1 or 2,
$R^1$ represents a C1-C10 chain hydrocarbon group, a (C1-C5 alkoxy)C2-C5 alkyl group, a (C1-C5 alkylsulfanyl)C2-C5 alkyl group, a (C1-C5 alkylsulfinyl)C2-C5 alkyl group, a (C1-C5 alkylsulfonyl)C2-C5 alkyl group {the C1-C10 chain hydrocarbon group, the (C1-C5 alkoxy)C2-C5 alkyl group, the (C1-C5 alkylsulfanyl)C2-C5 alkyl group, the (C1-C5 alkylsulfinyl)C2-C5 alkyl group, and the (C1-C5 alkylsulfonyl)C2-C5 alkyl group each independently have one or more substituents selected from the group consisting of a cyano group and a halogen atom}, a (C3-C7 cycloalkyl)C1-C3 alkyl group, or a C3-C7 cycloalkyl group {the (C3-C7 cycloalkyl)C1-C3 alkyl group and the C3-C7 cycloalkyl group each independently have one or more substituents selected from the group consisting of a cyano group, a halogen atom and a C1-C6 haloalkyl group},
$R^{30}$ represents a C1-C6 chain hydrocarbon group optionally having one or more halogen atoms, a halogen atom, $OR^{35}$, $NR^{35}R^{37}$, or a hydrogen atom, $R^{18}$ and $R^{35}$ are identical to or different from each other and each represents independently a C1-C6 chain hydrocarbon group optionally having one or more halogen atoms,
$R^8$, $R^{29}$, $R^{36}$, and $R^{37}$ are identical to or different from each other and each represents independently a C1-C6 chain hydrocarbon group optionally having one or more halogen atoms, or a hydrogen atom,
Group A: a group consisting of a C1-C6 alkyl group optionally having one or more halogen atoms, a C1-C6 alkoxy group optionally having one or more halogen atoms, a halogen atom, a cyano group and a nitro group.]
(hereinafter, referred to as "Intermediate compound D").
[26] A compound represented by formula (III):

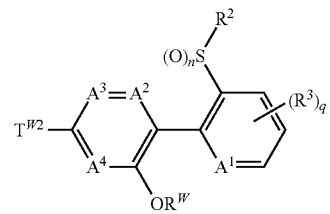

(III)

[wherein,
$R^2$ represents a C1-C6 alkyl group optionally having one or more halogen atoms, a cyclopropyl group or a cyclopropylmethyl group,
n is 0, 1 or 2,
$A^1$ represents a nitrogen atom or $CR^6$,
$A^2$ represents a nitrogen atom or $CR^{4a}$,
a combination of $A^3$ and $A^4$ represents a combination where $A^3$ represents a nitrogen atom, $A^4$ represents a nitrogen atom or $CR^{4c}$, or a combination where $A^3$ represents $CR^{4b}$, and $A^4$ represents a nitrogen atom,
$R^{4a}$, $R^{4b}$ and $R^{4c}$ are identical to or different from each other and each represents independently a C1-C6, chain hydrocarbon group optionally having one or more halogen atoms, a nitro group, $OR^{18}$, $NR^{18}R^{19}$, a cyano group, an amino group, a halogen atom, or a hydrogen atom,
$R^6$ represents a hydrogen atom or a halogen atom,
$R^w$ represents a C1-C6 chain hydrocarbon group optionally having one or more halogen atoms, a benzyl group optionally having one or more substituents selected from Group A, a C2-C7 alkylcarbonyl group, a (C1-C3 alkoxy)methyl group, or a hydrogen atom,
$T^{W2}$ represents a C1-C10 chain hydrocarbon group, a (C1-C5 alkoxy)C2-C5 alkyl group, a (C1-C5 alkylsulfanyl)C2-C5 alkyl group, a (C1-C5 alkylsulfinyl)C2-C5 alkyl group, a (C1-C5 alkylsulfonyl)C2-C5 alkyl group {the C1-C10 chain hydrocarbon group, the (C1-C5 alkoxy)C2-C5 alkyl group, the (C1-C5 alkylsulfanyl)C2-C5 alkyl group, the (C1-C5 alkylsulfinyl)C2-C5 alkyl group, and the (C1-C5 alkylsulfonyl)C2-C5 alkyl group each independently have one or more substituents selected from the group consisting of a cyano group and a halogen atom}, a (C3-C7 cycloalkyl)C1-C3 alkyl group or a C3-C7 cycloalkyl group {the (C3-C7 cycloalkyl)C1-C3 alkyl group and the C3-C7 cycloalkyl group each independently have one or more substituents selected from the group consisting of a cyano group, a halogen atom and a C1-C6 haloalkyl group}, $OR^1$, $S(O)_vR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by formula T-1, a group represented by formula T-2, a group represented by formula T-3, a group represented by formula T-4, a group represented by formula T-5, a group represented by formula T-6, a group represented by formula T-7, a group represented by formula T-8, a group represented by formula T-9, a group represented by formula T-10, a group represented by formula T-11, or a group represented by formula T-12, a halogen atom, a C1-C6 alkoxy group, a C1-C6 alkylsulfanyl group, a C1-C6 alkylsulfinyl group, a C1-C6 alkylsulfonyl group {the C1-C6 alkylsulfanyl group, the C1-C6 alkylsulfinyl group, and the C1-C6 alkylsulfonyl group each independently may optionally have a C3-C6 cycloalkyl group}, a C3-C6 cycloalkylsulfanyl group, a C3-C6 cycloalkylsulfinyl group, a C3-C6 cycloalkylsulfonyl group, a benzyloxy group optionally having one or more substituents selected from Group A, a C2-C7 alkylcarbonyloxy group optionally having one or more halogen atoms, a (C1-C3 alkoxy)methoxy group, or a hydroxy group,

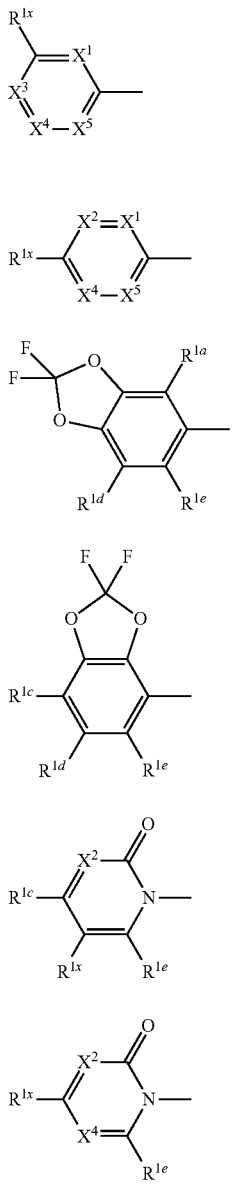

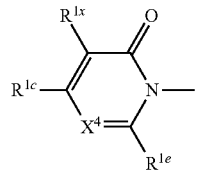

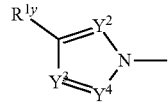

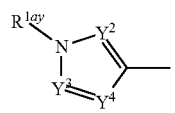

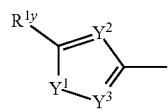

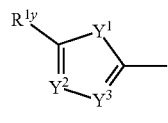

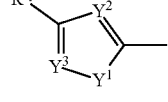

$X^1$ represents a nitrogen atom or $CR^{1a}$,
$X^2$ represents a nitrogen atom or $CR^{1b}$,
$X^3$ represents a nitrogen atom or $CR^{1c}$,
$X^4$ represents a nitrogen atom or $CR^{1d}$,
$X^5$ represents a nitrogen atom or $CR^{3e}$,
$R^{1x}$ represents a C1-C5 chain hydrocarbon group having one or more halogen atoms, $OR^7$, $OS(O)_2R^7$, $S(O)_mR^7$, $NR^8S(O)_2R^7$, or a halogen atom,
$R^{1a}$, $R^{1b}$, $R^{1c}$, $R^{1d}$, and $R^{1e}$ are identical to or different from each other and each represents independently a C1-C6 chain hydrocarbon group optionally having one or more halogen atoms, a C3-C6 cycloalkyl group optionally having one or more halogen atoms, a halogen atom, or a hydrogen atom,
$Y^1$ represents $NR^{25}$, an oxygen atom or a sulfur atom,
$Y^2$ represents a nitrogen atom or $CR^{26}$,
$Y^3$ represents a nitrogen atom or $CR^{27}$,
$Y^4$ represents a nitrogen atom or $CR^{28}$,
$R^{25}$, $R^{26}$, $R^{27}$ and $R^{28}$ are identical to or different from each other and each represents independently a C1-C6 chain hydrocarbon group optionally having one or more halogen atoms, a C3-C6 cycloalkyl group optionally having one or more halogen atoms, a halogen atom or a hydrogen atom,
$R^{1y}$ represents a C1-C5 chain hydrocarbon group having one or more halogen atoms, $OR^7$, $OS(O)_2R^7$, $S(O)_mR^7$, $NR^8S(O)_2R^7$, a cyano group, or a halogen atom,
$R^{1ay}$ and $R^7$ are identical to or different from each other and each represents independently a C1-C6 chain hydrocarbon group having one or more halogen atoms,
m and v are identical to or different from each other and each is 0, 1 or 2,
$R^1$ represents a C1-C10 chain hydrocarbon group, a (C1-C5 alkoxy)C2-C5 alkyl group, a (C1-C5 alkylsulfanyl)

C2-C5 alkyl group, a (C1-C5 alkylsulfinyl)C2-C5 alkyl group, a (C1-C5 alkylsulfonyl)C2-C5 alkyl group {the C1-C10 chain hydrocarbon group, the (C1-C5 alkoxy)C2-C5 alkyl group, the (C1-C5 alkylsulfanyl)C2-C5 alkyl group, the (C1-C5 alkylsulfinyl)C2-C5 alkyl group, and the (C1-C5 alkylsulfonyl)C2-C5 alkyl group each independently have one or more substituents selected from the group consisting of a cyano group and a halogen atom}, a (C3-C7 cycloalkyl)C1-C3 alkyl group, or a C3-C7 cycloalkyl group {the (C3-C7 cycloalkyl)C1-C3 alkyl group and the C3-C7 cycloalkyl group each independently have one or more substituents selected from the group consisting of a cyano group, a halogen atom and a C1-C6 haloalkyl group}, $R^{30}$ represents a C1-C6 chain hydrocarbon group optionally having one or more halogen atoms, a halogen atom, $OR^{35}$, $NR^{36}R^{37}$, or a hydrogen atom, $R^{18}$ and $R^{35}$ are identical to or different from each other and each represents independently a C1-C6 chain hydrocarbon group optionally having one or more halogen atoms, $R^3$ represents a C1-C6 chain hydrocarbon group optionally having one or more substituents selected from Group B, a C3-C7 cycloalkyl group optionally having one or more substituents selected from group E, a C3-C7 cycloalkenyl group optionally having one or more substituents selected from Group J, a phenyl group optionally having one or more substituents selected from Group H, a five or six membered aromatic heterocyclic group optionally having one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{15}R^{16}$, $NR^{24}NR^{11}C(O)NR^{15}R^{16}$, $N=CHNR^{15}R^{16}$, $N=S(O)_xR^{15}R^{16}$, $C(O)R^{17}$, $C(O)OR^{17}$, $C(O)NR^{15}R^{16}$, $CR^{24}=NOR^{17}$, $NR^{11}CR^{24}=NOR^{17}$, a cyano group, a nitro group, or a halogen atom, q is 0, 1, 2 or 3, and when q is 2 or 3, a plurality of $R^3$ may be identical to or different from each other, When two $R^3$ are adjacent to each other, said two $R^3$ may combined together with a carbon atom to which they are attached to form benzene ring, pyrrole ring, furan ring, thiophene ring, pyrazole ring, imidazole ring, triazole ring, oxazole ring, isoxazole ring, thiazole ring, oxadiazole ring, thiadiazole ring, pyridine ring, pyridazine ring, pyrimidine ring, or pyrazine ring {the benzene ring, the pyrrole ring, the furan ring, the thiophene ring, the pyrazole ring, the imidazole ring, the triazole ring, the oxazole ring, the isoxazole ring, the thiazole ring, the pyridine ring, the pyridazine ring, the pyrimidine ring, and the pyrazine ring each independently may optionally have one or more substituents selected from Group H}, $R^{17}$ represents a C1-C6 chain hydrocarbon group optionally having one or more halogen atoms, a phenyl group optionally having one or more substituents selected from Group D, or a hydrogen atom, $R^8$, $R^{11}$, $R^{19}$, $R^{24}$, $R^{29}$, $R^{36}$, and $R^{37}$ are identical to or different from each other and each represents independently a C1-C6 chain hydrocarbon group optionally having one or more halogen atoms, or a hydrogen atom, $R^{12}$ represents a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group, a six membered heterocyclic group {the phenyl group, and the six membered heterocyclic group each independently may optionally have one or more substituents selected from Group D}, a hydrogen atom, or a $S(O)_2R^{23}$, $R^{23}$ represents a C1-C6 chain hydrocarbon group optionally having one or more halogen atoms, or a phenyl group optionally having one or more substituents selected from Group D, $R^{11a}$ and $R^{12a}$ combine together with the nitrogen atom to which they are attached to form a three to seven membered nonaromatic heterocyclic group optionally having one or more substituents selected from group E, $R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D, $R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {the phenyl moiety in the phenyl C1-C3 alkyl group may optionally have one or more substituents selected from Group D}, $R^{15}$ represents a C1-C6 alkyl group optionally having one or more halogen atoms, or a hydrogen atom, $R^{16}$ represents a C1-C6 chain hydrocarbon group optionally having one or more substituents selected from Group F, a C3-C7 cycloalkyl group optionally having one or more substituents selected from Group J, $S(O)_2R^{23}$ or a hydrogen atom, x is 0 or 1, Group A: a group consisting of a C1-C6 alkyl group optionally having one or more halogen atoms, a C1-C6 alkoxy group optionally having one or more halogen atoms, a halogen atom, a cyano group and a nitro group, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom, Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NR^9R^{10}$, $C(O)R^{10}$, $OC(O)R^9$, $C(O)OR^9$, a cyano group, a nitro group, and a halogen atom, $R^9$ represents a C1-C6 alkyl group optionally having one or more halogen atoms, or a C3-C6 cycloalkyl group optionally having one or more halogen atoms, $R^{10}$ represents a C1-C6 alkyl group optionally having one or more halogen atoms, a C3-C6 cycloalkyl group optionally having one or more halogen atoms, or a hydrogen atom, Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C3-C6 cycloalkyl group optionally having one or more halogen atoms, a phenyl group or a six membered aromatic heterocyclic group {the phenyl group and the six membered aromatic heterocyclic group each independently may optionally have one or more substituents selected from Group D}, $OR^{10}$, an amino group, $NR^9R^{10}$, a halogen atom, a nitro group, and a cyano group;

Group H: a group consisting of a five or six membered aromatic heterocyclic group, a C1-C6 alkyl group optionally having one or more halogen atoms, a C3-C6 cycloalkyl group optionally having one or more halogen atoms, $OR^{10}$, an amino group, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, and a cyano group.

Group J: a group consisting of a C1-C6 alkyl group optionally having one or more halogen atoms, a halogen atom, a cyano group, a triazolyl group, and $NR^{10}C(O)R^9$. (hereinafter, referred to as "Intermediate compound E").

[27] A compound represented by formula (IV):

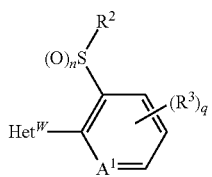

(IV)

[wherein, $R^2$ represents a C1-C6 alkyl group optionally having one or more halogen atoms, a cyclopropyl group or a cyclopropylmethyl group, n is 0, 1 or 2, $R^3$ represents a C1-C6 chain hydrocarbon group optionally having one or more substituents selected from Group B, a C3-C7 cycloalkyl group optionally having one or more substituents selected from group E, a C3-C7 cycloalkenyl group optionally having one or more substituents selected from Group J, a phenyl group optionally having one or more substituents selected from Group H, a five or six membered aromatic heterocyclic group optionally having one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{15}R^{16}$, $NR^{24}NR^{11}C(O)NR^{15}R^{16}$, $N=CHNR^{15}R^{16}$, $N=S(O)_xR^{15}R^{16}$, $C(O)R^{17}$, $C(O)OR^{17}$, $C(O)NR^{15}R^{16}$, $CR^{24}=NOR^{17}$, $NR^{11}CR^{24}=NOR^{17}$, a cyano group, a nitro group, or a halogen atom, q is 0, 1, 2 or 3, and when q is 2 or 3, a plurality of $R^3$ may be identical to or different from each other, When two $R^3$ are adjacent to each other, said two $R^3$ may combined together with a carbon atom to which they are attached to form benzene ring, pyrrole ring, furan ring, thiophene ring, pyrazole ring, imidazole ring, triazole ring, oxazole ring, isoxazole ring, thiazole ring, oxadiazole ring, thiadiazole ring, pyridine ring, pyridazine ring, pyrimidine ring, or pyrazine ring {the benzene ring, the pyrrole ring, the furan ring, the thiophene ring, the pyrazole ring, the imidazole ring, the triazole ring, the oxazole ring, the isoxazole ring, the thiazole ring, the pyridine ring, the pyridazine ring, the pyrimidine ring, and the pyrazine ring each independently may optionally have one or more substituents selected from Group H}, $Het^W$ represents a group represented by the following formula Het 3 or a group represented by the following formula Het 4:

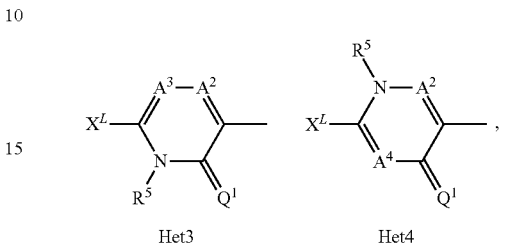

Het3            Het4

$A^1$ represents a nitrogen atom or $CR^6$,
$A^2$ represents a nitrogen atom or $CR^{4a}$,
$A^3$ represents a nitrogen atom or $CR^{4b}$,
$A^4$ represents a nitrogen atom or $CR^{4c}$,
$Q^1$ represents an oxygen atom or a sulfur atom,
$R^{20}$ represents a C1-C6 alkyl group optionally having one or more halogen atoms, or a hydrogen atom,
$R^5$ represents a C1-C6 chain hydrocarbon group optionally having one or more substituents selected from group F, a C3-C6 cycloalkyl group optionally having one or more substituents selected from Group J, a phenyl group optionally having one or more substituents selected from Group H, or a five or six membered aromatic heterocyclic group optionally having one or more substituents selected from Group H, $R^{4a}$, $R^{4b}$ and $R^{4c}$ are identical to or different from each other and each represents independently a C1-C6 chain hydrocarbon group optionally one or more halogen atoms, a nitro group, $OR^{18}$, $NR^{18}R^{19}$, a cyano group, an amino group, a halogen atom, or a hydrogen atom, $R^6$ represents a hydrogen atom or a halogen atom, $X^L$ represents a halogen atom, a C1-C6 alkoxy group, a C1-C6 alkylsulfanyl group, a C1-C6 alkylsulfinyl group, a C1-C6 alkylsulfonyl group {the C1-C6 alkylsulfanyl group, the C1-C6 alkylsulfinyl group, and the C1-C6 alkylsulfonyl group each independently may optionally have a C3-C6 cyaloalkyl group}, a C3-C6 cycloalkylsulfanyl group, a C3-C6 cycloalkylsulfinyl group, a C3-C6 cycloalkylsulfonyl group, a benzyloxy group optionally having one or more substituents selected from Group A, a C2-C7 alkylcarbonyloxy group optionally having one or more halogen atoms, a (C1-C3 alkoxy)methoxy group, or a hydroxy group, $R^{18}$ represents a C1-C6 chain hydrocarbon group optionally having one or more halogen atoms, $R^{17}$ represents a C1-C6 chain hydrocarbon group optionally having one or more halogen atoms, a phenyl group optionally having one or more substituents selected from Group D, or a hydrogen atom, $R^{11}$, $R^{19}$ and $R^{24}$ are identical to or different from each other and each represents independently a C1-C6 chain hydrocarbon group optionally one or more halogen atoms, or a hydrogen atom, $R^{12}$ represents a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group, or six membered heterocyclic group {the phenyl group, and the six membered heterocyclic group each independently may have optionally one or more substituents selected from Group D}, a hydrogen atom, or $S(O)_2R^{23}$, $R^{23}$ represents a C1-C6 chain hydrocarbon group optionally having one or more halogen atoms, or a phenyl group optionally having one or more substituents selected from Group D, $R^{11a}$ and $R^{12a}$ combine together with the nitrogen atom to which they are attached to form a three to seven membered nonaromatic heterocyclic group optionally having one or more substituents selected from group E, $R^{13}$ represents a hydrogen atom, a C1-C6 Chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D, $R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {the phenyl moiety in the phenyl C1-C3 alkyl group may optionally have one or more substituents selected from Group D}, $R^{15}$ represents a C1-C6 alkyl group optionally having one or more halogen atoms, or a hydrogen atom, $R^{16}$ represents a C1-C6 chain hydrocarbon group optionally having one or more substituents selected from Group F, a C3-C7 cycloalkyl group optionally having one or more substituents selected from Group J, $S(O)_2R^{23}$ or a hydrogen atom, x is 0 or 1, Group A; a group consisting of a C1-C6 alkyl group optionally having one or more halogen atoms, a C1-C6 alkoxy group optionally having one or more halogen atoms, a halogen atom, a cyano group and a nitro group, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen at Group D: a group consisting of a C1-C6 chain hydrocarbon group optionally having one or lore halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NR^9R^{10}$, $C(O)R^{10}$, $OC(O)R^9$, $C(O)OR^9$, a cyano group, a nitro group, and a halogen atom, $R^9$ represents a C1-C6 alkyl group optionally having one or more halogen atoms, or a C3-C5 cycloalkyl group optionally having one or more halogen atoms, $R^{10}$ represents a C1-C6 alkyl group optionally having one or more halogen atoms, a C3-C6 cycloalkyl group optionally having one or more halogen atoms, or a hydrogen atom, Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C3-C6 cycloalkyl group optionally having one or more halogen atoms, a phenyl group or a six membered aromatic heterocyclic group {the phenyl group and the six membered aromatic heterocyclic group each independently may optionally have one or more substituents selected from Group n}, $OR^{10}$, an amino group, $NR^9R^{10}$, a halogen atom, a nitro group, and a cyano group;

Group H: a group consisting of a five or six membered aromatic heterocyclic group, a C1-C6 alkyl group optionally having one or more halogen atoms, a C3-C6 cycloalkyl group optionally having one or more halogen atoms, $OR^{10}$, an amino group, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, and a cyano group.

Group J: a group consisting of a C1-C6 alkyl group optionally having one or more halogen atoms, a halogen atom, a cyano group, a triazolyl group, and $NR^{10}C(O)R^9$].

(hereinafter, referred to as "Intermediate compound F").

Effect of Invention

The present invention can control harmful arthropods.

MODE FOR CARRYING OUT THE INVENTION

The substituent(s) as described herein is/are explained.

The term "halogen atom" represents fluorine atom, chlorine atom, bromine atom, or iodine atom.

When the substituents have two or more halogen atoms, these halogen atoms may be identical to or different from each other.

The expression of "CX-CY" as used herein represents that the number of carbon atom is from X to Y. For example, the expression of "C1-C6" represents that the number of carbon atom is from 1 to 6, The term of "chain hydrocarbon group" represents an alkyl group, an alkenyl group, or an alkynyl group.

Example of the term of "alkyl group" include methyl group, ethyl group, propyl group, isopropyl group, 1,1-dimethylpropyl group, 1,2-dimethylpropyl group, 1-ethylpropyl group, butyl group, sec-butyl group, tert-butyl group, pentyl group, hexyl group, octyl group, nonyl group, and decyl group.

Example of the term of "alkenyl group" include vinyl group, 1-propenyl group, 2-propenyl group, 1-methyl-1-propenyl group, 1-methyl-2-propenyl group, 1,2-dimethyl-1-propenyl group, 1-ethyl-2-propenyl group, 3-butenyl group, 4-pentenyl group, 5-hexenyl group, 7-octenyl group, 8-nonenyl group, and 9-decenyl group.

Example of the term of "alkynyl group" includes ethynyl group, 1-propynyl group, 2-propynyl group, 1-methyl-2-propynyl group, 1,1-dimethyl-2-propynyl group, 1-ethyl-2- propynyl group, 2-butynyl group, 4-pentynyl group, 5-hexynyl group, 7-octynyl group, 8-nonynyl group, and 9-decynyl group.

Example of the term of "C1-C6 alkyl group optionally having one or more halogen atoms" or "C1-C6 haloalkyl group" include trifluoromethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, and perfluorohexyl group.

Example of the term of "cycloalkyl group" includes cyclopropyl group, cyclobutyl group, cyclopentyl group, cyclohexyl group and cycloheptyl group.

Example of the term of "cycloalkenyl group" includes cyclopropenyl group, cyclobutenyl group, cyclopentenyl group, cyclohexenyl group, and cycloheptenyl group. Examples of the term of "C3-C6 cycloalkyl group optionally having one or more halogen atoms" includes 2,2-difluorocyclopropyl group, 1-(2,2,2-trifluoroethyl)cyclopropyl group, and 4-(trifluoromethyl)cyclohexyl group.

Examples of the term of "alkoxy group" includes methoxy group, ethoxy group, propoxy group, butoxy group, pentoxy group, and hexyloxy group.

The term of "C1-C6 alkoxy group optionally having one or more halogen atoms" represents a C1-C6 alkoxy group wherein one or more halogen atoms are replaced by a halogen atom, and includes, for example, trifluoromethoxy group, difluoromethoxy group, 2,2,2-trichloroethoxy group, and 2,2,2-trifluoroethoxy group.

The terms of "alkylsulfanyl", "alkylsulfinyl", and "alkylsulfonyl" represent an alkyl group containing a $S(O)_z$ moiety, respectively.

For example, examples of the "alkylsulfanyl" when z is 0 include methylsulfanyl group, ethylsulfanyl group, propylsulfanyl group, and isopropylsulfanyl group.

For example, examples of the "alkylsulfinyl" when z is 1 include methylsulfinyl group, ethylsulfinyl group, propylsulfinyl group, and isopropylsulfinyl group.

For example, examples of the "alkylsulfonyl" when z is include methylsulfonyl group, ethylsulfonyl group, propylsulfonyl group, and isopropylsulfonyl group.

Examples of the term of "three (3) to seven (7) membered nonaromatic heterocyclic group" include aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiazinane ring, thiomorpholine ring, and 1,4-thiazepane ring. Examples of the three to seven membered nonaromatic heterocyclic group optionally having one or more substituents selected from Group E include the followings:

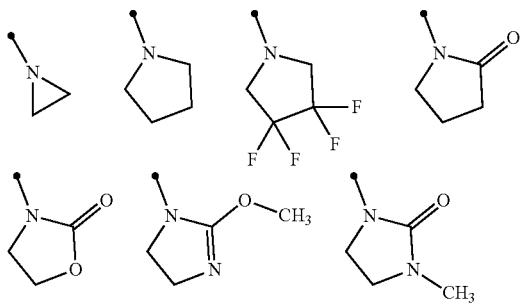

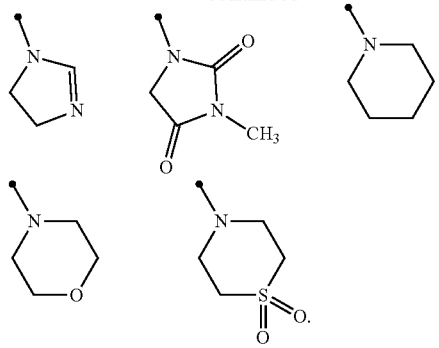

The term of "(C1-C5 alkoxy)C2-C5 alkyl group having one or more halogen atom" represents a group wherein the (C1-C5 alkoxy) and/or the (C2-C5 alkyl) has/have one or more halogen atoms, and includes, for example, 2-(trifluoromethoxy)ethyl group, 2,2-difluoro-3-methoxypropyl group, 2,2-difluoro-3-(2,2,2-trifluoroethoxy)propyl group, and 3-(2-chloroethoxy)propyl group.

The term of "(C1-C5 alkylsulfanyl)C2-C5 alkyl group having one or more halogen atoms" represents a group wherein the (C1-C5 alkylsulfanyl) and/or the (C2-C5 alkyl) has/have one or more halogen atoms, and includes, for example, 2,2-difluoro-2-(trifluoromethylthio)ethyl group.

The term of "(C1-C5 alkylsulfinyl)C2-C5 alkyl group having one or more halogen atoms" represents a group wherein the (C1-C5 alkylsulfinyl) and/or the (C2-C5 alkyl) has/have one or more halogen atoms, and includes, for example, 2,2-difluoro-2-(trifluoromethansulfinyl)ethyl group.

The term of "(C1-C5 alkylsulfonyl)C2-C5 alkyl group having one or more halogen atoms" represents a group wherein the (C1-C5 alkylsulfonyl) and/or the (C2-C5 alkyl) has/have one or more halogen atoms, and includes, for example, 2,2-difluoro-2-(trifluoromethansulfonyl) ethyl group.

The term of "(C3-C7 cycloalkyl)C1-C3 alkyl group optionally having one or more halogen atoms" represents a group wherein the (C3-C7 cycloalkyl) and/or the (C1-C3 alkyl) has/have one car more halogen atoms, and includes, for example, (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The term of "(C3-C7 cycloalkyl)C1-C3 alkyl group having one or tore substituents selected from Group G" represents a group wherein the (C3-C7 cycloalkyl) and/or the (C1-C3 alkyl) has/have one or more substituents selected from Group G, and includes, example, (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2-tetrafluoroethyl group, 2-cyclopropyl-3,3,3-trifluoropropyl group, and 1,1,2,2, tetrafluoro-2-[2-(trifluoromethyl)cyclopropyl]ethyl group.

Examples of the term of "phenyl C1-C3 alkyl group {the phenyl moiety in the phenyl C1-C3 alkyl group may optionally have one or more substituents selected from Group D}" include benzyl group, 2-fluorobenzyl group, 4-chlorobenzyl group, 4-(trifluoromethyl)benzyl group, and 2-[4-(trifluoromethyl)phenyl]ethyl group.

The term of "five (5) or six (6) membered aromatic heterocyclic group" represents a five membered aromatic heterocyclic group or a six membered aromatic heterocyclic group, and examples of the five membered aromatic heterocyclic group include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group. As the five membered aromatic heterocyclic group, a five membered aromatic heterocyclic group containing 1 to 4 nitrogen atoms, that is, pyrrolyl group, pyrazolyl group, imidazolyl group, 1,2,4-triazolyl group, 1,2,3-triazolyl group, or tetrazolyl group is preferably included. Examples of the six membered aromatic heterocyclic group include pyridyl group, pyridazinyl group, pyrimidinyl group, pyrazinyl group, and triazinyl group.

The term of "when two $R^3$ are adjacent to each other, said two $R^3$ combine together with a carbon atom to which they are attached to form benzene ring, pyrrole ring, furan ring, thiophene ring, pyrazole ring, imidazole ring, triazole ring, oxazole ring, isoxazole ring, thiazole ring, oxadiazole ring, thiadiazole ring, pyridine ring, pyridazine ring, pyrimidine ring, or pyrazine ring" represents, for example, the following compounds when pyrrole ring is formed.

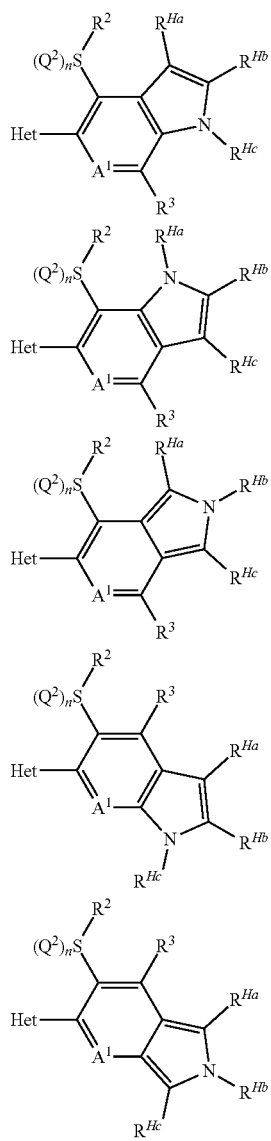

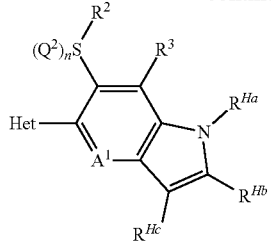

(wherein, $R^{Ha}$, $R^{Hb}$, and $R^{Hc}$ are identical to or different from each other and each represents independently a five or six membered aromatic heterocyclic group, a C1-C6 alkyl group optionally having one or more halogen atoms, a C3-C6 cycloalkyl group optionally having one or more halogen atoms, $OR^{10}$, an amino group, $NR^9R^{10}$, $C(O)R^{10}$, $C(O)NR^9R^{10}$, $OC(O)R^9$, $OC(O)CR^9$, $NR^{10}C(O)R^9$, $NR^{10}C(O)OR^9$, $C(O)OR^{10}$, a halogen atom, a nitro group, or a cyano group, and the other symbols are the same as defined above.]

Examples of the embodiment of the compound of the present invention include the following compounds.

When "Present compound Z of the present invention" is described herein, encompasses "Present compound of the present invention" unless specified otherwise.

Embodiment 1

A compound of the present invention wherein $A^1$ represents a nitrogen atom or CH.

Embodiment 2

The compound described in Embodiment 1 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$ or a halogen atom, $R^{4a}$, $R^{4b}$ and $R^{4c}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 3

A compound of the present invention wherein $A^1$ represents a nitrogen atom.

Embodiment 4

The compound described in Embodiment 3 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently

Embodiment 5

The compound described in Embodiment 3 wherein $R^2$ represents a C1-C6 alkyl group, $R^{4a}$, $R^{4b}$ and $R^{4c}$ represent a hydrogen atom or a halogen atom, q is 0 or 1, and $Q^1$ and $Q^2$ represent an oxygen atom.

Embodiment 6

The compound described in Embodiment 5 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$ or a halogen atom, and $R^5$ represents a C1-C6 alkyl group optionally having one or more halogen atoms.

Embodiment 7

The compound described in Embodiment 3 wherein $R^2$ represents a C1-C6 alkyl group, $R^3$ represents a C1-C6 alkyl group, C3-C7 cycloalkyl group {the C1-C6 alkyl group and the C3-C7 cycloalkyl group each independently may optionally have one or more substituents selected from the group consisting of a halogen atom and a cyano group}, a phenyl group, a pyridyl group {the phenyl group and the pyridyl group each independently may optionally have one or more substituents selected from Group G}, or a halogen atom, $R^{4a}$, $R^{4b}$ and $R^{4c}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 8

A compound of the present invention wherein $A^1$ represents CH.

Embodiment 9

The compound described in Embodiment 8 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$, $R^{4b}$ and $R^{4c}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 10

A compound of the present invention wherein Het represents Het 1.

Embodiment 11

The compound described in Embodiment 10 wherein $A^1$ represents a nitrogen atom or CH.

Embodiment 12

The compound described in Embodiment 11 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O) OR^{14}$, or a halogen atom, $R^{4a}$ and $R^{4b}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 13

The compound described in Embodiment 10 wherein $A^1$ represents a nitrogen atom.

Embodiment 14

The compound described in Embodiment 13 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O) OR^{14}$ or a halogen atom.

Embodiment 15

The compound described in Embodiment wherein $R^2$ represents a C1-C6 alkyl group, $R^{4a}$ and $R^{4b}$ represent a hydrogen atom or a halogen atom, q is 0 or 1, and $Q^1$ and $Q^2$ represent an oxygen atom.

Embodiment 16

The compound described in Embodiment 15 wherein $R^3$ represents a C1-C6 alkyl group optionally having one or more substituents selected from Group B, a C3-C7 cycloalkyl group optionally having one or more substituents selected from Group E, a phenyl group, a pyridyl group, pyrimidinyl group, a pyrazolyl group, a triazolyl group {the phenyl group, the pyridyl group, the pyrimidinyl group, the pyrazolyl group, and the triazolyl group each independently may optionally have one or more substituent: selected from Group J}, $OR^{12}$, $NR^{11}R^{12}$, $NR^{11}C(O)OR^{14}$, or a halogen atom, and $R^5$ represents a C1-C6 alkyl group optionally having one or more halogen atoms.

Embodiment 17

The compound described in Embodiment 13 wherein $R^2$ represents a C1-C6 alkyl group, $R^3$ represents a C1-C6 alkyl group, a C3-C7 cycloalkyl group {the C1-CG alkyl group and the C3-C7 cycloalkyl group each independently may optionally have one or more substituents selected from the group consisting of a halogen atom and a cyano group}, a phenyl group, a pyridyl group {the phenyl group, and the pyridyl group each independently may optionally have one or more substituents selected from Group G}, or a halogen atom, $R^{4a}$ and $R^{4b}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 18

The compound described in Embodiment 10 wherein $A^1$ represents CH.

Embodiment 19

The compound described in Embodiment 18 wherein $R^2$ represents an ethyl group, $R^3$ represents a C1-C6 alkyl optionally having one or more substituents selected from group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$ and $R^{4b}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 20

The compound described in Embodiment 10 wherein $A^2$ represents $CR^{4a}$, and $A^3$ represents $CR^{4b}$.

Embodiment 21

The compound described in Embodiment 11 wherein $A^2$ represents $CR^{4a}$ and $A^3$ represents $CR^{4b}$.

Embodiment 22

The compound described in Embodiment 12 wherein $A^2$ represents $CR^{4a}$ and $A^3$ represents $CR^{4b}$.

Embodiment 23

The compound described in Embodiment 13 wherein $A^2$ represents $CR^{4a}$ and $A^3$ represents $CR^{4b}$.

Embodiment 24

The compound described in Embodiment 14 wherein $A^2$ represents $CR^{4a}$ and $A^3$ represents $CR^{4b}$.

Embodiment 25

The compound described in Embodiment 15 wherein $A^2$ represents $CR^{4a}$ and $A^3$ represents $CR^{4b}$.

Embodiment 26

The compound described in Embodiment 16 wherein $A^2$ represents $CR^{4a}$ and $A^3$ represents $CR^{4b}$.

Embodiment 27

The compound described in Embodiment 17 wherein $A^2$ represents $CR^{4a}$ and $A^3$ represents $CR^{4b}$.

Embodiment 28

The compound described in Embodiment 18 wherein $A^2$ represents $CR^{4a}$ and $A^3$ represents $CR^{4b}$.

Embodiment 29

The compound described in Embodiment 19 wherein $A^2$ represents $CR^{4a}$ and $A^3$ represents $CR^{4b}$.

Embodiment 30

A compound of the present invention wherein Het represents a group represented by formula Het 1, $A^2$ represents $CR^{4a}$, and $A^3$ represents a nitrogen atom.

Embodiment 31

The compound described in Embodiment 30 wherein $A^1$ represents a nitrogen atom or CH.

Embodiment 32

The compound described in Embodiment 31 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 33

The compound described in Embodiment 30 wherein $A^1$ represents a nitrogen atom.

Embodiment 34

The compound described in Embodiment 33 wherein $R^3$ represents a C1-C6 alkyl group optionally having one or more substituents selected from Group B, a 03-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom.

Embodiment 35

The compound described in Embodiment 33 wherein $R^2$ represents a C1-C6 alkyl group, $R^{4a}$ represents a hydrogen atom or a halogen atom, q is 0 or 1, and $Q^1$ and $Q^2$ represent an oxygen atom.

Embodiment 36

The compound described in Embodiment 35 wherein $R^3$ represents a C1-C6 alkyl group optionally having one or more substituents selected from Group B, a C3-C7 cycloalkyl group optionally having one or more substituents selected from group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from group J}, $OR^{12}$, $NR^{11}R^{12}$, $NR^{11}C(O)OR^{14}$, or a halogen atom, and $R^5$ represents a C1-C6 alkyl group optionally having one or more halogen atoms.

Embodiment 37

The compound described in Embodiment 33 wherein $R^2$ represents a C1-C6 alkyl group, $R^3$ represents a C1-C6 alkyl group, a C3-C7 cycloalkyl group {the C1-C6 alkyl group and the C3-C7 cycloalkyl group each independently may optionally have one or more substituents selected from the group consisting of a halogen atom and a cyano group}, a phenyl group, a pyridyl group {the phenyl group and the pyridyl group each independently may optionally have one or more substituents selected from Group G}, or a halogen atom, $R^{4a}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 38

The compound described in Embodiment 30 wherein $A^1$ represents CH.

Embodiment 39

The compound described in Embodiment 38 wherein $R^2$ represents an ethyl group, $R^3$ represents a C1-C6 alkyl group optionally having one or more substituents selected from group B, a C3-C7 cycloalkyl group optionally having one or more substituents selected from Group E, a phenyl group, a pyridyl group, a pyrimidinyl group, a pyrazolyl group, triazolyl group the {the phenyl group, the pyridyl group, the pyrimidinyl group, the pyrazolyl group, and the triazolyl group each independently may optionally have one or more substituents selected from group J}, $OR^{12}$, $NR^{11}R^{12}$, $NR^{11}C(O)OR^{14}$, or a halogen atom, $R^{4a}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 40

A compound of the present invention wherein Het represents a group represented by formula Het1, $A^2$ represents a nitrogen atom, and $A^3$ represents $CR^{4b}$.

Embodiment 41

The compound described in Embodiment 40 wherein $A^1$ represents a nitrogen atom or a CH.

Embodiment 42

The compound described in Embodiment 41 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4b}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 43

The compound described in Embodiment 40 wherein $A^1$ represents a nitrogen atom.

Embodiment 44

The compound described in Embodiment 43 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom.

Embodiment 45

The compound described in Embodiment 43 wherein $R^2$ represents a C1-C6 alkyl group, $R^{4b}$ represents a hydrogen atom or a halogen atom, q is 0 or 1, and $Q^1$ and $Q^2$ represent an oxygen atom.

Embodiment 46

The compound described in Embodiment 45 wherein $R^3$ represents a C1-C6 alkyl group optionally having one or ore substituents selected from Group B, a C3-C7 cycloalkyl group optionally having one or more substituents selected from Group E, a phenyl group, a pyridyl group a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, and $R^5$ represents a C1-C6 alkyl group optionally having one or more halogen atoms.

Embodiment 47

The compound described in Embodiment 43 wherein $R^2$ represents a C1-C6 alkyl group, $R^3$ represents a C1-C6 alkyl group, a C3-C7 cycloalkyl group {the C1-C6 alkyl group and the C3-C7 cycloalkyl group each independently may optionally have one or more substituents selected from the group consisting of a halogen atom and a cyano group}, a phenyl group, a pyridyl group {the phenyl group and the pyridyl group each independently may optionally have one or more substituents selected from Group G}, or a halogen atom, $R^{4b}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 48

The compound described in Embodiment 40 wherein $A^1$ represents CH.

Embodiment 49

The compound described in Embodiment 48 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or halogen atom, $R^{4b}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 50

A compound of the present invention wherein Het represents a group represented by formula Het1, and $A^2$ and $A^3$ represent a nitrogen atom.

Embodiment 51

The compound described in Embodiment 50 wherein $A^1$ represents a nitrogen atom or CH.

Embodiment 52

The compound described in Embodiment 51 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group L}, $OR^{12}$, $NR^{11}R^{12}$, $NR^{11}C(O)OR^{14}$, or a halogen atom, $R^5$ represents a C1-C6 alkyl group optionally having one or more halogen atoms, q is 0 or 1, and $Q^1$ and $Q^2$ represent an oxygen atom.

Embodiment 53

The compound described in Embodiment 50 wherein $A^1$ represent a nitrogen atom.

Embodiment 54

The compound described in Embodiment 53 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyi group each independently may optionally have one or more substituents selected from Group J}, $OR^{12}$, $NR^{11}R^{12}$, $NR^{11}C(O)OR^{14}$, or a halogen atom.

Embodiment 55

The compound described in Embodiment 53 wherein $R^2$ represent, a C1-C6 alkyl group, q is 0 or 1, and $Q^1$ and $Q^2$ represent an oxygen atom.

Embodiment 56

The compound described in Embodiment 55 wherein $R^3$ represents a C1-C6 alkyl group optionally having one or more substituents selected from Group B, or a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, and $R^5$ represents a C1-C6 alkyl group optionally having one or more halogen atoms.

Embodiment 57

The compound described in Embodiment 53 wherein $R^2$ represents a C1-C6 alkyl group, $R^3$ represents a C1-C6 alkyl group, a C3-C7 cycloalkyl group {the C1-C6 alkyl group and the C3-C7 cycloalkyl group each independently may optionally have one or more substituents selected from the group consisting of a halogen atom and a cyano group}, a phenyl group, a pyridyl group {the phenyl group and the pyridyl group each independently may optionally have one or more substituents selected from Group G}, or a halogen atom, $R^5$ represents a C1-C6 alkyl group optionally having one or more halogen atoms, q is 0 or 1, and $Q^1$ and $Q^2$ represent an oxygen atom.

Embodiment 58

The compound described in Embodiment 50 wherein $A^1$ represents CH.

Embodiment 59

The compound described in Embodiment 58 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^5$ represents a C1-C6 alkyl group optionally having one or more halogen atoms, q is 0 or 1, and $Q^1$ and $Q^2$ represent an oxygen atom.

Embodiment 60

A compound of the present invention wherein Het represents a group represented by formula Het2.

Embodiment 61

The compound described in Embodiment 60 wherein $A^1$ represents a nitrogen atom or CH.

Embodiment 62

The compound described in Embodiment 61 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$ and $R^{4c}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 63

The compound described in Embodiment 60 wherein $A^1$ represents a nitrogen atom.

Embodiment 64

The compound described in Embodiment 63 wherein $R^3$ represents a C1-C6 alkyl group optionally having one or more substituents selected from Group B, a C3-C7 cycloalkyl group optionally having one or more substituents selected from Group E, a phenyl group, a pyridyl group, pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom.

Embodiment 65

The compound described in Embodiment 63 wherein $R^2$ represents a C1-C6 alkyl group, $R^{4a}$ and $R^{4c}$ represent a hydrogen atom or a halogen atom, q is 0 or 1, and $Q^1$ and $Q^2$ represent an oxygen atom.

Embodiment 66

The compound described in Embodiment 65 wherein $R^3$ represents a C1-C6 alkyl group optionally having one or more substituents selected from Group B, a C3-C7 cycloalkyl group optionally having one or pore substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, and $R^5$ represents a C1-C6 alkyl group optionally having one or more halogen atoms.

Embodiment 67

The compound described in Embodiment 63 wherein $R^2$ represents a C1-C6 alkyl group, $R^3$ represents a C1-C6 alkyl group, a C3-C7 cycloalkyl group {the C1-C6 alkyl group and the C3-C7 cycloalkyl group each independently may optionally have one or more substituents selected from the group consisting of a halogen atom and a cyano group}, a phenyl group, a pyridyl group {the phenyl group and the pyridyl group each independently may optionally have one or more substituents selected from Group G}, or a halogen atom, $R^{4a}$ and $R^{4c}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 68

The compound described in Embodiment 60 wherein $A^1$ represents a CH.

Embodiment 69

The compound described in Embodiment 68 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$ and $R^{4c}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 70

The compound described in Embodiment 60 wherein $A^2$ represents $CR^{4a}$ and $A^4$ represents $CR^{4c}$.

Embodiment 71

The compound described in Embodiment 61 wherein $A^2$ represents $CR^{4a}$ and $A^4$ represents $CR^{4c}$.

Embodiment 72

The compound described in Embodiment 62 wherein $A^2$ represents $CR^{4a}$ and $A^4$ represents $CR^{4c}$.

Embodiment 73

The compound described in Embodiment 63 wherein $A^2$ represents $CR^{4a}$ and $A^4$ represents $CR^{4c}$.

Embodiment 74

The compound described in Embodiment 64 wherein $A^2$ represents $CR^{4a}$ and $A^4$ represents $CR^{4c}$.

Embodiment 75

The compound described in Embodiment 65 wherein $A^2$ represents $CR^{4a}$ and $A^4$ represents $CR^{4c}$.

Embodiment 76

The compound described in Embodiment 66 wherein $A^2$ represents $CR^{4a}$ and $A^4$ represents $CR^{4c}$.

Embodiment 77

The compound described in Embodiment 67 wherein $A^2$ represents $CR^{4a}$ and $A^4$ represents $CR^{4c}$.

Embodiment 78

The compound described in Embodiment 68 wherein $A^2$ represents $CR^{4a}$ and $A^4$ represents $CR^{4c}$.

Embodiment 79

The compound described in Embodiment 69 wherein $A^2$ represents $CR^{4a}$ and $A^4$ represents $CR^{4c}$.

Embodiment 80

A compound of the present invention wherein Het represents a group represented by formula Het2, $A^2$ represents $CR^{4a}$ and $A^4$ represents a nitrogen atom.

Embodiment 81

The compound described in Embodiment 80 wherein $A^1$ represents a nitrogen atom or CH.

Embodiment 82

The compound described in Embodiment 81 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 83

The compound described in Embodiment 80 wherein $A^1$ represents a nitrogen atom.

Embodiment 84

The compound described in Embodiment 83 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom.

Embodiment 85

The compound described in Embodiment 83 wherein $R^2$ represents a C1-C6 alkyl group, $R^{4a}$ represents a hydrogen atom or a halogen atom, q is 0 or 1, $Q^1$ and $Q^2$ represent an oxygen atom.

Embodiment 86

The compound described in Embodiment 85 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^5$ represents a C1-C6 alkyl group optionally having one or more halogen atoms.

Embodiment 87

The compound described in Embodiment 83 wherein $R^2$ represents a C1-C6 alkyl group, $R^3$ represents a C1-C6 alkyl group, a C3-C7 cycloalkyl group {the C1-C6 alkyl group and the C3-C7 cycloalkyl group each independently may optionally have one or more substituents selected from the group consisting of a halogen atom and a cyano group}, a phenyl group, a pyridyl group {the phenyl group and the pyridyl group each independently may optionally have one or more substituents selected from Group G}, or a halogen atom, $R^{4a}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 88

The compound described in Embodiment 80 wherein $A^1$ represents CH.

Embodiment 89

The compound described in Embodiment 88 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 90

A compound of the present invention wherein Het represents a group represented by formula Het2, $A^2$ represents a nitrogen atom, and $A^4$ represents $CR^{4c}$.

Embodiment 91

The compound described in Embodiment 90 wherein $A^1$ represents a nitrogen atom or CH.

Embodiment 92

The compound described in Embodiment 91 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4c}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 93

The compound described in Embodiment 90 wherein $A^1$ represents a nitrogen atom.

Embodiment 94

The compound described in Embodiment 93 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom.

Embodiment 95

The compound described in Embodiment 93 wherein $R^2$ represents a C1-C6 alkyl group, $R^{4c}$ represents a hydrogen atom or a halogen atom, q is 0 or 1, and $Q^1$ and $Q^2$ represent an oxygen atom.

Embodiment 96

The compound described in Embodiment 95 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^5$ represents a C1-C6 alkyl group optionally having one or more halogen atoms, and $Q^1$ and $Q^2$ represent an oxygen atom.

Embodiment 97

The compound described in Embodiment 93 wherein $R^2$ represents a C1-C6 alkyl group, $R^3$ represents a C1-C6 alkyl group, a C3-C7 cycloalkyl group {the C1-C6 alkyl group and the C3-C7 cycloalkyl group each independently may optionally have one or more substituents selected from the group consisting of a halogen atom and a cyano group}, a phenyl group, a pyridyl group {the phenyl group and the pyridyl group each independently may optionally have one or more substituents selected from Group G}, or a halogen atom, $R^{4c}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 98

The compound described in Embodiment 90 wherein $A^1$ represents CH.

Embodiment 99

The compound described in Embodiment 98 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4c}$ represents a hydrogen atom, $R^5$ represents a C1-C6 alkyl group optionally having one or more halogen atoms, q is 0 or 1, and $Q^1$ and $Q^2$ represent an oxygen atom.

Embodiment 100

A compound of the present invention wherein Het represents a group represented by formula Het2 and $A^2$ and $A^4$ represent a nitrogen atom.

Embodiment 101

The compound described in Embodiment 100 wherein $A^1$ represents a nitrogen atom or CH.

Embodiment 102

The compound described in Embodiment 101 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^5$ represents a C1-C6 alkyl group optionally having one or more halogen atoms, q is 0 or 1, and $Q^1$ and $Q^2$ represent an oxygen atom.

Embodiment 103

The compound described in Embodiment 100 wherein $A^1$ represents a nitrogen atom.

Embodiment 104

The compound described in Embodiment 103 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently

Embodiment 105

The compound described in Embodiment 103 wherein $R^2$ represents a C1-C6 alkyl group, q is 0 or 1, and $Q^1$ and $Q^2$ represent an oxygen atom.

Embodiment 106

The compound described in Embodiment 105 wherein $R^3$ represents a C1-C6 alkyl group optionally having one or more substituents selected from Group B, a C3-C7 cycloalkyl group optionally having one or more substituents selected from Group B, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, and $R^5$ represents a C1-C6 alkyl group optionally having one or more halogen atoms.

Embodiment 107

The compound described in Embodiment 103 wherein $R^2$ represents a C1-C6 alkyl group, $R^3$ represents a C1-C6 alkyl group, a C3-C7 cycloalkyl group {the C1-C6 alkyl group and the C3-C7 cycloalkyl group each independently may optionally have one or more substituents selected from the group consisting of a halogen atom and a cyano group}, phenyl group, a pyridyl group {the phenyl group and the pyridyl group each independently may optionally have one or more substituents selected from Group G}, or a halogen atom, $R^5$ represents a C1-C6 alkyl group optionally having one or more halogen atoms, q is 0 or 1, and $Q^1$ and $Q^2$ represent an oxygen atom.

Embodiment 108

The compound described in Embodiment 100 wherein $A^1$ represents CH.

Embodiment 109

The compound described in Embodiment 108 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^5$ represents a C1-C6 alkyl group optionally having one or more halogen atoms, q is 0 or 1, and $Q^1$ and $Q^2$ represent an oxygen atom.

Embodiment 110

A compound of the present invention wherein Het represents a group represented by formula Het1, $A^2$ represents $CR^{4a}$, $A^3$ represents $CR^{4b}$, and when Het represent a group represented by Het2, $A^2$ represents $CR^{4a}$ and $A^4$ represents $CR^{4c}$.

Embodiment 111

The compound described in Embodiment 110 wherein $A^1$ represents a nitrogen atom or CH.

Embodiment 112

The compound described in Embodiment 111 wherein $R^2$ represents an ethyl group, $R^3$ represents a C1-C6 alkyl group optionally having one or more substituent selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$, $R^{4b}$ and $R^{4c}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 113

The compound described in Embodiment 110 wherein $A^1$ represents a nitrogen atom.

Embodiment 114

The compound described in Embodiment 113 wherein $R^3$ representsa C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom.

Embodiment 115

The compound described in Embodiment 113 wherein $R^2$ represents a C1-C6 alkyl group, $R^{4a}$, $R^{4b}$ and $R^{4c}$ represent a hydrogen atom or a halogen atom, q is 0 or 1, and $Q^1$ and $Q^2$ represent an oxygen atom.

Embodiment 116

The compound described in Embodiment 115 wherein $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, and $R^5$ represents a C1-C6 alkyl group optionally having one or more halogen atoms.

Embodiment 117

The compound described in Embodiment 113 wherein $R^2$ represents a C1-C6 alkyl group, $R^3$ represents a C1-C6 alkyl group, a C3-C7 cycloalkyl group {the C1-C6 alkyl group and the C3-C7 cycloalkyl group each independently may optionally have one or more substituents selected from the group consisting of a halogen atom and a cyano group}, a phenyl group, a pyridyl group {the phenyl group and the pyridyl group each independently may optionally have one or more substituents selected from Group G}, or a halogen atom, $R^{4a}$, $R^{4b}$, $R^{4c}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 118

The compound described in Embodiment 113 wherein $R^2$ represents an ethyl group, $R^3$, $R^{4a}$, $R^{4b}$ and $R^{4c}$ represent a hydrogen atom, $R^5$ represents a C1-C6 alkyl group, q is 0, n is 2, and $Q^1$ and $Q^2$ represent an oxygen atom.

Embodiment 119

The compound described in Embodiment 110 wherein $A^1$ represents CH.

Embodiment 120

The compound described in Embodiment 119 wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$, $R^{4b}$ and $R^{4c}$ represent a hydrogen atom, $R^5$ represents a C1-C6 alkyl group optionally having one or more halogen atoms, q is 0 or 1, and $Q^1$ and $Q^2$ represent an oxygen atom.

Embodiment 121

A compound of the present invention wherein $A^1$ represents a nitrogen atom or CH, $R^2$ represents an ethyl group, $R^3$ represents a C1-C5 alkyl group, a C3-C7 cycloalkyl group {the C1-C6 alkyl group and the C3-C7 cycloalkyl group each independently may optionally have one or more substituents selected from the group consisting of a halogen atom and a cyano group}, a phenyl group, a pyrazolyl group, a pyridyl group {the phenyl group, the pyrazolyl group, and the pyridyl group each independently may optionally have one or more substituents selected from Group G}, or a halogen atom, $R^{4a}$, $R^{4b}$ and $R^{4c}$ represent a hydrogen atom, $R^5$ represents a C1-C6 alkyl group or a C3-C6 cycloalkyl group, q is 0 or 1, n is 2, and $Q^1$ and $Q^2$ represent an oxygen atom.

Embodiment 122

A compound of the present invention wherein $A^1$ represents a nitrogen atom or CH, $R^2$ represents an ethyl group, $R^3$ represents a C1-C6 alkyl group, a C3-C7 cycloalkyl group {the C1-C6 alkyl group and the C3-C7 cycloalkyl group each independently may optionally have one or more substituents selected from the group consisting a halogen atom and a cyano group}, a phenyl group, a pyridyl group {the phenyl group, the pyrimidinyl group, and the pyridyl group each independently may optionally have one or more substituents selected from Group G}, or a halogen atom, $R^{4a}$, $R^{4b}$ and $R^{4c}$ represent a hydrogen atom, $R^5$ represents a C1-C6 alkyl group, q is 0 or 1, n is 2, and $Q^2$ and $Q^2$ represent an oxygen atom.

Embodiment 123

A compound of the present invention wherein T represents a C1-C5 chain hydrocarbon group having one or more halogen atoms, $OR^1$, $S(O)_xR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by formula T-1, a group represented by formula T-2, a group represented by formula T-3, a group represented by formula T-4, a group represented by formula T-5, a group represented by formula T-6, a group represented by formula T-7, a group represented by formula T-8, a group represented by formula T-9, a group represented by formula T-10, a group represented by formula T-11, or a group represented by formula T-12, and $R^1$, $R^{1x}$, $R^{1y}$ and $R^{1ay}$ are identical to or different from each other and each represents independently a C1-C5 chain hydrocarbon group having one more halogen atoms.

Embodiment 124

A compound of the present invention wherein T represents a C1-C5 alkyl group having three or more fluorine atoms, $OR^1$, $S(O)_xR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by formula T-1, a group represented by formula T-2, a group represented by formula T-3, a group represented by formula T-4, a group represented by formula T-5, a group represented by formula T-6, a group represented by formula T-7, a group represented by formula T-8, a group represented by formula T-9, a group represented by formula T-10, a group represented by formula T-11, or a group represented by formula T-12, and $R^1$, $R^{1x}$, $R^{1y}$ and $R^{1ay}$ are identical to or different from each other and each represents independently a C1-C5 alkyl group having three or more fluorine atoms.

Embodiment 125

A compound of the present invention wherein T represents a C1-C5 chain hydrocarbon group having one or more halogen atoms, $OR^1$, $S(O)_xR^1$, $OS(O)_2R^1$, $NR^1R^{29}$, a group represented by formula T-1, a group represented by formula T-2, a group represented by formula T-3, a group represented by formula T-4, or a group represented by formula T-8, and $R^1$, $R^{1x}$ and $R^{1y}$ are identical to or different from each other and each represents independently a C1-C5 chain hydrocarbon group having one or more halogen atoms.

Embodiment 126

A compound of the present invention wherein T represents a C1-C5 alkyl group having three or more fluorine atoms, $OR^1$, $S(O)_xR^1$, $OS(O)_2R^1$, $NR^1R^{29}$, a group represented by formula T-1, a group represented by formula T-2, a group represented by formula T-3, a group represented by formula T-4, or a group represented by formula T-8, and $R^1$, $R^{1x}$ and $R^{1y}$ are identical to or different from each other and each represents independently a C1-C5 alkyl group having three or more fluorine atoms.

Embodiment 127

A compound of the present invention wherein T represents a C1-C5 chain hydrocarbon group having one or more halogen atoms, $OR^1$, $S(O)_vR^1$, $OS(O)_2R^1$, $NR^1R^{29}$, and $R^1$ represents a C1-C5 chain hydrocarbon group having one more halogen atoms.

Embodiment 128

A compound of the present invention wherein T represents a C1-C5 alkyl group having three or more fluorine atoms, $OR^1$, $S(O)_vR^1$, $OS(O)_2R^1$, $NR^1R^{29}$, and $R^1$ represents a C1-C5 alkyl group having three or more fluorine atoms.

Embodiment 129

A compound of the present invention wherein T represents $OR^1$.

Embodiment 130

The compound described in Embodiment 129 wherein $R^1$ represents a C1-C5 chain hydrocarbon group having one or more halogen atoms.

Embodiment 131

The compound described in Embodiment 129 wherein $R^1$ represents a C1-C5 alkyl group having three or more fluorine atoms.

Embodiment 132

A compound of the present invention wherein T represents a group represented by formula T-1, a group represented by formula T-2, a group represented by formula T-3, a group represented by formula T-4, or a group represented by formula T-8.

Embodiment 133

The compound described in Embodiment 132 wherein $R^{1x}$ and $R^{1y}$ are identical to or different from each other and each represents independently a C1-C5 chain hydrocarbon group having one or more halogen atoms.

Embodiment 134

The compound described in Embodiment 132 wherein $R^{1x}$ and $R^{1y}$ are identical to or different from each other and each represents independently a C1-C5 alkyl group having three or more fluorine atoms.

Embodiment 135

The compound described in anyone of Embodiments 1 to 121 or 122 wherein T represents a C1-C5 chain hydrocarbon group having one or more halogen atoms, $OR^1$, $S(O)_vR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by formula T-1, a group represented by formula T-2, a group represented by formula T-3, a group represented by formula T-4, a group represented by formula T-5, a group represented by formula T-6, a group represented by formula T-7, a group represented by formula T-8, a group represented by formula T-9, a group represented by formula T-10, a group represented by formula T-11, or a group represented by formula T-12, and $R^1$, $R^{1x}$, $R^{1y}$ and $R^{1ay}$ are identical to or different from each other and each represents independently a C1-C5 chain hydrocarbon group having one or more halogen atoms.

Embodiment 136

The compound described in Embodiments 1 to 121 or 122 wherein T represents a C1-C5 alkyl group having three or more fluorine atoms, $OR^1$, $S(O)_vR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by formula T-1, a group represented by formula T-2, a group represented by formula T-3, a group represented by formula T-4, a group represented by formula T-5, a group represented by formula T-6, a group represented by formula T-7, a group represented by formula T-8, a group represented by formula T-9, a group represented by formula T-10, a group represented by formula T-11, or a group represented by formula T-12, and $R^1$, $R^{1x}$, $R^{1y}$ and $R^{1ay}$ are identical to or different from each other and each represents independently a C1-C5 alkyl group having three or more fluorine atoms.

Embodiment 137

The compound described in anyone of Embodiments 1 to 121 or 122 wherein T represents a C1-C5 chain hydrocarbon group having one or more halogen atoms, $OR^1$, $S(O)_vR^1$, $OS(O)_2R^1$, $NR^1R^{29}$, a group represented by formula T-1, a group represented by formula T-2, a group represented by formula T-3, a group represented by formula T-4, or a group represented by formula T-8, and $R^1$, $R^{1x}$, and $R^{1y}$ are identical to or different from each other and each represents independently a C1-C5 chain hydrocarbon group having one or more halogen atoms.

Embodiment 138

The compound described in anyone of Embodiments 1 to 121 or 122 wherein T represents a C1-C5 alkyl group having three or more fluorine atoms, $OR^1$, $S(O)_vR^1$, $OS(O)_2R^1$, $NR^1R^{29}$, a group represented by formula T-1, a group represented by formula T-2, a group represented by formula T-3, a group represented by formula T-4, or a group represented by formula T-8, and $R^1$, $R^{1x}$, and $R^{1y}$ are identical to or different from each other and each represents independently a C1-C5 alkyl group having three or more fluorine atoms.

Embodiment 139

The compound described in anyone or more Embodiments 1 to 121 or 122 wherein T represents a C1-C5 chain hydrocarbon group having one or more halogen atoms, $OR^1$, $S(O)_vR^1$, $OS(O)_2R^1$, $NR^1R^{29}$, anal $R^1$ represents a C1-C5 chain hydrocarbon group having one or more halogen atoms.

Embodiment 140

The compound described in anyone of Embodiments 1 to 121 or 122 wherein T represents a C1-C5 alkyl group having three or more fluorine atoms, $OR^1$, $S(O)_vR^1$, $OS(O)_2R^1$, or $NR^1R^{29}$, and $R^1$ represents a C1-C5 alkyl group having three or more fluorine atoms.

Embodiment 141

The compound described in anyone of Embodiments 1 to 121 or 122 wherein T represents $OR^1$.

Embodiment 142

The compound described in anyone of Embodiments 1 to 121 or 122 wherein T represents $OR^1$, and $R^1$ represents a C1-C5 chain hydrocarbon group having one or more halogen atoms.

Embodiment 143

The compound described in anyone of Embodiments 1 to 121 or 122 wherein T represents $OR^{10}$, and $R^1$ represents a C1-C5 alkyl group having three or more fluorine atoms.

Embodiment 144

The compound described in anyone of Embodiments 1 to 121 or 122 wherein T represents a group represented by formula T-1, a group represented by formula T-2, a group represented by formula T-3, a group represented by formula T-4, or a group represented by formula T-8.

Embodiment 145

The compound described in anyone of Embodiments 1 to 121 or 122 wherein T represents a group represented by formula T-1, a group represented by formula T-2, a group represented by formula T-3, a group represented by formula T-4, or a group represented by formula T-8, and $R^{1x}$ and $R^{1y}$ are identical to or different from each other and each represents independently a C1-C5 chain hydrocarbon group having one or more halogen atoms.

Embodiment 146

The compound described in anyone of Embodiments 1 to 121 or 122 wherein T represents a group represented by formula T-1, a group represented by formula T-2, a group represented by formula T-3, a group represented by formula T-4, or a up represented by formula T-8, and $R^{1x}$ and $R^{1y}$ are identical to or different from each other and each represent independently a C1-C5 alkyl group having three or more fluorine atoms.

Embodiment 147

The compound described in Embodiments 1 to 121 or 122 wherein T represents $OR^1$, a group represented by formula T-1, a group represented by formula T-2, or a group represented by formula T-8, $R^1$, $R^{1x}$ and $R^{1y}$ are identical to or different from each other and each represents independently a C1-C5 alkyl group having one or more fluorine atoms, $X^1$ represents $CR^{1a}$, $X^2$ represents $CR^{1b}$, $X^3$ represents $CR^{1c}$ and $X^5$ represents $CR^{1e}$.

Examples of the embodiment of the compound Z of the present invention include the following compounds.

Embodiment 148

A compound Z of the present invention wherein $R^2$ represents an ethyl group, $R^3$ represents a C1-C6 alkyl group optionally having one or more substituents selected from Group B, a C3-C7 cycloalkyl group optionally having one or more substituents selected from Group E, a phenyl group, a pyridyl group, a pyrimidinyl group, pyrazolyl group, a triazolyl group {the phenyl group, the pyridyl group, the pyrimidinyl group, the pyrazolyl group, and the triazolyl group each independently may optionally have one or more substituents selected from Group J}, $OR^{12}$, $NR^{11}R^{12}$, $NR^{11}C(O)OR^{14}$, or a halogen atom, $R^{4a}$, $R^{4b}$ and $R^{4c}$ represent a hydrogen atom, $R^5$ represents a C1-C6 alkyl group optionally having one or more halogen atoms, q is 0 or 1, n is 2, and $Q^1$ and $Q^2$ represent an oxygen atom.

Embodiment 149

The compound described in Embodiment 148 wherein $A^1$ represents a nitrogen atom, T represents a C1-C5 alkyl group having one or more substituents selected from the group consisting of a cyano group and a halogen atom, $OR^1$, $S(O)_vR^1$, $OS(O)_2R^1$, $NR^1R^{29}$, a group represented by formula T-1, a group represented by formula T-2, a group represented by formula T-3, a group represented by formula T-4, or a group represented by formula T-8, and $R^1$, $R^{1x}$ and $R^{1y}$ are identical to or different from each other and each represents independently a C1-C5 alkyl group optionally having one or more substituents selected from the group consisting of a cyano group and a halogen atom.

Embodiment 150

The compound described in Embodiment 148 wherein $A^1$ represents a nitrogen atom or CH, T represents a C1-C5 alkyl group having one or more substituents selected from the group consisting of a cyano group and a halogen atom, $OR^1$, $S(O)_vR^1$, $OS(O)_2R^1$, or $NR^1R^{29}$, and $R^1$ represent a C1-C5 alkyl group having one or more substituents selected from the group consisting of a cyano group and a halogen atom.

Embodiment 151

The compound described in Embodiment 148 wherein $A^1$ represents a nitrogen atom, T represents a group represented by formula T-1, a group represented by formula T-2, a group represented by formula T-3, a group represented by formula T-4, or a group represented by formula T-8, and $R^{1x}$ and $R^{1y}$ are identical to or different from each other and each represents independently a C1-C5 alkyl group optionally having one or more substituents selected from the group consisting of a cyano group and a halogen atom.

Embodiment 152

The compound described in Embodiment 148 wherein $A^1$ represents a nitrogen atom, and T represents a C1-C5 alkoxy group having one or more substituents selected from the group consisting of a cyano group and a halogen atom.

Embodiment 153

The compound described in Embodiment 148 wherein $R^5$ represents a C1-C6 alkyl group optionally having one or more halogen atoms.

Embodiment 154

The compound described in Embodiment 153 wherein $A^1$ represents a nitrogen atom or CH, T represents a C1-C5 alkyl group having one or more substituents selected from the group consisting of a cyano group and a halogen atom, $OR^1$, $S(O)_vR^1$, $OS(O)_2R^1$, $NR^1R^{29}$, a group represented by formula T-1, a group represented by formula T-2, a group represented by formula T-3, a group represented by formula T-4, or a group represented by formula T-8, and $R^1$, $R^{1x}$ and $R^{1y}$ are identical to or different from each other and each represents independently a C1-C5 alkyl group optionally having one or more substituents selected from the group consisting of a cyano group and a halogen atom.

Embodiment 155

The compound described in Embodiment 154 wherein $A^1$ represents a nitrogen atom.

Embodiment 156

The compound described in Embodiment 153 wherein $A^1$ represents a nitrogen atom or CH, T represents a C1-C5 alkyl group having one or more substituents selected from the group consisting of a cyano group and a halogen atom, $OR^1$, $S(O)_vR^1$, $OS(O)_2R^1$, or $NR^1R^{29}$, and $R^1$ represents C1-C5 alkyl group optionally having one or more substituents selected from the group consisting of a cyano group and a halogen atom.

Embodiment 157

The compound described in Embodiment 156 wherein $A^1$ represents a nitrogen atom.

Embodiment 158

The compound described in Embodiment 153 wherein $A^1$ represents a nitrogen atom or CH, T represents a group represented by formula T-1, a group represented by formula T-2, a group represented by formula T-3, a group represented by formula T-4, or a group represented by formula T-8, and $R^{1x}$ and $R^{1y}$ are identical to or different from each other and each represents independently a C1-C5 alkyl group optionally having one or more substituents selected from the group consisting of a cyano group and a halogen atom.

Embodiment 159

The compound described in Embodiment 158 wherein $A^1$ represents a nitrogen atom.

Embodiment 160

The compound described in Embodiment 153 wherein $A^1$ represents a nitrogen atom or CH, and T represents a C1-C5 alkoxy group having one or more substituents selected from the group consisting of a cyano group and a halogen atom.

Embodiment 161

The compound described in Embodiment 160 wherein $A^1$ represents a nitrogen atom.

Examples of the embodiment of the intermediate compound D include the following compounds.

Embodiment 162

An intermediate compound D wherein $R^2$ represents a C1-C6 alkyl group optionally having one or more halogen atoms, n is 2, $R^w$ represents C1-C6 chain hydrocarbon group optionally having one or more halogen atoms, $T^w$ represents a halogen atom, a C1-C6 alkylsulfanyl group, a C1-C6 alkylsulfinyl group, a C1-C6 alkylsulfonyl group, and $R^{4a}$, $R^{4b}$ and $R^{4c}$ each represents a hydrogen atom.

Embodiment 163

The compound described in Embodiment 162 wherein $A^2$ represents CH, $A^3$ represents a nitrogen atom or CH, and $A^4$ represents a nitrogen atom or CH.

Embodiment 164

The compound described in Embodiment 162 wherein $A^2$ represents CH, $A^3$ represents CH, and $A^4$ represents a nitrogen atom.

Embodiment 165

The compound described in Embodiment 162 wherein $A^2$ represents CH, $A^3$ represents a nitrogen atom, and $A^4$ represents CH.

Embodiment 166

The compound described in Embodiments 162 to 165 wherein $R^2$ represents an ethyl group, $R^w$ represents a C1-C3 alkyl group, and $T^w$ represents a halogen atom or a C1-C3 alkylsulfanyl group.

Embodiment 167

The compound described in Embodiments 162 to 165 wherein $R^2$ represents an ethyl group, $R^w$ represents a C1-C3 alkyl group, and $T^w$ represents a halogen atom.

Examples of the embodiment of the intermediate compound E include the following compounds.

Embodiment 168

An intermediate compound E wherein $R^2$ represents a C1-C6 alkyl group optionally having one or more halogen atoms, n is 0 or 2, $R^w$ represents a C1-C6 chain hydrocarbon group optionally having one or more halogen atoms, a benzyl group optionally having one or more substituents selected from Group A, or a hydrogen atom, $T^{w2}$ represents a halogen atom, a C1-C6 alkylsulfanyl group, a C1-C6 alkylsulfinyl group, or a C1-C6 alkylsulfonyl group, $R^3$ represents a C1-C6 alkyl group optionally having one or more substituents selected from Group B, or a hydrogen atom, and $R^{4a}$, $R^{4b}$ and $R^{4c}$ each represents a hydrogen atom.

Embodiment 169

The compound described in Embodiment 168 wherein $A^2$ represents CH, $A^3$ represents a nitrogen atom or CH, and $A^4$ represents a nitrogen atom or CH.

Embodiment 170

The compound described in Embodiment 168 wherein $A^2$ represents CH, $A^3$ represents CH, and $A^4$ represents a nitrogen atom.

Embodiment 171

The compound described in Embodiment 168 wherein $A^2$ represents CH, $A^3$ represents a nitrogen atom, and $A^4$ represents CH.

Embodiment 172

The compound described in Embodiments 168 to 171 wherein $R^2$ represents an ethyl group, $R^w$ represents a C1-C3 alkyl group or a benzyl group, $T^{w2}$ represents a halogen atom or a C1-C3 alkylsulfanyl group, and q is 0 or 1.

Embodiment 173

The compound described in Embodiments 168 to 171 wherein $R^2$ represents an ethyl group, $R^w$ represents a C1-C3 alkyl group or a benzyl group, $T^{w2}$ represents a halogen atom, and q is 0 or 1.

Examples of the embodiment of the intermediate compound F include the following compounds.

Embodiment 174

An intermediate compound F wherein $A^1$ represents a nitrogen atom or CH, $R^2$ represents a C1-C6 alkyl group optionally having one or more halogen atoms, n is 0 or 2, $X^L$ represents a halogen atom, a hydroxy group, a C1-C6 alkylsulfanyl group, a C1-C6 alkylsulfinyl group, a C1-C6 alkylsulfonyl group, $R^3$ represents a C1-C6 alkyl group optionally having one or more substituents selected from Group B, a halogen atom or $NR^{11}R^{11}$, and $R^{4a}$, $R^{4b}$ and $R^{4c}$ each represents a hydrogen atom.

Embodiment 175

The compound described in Embodiment 175 wherein $A^2$ represents CH, $A^3$ represents a nitrogen atom or CH, and $A^4$ represents a nitrogen atom or CH.

Embodiment 176

The compound described in Embodiment 174 wherein $A^2$ represents CH, $A^3$ represents CH, and $A^4$ represents a nitrogen atom.

Embodiment 177

The compound described in Embodiment 174 wherein $A^2$ represents CH, $A^3$ represents a nitrogen atom, and $A^4$ represents CH.

Embodiment 178

The compound described in Embodiments 174 to 177 wherein $R^2$ represents an ethyl group, $X^L$ represents a halogen atom, a C1-C3 alkylsulfanyl group or a C1-C3 alkylsulfonyl group, and q is 0 or 1.

Embodiment 179

The compound described in Embodiments 174 to 177 wherein Q represents an oxygen atom.

Embodiment 180

The compound described in Embodiments 174 to 177 wherein $R^5$ represents a C1-C6 chain hydrocarbon group {the C1-C6 chain hydrocarbon group have one or more substituents selected from the group consisting of a halogen atom, a cyclopropyl group, a phenyl group, and a cyclothiazolyl group} or a C3-C6 cycloalkyl group.

Next, a process for preparing the compound Z of the present invention is explained.

Process 1

A compound represented by formula (Ib) (hereinafter, referred to as Compound (Ib)) or a compound represented by formula (Ic) (hereinafter, referred to as Compound (Ic)) may be prepared by oxidizing a compound represented by formula (Ia) (hereinafter, referred to as Compound (Ia)).

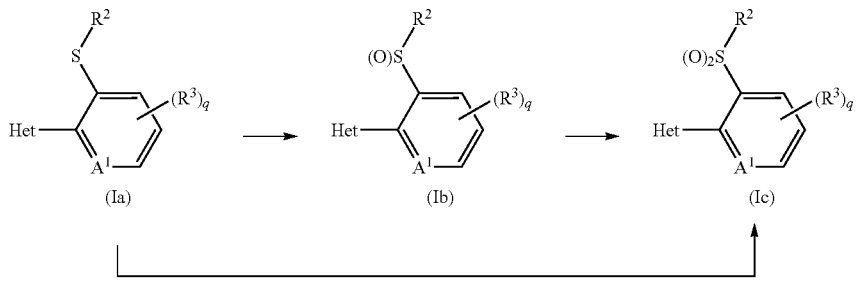

[wherein the symbols are the same as defined above]

First, a process for preparing the Compound (Ib) from the Compound (Ia) is described.

The reaction is usually carried out in a solvent.

Examples of the solvent to be used in the reaction include halogenated hydrocarbons such as dichloromethane and chloroform (hereinafter, collectively referred to as halogenated hydrocarbons); nitriles such as acetonitrile (hereinafter collectively referred to nitriles); alcohols such as methanol and ethanol (hereinafter, collectively referred to as alcohols); acetic acid; water; and mixed solvents thereof.

Examples of the oxidizing agent to be used in the reaction include sodium periodate, m-chloroperoxybenzoic acid (hereinafter, referred to as mCPBA) and hydrogen peroxide. When hydrogen peroxide is used as an oxidizing agent, sodium carbonate or a catalyst may be added as needed.

Examples of the catalyst to be used in the reaction include tungstic acid, and sodium tungstate.

In the reaction, the oxidizing agent is used usually within a range of 1 to 1.2 molar ratio(s), the base is used usually within a range of 0.01 to 1 molar ratio(s), and the catalyst is used usually within a range of 0.01 to 0.5 molar ratios, as opposed to 1 mole of the compound (Ia).

The reaction temperature of the reaction is usually within a range of −20 to 80° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to give the compound (Ib).

Next, a process for preparing the compound (IC) from the compound (Ib) is described.

The reaction is usually carried out in a solvent. Examples of the solvent to be used in the reaction include halogenated hydrocarbons, nitriles, alcohols, acetic acid, water, and mixed solvents thereof.

Examples of the oxidizing agent to be used in the reaction include mCPBA and peroxide hydrogen. When peroxide hydrogen is used as an oxidizing agent, a base or a catalyst may be added as needed.

Examples of the base to be used in the reaction include sodium carbonate.

Examples of the catalyst to be used in the reaction include sodium tungstate.

In the reaction, the oxidizing agent is used usually within a range of 1 to 2 molar ratio(s), the base is used usually within a range of 0.01 to 1 molar ratio(s), and the catalyst is used usually within a range of 0.01 to 0.5 molar ratios, as opposed to 1 mole of the compound (Ib).

The reaction temperature of the reaction is usually within a range of −20 to 120° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to give the compound (Ic).

Also, the compound (Ic) may be prepared by reacting the compound (Ia) with an oxidizing agent in one step (one pot).

The reaction may be carried out by using the oxidizing agent in a ratio of usually 2 to 5 molar ratios as opposed to 1 mole of the compound (Ia) according to the method for preparing the compound (Ic) from the compound (Ib).

Process 2

A compound represented by formula (Id-2) (hereinafter, referred to as Compound (Id-2)) may be prepared by reacting a compound represented by formula (M-2) (hereinafter, referred to as Compound (M-2)) and a compound represented by formula (R-1) (hereinafter, referred to as Compound (R-1)) in the presence of a base.

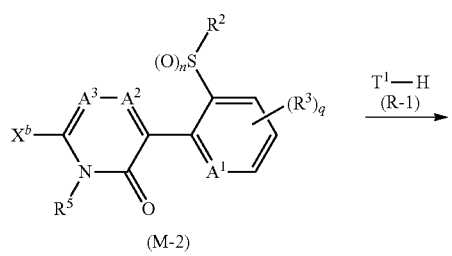

(M-2)

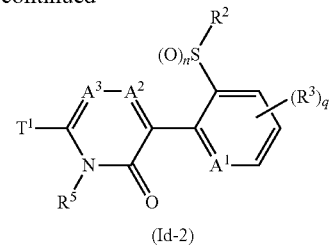

(Id-2)

[wherein $X^b$ represents a chlorine atom or a bromine atom, $T^1$ represents $OR^1$, $NR^1R^{29}$ a group represented by formula T-5, a group represented by formula T-6, a group represented by formula T-7, or a group represented by formula T-8, and the other symbols are the same as defined above.]

The reaction is usually carried out in the presence of a solvent. Examples of the solvents to be used in the reaction include ethers such as tetrahydrofuran (hereinafter, sometimes referred to as THF) and methyl tert-butyl ether (hereinafter, referred to as MTBE) (hereinafter, collectively referred to as ethers); aromatic hydrocarbons such as toluene and xylene (hereinafter, collectively referred to as aromatic hydrocarbons); nitriles; N-methyl pyrrolidone (hereinafter, referred to as NMP); and aprotic polar solvents such as dimethylformamide (hereinafter, referred to as DMF) and dimethyl sulfoxide (hereinafter, referred to DMSO) (hereinafter, collectively referred to as polar aprotic solvent); and mixed solvents thereof.

Examples of the base to be used in the reaction include alkali metal carbonates (such as potassium carbonate) (hereinafter, collectively referred to as alkali metal carbonates); and alkali metal hydrides such as sodium hydride (hereinafter, collectively referred to as alkali metal hydrides).

In the reaction, the compound (R-1) is used usually within a range of 1 to 2 molar ratio(s), and the base is used usually within a range of 1 to 10 molar ratio(s), as opposed to 1 mole of the compound (M-2)

The reaction temperature of the reaction is usually within a range of −20 to 150° C. The reaction period the reaction is usually within a range of 0.5 to 24 hours.

When the reaction is completed, water is added to reaction mixtures, and the reaction mixtures are extracted with organic solvent(s), and the organic layers are worked up (for example, drying and concentration) to give the compound (Id-2).

Process 3

A compound represented by formula (Id-4) may be Prepared by reacting a compound represented by formula (M-3) (hereinafter, referred to as Compound (M-3)) with the compound (R-1) in the presence of a base.

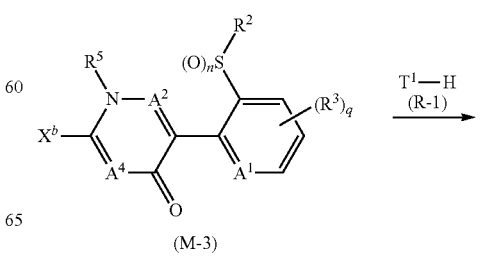

(M-3)

-continued

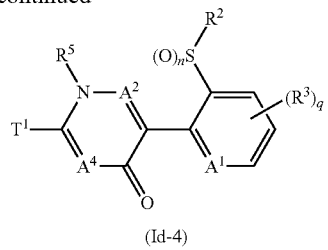

(Id-4)

[wherein the symbols are the same as defined above]

The reaction may be carried out according to the method described in Process 2.

Process 4

A compound represented by formula (Ie-2) (hereinafter, referred to Compound (Ie-2)) may be prepared by reacting the compound (M-2) with a compound represented by formula (R-2) (hereinafter, referred to Compound (R-2)) in the presence of a metal catalyst.

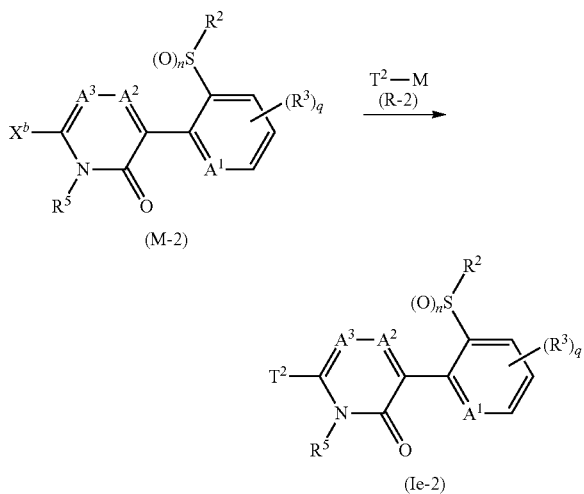

[wherein $T^2$ represents a group represented by formula T-1, a group represented by formula T-2, group represented by formula T-3, a group represented by formula T-4, a group represented by formula T-9, a group represented by formula T-10, a group represented by formula T-11, or a group represented by formula T-12, M represents 9-borabiclo[3,3,1]nonan-9-yl, a borono group, a 4,4,5,5,-tetramethyl-1,3,2-dioxaborolan-2-yl, a tributylstannyl group, ZnCl, MgCl, or MgBr; and the other symbols are the same as defined above]

The reaction is usually carried out in the presence of a solvent. Examples of the solvent to be used in the reaction include ethers, aromatic hydrocarbons, aprotic polar solvents, water, and mixed solvents thereof.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0), and palladium(II) acetate; nickel catalysts such as bis(cyclooctadiene)nickel(0) and nickel (II) chloride; and copper catalyst such as copper (I) iodide and copper(I) chloride.

A ligand, a base and/or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline.

Examples of the base to be used in the reaction include alkali metal hydrides; alkali metal carbonates; and organic bases such as triethylamine, diisopropylethylamine, pyridine, and 4-(dimethylanino)pyridine.

Examples of the inorganic halogenated compounds include alkali metal fluorides such as potassium fluoride, and sodium fluoride; and alkali metal chlorides such as lithium chloride, and sodium chloride.

In the reaction, the compound (R-2) is usually used within a range of 1 to 10 molar ratio(s), the metal catalyst is usually used within a range of 0.01 to 0.5 molar ratios, the ligand is usually used within a range of 0.01 to 1 molar ratio(s), the base is usually used within a range of 0.1 to 1 molar ratio(s), and the inorganic halogenated compound is usually used within a range of 0.1 to 5 molar ratios, as opposed to 1 mole of the compound (M-2).

The reaction temperature is usually within a range of −20 to 200° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (Ie-2).

The compound (R-2) is a commercially available compound, or can be prepared by using a known method.

Process 5

A compound represented by formula (Ie-4) may be prepared by reacting the compound (M-3) with the compound (R-2) in the presence of a metal catalyst.

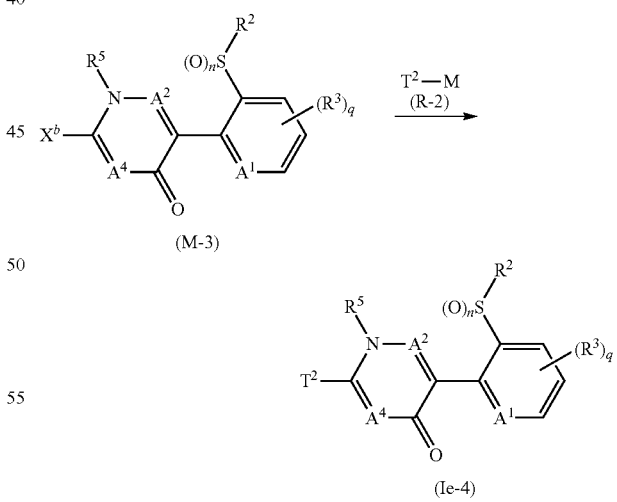

[wherein the symbols are the same as defined above.]

The reaction may be carried out according to the method described in Process 4.

Process 6

A compound represented by formula (If-2) may be prepared by reacting a compound represented by formula (M-4) (hereinafter, referred to as Compound (M-4)) with a compound represented by formula (R-3) (hereinafter, referred to as Compound (R-3)) in the presence of a base.

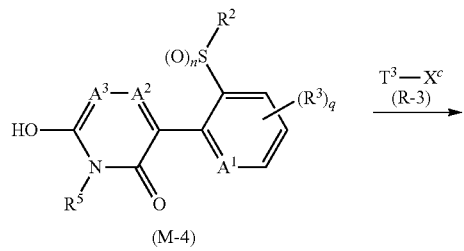

(M-4)

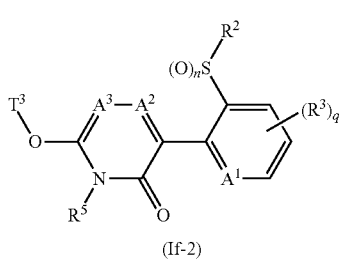

(If-2)

[wherein $X^c$ represents a chlorine atom, a bromine atom or an iodine atom, $T^3$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, or $S(O)_2R^1$, and the other symbols are the same as defined above.]

The reaction may be carried out by using the compound (M-4) in place of the compound (R-1), and the compound (R-3) in place of the compound (M-2) according to the method described in Process 2.

The compound (R-3) is a commercially available compound, or can be prepared by using a known method.

Process 7

A compound represented by formula (If-4) may be prepared by reacting a compound represented by formula (M-5) (hereinafter, referred to Compound (M-5)) with the compound (R-3) in the presence of a base.

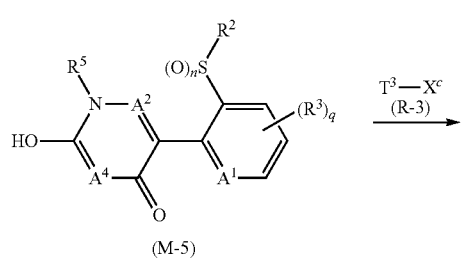

(M-5)

-continued

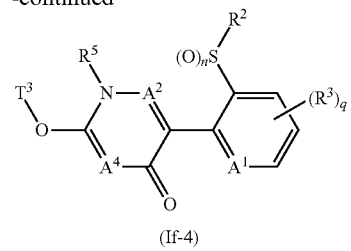

(If-4)

[wherein the symbols are the same as defined above.]

The reaction may be carried out according to the method described in Process 6.

Process 8

A compound represented by formula (Ig-2) (hereinafter, referred to as Compound (Ig-2)) may be prepared by reacting the compound (M-2) with a compound represented by formula (R-4) (hereinafter, referred to as Compound (R-4)) in the presence of a copper.

(M-2)

(Ig-2)

[wherein, $T^4$ represents a C1-C10 chain hydrocarbon group having one or more halogen atoms, a (C1-C5 alkoxy)C2-C5 alkyl group having one or more halogen atoms, (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G, and the other symbols are the same as defined above.]

The compound (R-4) is a commercially available compound, or can be prepared by using a known method.

The reaction is usually carried out in the presence of a solvent. Examples of the solvent to be used in the reaction include aromatic hydrocarbons, aprotic polar solvents, and mixed solvents thereof.

In the reaction, the compound (R-4) is usually used within a range of 1 to 10 molar ratio (s), and the copper is usually used within a range of 1 to 10 molar ratio(s), as opposed to 1 mole of the compound (M-2).

The reaction temperature is usually within a range of 40 to 200° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (Ig-2).

Process 9

The compound represented by formula (Ig-4) may be prepared by reacting the compound (M-3) with the compound (R-4) in the presence of a copper.

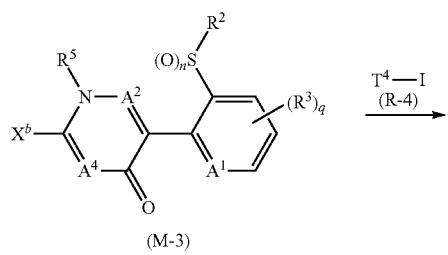

(M-3)

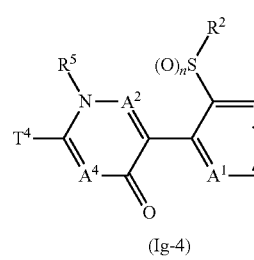

(Ig-4)

[wherein the symbols are the same as defined above.]

The reaction may be carried out according to the method described in Process 8.

Process 10

A compound represented by formula (Ih-2) (hereinafter, referred to Compound (Ih-2)) may be prepared by reacting the compound (M-2) with a compound represented by formula (R-5) (hereinafter, referred to as Compound (R-5)) in the presence of a base.

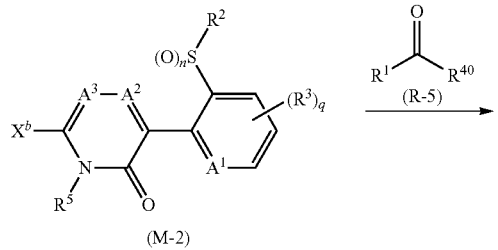

(M-2)

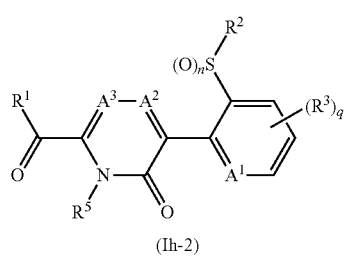

(Ih-2)

[wherein, $R^{40}$ represents a methoxy group, an ethoxy group, a phenoxy group, or $N(CH_3)CH_3$, and the other symbols are the same as defined above.]

The compound (R-5) is a commercially available compound, or can be prepared by using a known method.

The reaction is usually carried out in the presence of a solvent. Examples of the solvent to be used in the reaction include ethers, and aromatic hydrocarbons.

Examples of the base to be used in the reaction include butyl lithium, lithium diisopropylamide, lithium tetramethylpiperidide, lithium bis(trimethylsilyl)amide and the like.

In the reaction, the compound (R-5) is usually used within a range of 1 to 10 molar ratio(s), and the base is usually used within a range of 1.0 to 2.0 molar ratio(s), as opposed to 1 mole of the compound (M-2).

The reaction temperature is usually within a range of −100 to 60° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (Ih-2).

Process 11

A compound represented by formula (Ih-4) may be prepared by reacting the compound (M-3) with the compound (R-5) in the presence of a base.

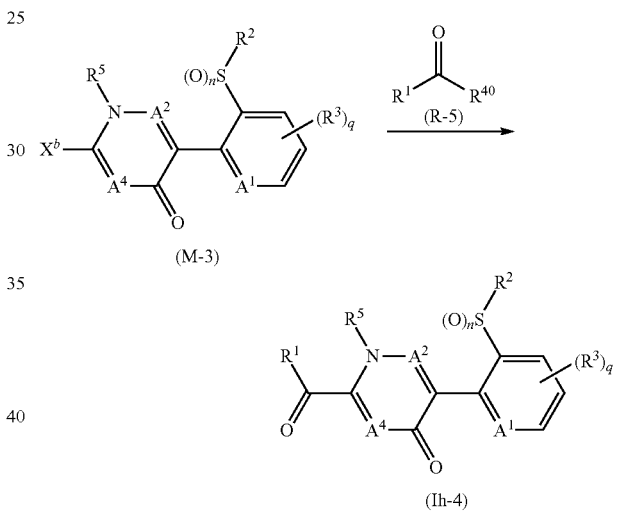

(M-3)

(Ih-4)

[wherein the symbols are the same as defined above.]

The reaction may be carried out according to the method described in Process 10.

Process 12

A compound represented by formula (Ii-2) (hereinafter, referred to as Compound (Ii-2)) may be prepared by reacting compound represented by formula (M-6) (hereinafter, referred to as Compound (M-6)) with a compound represented by formula (R-6) (hereinafter, referred to as Compound (R-6)) in the presence of a condensing agent.

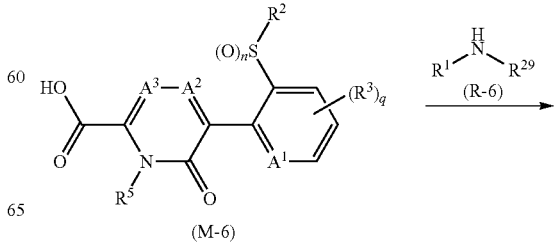

(M-6)

-continued

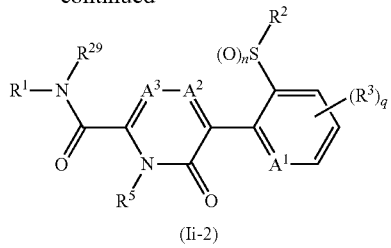

(Ii-2)

[wherein the symbols are the same as defined above.]

The compound (R-6) is a commercially available compound, or can be prepared by using a known method.

The reaction is usually carried out in a solvent. Examples of the solvent to be used in the reaction include ethers, halogenated hydrocarbons, aromatic hydrocarbons, aprotic polar solvents, and mixed solvents thereof.

Examples of the condensing agent to be used in the reaction include 1-ethyl-3-(3-dimethylaminopropyl)carbodiimide hydrochloride and the like.

A base may be added to the reaction as needed, and examples of the bases include organic bases.

In the reaction, the compound (R-6) is used usually within a range of 1 to 10 molar ratio(s), the condensing agent is used usually within a range of 1 to 5 molar ration(s), and the base is used usually within a range of 0.1 to 10 molar ratios, as opposed to 1 mole of the compound (M-6).

The reaction temperature of the reaction is usually within a range of −20 to 120° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (Ii-2).

Process 13

A compound represented by formula (Ii-4) may be prepared by reacting a compound represented by formula (M-7) (hereinafter, referred to as Compound (M-7)) with the compound (R-6) in the presence a condensing agent.

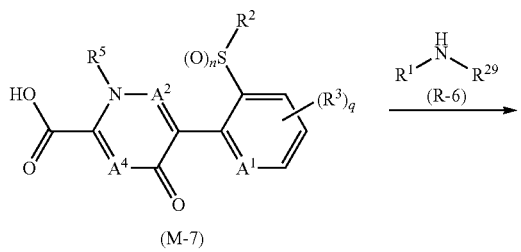

(M-7)

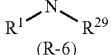

(R-6)

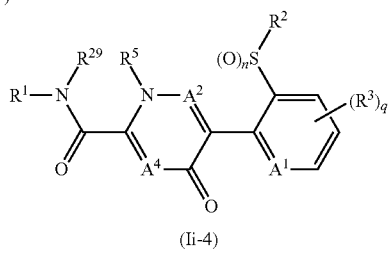

(Ii-4)

[wherein the symbols are the same as defined above.]

The reaction may be carried out according to the method described in Process 12.

Process 14

A compound represented by formula (Ij-2) (hereinafter, referred to as Compound (Ij-2)) may be prepared by reacting a compound represented by formula (M-8) (hereinafter, referred to as Compound (M-8)) with a compound represented by formula (R-7) (hereinafter, referred to as Compound (R-7)) in the presence of a base.

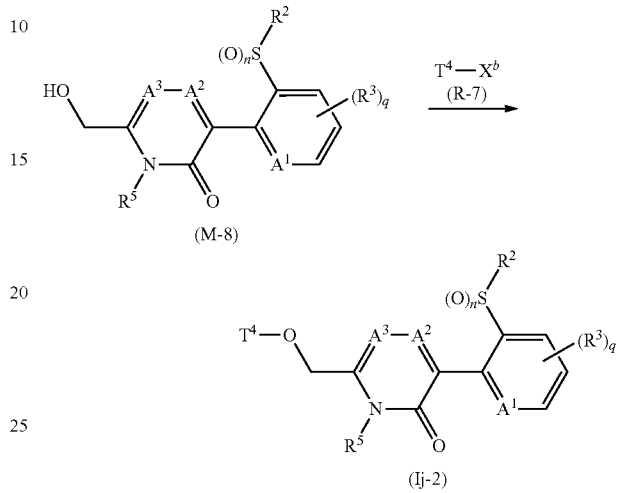

(M-8)

(Ij-2)

[wherein the symbols are the same as defined above.]

The compound (R-7) is a commercially available compound, or can be prepared by a known method.

The reaction is usually carried out in a solvent. Examples of the solvent to be used in the reaction include ethers, aromatic hydrocarbons, aprotic polar solvents, and mixed solvents thereof.

Examples of the base to be used in the reaction include organic bases, alkali metal hydrides, and alkali metal carbonates.

In the reaction, the compound (R-7) is used usually within a range of 1 to 10 molar ratio(s), and the base is used usually within a range of 0.1 to 5 molar ratios, as opposed to 1 mole of the compound (M-8).

The reaction temperature of the reaction is usually within a range of −20 to 120° C. The reaction period of the react usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (Ij2)

Process 15

A compound represented by formula (Ij-4) may be prepared by reacting a compound represented by formula (M-9) (hereinafter, referred to as Compound (M-9)) with the compound (R-7) in the presence of a base.

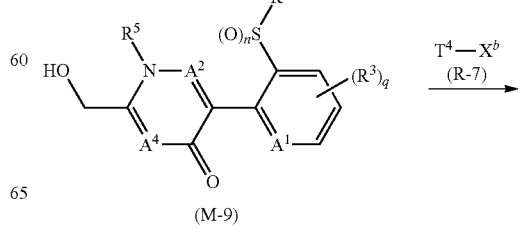

(M-9)

61

-continued

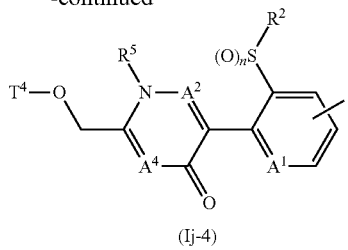

(Ij-4)

[wherein the symbols are the same as defined above.]

The reaction may be carried out according to the method described in Process 14.

Process 16

A compound represented by formula (Ik-2) (hereinafter, referred to as Compound (Ik-2)) may be prepared by reacting a compound represented by formula (M-10) (hereinafter, referred to as Compound (M-10)) with a compound represented by formula (R-8) (hereinafter, referred to as Compound (R-8)).

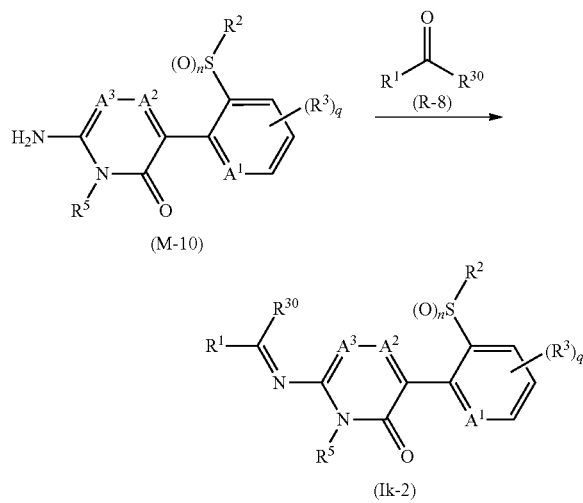

[wherein the symbols are the same as defined above.]

The compound (R-8) is a commercially available compound, or can be prepared by using a known method.

The reaction is usually carried out in the presence of a solvent. Examples of the solvent to be used in the reaction include ethers, halogenated hydrocarbons, aromatic hydrocarbons, aprotic polar solvents, and mixed solvents thereof.

An acid may be added to the reaction as needed, and examples of the acid include p-toluenesulfonic acid and 10-camphorsulfonic acid and the others.

In the reaction, the compound (R-8) is used usually within a range of 1 to 10 molar ratio(s), and the acid is used usually within a range of 0.1 to 10 molar ratios, as opposed to 1 mole of the compound (M-10).

The reaction temperature is usually within a range of −20 to 180° C. The reaction period of the reaction is usually within a range of 0.1 to 24 hours.

When the reaction is completed, water is added to the reaction mixtures, and the reaction mixtures are extracted with organic solvent (s), and the organic solvents are worked up (for example, drying and concentration) to give the compound (Ik-2).

62

Process 17

The compound (Ik-4) may be prepared by reacting compound represented by formula (M-11) (hereinafter, referred to as Compound (M-11)) with the compound (R-8).

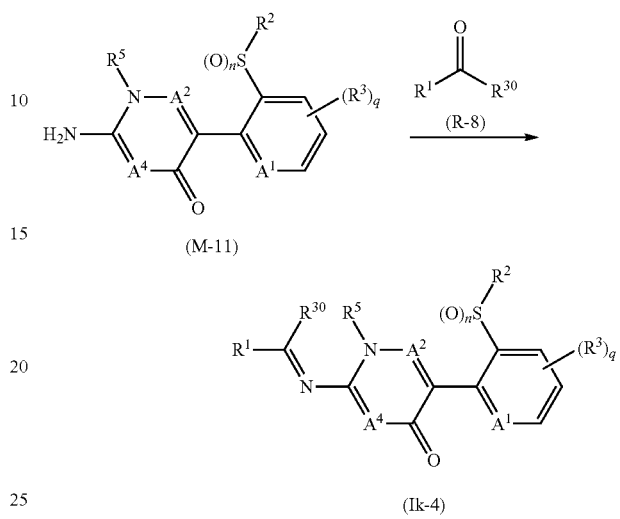

[wherein the symbols are the same as defined above.]

The reaction may be carried out according to the method described in Process 16.

Process 18

A compound represented by formula (Im-2) (hereinafter, referred to as Compound (Im-2)) may be prepared by reaction a compound represented by formula (M-12) (hereinafter, referred to as Compound (M-12)) with a compound represented by formula (R-9) (hereinafter, referred to as Compound (R-9)).

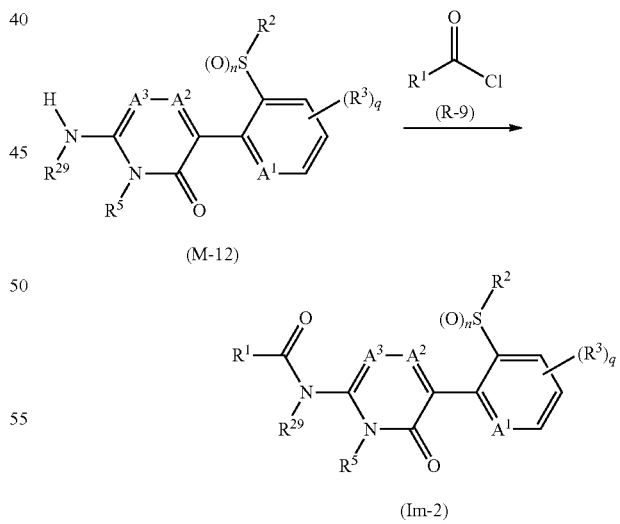

[wherein the symbols are the same as defined above.]

The compound (R-9) is a commercially available compound, or can be prepared by using a known method.

The reaction is usually carried out in the presence of a solvent. Examples of the solvent to be used in the reaction include ethers, halogenated hydrocarbons, aromatic hydrocarbons, aprotic polar solvents, and mixed solvents thereof.

A base may be added to the reaction as needed, and examples of the base include organic bases.

In the reaction, the compound (R-9) is used usually within a range of 1 to 10 molar ratio(s), and the base is used usually within a range of 0.1 to 10 molar ratios, as opposed to 1 mole of the compound (M-12).

The reaction temperature is usually within a range of −20 to 120° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (Im-2).

Process 19

The compound represented by formula (Im-4)) may be prepared by reacting a compound represented by formula (M-13) (hereinafter, referred to as Compound (M-13)) with the compound (R-9).

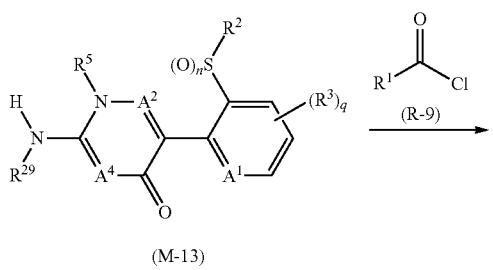

(M-13)

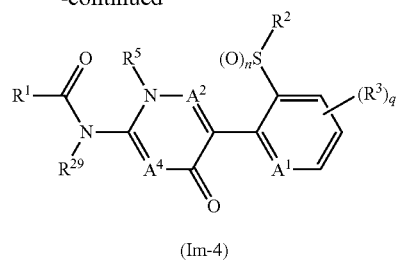

(Im-4)

[wherein the symbols are the same as defined above.]

The reaction nay be carried out according to the method described in Process 18.

Process 20

A compound represented by formula (In-2) (hereinafter, referred to as Compound (In-2)), a compound represented by formula (Io-2) (hereinafter, referred to as Compound (Io-2)) and a compound represented by formula (Ip-2) (hereinafter, referred to as Compound (Ip-2)) may be prepared according to the following method.

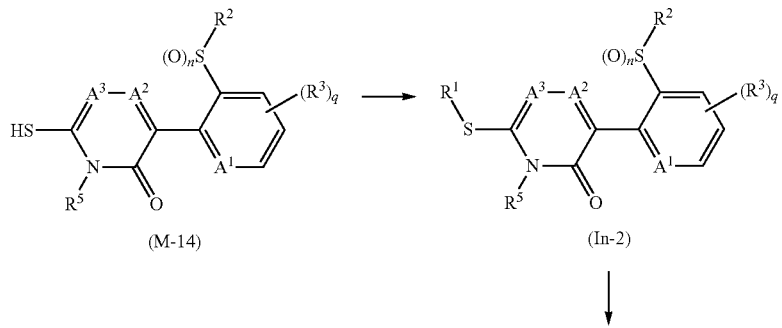

[wherein the symbols are the same as defined above.]

First, the process for preparing the compound (In-2) is described.

The compound (In-2)) may be prepared by using a compound represented by formula (M-14) (hereinafter, referred to as Compound (M-14)) in place of the compound (M-8) according to the method described in Process 14.

Next, the process for preparing the compound (Io-2) is described.

The compound (Io-2) can be prepared by using the compound (In-2) in place of the compound (Ia) according to the method described in Process 1.

Next, the process for preparing the compound (Ip-2) is described.

The compound (Ip-2) can be prepared by using the compound (Io-2) in place of the compound (Ib) according to the method described in Process 1.

Process 21

A compound represented by formula (In-4) (hereinafter, referred to as Compound (In-4)), a compound represented by formula (Io-4) (hereinafter, referred to as Compound (Io-4)), and a compound represented by formula (Ip-4) (hereinafter referred to as Compound (Ip-4)) can be prepared according to the following method.

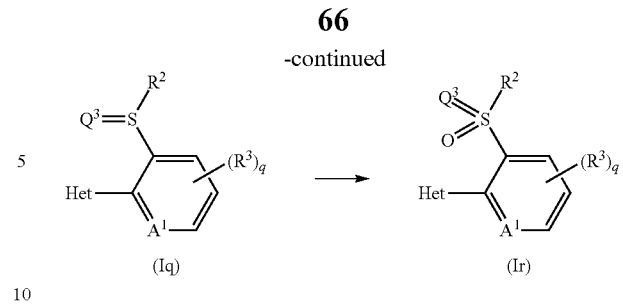

[wherein $Q^3$ represents N—CN, N—NO$_2$, NR$^5$, N—C(O)R$^5$ or N—C(O)OR$^{15}$, and the other symbols are the same as defined above.]

The compound (Iq) may be prepared by using the compound (Ia) according to the method described in Organic Letters, 9(19), 3809, 2007.

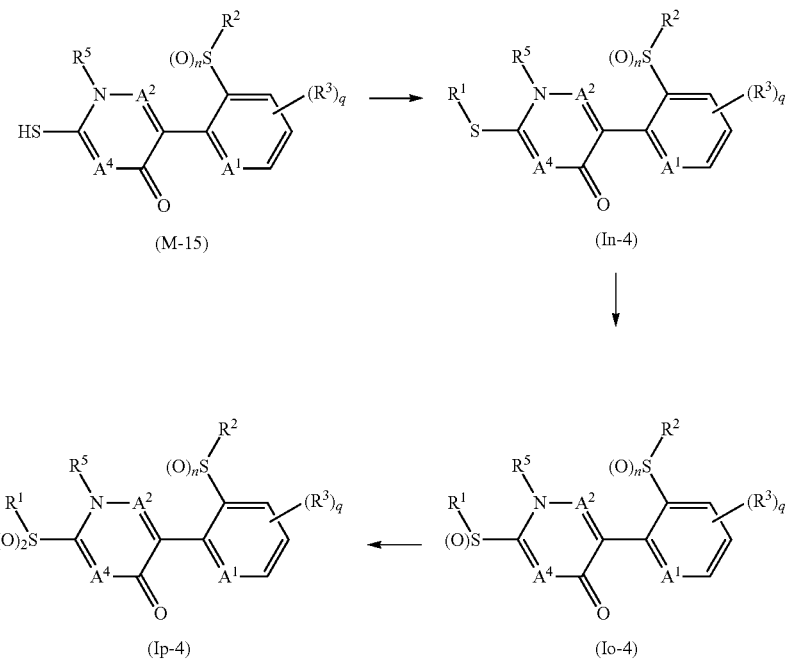

[wherein the symbols are the same as defined above.]

The reaction may be carried out according to the method described in Process 20.

Process 22

A compound represented by formula (Iq) (hereinafter, referred to as Compound (Iq)) and a compound represented by formula (Ir) (hereinafter, referred to as Compound (Ir)) may be prepared according to the following scheme.

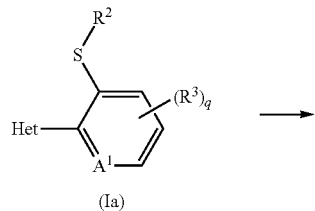

The compound (Ir) may be prepared by using the compound (Iq) according to the method described in Process 1 for preparing the compound (Ib) from the compound (Ia).

Process 23

A compound represented by formula (Is) (hereinafter, referred to as Compound (Is)) and a compound represented by formula (It) (hereinafter, referred to as Compound (It)) may be prepared according to the following scheme.

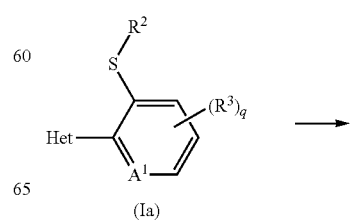

-continued

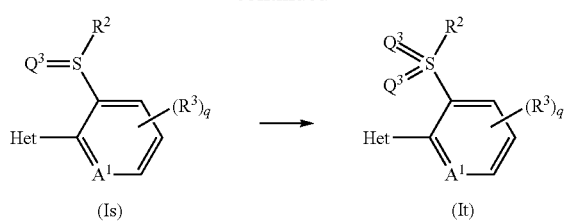

(Is) → (It)

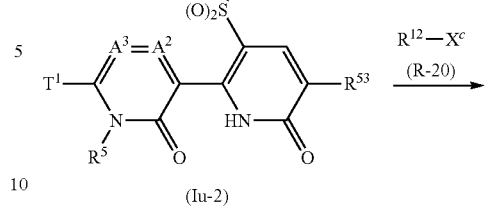

(Iu-2) → (R-20)

[wherein the symbols are the same as defined above.]

The compound (Is) may be prepared by using the compound (Ia), or the compound (It) may be prepared by using the compound (Is), each according to the method described in Russian Journal of Organic Chemistry, Vol, No. 5, 778-779, 2013.

Process 24

A compound represented by formula (Iu-2) (hereinafter, referred to as Compound (Iu-2)) may be prepared by reacting a compound represented by formula (M-25) (hereinafter, referred to as Compound (M-25)) with trifluoroacetic anhydride in the presence of organic bases. Also, the compound (Iu-2) may be prepared by reacting the compound (M-25) with acetic anhydride, followed by reacting with methanol.

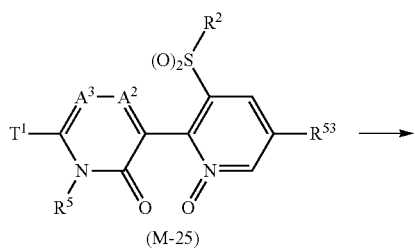

(M-25) → (Iu-2)

[wherein the symbols are the same as defined above.]

The reaction may be carried out by using the compound (Iu-2) in place of the compound (M-4) and using the compound (R-20) in place of the compound (R-3) according to the method described in Process 6.

The compound (R-20) is a commercially available compound, or can be prepared by using a known method.

Process 26

A compound presented by formula (Iw-2) can be prepared by reacting a compound represented by formula (Iv-2-1) (hereinafter, referred to as Compound (Iv-2-1)) and a compound represented by formula (R-21) (hereinafter, referred to as Compound (R-21)) in the presence of metal catalyst.

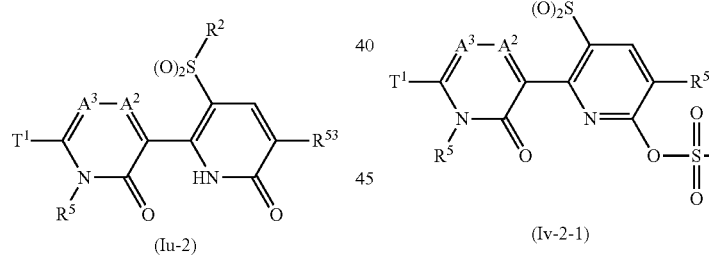

(Iv-2-1) → (R-21)

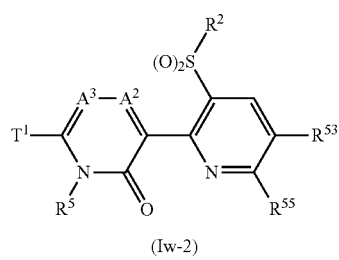

(Iw-2)

[wherein, $R^{53}$ represents a C1-C6 alkyl group optionally having one or more substituents selected from Group B, a C3-C7 cycloalkyl group optionally having one or more substituents selected from Group E, a phenyl group optionally having one or more substituents selected from Group H, or a five or six membered aromatic heterocyclic group optionally having one or more substituents selected from Group H, and the other symbols are the same as defined above.]

The reaction may be carried out according to the method described in WO 2009/076387.

Process 25

A compound represented by formula (Iv-2) may be prepared by reacting the compound (Iu-2) with a compound represented by formula (R-20) (hereinafter, referred to as Compound (R-20)) in the presence of a base.

[where, $R^{55}$ represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, or a five or six membered aromatic heterocyclic group optionally having one or more substituents selected from Group H, and the other symbols are the same as defined above.]

The reaction may be carried out by using the compound (Iv-2-1) in place of the compound (M-2) and using the compound (R-21) in place of the compound (R-2) according to the method described in Process 4.

The compound (R-21) is a commercially available compound, or can be prepared by using a known method.

Process 27

A compound represented by formula (Iu-4) (hereinafter, referred to as Compound (Iu-4)) may be prepared by reacting a compound represented by formula (M-29) (hereinafter, referred to as Compound (M-29)) with trifluroacetic anhydride in the presence of organic bases. Also, the compound (Iu-4) may be prepared by reacting the compound (M-29) with acetic anhydride, followed by reacting with methanol.

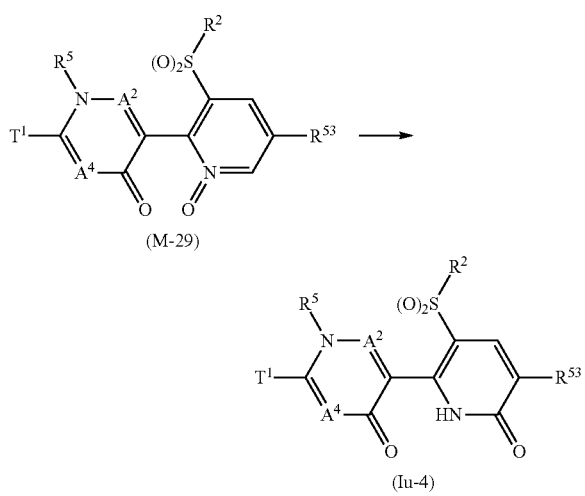

[wherein the symbols are the same as defined above.]

The reaction may be carried out according to the method described in WO 2009/076387.

Process 28

A compound represented by formula (Iv-4) may be prepared by reacting the compound (Iu-4) with the compound (R-20) in the presence of a base.

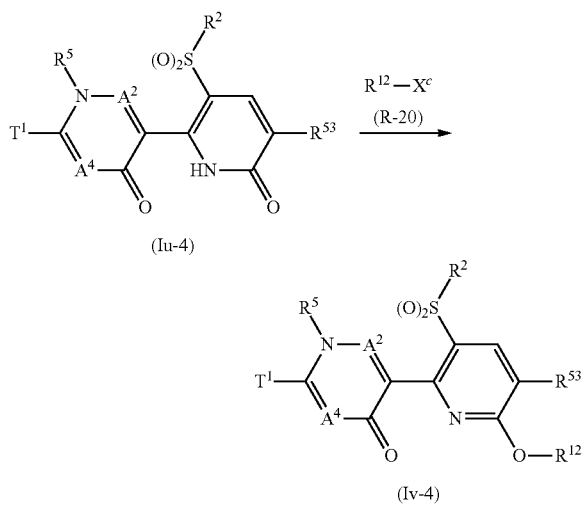

[wherein the symbols are the same as defined above.]

The reaction may be carried out by using the compound (Iu-4) in place of the compound (M-4) and using the compound. (R-20) in place of the compound (R-3) according to the method described in Process 6.

Process 29

A compound represented by formula (Iw-4) ray be prepared by reacting a compound represented by formula (Iv-4-1) (hereinafter, referred to as Compound (Iv-4-1)) with the compound (R-21) in the presence of a metal catalyst.

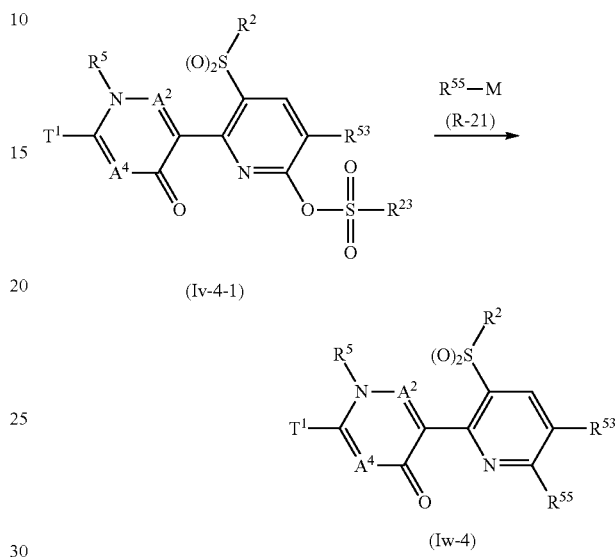

[wherein the symbols are the same as defined above.]

The reaction may be carried out by using the compound (Iv-4-1) in place of the compound (M-2) and using the compound (R-21) in place of the compound (R-2) according to the method described Process 4.

Process 30

The compound may be prepared by reacting a compound represented by formula (M-30) (hereinafter, referred to as Compound (M-30)) with a compound represented by formula (R-16) (hereinafter, referred to as Compound (R-16)) in the presence of a base.

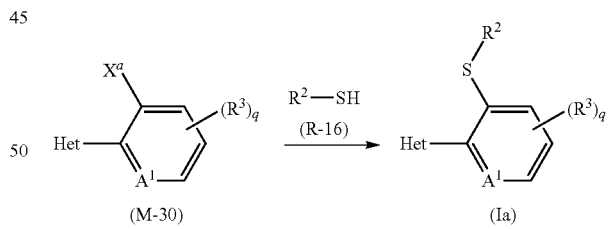

[wherein $x^a$ represents a fluorine atom or a chlorine atom, and the other symbols are the same as defined above.]

The reaction may be carried out by using the compound (M-30) in place of the compound (M-2) and using the compound (R-16) in place of the compound (R-1) according to the method described in Process 2.

The compound (R-16) is a commercially available compound, or can be prepared by using a known method.

Process 31

A compound represented by formula (Ix-2) (hereinafter, referred to as Compound (Ix-2)) may be prepared by reacting a compound represented by formula (M-31) (hereinafter, referred to as Compound (M-31)) with a compound represented by formula (M-1) (hereinafter, referred to as Compound (M-1)) in the presence of a metal catalyst.

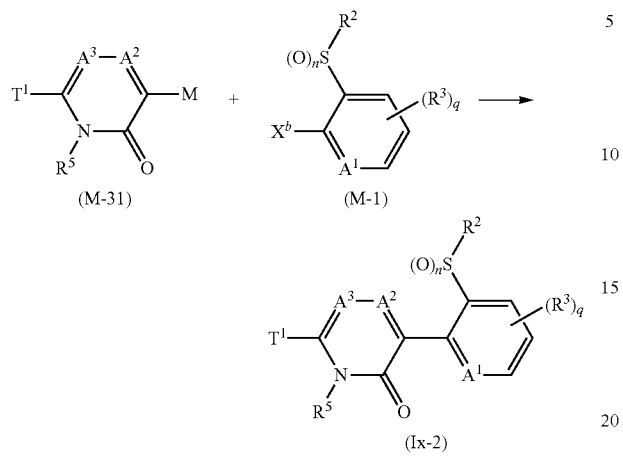

(M-31)  (M-1)

(Ix-2)

[wherein the symbols are the same as defined above.]

The reaction may be carried out by using the compound (M-31) in place of the compound (R-2) and using the compound (M-1) in place of the compound (M-2) according to the method described in Process 4.

The compound (M-31) can be prepared by using the method described in the reference process 31 or a known method.

Process 32

A compound represented by formula (4) (hereinafter, referred to as Compound (Ix-4)) may be prepared by reacting a compound represented by formula (M-32) (hereinafter, referred to as Compound (M-32)) with the compound (M-1) in the presence of a metal catalyst.

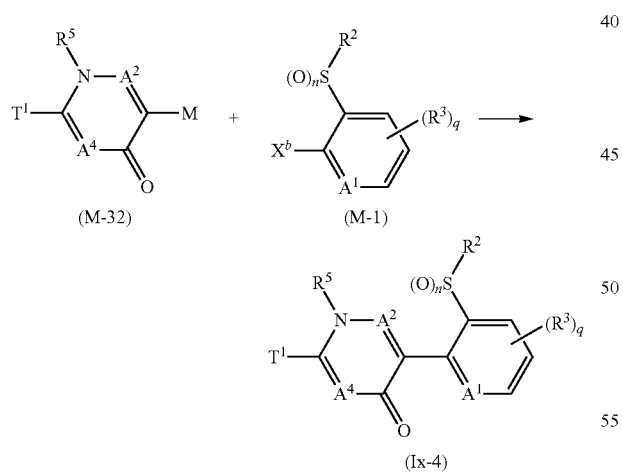

(M-32)  (M-1)

(Ix-4)

[wherein the symbols are the same as defined above.]

The reaction may be carried out by using the compound (M-32) in place of the compound (R-2) and using the compound (M-1) in place of the compound (M-2) according to the method described in Process 4.

The compound (M-32) can be prepared by using the method described in the reference process 32 or a known method, Process 33

The compound (Id-2) may be prepared by reacting a compound represented by formula (M-43) (hereinafter, referred to as Compound (M-43)) with the compound (R-1) in the presence of a base.

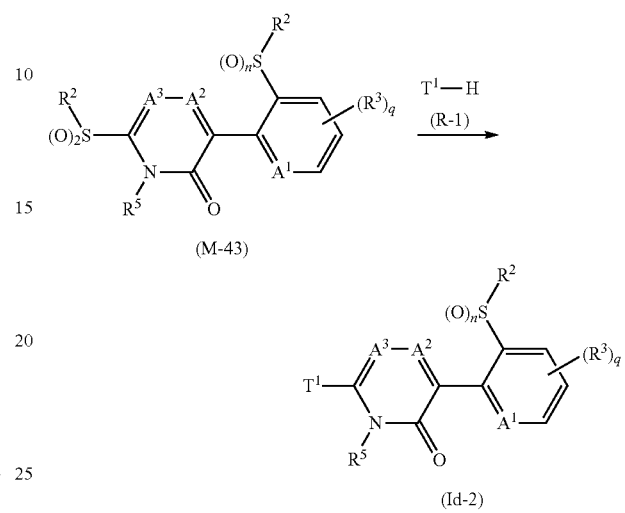

(M-43)

(Id-2)

[wherein the symbols are the same as defined above.]

The reaction may be carried out by using the compound (M-43) in place of the compound (M-2) according to the method described in Process 2.

Process 34

The compound (Id-4) may be prepared by reacting a compound represented by formula (M-46) (hereinafter, referred to as Compound (M-46)) with the compound (R-1) in the presence of a base.

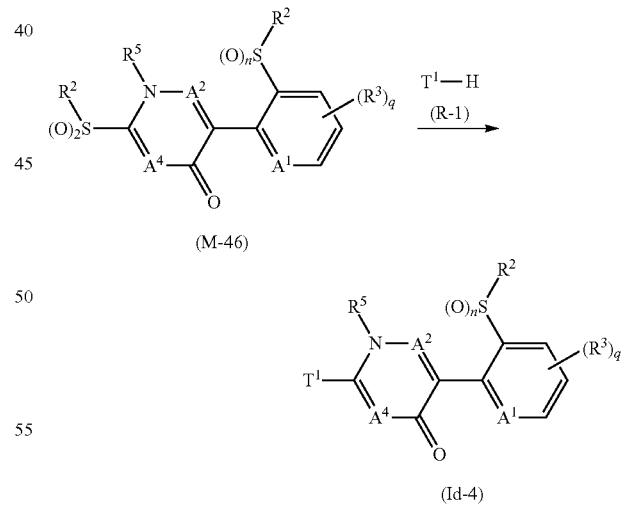

(M-46)

(Id-4)

[wherein the symbols are the same as defined above.]

The reaction may be carried out by using the compound (M46) in place of the compound (M-2) according to the method described in Process 1.

Reference Process 1

The compound (M-2) May be prepared by reacting a compound represented by formula (M-2c) (hereinafter, referred to as Compound (M-2c)) with compound represented by formula (R-10) (hereinafter, referred to as Compound (R-10)) in the presence of a base.

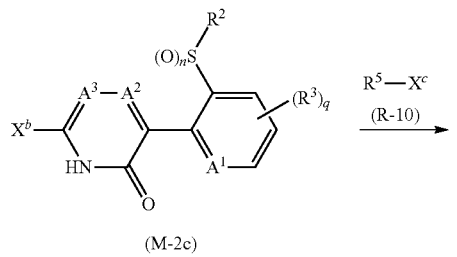

(M-2c)

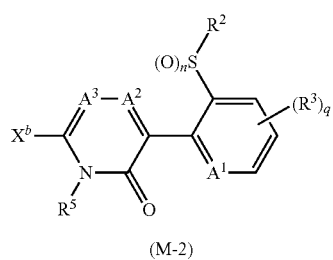

(M-2)

[wherein the symbols are the same as defined above.]

The reaction may be carried out by using the compound (R-10) in place of the compound (M-2) and using the compound (M-2c) in place of the compound (R-1) according to the method described in Process 2.

The compound (R-10) is a commercially available compound, or can be prepared by using a known method.
Reference Process 2

The compound (M-2c) may be prepared according to the following scheme.

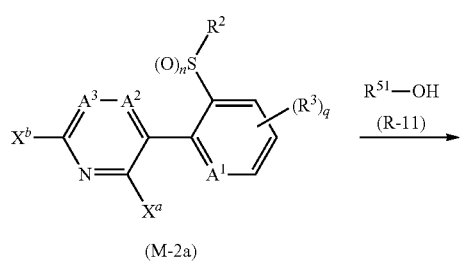

(M-2a)

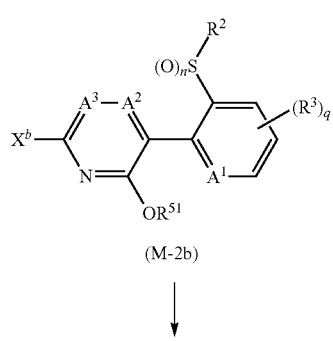

(M-2b)

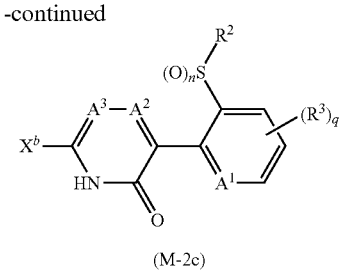

(M-2c)

[wherein, $R^{51}$ represents a methyl group, an ethyl group, or a benzyl group, and the other symbols are the same as defined above.]

A compound represented by formula (M-2b) (hereinafter, referred to as Compound (M-2b)) may be prepared by reacting a compound represented by formula (M-2a) (hereinafter, referred to as Compound (M-2a)) with a compound represented by formula (R-11) (hereinafter, referred to as Compound (R-11) in the presence of a base. The reaction may be carried out according to method described in Process 2.

The compound (M-2c) may be prepared by reacting the compound (M-2b) with an acid. The reaction may be carried out according to the method described in, for example, WO 2016/052455.

The compound (R-11) is a commercially available compound, or can be prepared by using a known method.
Reference Process 3

The compound (M-2a) may be prepared by reacting a compound represented by formula (R-12) (hereinafter, referred to as Compound (R-12)) with the compound (M-1) in the presence of a metal catalyst.

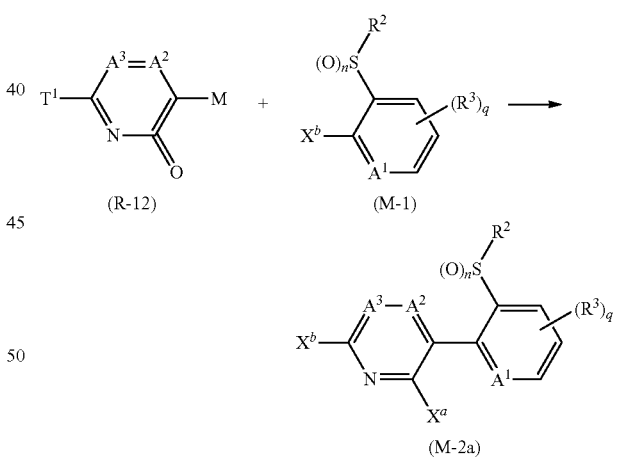

[wherein the symbols are the same as defined above.]

The reaction may be carried out by using the compound (M-1) in place of the compound (M-2) and using the compound (R-12) in place of the compound (R-2) according to the method described in Process 4.

The compound (R-12) is a commercially available compound, or can be prepared by using known method.
Reference Process 4

The compound (M-3) may be prepared by reacting a compound represented by formula (M-3c) (hereinafter, referred to as Compound (M-3c)) with the compound (R-10) in the presence of a base.

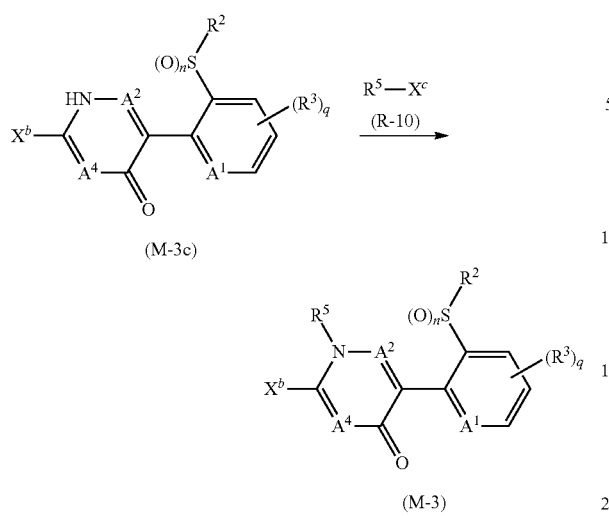

[wherein the symbols are the same as defined.]

The reaction may be carried out according to the method described in Reference Process 1.

Reference Process 5

The compound (M-3c) may be prepared according to the following scheme.

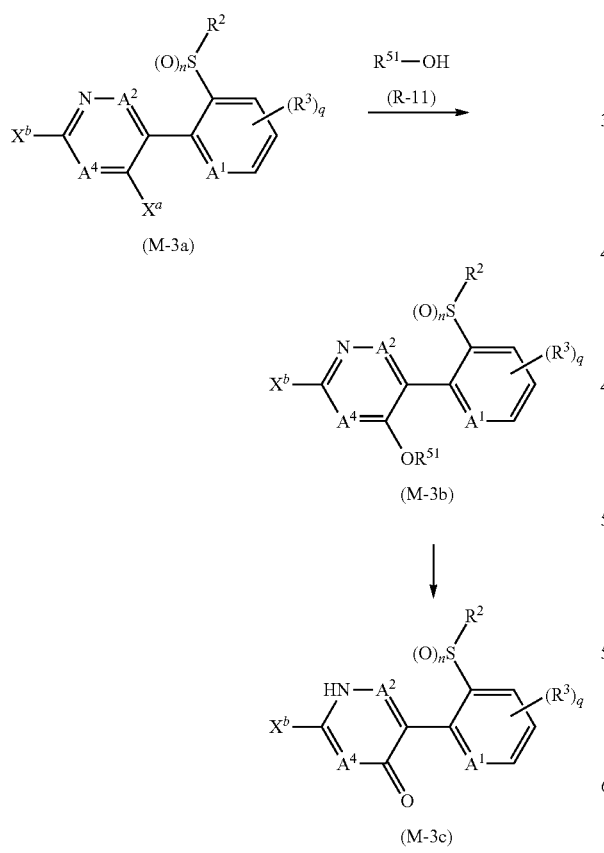

[wherein the symbols are the same as defined above.]

These reactions may be carried out according to the methods described in Reference Process 2.

Reference Process 6

A compound represented by formula (M-3a) may be prepared by reacting a compound represented by formula (R-13) (hereinafter, referred to as Compound (R-13)) with the compound (M-1) in the presence of a metal catalyst.

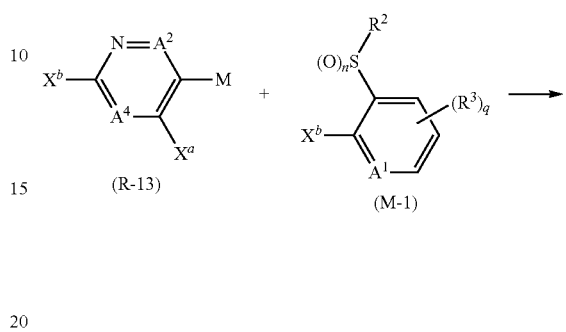

[wherein the symbols are the same as defined above.]

The reaction may be carried out according to the method described in Reference Process 3.

The compound (R-13) is a commercially available compound, or can be prepared by using a known method.

Reference Process 7

The compound (M-4) may be prepared according to the following scheme.

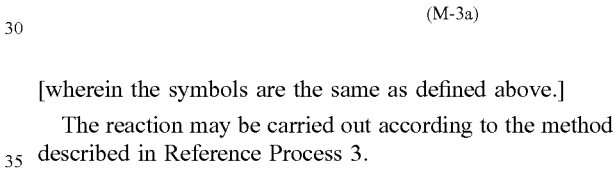

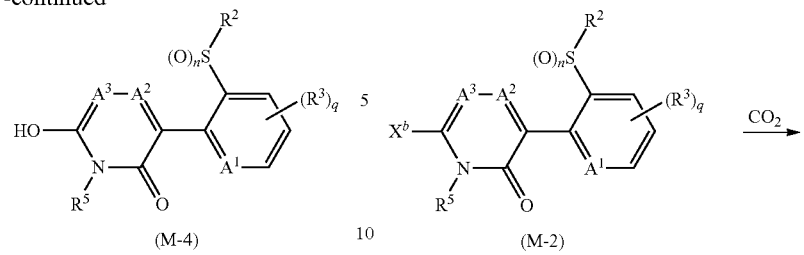

[wherein the symbols are the same as defined above.]

These reactions may be carried out according to the methods described in Reference Process 2.

Reference Process 8

The compound (M-5) may be prepared according to the following scheme.

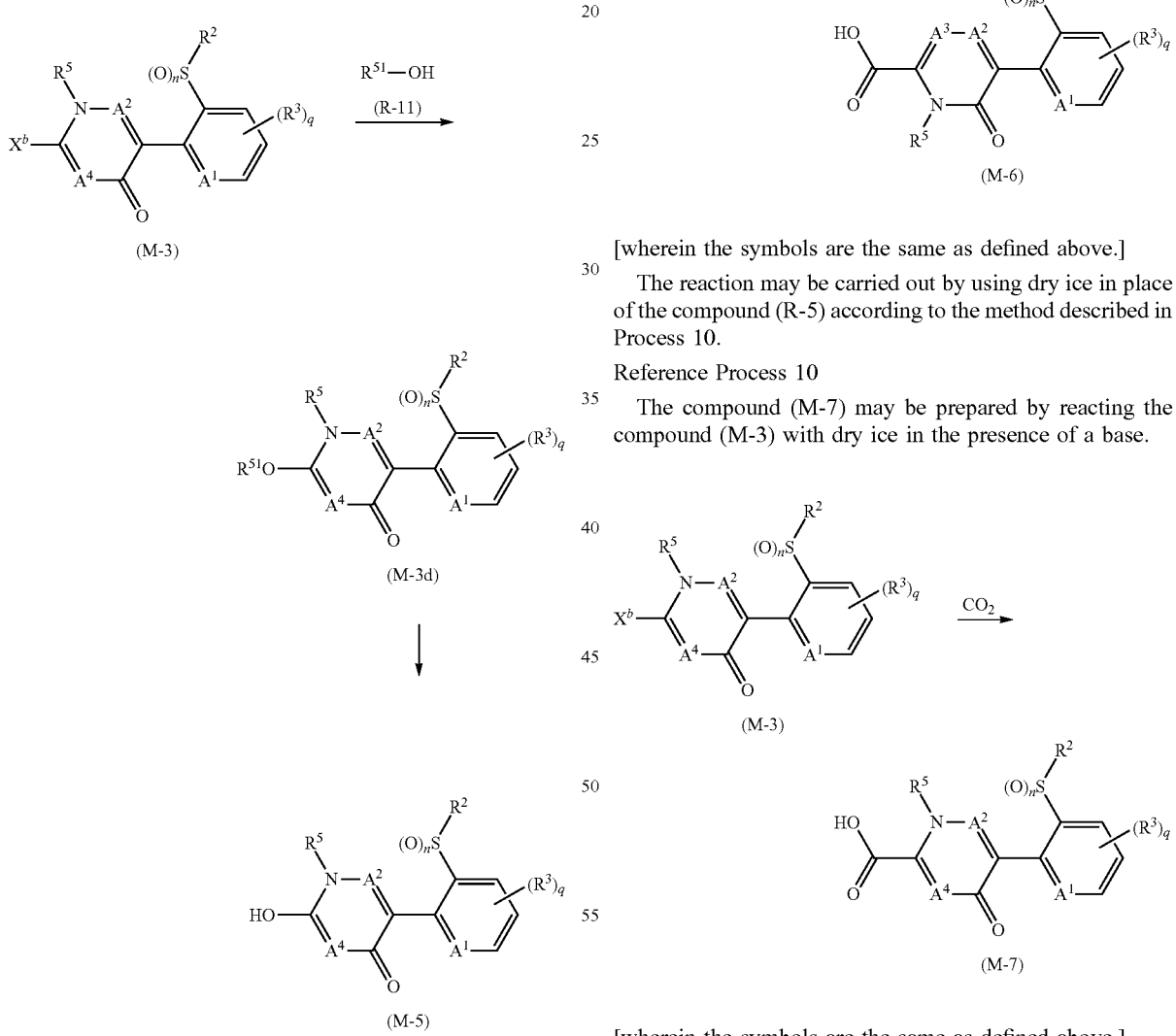

[wherein the symbols are the same as defined above.]

These reactions may be carried out according to the methods described in Reference Process 2.

Reference Process 9

The compound (M-6) may be prepared by reacting the compound (M-2) with dry ice in the presence of a base.

[wherein the symbols are the same as defined above.]

The reaction may be carried out by using dry ice in place of the compound (R-5) according to the method described in Process 10.

Reference Process 10

The compound (M-7) may be prepared by reacting the compound (M-3) with dry ice in the presence of a base.

[wherein the symbols are the same as defined above.]

The reaction may be carried out by using dry ice in place of the compound (R-5) according to the method described in Process 10.

Reference Process 11

The compound (M-3) may be prepared by reacting the compound (M-6) with a reducing agent.

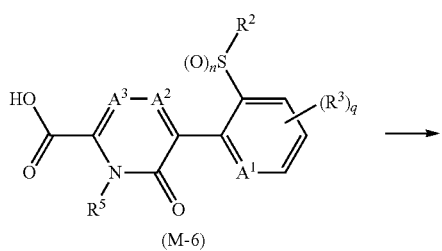

(M-6)

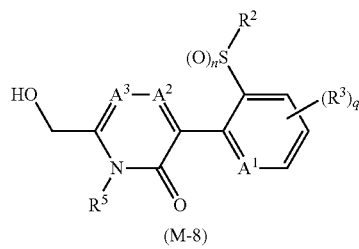

(M-8)

[wherein the symbols are the same as defined above.]

The reaction is usually carried out in a solvent.

Examples of the solvent to be used in the reaction include ethers, aliphatic hydrocarbons, aromatic hydrocarbons, alcohols, and mixed solvents thereof.

Examples of the reducing agent to be used in the reaction include sodium borohydride, lithium borohydride, lithium aluminium hydride, diisobutylaluminum hydride, and the others.

In the reaction, the reducing agent is used usually within a range of 1 to 5 molar ratio(s), as opposed to 1 mole of the compound (M-6).

The reaction temperature of the reaction is usually within a range of −20 to 120° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (M-8).

Reference Process 12

The compound (M-9) may be prepared by reacting the compound (M-7) with a reducing agent.

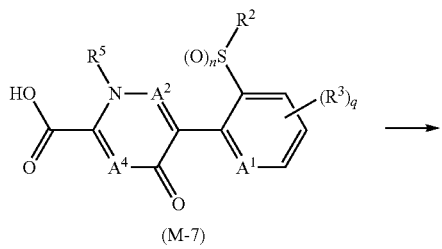

(M-7)

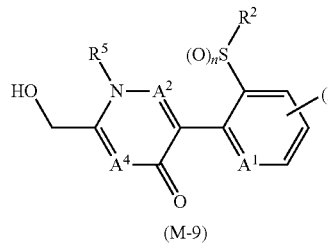

(M-9)

[wherein the symbols are the same as defined above.]

These reactions may be carried out according to the methods described in Reference Process 11.

Reference Process 13

The compound (M-10) may be prepared according to the following scheme.

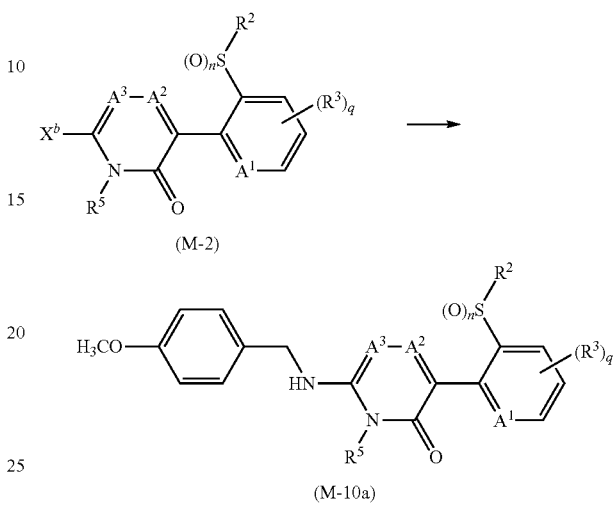

(M-2)

(M-10a)

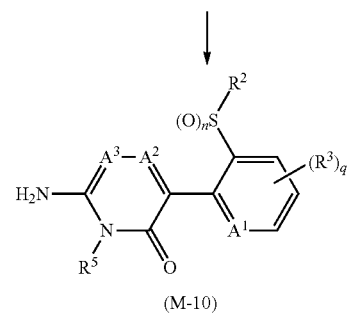

(M-10)

[wherein the symbols are the same as defined above.]

A compound represented by formula (M-10a) (hereinafter, referred to as compound (M-10a)) may be prepared by using the compound (M-2) in place of the compound (M-2a) and using p-methoxybenzylamine to in place of the compound (R-11) according to the method described in Reference Process 2.

The compound (M-10) may be prepared by using the compound (M-10a) in place of the compound (M-2b) according to the method described in Reference Process 2.

Reference Process 14

The compound (M-11) may be prepared according to the following scheme.

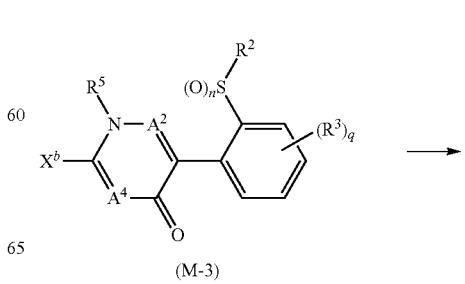

(M-3)

-continued

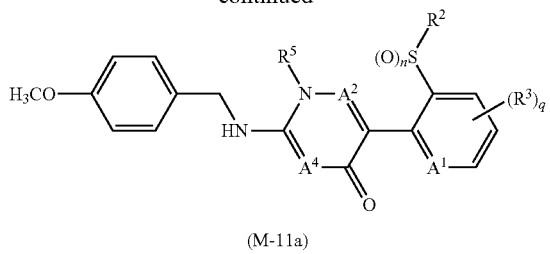

(M-11a)

↓

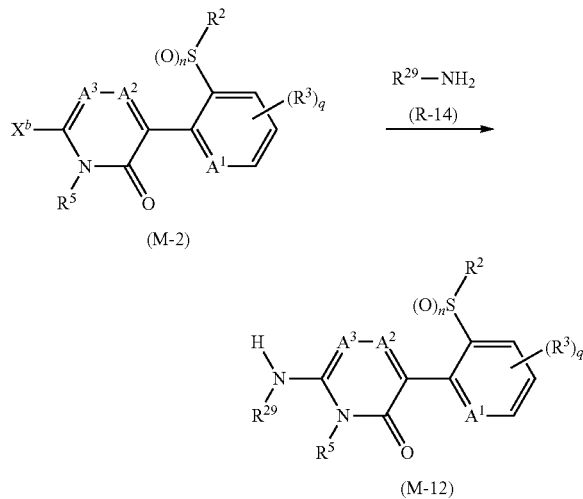

[wherein the symbols are the same as defined above.]

These reactions may be carried out according to the methods described in Reference Process 13.

Reference Process 15

The compound (M-12) may be prepared by reacting the compound (M-2) with a compound represented by formula (R-14) (hereinafter, referred to as Compound (R-14)) in the presence of a base.

[wherein the symbols are the same as defined above.]

The compound (R-14) is a commercially available compound, or can be prepared by using a known method.

The reaction is usually carried out in a solvent.

Examples of the solvent to be used in the reaction include ethers, aromatic hydrocarbons, polar aprotic solvent, and mixed solvents thereof.

Examples of the palladium catalyst include aryl palladium (II) chloride.

In the reaction, phenol as the additive, and potassium tert-butoxide as the base are used.

In the reaction, the compound (R-14) is usually used within a range of 1 to 10 molar ratio(s), the palladium catalyst is usually used within a range of 0.01 to 1 molar ratio(s), phenol is usually used within a range of 1 to 5 molar ratio(s) and potassium tert-butoxide is usually used within a range of 0.1 to 10 molar ratios, as opposed to 1 mole of the compound (M-2).

The reaction temperature of the reaction is usually within a range of 40 to 180° C. The reaction period of the reaction is usually within a range of 0.1 to 24 hours.

When the reaction is completed, water is added to reaction mixtures, and the reaction mixtures are extracted with organic solvent(s), and the organic layers are worked up (for example, drying and concentration) to give the compound (M-12).

Reference Process 16

The compound (M-13) may be prepared by reacting the compound (M-3) with the compound (R-14) in the presence of a base.

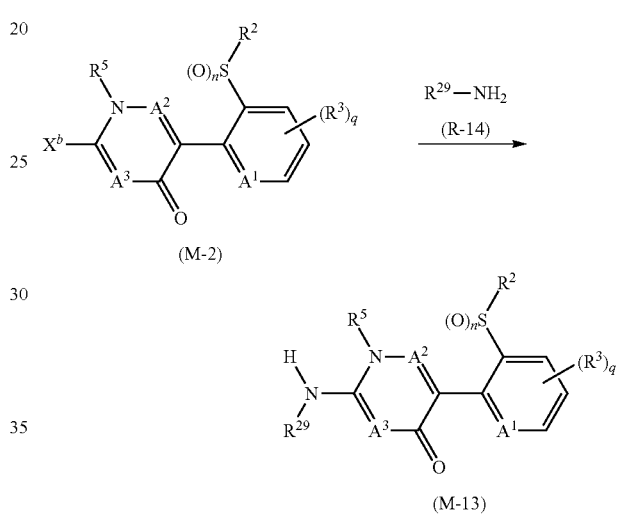

[wherein the symbols are the same as defined above.]

The reaction may be carried out according to the method described in Reference process 15.

Reference Process 17

The compound (M-14) may be prepared according to the following scheme.

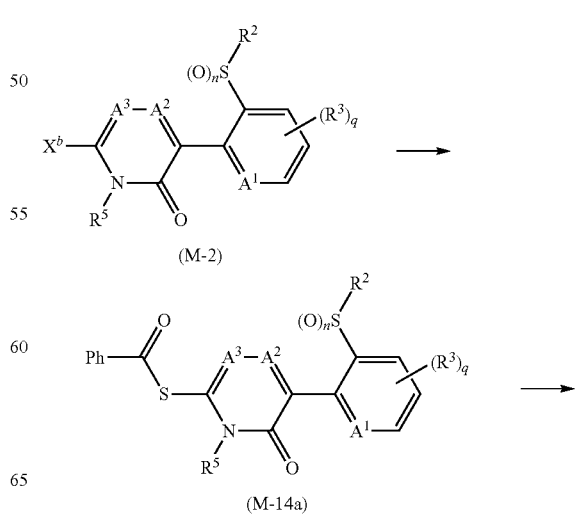

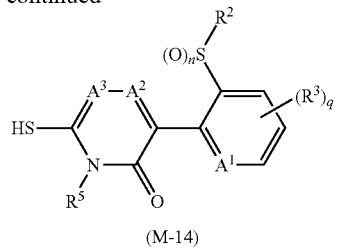

(M-14)

[wherein the symbols are the same as defined above.]

First, a process for preparing a compound represented by formula (M-14a) (hereinafter, referred to as Compound (M-14a)) is described.

The compound (M-14a) may be prepared by reacting the compound (M-2) with thiobenzoic acid in the presence of a copper catalyst and a base.

The reaction is usually carried out in the presence of a solvent. Examples of the solvent to be used in the reaction include ethers, aromatic hydrocarbons, aprotic polar solvents, water, and mixed solvents thereof.

Examples of the copper catalyst to be used in the reaction include copper chloride, copper bromide, and copper iodide.

Examples of the base to be used in the reaction include alkali metal hydrides, alkali metal carbonates, and organic bases.

A ligand may be added to the reaction as needed. Examples of the ligand to be used in the reaction include 2,2'-bipyridine, 2-aminoethanol, 8-hydroxyquinoline, 1,10-phenanthroline, and the others.

In the reaction, thiobenzoic acid is usually used within a range of 1 to 10 molar ratio(s), the copper catalyst is usually used within a range of 0.01 to 0.5 molar ratios, the ligand is usually used within a range of 0.01 to 1 molar ratio(s), and the base is usually used with a range of 0.1 to 5 molar ratios, as opposed to 1 mole of the compound (M-2)

The reaction temperature is usually within a range of −20 to 200° C. The reaction period of the reaction is usually within a range of 0.1 to 24 hours.

When the reaction is completed, water is added to reaction mixtures, and the reaction mixtures are extracted with organic solvent(s), and the organic layers are worked up (for example, drying and concentration) to give the compound (M-14a).

Next, the process for preparing the compound (M-14) is described.

The compound (M-14) may be prepared, for example, according to the method described WO 2011/068171 or the method described in Journal of Organic Chemistry, 1978, 43(6), 1190-1192.

Reference Process 18

The compound (M-15) may be prepared according to the following scheme.

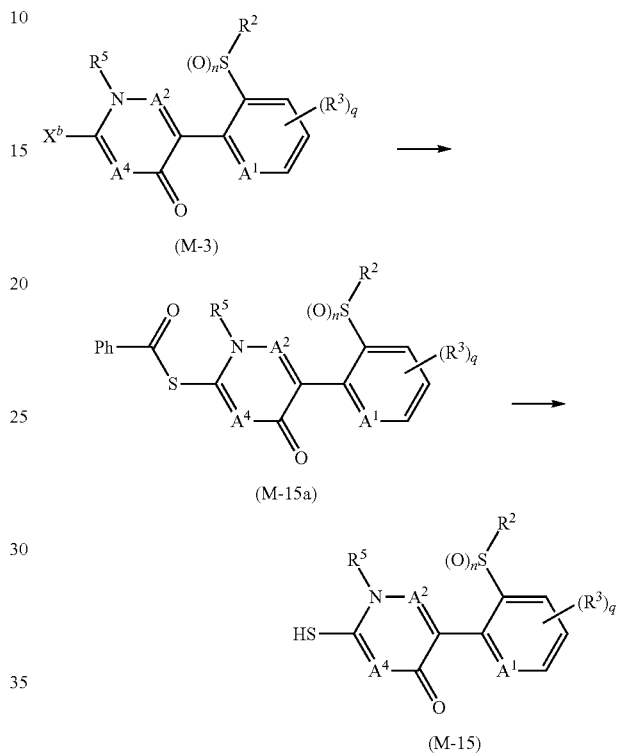

[wherein the symbols are the same as defined above.]

These reactions may be carried out according to the methods described in Reference Process 17.

Reference Process 19

A compound represented by formula (M-1b) and a compound represented by formula (M-1c) may be prepared by oxidizing a compound represented by formula (M-1a) (hereinafter, referred to as Compound (M-1a)).

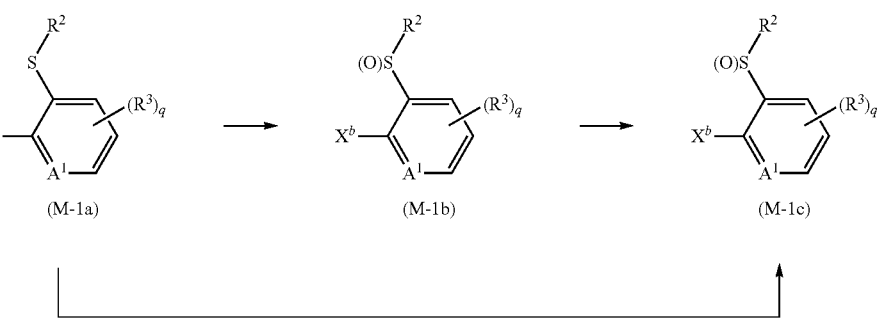

[wherein the symbols are the same as defined above.]

These reactions may be carried out according to the methods described in Process 1.

Reference Process 20

The compound (M-1a) may be prepared by reacting a compound represented by formula (R-15) (hereinafter, referred to as Compound (R-15)) with the compound (R-16) in the presence of a base.

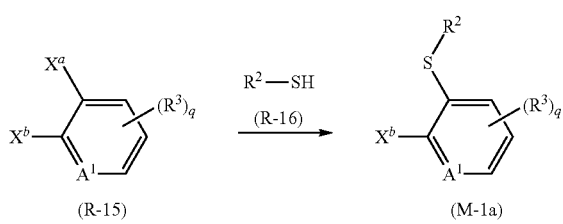

(R-15)     (M-1a)

[wherein the symbols are the same as defined above.]

The reaction may be carried out according to the method described in Process 2.

The compound (R-15) is commercially available compounds, or can be prepared by using a known method.

Reference Process 21

A compound represented by formula (M-2b-1) (hereinafter, referred to as Compound (M-2b-1)) may be prepared according to the following scheme.

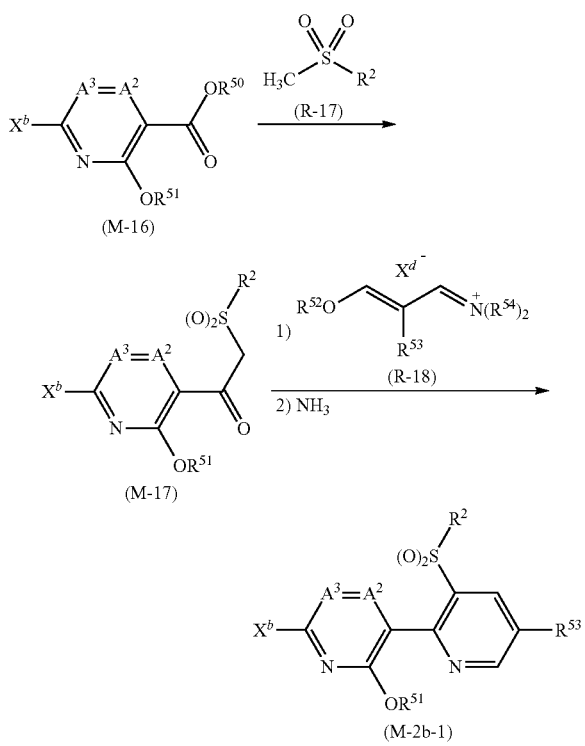

[wherein $R^{50}$ represents a methyl group or an ethyl group, $R^{52}$ and $R^{54}$ are identical to or different from each other and each represents independently a C1-C6 alkyl group, $X^d$ represents a fluorine atom, a chlorine atom, a bromine atom, an iodine atom, $BF_4$, or $PF_6$, and the other symbols are the same as defined above.]

A compound represented by formula (M-17) (hereinafter, referred to as Compound (M-17)) may be prepared by reacting a compound represented by formula (M-16) (hereinafter, referred to as Compound (M-16)) with a compound represented by formula (R-17) (hereinafter, referred to as Compound (R-17)) in the presence of a base.

The reaction is usually carried out in the presence of a solvent. Examples of the solvent to be used in the reaction include alcohols, ethers, aromatic hydrocarbons, aprotic polar solvents, and mixed solvents thereof.

Examples of the base to be used in the reaction include n-butyl lithium, s-butyl lithium, t-butyl lithium, lithium diisopropylamide, lithium bis(trimethylsilyl)amide, sodium bis(trimethylsilyl)amide, potassium bis(trimethylsilyl)amide, potassium t-butoxide, sodium methoxide, sodium ethoxide, and alkali metal hydrides.

In the reaction, the compound (R-17) is usually used within a range of 1 to 5 molar ratio(s), and the base is usually used within a range of 1 to 5 molar ratio(s), as opposed to 1 mole of the compound (M-16). Preferably, the compound (R-17) is used within a range of 1.0 to 1.1 molar ratio(s), and the base is used within a range of 1 to 2 molar ratio(s), as opposed to 1 mole of the compound (M-16).

The reaction temperature of the reaction is usually within a range of −78 to 100° C. The reaction period of the reaction is usually within a range of 0.5 to 12 hours.

When the reaction is completed, water is added to reaction mixtures, and the reaction mixtures are extracted with organic solvent(s), and the organic layers are worked up (for example, drying and concentration) to give the compound (M-17).

The compound (M-16) is a commercially available compound, or can be prepared by using a known method.

The compound (R-17) is a commercially available compound, or can be prepared by using the method described in Journal of Molecular Catalysis A: Chemical, 2011, 341(1-2), 57.

The compound (M-2b-1) may be prepared by reacting the compound (M-17) with a compound represented by formula (R-18) (hereinafter, referred to as Compound (R-18)), followed by reacting with ammonia.

The step 1 in which the compound (M-17) is reacted with the compound (R-18) is described.

The reaction is usually carried out in a solvent.

Examples of the solvent to be used in the reaction include ethers; aromatic hydrocarbons; halogenated hydrocarbons (such as dichloromethane and chloroform) (hereinafter, collectively referred to as aliphatic hydrocarbons); alcohols; esters; nitriles; aprotic polar solvents; nitrogen-containing aromatic compounds such as pyridine and 2,6-lutidine (hereinafter, collectively referred to as nitrogen-containing aromatic compounds); and mixed solvents thereof.

A base may be used in the reaction, and examples of the base include alkali metal carbonates, alkali metal hydrides, and organic bases.

When a base is used in the reaction, the base is usually used within a range of 1 to 10 molar ratio(s), as opposed to 1 mole of the compound (M-17).

In the reaction, the compound (R-18) is usually used within a range of 1 to 10 molar ratio(s), as opposed to 1 mole of the compound (M-17).

The reaction temperature of the reaction is usually within a range of −50 to 200° C. The reaction period of the reaction is usually within a range of 0.1 to 24 hours.

When the reaction is completed, the reaction mixtures are concentrated to obtain the residues and then the residues are used as itself in the second step, or alternatively, water is added to the reaction mixtures and the mixtures are extracted with organic solvents(s), and the organic layers are worked up (for example, drying and concentration) to obtain the residues, and then the residues may be used as itself in the second step.

Next, the step 2 in which the residues obtained in the step 1 is reacted with ammonia to obtain the compound (M-2b-1) is described.

The reaction is usually carried out in the presence of a solvent. Examples of the solvents to be used in the reaction include ethers, nitriles, alcohols, aprotic polar solvents, nitrogen-containing aromatic compounds, and mixed solvents thereof.

Ammonia to be used in the reaction may be used as an aqueous solution or an alcoholic solution thereof.

In the reaction, ammonia is usually used within a range of 1 to 100 molar ratio(s), as opposed to 1 mole of the compound (M-17) used in the step 1.

The reaction temperature of the reaction is usually within a range of 0 to 100° C. The reaction period of the reaction is usually within a range of 0.1 to 24 hours.

When the reaction is completed, water is added to reaction mixtures, and the reaction mixtures are extracted with organic solvent(s), and the organic layers are worked up (for example, drying and concentration) to give the compound (M-2b-1).

The compound (R-18) may be prepared according to the method described in WO 2009/054742.

Reference Process 29

A compound represented by formula (M-2b-2) (hereinafter, referred to Compound (M-2b-2)) may be prepared according to the following scheme.

A compound represented by formula (M-20) (hereinafter, referred to as Compound (M-20)) may be prepared by reacting the compound (M-17) with ammonia.

The reaction is usually carried out in the presence of a solvent. Examples of the solvents to be used in the reaction include ethers, aromatic hydrocarbons, nitriles, alcohols, aprotic polar solvents, water, and mixed solvents thereof.

Ammonia to be used in the reaction may be used as ammoia gas, or may be used as an aqueous solution or an alcoholic solution thereof. Also, ammonium salts including ammonium carboxylate such as ammonium acetate; ammonium phosphate such as ammonium dihydrogen phosphate; ammonium carbonate; and ammonium chloride may be used.

In the reaction, ammonia is usually used within a range of 0.1 to 100 molar ratios, as opposed to 1 mole of the compound (M-17).

The reaction temperature of the reaction is usually within a range of 0 to 200° C. The reaction period of the reaction is usually within a range of 0.5 to 24 hours.

When the reaction is completed, water is added to reaction mixtures, and the reaction mixtures are extracted with organic solvent(s), and the organic layers are worked up (for example, drying and concentration) to give the compound (M-20).

The compound (M-2b-2) may be prepared by reacting the compound (M-20) with a compound represented by formula (R-19) (hereinafter, referred to as Compound (R-19)).

The reaction is usually carried out in the presence of a solvent. Examples of the solvents to be used in the reaction include ethers, aromatic hydrocarbons, halogenated hydrocarbons, alcohols, esters, nitriles, aprotic polar solvents, nitrogen-containing aromatic compounds, and mixed solvents thereof.

A base may be used in the reaction, and examples of the base include alkali metal carbonates, alkali metal hydrides, and organic bases.

When a base may be used in the reaction, the base is usually used within a range of 1 to 10 molar ratio(s), as opposed to 1 mole of the compound (M-20).

In the reaction, the compound (R-19) is usually used within a range of 1 to 10 molar ratio(s), as opposed to 1 mole of the compound (M-20).

The reaction temperature of the reaction is usually within a range of −50 to 200° C. The reaction period of the reaction is usually within a range of 0.1 to 24 hours.

When the reaction is completed, water is added to reaction mixtures, and the reaction mixtures are extracted with organic solvent(s), and the organic layers are worked up (for example, drying and concentration) to give the compound (M-2b-2).

The compound (R-19) may be prepared according to the method described in Organic Process Research & Development, 2005, 9, 141, or The Journal of Organic Chemistry 2000, 65, 4571-4574.

Reference process 23

A compound represented by formula (M-3b-1) (hereinafter, referred to as Compound (M-3b-1)) may be prepared according to the following scheme.

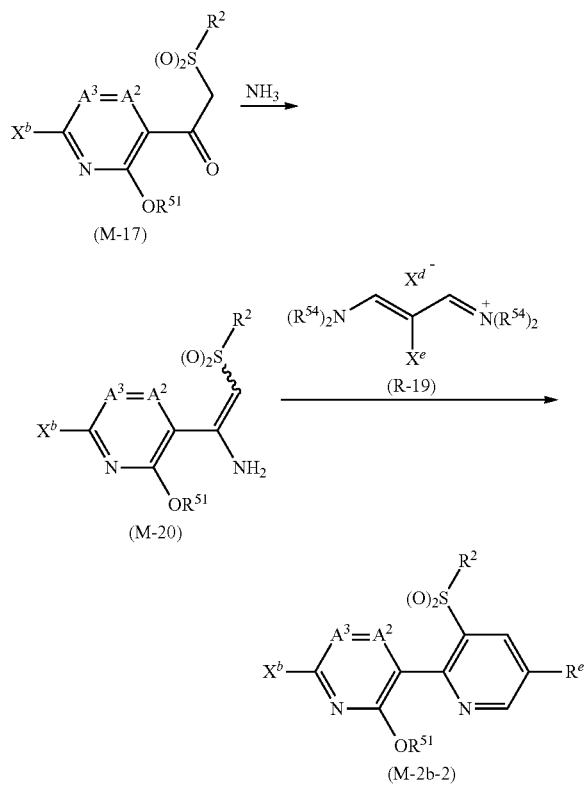

[wherein $X^e$ represents a chlorine atom, a bromine atom, an iodine atom, a methyl group, a nitro group, or a trifluoromethyl group, and the other symbols are the same as defined above.]

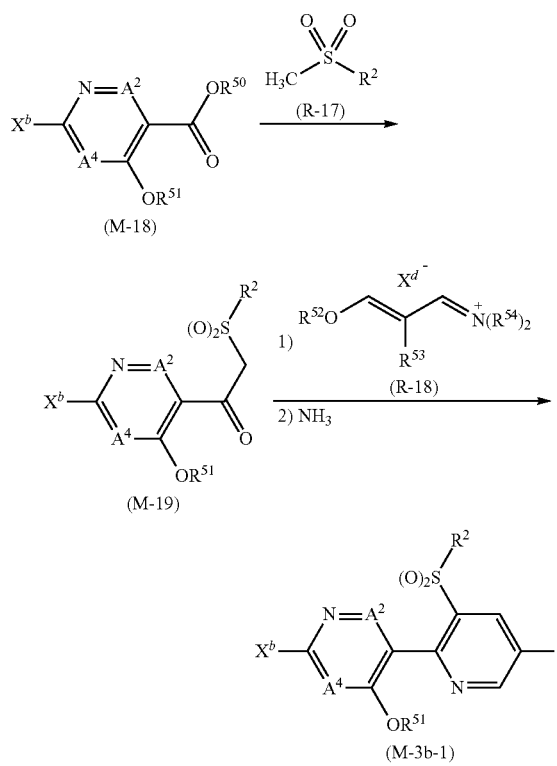

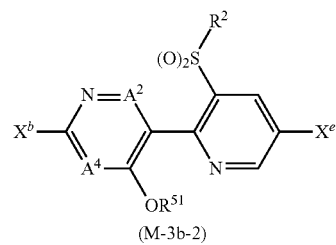

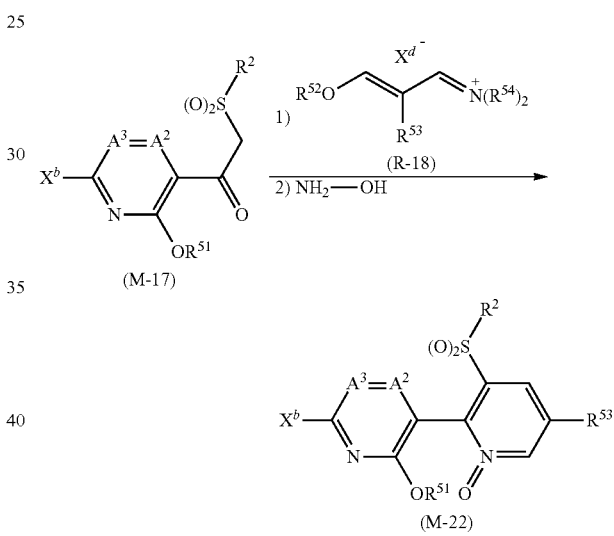

[wherein the symbols are the same as defined above.]

These reactions may be carried out by using the compound (M-18) in place of the compound (M-16) according to the methods described in Reference Process 21.

Reference process 24

A compound represented by formula (M-3b-2) (hereinafter, referred to as Compound (M-3b-2)) may be prepared according to the following scheme.

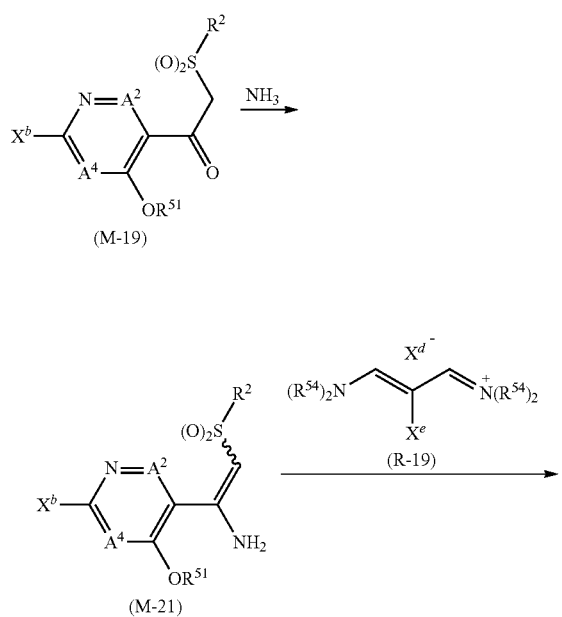

[wherein the symbols are the same as defined above.]

These reactions may be carried out by using the compound (M-19) in place of the compound (M-17) according to the methods described in Reference Process 22.

Reference Process 25

A compound represented by formula (M-22) (hereinafter, referred to as Compound (M-22)) may be prepared by reacting the compound (M-17) with the compound (R-18), followed by reacting with hydroxyl amine.

[wherein the symbols are the same as defined above.]

The reaction may be carried out by using hydroxyl amine in place of ammonia according to the method described in Reference Process 21 for preparing the compound (M-2b-1) from the compound (M-17).

Reference Process 26

The compound (M-25) may be prepared according to the following scheme.

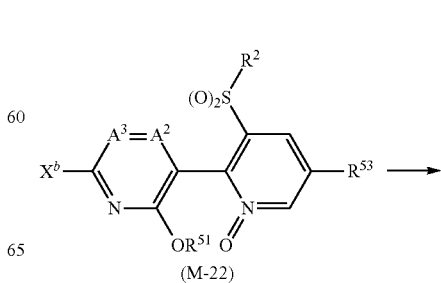

-continued

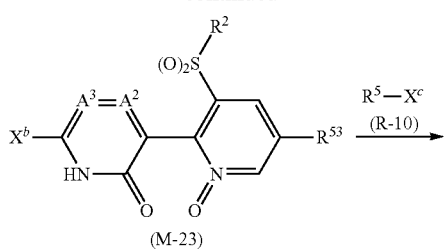
(M-23)

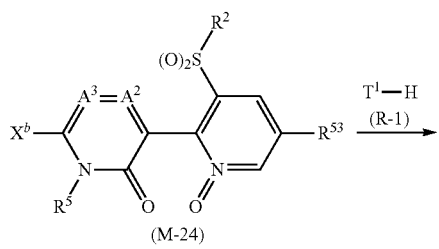
(M-24)

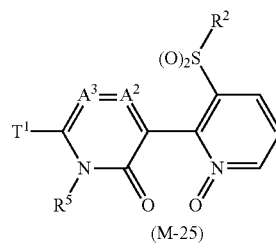
(M-25)

[wherein the symbols are the same as defined above.]

A compound represented by formula (M-23) (hereinafter, referred to as Compound (M-23)) may be prepared by using the compound (M-22) in place of the compound (M-2b) according to the method described in Reference Process 2.

A compound represented by formula (M-24) (hereinafter, referred to as Compound (M-24)) may be prepared by using the compound (M-23) in place of the compound (M-2c) according to the method described in Reference Process 2.

The compound (M-25) may be prepared by using the compound (M-24) in place of the compound (M-2) according to the method described in Process 2.

Reference Process 27

A compound represented by formula (M-26) (hereinafter, referred to as Compound (M-26)) may be prepared by reacting the compound (M-19) with the compound (M-18), followed by reacting with hydroxyl amine.

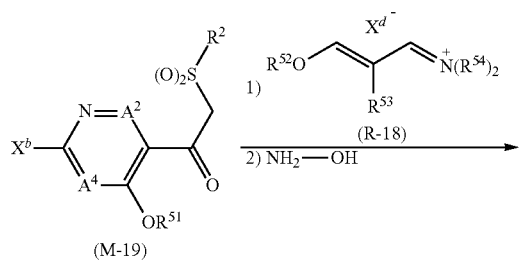
(M-19)

-continued

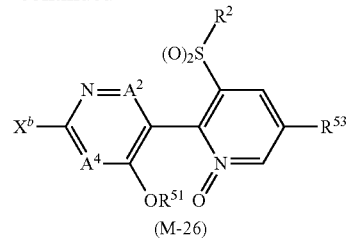
(M-26)

[wherein the symbols are the same as defined above.]

The reaction may be carried out by using the compound (M-19) in place of the compound (M-16) and using hydroxyl amine in place of ammonia, according to the method described in Reference Process 21 for preparing the compound (M-2b-1) from the compound (M-17).

Reference Process 28

The compound (M-29) may be prepared according to the following scheme.

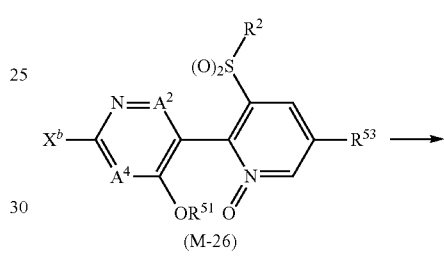
(M-26)

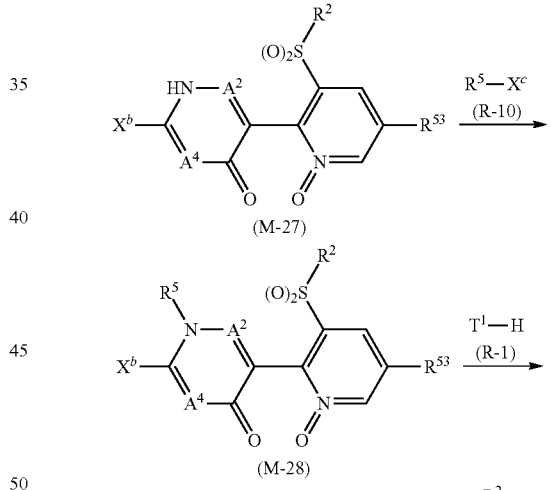
(M-27)

(M-28)

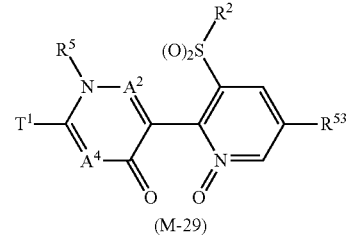
(M-29)

[wherein the symbols are the same as defined above.]

A compound represented by formula (M-27) (hereinafter, referred to as Compound (M-27)) may be prepared by using the compound (M-26) in place of the compound (M-2b) according to the method described in Reference Process 2.

A compound represented by formula (M-28) (hereinafter, referred to as Compound (M-28)) may be prepared by using the compound (M-27) in place of the compound (M-2c) according to the method described in Reference Process 2.

A compound represented by formula (M-29) may be prepared by using the compound (M-28) in place of the compound (M-2) according to the method described in Process 2.

Reference Process 29

Among the compound (M-30), a compound represented by formula (M-33) wherein Het represents a group represented by formula Het 1 can be prepared by reacting the compound (M-31) and the compound (R-15).

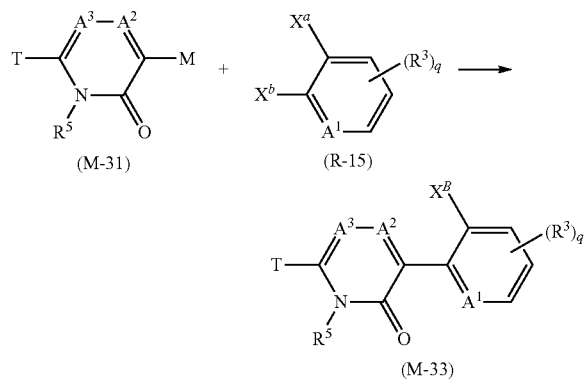

[wherein the symbols are the same as defined above.]

The reaction may be carried out by using the compound (M-31) in place of the compound (R-2) and using the compound (R-15) in place of the compound (M-2) according to the method described in the Process 4.

Reference Process 30

Among the compound (M-30), a compound represented by formula (M-34) wherein Het represents a group represented by formula Het 2 can be prepared by reacting the compound (M-32) and the compound (R-15).

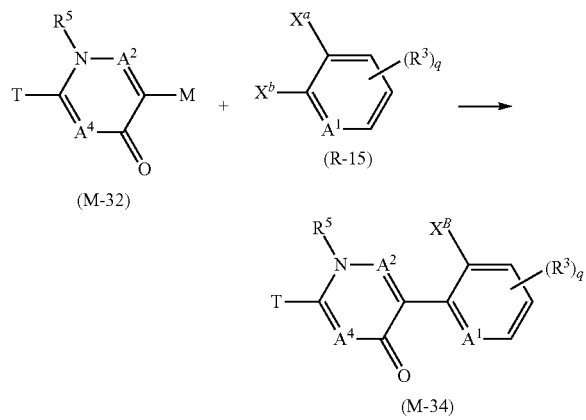

[wherein the symbols are the same as defined above.]

The reaction may be carried out by using the compound (M-32) in place of the compound (R-2) and using the compound (R-15) in place of the compound (M-2) according to the method described in the Process 4.

Reference Process 31

A compound represented by formula (M-37) (hereinafter, referred to as Compound (M-37)) can be prepared according to the following scheme.

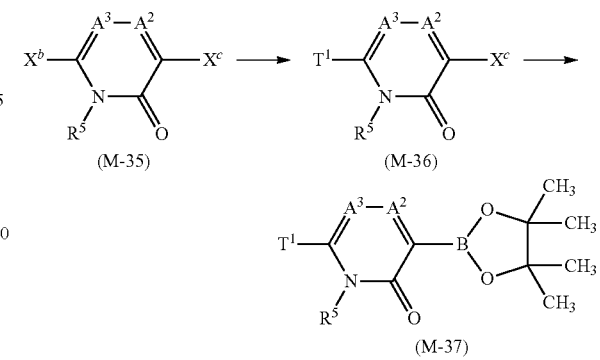

[wherein the symbols are the same as defined above.]

A compound represented by formula (M-36) (hereinafter, referred to as Compound (M-36)) can be prepared by reacting a compound represented by formula (M-35) (hereinafter, referred to as Compound (M-35)) and the compound (R-1). The reaction can be carried out by using the compound (M-35) in place of the compound (M-2) according to the method described in the Process 2.

The compound (M-37) can be prepared by reacting the compound (M-36 and bis(pinacolato)diboron in the presence of a palladium catalyst and a base. The reaction can be carried out, for example, according the method described in Journal of Organic Chemistry, 1995, (60), 7508-7510.

The compound (M-35) is a commercially available compound, or can be prepared by using a known method.

Reference Process 32

A compound represented by formula (M-40) (hereinafter, referred to as Compound (M-40)) can be prepared according to the following scheme.

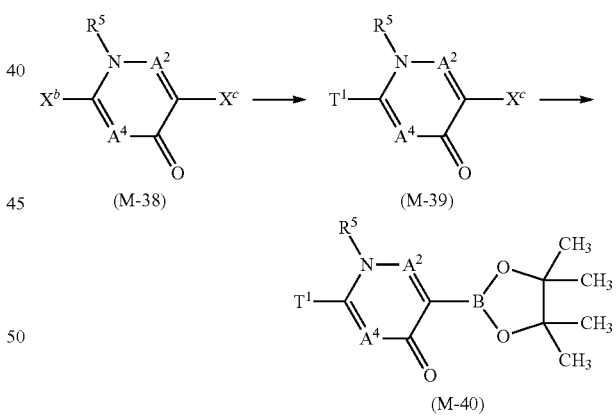

[wherein the symbols are the same as defined above.]

A compound represented by formula (M-39) (hereinafter, referred to as Compound (M-39)) can be prepared by reacting a compound represented by formula (M-38) (hereinafter, referred to as Compound (M-38)) and the compound (R-1). The reaction can be carried out by using the compound (M-38) in place of the compound (M-2) according to the method described in the Process 2.

The compound (M-40) can be prepared by reacting the compound (M-39) and bis(pinacolato)diboron in the presence of a palladium catalyst and a base. The reaction can be carried out, for example, according to the method described in Journal of Organic Chemistry, 1995, (60), 7508-7510.

The compound (M-38) is a commercially available compound, or can be prepared by using a known method.

Reference Process 33

A compound represented by formula (M-41) (hereinafter, referred to as Compound (M-41)), a compound represented by formula (M-42) (hereinafter, referred to as Compound (M-42)), and the compound (M-43) can be prepared according to the following scheme.

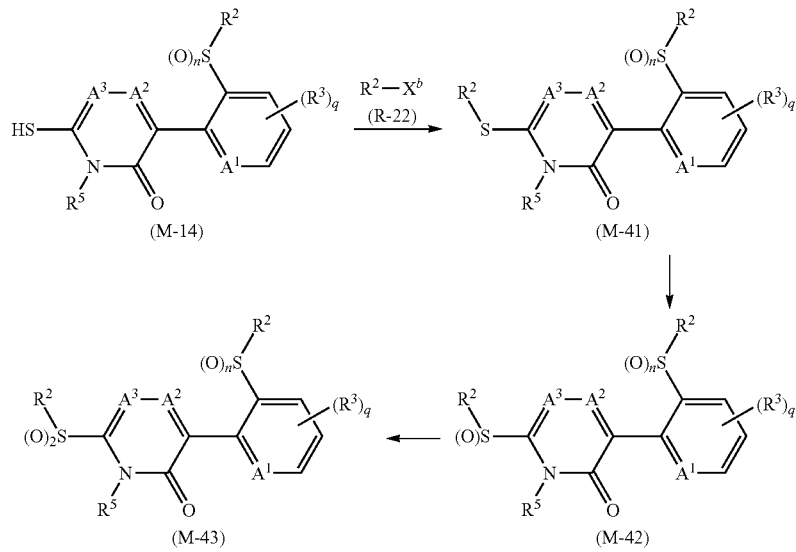

[wherein the symbols are the same as defined above.]

The reaction can be carried out according to the method described in the Process 20.

The compound (R-22) is a commercially available compound, or can be prepared by using a known method.

Reference Process 34

A compound represented by formula (M-44) (hereinafter, referred to as Compound (M-44)), a compound represented by formula (M-45) (hereinafter, referred to as Compound (M-45)), and the compound (M-46) can be prepared according to the following scheme.

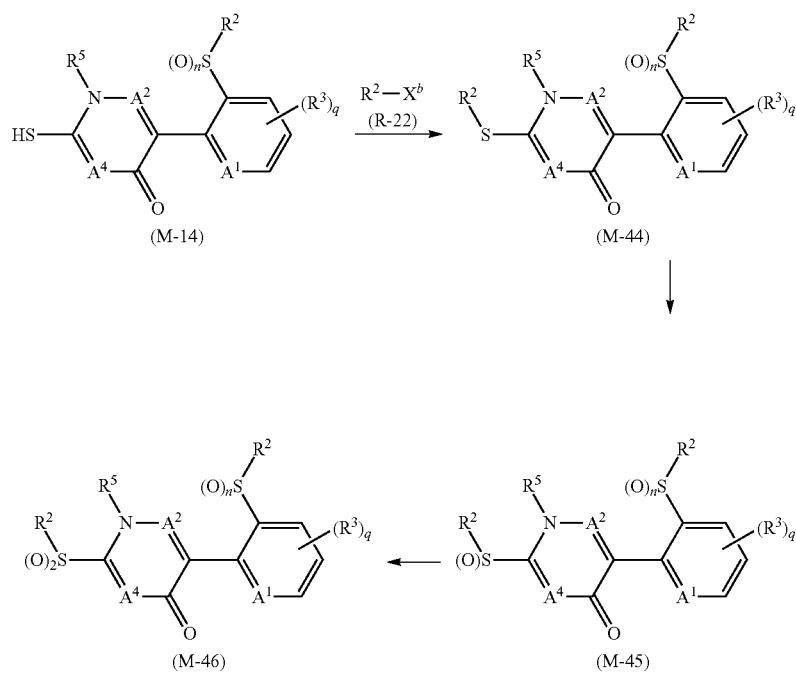

[wherein the symbols are the same as defined above.]

The reaction can be carried out according to the method described in the Process 20.

Examples of the embodiment of the compound (M-36) include the following compounds.

Reference Process 35

The compound (M-41) can be prepared by reacting the compound (M-2) and the compound (R-16) in the presence of a base.

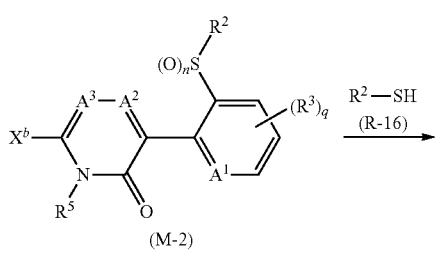

[wherein the symbols are the same as defined above.]

The reaction can be carried out by using the compound (R-16) in place of the compound (R-1) according to the method described in the process 2.

Reference Process 36

The compound (M-44) can be Prepared by reacting the compound (M-3) and the compound (R-16) in the presence of a base.

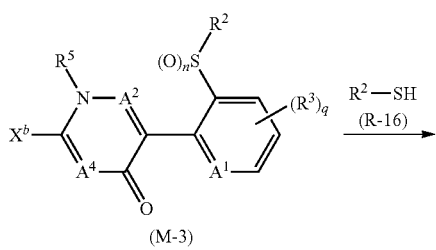

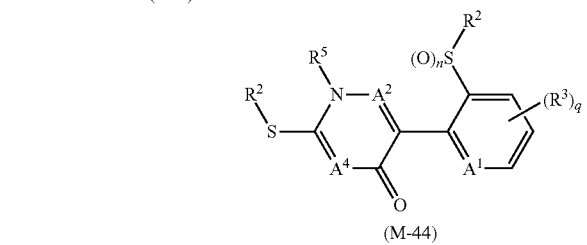

[wherein the symbols are the dame as defined above.]

The reaction can be carried out by using the compound (R-16) in place of the compound (R-1) according to the method described in the process 2.

Embodiment M1

The compound (M-36) wherein $A^2$ represents a nitrogen atom or CH, $A^3$ represent a nitrogen atom or CH, $R^5$ represents a C1-C3 alky group, and $T^1$ represents a C2-C6 alkoxy group having one or more halogen atoms.

Embodiment M2

The compound according to the embodiment M1 wherein $A^2$ represents CH, and $A^3$ represents CH.

Embodiment M3

The compound according to the embodiment M1 wherein $A^2$ represents CH, and $A^3$ represent, a nitrogen atom.

Examples of the embodiment of the compound (M-39) include the following compounds.

Embodiment M4

The compound (M-39) wherein $A^2$ represents a nitrogen atom or CH, $A^4$ represents a nitrogen atom or CH, $R^5$ represents a C1-C3 alkyl group, and $T^1$ represents a C2-C6 alkoxy group having one or more halogen atoms.

Embodiment M5

The compound according to the embodiment M4 wherein $A^2$ represents CH, and $A^4$ represents CH.

Embodiment M6

The compound according to the embodiment M4 wherein $A^2$ represents CH, and $A^4$ represents a nitrogen atom.

Examples of the embodiment of the compound (M-31) includes the following compounds.

Embodiment M7

The compound (M-31) wherein $A^2$ represents a nitrogen atom or CH, $A^3$ represents a nitrogen atom or CH, $R^5$ represents a C1-C3 alkyl group, and T represents a C2-C6 alkoxy group having one or more halogen atoms.

Embodiment M8

The compound according to the embodiment M7 wherein $A^2$ represents CH, and $A^3$ represents CH.

Embodiment M9

The compound according to the embodiment M7 wherein $A^2$ represents CH, and $A^3$ represents a nitrogen atom.

Embodiment M10

The compound according to the embodiment M7 wherein M represents a 9-borabicyclo[3,3,1]nonan-9-yl, a borono group, a 4,4,5,5,-tetramethyl-1,3,2-dioxaborolan-2-yl, or a tributylstannyl group.

Examples of the embodiment of the compound (M-32) include the following compounds.

Embodiment M11

The compound (M-32) wherein $A^2$ represents a nitrogen atom or CH, $A^4$ represents a nitrogen atom or CH, $R^5$ represents a C1-C3 alkyl group, and T represents a C2-C6 alkoxy group having one or more halogen atoms.

Embodiment M12

The compound according to the embodiment M11 wherein $A^2$ represents CH, and $A^4$ represents CH.

Embodiment M13

The compound according to the embodiment M11 wherein $A^2$ represents CH, and $A^4$ represents a nitrogen atom.

Embodiment M14

The compound according to the embodiment M11 wherein M represents a 9-borabiclo[3,3,1]nonan-9-yl, a borono group, a 4,4,5,5,-tetramethyl-1,3,2-dioxaborolan-2-yl, or a tributylstannyl group.

Next, specific examples of the compound Z of the present invention are indicated below.

Herein, Me represents a methyl group, Et represents an ethyl group, Pr represents a propyl group, i-Pr represents an isopropyl group, Bu represents a butyl group, c-Pr represents a cyclopropyl group, 1-CN-c-Pr represents a 1-cyano-cyclopropyl group, Ph represents a phenyl group, Py2 represents a 2-pyridyl group, Py3 represents a 3-pyridyl group, Py4 represents a 4-pyridyl group, and Bn represents a benzyl group. When the Ph, Py2, Py3, and Py4 have any substituent(s), the substituent(s) is described together with a substitution position before the symbol. For example, 4-$CF_3$-Py2 represents a 4-(trifluoromethyl)-2-pyridyl group, and 3,5-$(CF_3)_2$-Ph represents a 3,5-bis(trifluoromethyl) phenyl group.

A compound represented by formula (L-1):

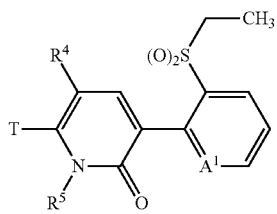

(L-1)

(hereinafter, referred to as Compound (L-1)) wherein $A^1$ represents CH, $R^4$ represents a hydrogen atom, $R^5$ represents a methyl group, and T represents any substituents indicated in Table 1 to Table 6 (hereinafter, referred to as Compound Class $SX_1$).

TABLE 1

$CF_3$
$CHF_2$
$CH_2CF_3$
$CF_2CF_3$
$CH_2CF_2CF_3$
$CF_2CF_2CF_3$
$CF_2CF_2CF_2CF_3$
$CF_2CF_2CF_2CF_2CF_3$
$OCF_3$
$OCHF_2$
$OCH_2CF_3$
$OCH_2CHF_2$
$OCF_2CF_3$

TABLE 1-continued $OCH(CH_3)CF_3$
$OCH_2CF_2CHF_2$
$OCH_2CF_2CF_3$
$OCF_2CF_2CF_3$
$OCH_2CF_2CHFCF_3$
$OCH_2CF_2CF_2CF_3$
$OCF_2CF_2CF_2CF_3$
$OCH_2CF_2CF_2CF_2CF_3$
$OCH_2CMe_2CN$

TABLE 2

$SCF_3$
$SCH_2CF_3$
$SCF_2CF_3$
$SCH_2CF_2CF_3$
$SCF_2CF_2CF_3$
$SCH_2CF_2CF_2CF_3$
$SCF_2CF_2CF_2CF_3$
$S(O)CF_3$
$S(O)CH_2CF_3$
$S(O)CF_2CF_3$
$S(O)CH_2CF_2CF_3$
$S(O)CF_2CF_2CF_3$
$S(O)CH_2CF_2CF_2CF_3$
$S(O)CF_2CF_2CF_2CF_3$
$S(O)_2CF_3$
$S(O)_2CH_2CF_3$
$S(O)_2CF_2CF_3$
$S(O)_2CH_2CF_2CF_3$
$S(O)_2CF_2CF_2CF_3$
$S(O)_2CH_2CF_2CF_2CF_3$
$S(O)_2CF_2CF_2CF_2CF_3$
$OCH_2$(1-CN-c-Pr)

TABLE 3

$NHCH_2CF_3$
$NHCH_2CF_2CF_3$
$NHCH_2CF_2CF_2CF_3$
$NMeCH_2CF_3$
$NMeCH_2CF_2CF_3$
$NMeCH_2CF_2CF_2CF_3$
$NEtCH_2CF_3$
$NEtCH_2CF_2CF_3$
$NEtCH_2CF_2CF_2CF_3$
$OS(O)_2CF_3$
$OS(O)_2CF_2CF_3$
$OS(O)_2CF_2CF_2CF_3$
$CH_2OCF_3$
$CH_2OCH_2CF_3$
$CH_2OCF_2CF_3$
$C(O)CF_3$
$C(O)CF_2CF_3$
$C(O)CF_2CF_2CF_3$
$C(O)NMeCH_2CF_3$
$NMeC(O)CF_3$
$N=CEtCH_2CF_3$
$OCH_2$(1-CN-c-Bu)

TABLE 4

3-$CF_3$—Ph
4-$CF_3$—Ph
3,5-$(CF_3)_2$—Ph
3-$SCF_3$—Ph
3-$S(O)CF_3$—Ph
3-$S(O)_2CF_3$—Ph
4-$SCF_3$—Ph
4-$S(O)CF_3$—Ph
4-$S(O)_2CF_3$—Ph

TABLE 4-continued

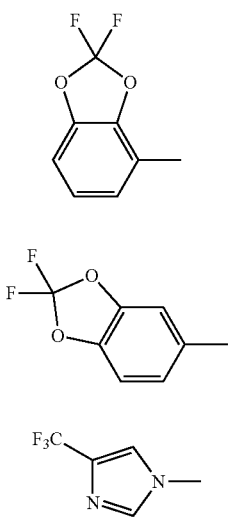

TABLE 5

4-CF₃—Py2
5-CF₃—Py2
4-SCF₃—Py2
4-S(O)CF₃—Py2
4-S(O)₂CF₃—Py2
5-SCF₃—Py2
5-S(O)CF₃—Py2
5-S(O)₂CF₃—Py2
5-NMeCH₂CF₃—Py2

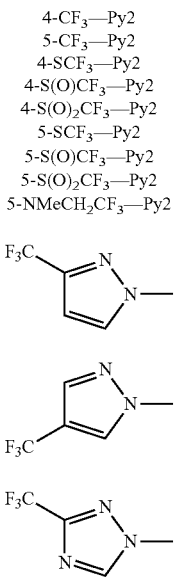

TABLE 6

5-CF₃—Py3
6-CF₃—Py3
5-SCF₃—Py3
5-S(O)CF₃—Py3
5-S(O)₂CF₃—Py3
6-SCF₃—Py3
6-S(O)CF₃—Py3
6-S(O)₂CF₃—Py3
6-NMeCH₂CF₃—Py3

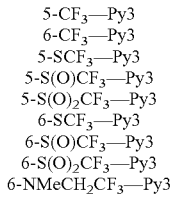

TABLE 6-continued

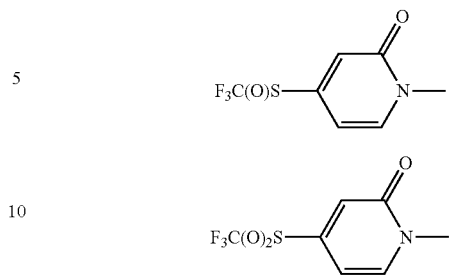

A compound (L-1) wherein $A^1$ represents CH, $R^4$ represents a hydrogen atom, $R^5$ represents an ethyl group, and T represents any substituents indicated in Table 1 to Table 6 (hereinafter, referred to as Compound Class $SX_2$).

A compound (L-1) wherein $A^1$ represents a nitrogen atom, $R^4$ represents a hydrogen atom, $R^5$ represents a methyl group, and T represents any substituents indicated in Table 1 to Table 6 (hereinafter, referred to as Compound Class $SX_3$).

A compound (L-1) wherein $A^1$ represents a nitrogen atom, $R^4$ represents a hydrogen atom, $R^5$ represents an ethyl group, and T represents any substituents indicated in Table 1 to Table 6 (hereinafter, referred to as Compound Class $SX_4$).

A compound (L-1) wherein $A^1$ represents a nitrogen atom, $R^4$ represents a hydrogen atom, $R^5$ represents a propyl group, and T represents any substituents indicated in Table 1 to Table 6 (hereinafter, referred to as Compound Class $SX_5$).

A compound (L-1) wherein $A^1$ represents a nitrogen atom, $R^4$ represents a hydrogen atom, $R^5$ represents an isopropyl group, and T represents any substituents indicated in Table 1 to Table 6 (hereinafter, referred to as Compound Class $SX_6$).

A compound (L-1) wherein $A^1$ represents a nitrogen atom, $R^4$ represents a hydrogen atom, $R^5$ represents a cyclopropyl group, and T represents any substituents indicated in Table 1 to Table 6 (hereinafter, referred to as Compound Class $SX_7$).

A compound (L-1) wherein $A^1$ represents a nitrogen atom, $R^4$ represents a chlorine atom, $R^5$ represents a methyl group, and T represents any substituents indicated in Table 1 to Table 6 (hereinafter, referred to as Compound Class $SX_8$).

A compound (L-1) wherein $A^1$ represents a nitrogen atom, $R^4$ represents a chlorine atom, $R^5$ represents an ethyl group, and T represents any substituents indicated in Table 1 to Table 6 (hereinafter, referred to as Compound Class $SX_9$).

A compound (L-1) wherein $A^1$ represents a nitrogen atom, $R^4$ represents a chlorine atom, $R^5$ represents a propyl group, and T represents any substituents indicated in Table 1 to Table 6 (hereinafter, referred to as Compound Class $SX_{10}$).

A compound (L-1) wherein $A^1$ represents a nitrogen atom, $R^4$ represents a chlorine atom, $R^5$ represents an isopropyl group, and T represents any substituents indicated in Table 1 to Table 6 (hereinafter, referred to as Compound Class $SX_{11}$).

A compound (L-1) wherein $A^1$ represents a nitrogen atom, $R^4$ represents a chlorine atom, $R^5$ represents a cyclopropyl group, and T represents any substituents indicated in Table 1 to Table 6 (hereinafter, referred to as Compound Class $SX_{12}$).

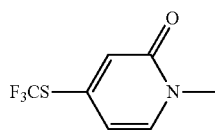

A compound represented by formula (L-2):

$$\text{(L-2)}$$

(hereinafter, referred to as Compound (L-2)) wherein $A^1$ represents CH, $R^5$ represents a methyl group, and T represents any substituents indicated in Table 1 to Table 6 (hereinafter, referred to as Compound Class $SX_{13}$).

A compound (L-2) wherein $A^1$ represents CH, $R^5$ represents an ethyl group, and T represents any substituents indicated in Table 1 to Table 6 (hereinafter, referred to as Compound Class $SX_{14}$).

A compound (L-2) wherein $A^1$ represents a nitrogen atom, $R^5$ represents a methyl group, and T represents any substituents indicated in Table 1 to Table 6 (hereinafter, referred to as Compound Class $SX_{15}$).

A compound (L-2) wherein $A^1$ represents a nitrogen atom, $R^5$ represents an ethyl group, and T represents any substituents indicated in Table 1 to Table 6 (hereinafter, referred to as Compound Class $SX_{16}$).

A compound (L-2) wherein $A^1$ represents a nitrogen atom, $R^5$ represents a propyl group, and T represents any substituents indicated in Table 1 to Table 6 (hereinafter, referred to as Compound Class $SX_{17}$).

A compound (L-2) wherein $A^1$ represents a nitrogen atom, $R^5$ represents an isopropyl group, and T represents any substituents indicated in Table 1 to Table 6 (hereinafter, referred to as Compound Class $SX_{18}$).

A compound (L-2) wherein $A^1$ represents a nitrogen atom, $R^5$ represents a cyclopropyl group, and T represents any substituents indicated in Table 1 to Table 6 (hereinafter, referred to as Compound Class $SX_{19}$).

A compound represented by formula (L-3):

$$\text{(L-3)}$$

(hereinafter, referred to as Compound (L-3)) wherein $A^1$ represents CH, $R^4$ represents a hydrogen atom, $R^5$ represents a methyl group, and T represents any substituents indicated in Table 1 to Table 6 (hereinafter, referred to as Compound Class $SX_{20}$).

A compound (L-3) wherein $A^1$ represents CH, $R^4$ represents a hydrogen atom, $R^5$ represents an ethyl group, and T represents any substituents indicated in Table 1 to Table 6 (hereinafter, referred to as Compound Class $SX_{21}$).

A compound (L-3) wherein $A^1$ represents a nitrogen atom, $R^4$ represents a hydrogen atom, $R^5$ represents a methyl group, and T represents any substituents indicated in Table 1 to Table 6 (hereinafter, referred to as Compound Class $SX_{22}$).

A compound (L-3) wherein $A^1$ represents a nitrogen atom, $R^4$ represents a hydrogen atom, $R^5$ represents an ethyl group, and T represents any substituents indicated in Table 1 to Table 6 (hereinafter, referred to as Compound Class $SX_{23}$).

A compound (L-3) wherein $A^1$ represents a nitrogen atom, $R^4$ represents a hydrogen atom, $R^5$ represents a propyl group, and T represents any substituents indicated in Table 1 to Table 6 (hereinafter, referred to as Compound Class $SX_{24}$).

A compound (L-3) wherein $A^1$ represents a nitrogen atom, $R^4$ represents a hydrogen atom, $R^5$ represents an isopropyl group, and T represents any substituents indicated in Table 1 to Table 6 (hereinafter, referred to as Compound Class $SX_{25}$).

A compound (L-3) wherein $A^1$ represents a nitrogen atom, $R^4$ represents a hydrogen atom, $R^5$ represents a cyclopropyl group, and T represents any substituents indicated in Table 1 to Table 6 (hereinafter, referred to as Compound Class $SX_{26}$).

A compound (L-3) wherein $A^1$ represents a nitrogen atom, $R^4$ represents a chlorine atom, $R^5$ represents a methyl group, and T represents any substituents indicated in Table 1 to Table 6 (hereinafter, referred to as Compound Class $SX_{27}$).

A compound (L-3) wherein $A^1$ represents a nitrogen atom, $R^4$ represents a chlorine atom, $R^5$ represents an ethyl group, and T represents any substituents indicated in Table 1 to Table 6 (hereinafter, referred to as Compound Class $SX_{28}$).

A compound (L-3) wherein $A^1$ represents a nitrogen atom, $R^4$ represents a chlorine atom, $R^5$ represents a propyl group, and T represents any substituents indicated in Table 1 to Table 6 (hereinafter, referred to as Compound Class $SX_{29}$).

A compound (L-3) wherein $A^1$ represents a nitrogen atom, $R^4$ represents a chlorine atom, $R^5$ represents an isopropyl group, and T represents any substituents indicated in Table 1 to Table 6 (hereinafter, referred to as Compound Class $SX_{30}$).

A compound (L-3) wherein $A^1$ represents a nitrogen atom, $R^4$ represents a chlorine atom, $R^5$ represents a cyclopropyl group, and T represents any substituents indicated in Table 1 to Table 6 (hereinafter, referred to as Compound Class $SX_{31}$).

A compound represented by formula (L-4):

$$\text{(L-4)}$$

(hereinafter, referred to as Compound (L-4)) wherein $A^1$ represents CH, $R^5$ represents a methyl group, and T represents any substituents indicated in Table 1 to Table 6 (hereinafter, referred to as Compound Class $SX_{32}$).

A compound (L-4) wherein $A^1$ represents CH, $R^5$ represents an ethyl group, and T represents any substituents indicated in Table 1 to Table 6 (hereinafter, referred to as Compound Class $SX_{33}$).

A compound (L-4) wherein $A^1$ represents a nitrogen atom, represents a methyl group, and T represent any substituents indicated in Table 1 to Table 6 (hereinafter, referred to as Compound Class $SX_{34}$).

A compound (L-4) wherein $A^1$ represents a nitrogen atom, $R^5$ represents an ethyl group, and T represents any substituents indicated in Table 1 to Table 6 (hereinafter, referred to as Compound Class $SX_{35}$).

A compound (L-4) wherein $A^1$ represents a nitrogen atom, $R^5$ represents a propyl group, and T represents any substituents indicated in Table 1 to Table 6 (hereinafter, referred to as Compound Class $SX_{36}$).

A compound (L-4) wherein $A^1$ represents a nitrogen atom, $R^5$ represents an isopropyl group, and T represents any substituents indicated in Table 1 to Table 6 (hereinafter, referred to as Compound Class $SX_{37}$).

A compound (L-4) wherein $A^1$ represents a nitrogen atom, $R^5$ represents a cyclopropyl group, and T represents any substituents indicated in Table 1 to Table 6 (hereinafter, referred to as Compound Class $SX_{38}$).

A compound represented by formula (L-5):

(L-5)

(hereinafter, referred to as Compound (L-5)) wherein $A^1$ represents CH, $R^4$ represents a hydrogen atom, $R^5$ represents a methyl group, and T represents any substituents indicated in Table 1 to Table 6 (hereinafter, referred to as Compound Class $SX_{39}$).

A compound (L-5) wherein $A^1$ represents CH, $R^4$ represents a hydrogen atom, $R^5$ represents an ethyl group, and represents any substituents indicated in Table 1 to Table 6 (hereinafter, referred to as Compound Class $SX_{40}$).

A compound (L-5) wherein $A^1$ represents a nitrogen atom, $R^4$ represents a hydrogen atom, $R^5$ represents a methyl group, and T represents any substituents indicated in Table 1 to Table 6 (hereinafter, referred to as Compound Class $SX_{41}$).

A compound (L-5) wherein $A^1$ represents a nitrogen atom, $R^4$ represents a hydrogen atom, $R^5$ represents an ethyl group, and T represents any substituents indicated in Table 1 to Table 6 (hereinafter, referred to as Compound Class $SX_{42}$).

A compound (L-5) wherein $A^1$ represents a nitrogen atom, $R^4$ represents a hydrogen atom, $R^5$ represents a propyl group, and T represents any substituents indicated in Table 1 to Table 6 (hereinafter, referred to as Compound Class $SX_{43}$).

A compound (L-5) wherein $A^1$ represents a nitrogen atom, $R^4$ represents a hydrogen atom, $R^5$ represents an isopropyl group, and T represents any substituents indicated in Table 1 to Table 6 (hereinafter, referred to as Compound Class $SX_{14}$).

A compound (L-5) wherein $A^1$ represents a nitrogen atom, $R^4$ represents a hydrogen atom, $R^5$ represents a cyclopropyl group, and T represents any substituents indicated in Table 1 to Table 6 (hereinafter, referred to as Compound Class $SX_{45}$).

A compound (L-5) wherein $A^1$ represents a nitrogen atom, $R^4$ represents chlorine atom, $R^5$ represents a methyl group, and T represents any substituents indicated in Table 1 to Table 6 (hereinafter, referred to as Compound Class $SX_{46}$).

A compound (L-5) wherein $A^1$ represents a nitrogen atom, $R^4$ represents a chlorine atom, $R^5$ represents an ethyl group, and T represents any substituents indicated in Table 1 to Table 6 (hereinafter, referred to as Compound Class $SX_{47}$).

A compound (L-5) wherein $A^1$ represents a nitrogen atom, $R^4$ represents a chlorine atom, $R^5$ represents a propyl group, and T represents any substituents indicated in Table 1 to Table 6 (hereinafter, referred to as Compound Class $SX_{48}$).

A compound (L-5) wherein $A^1$ represents a nitrogen atom, $R^4$ represents a chlorine atom, $R^5$ represents an isopropyl group, and T represents any substituents indicated in Table 1 to Table 6 (hereinafter, referred to as Compound Class $SX_{49}$).

A compound (L-5) wherein $A^1$ represents a nitrogen atom, $R^4$ represents a chlorine atom, $R^5$ represents a cyclopropyl group, and T represents any substituents indicated in Table 1 to Table 6 (hereinafter, referred to as Compound Class $SX_{50}$).

A compound represented by formula (L-6):

(L-6)

(hereinafter, referred to as Compound (L-6)) wherein $A^1$ represents CH, $R^5$ represents a methyl group, and T represents any substituents indicated in Table 1 to Table 6 (hereinafter, referred to as Compound Class $SX_{51}$).

A compound (L-6) wherein $A^1$ represents CH, $R^5$ represents an ethyl group, and T represents any substituents indicated in Table 1 to Table 6 (hereinafter, referred to as Compound Class $SX_{52}$).

A compound (L-6) wherein $A^1$ represents a nitrogen atom, $R^5$ represents a methyl group, and T represents any substituents indicated in Table 1 to Table 6 (hereinafter, referred to as Compound Class $SX_{53}$).

A compound (L-6) wherein $A^1$ represents a nitrogen atom, $R^5$ represents an ethyl group, and T represents any substituents indicated in Table 1 to Table 6 (hereinafter, referred to as Compound Class $SX_{54}$).

A compound (L-6) wherein $A^1$ represents a nitrogen atom, $R^5$ represents a propyl group, and T represents any substituents indicated in Table 1 to Table 6 (hereinafter, referred to as Compound Class $SX_{55}$).

A compound (L-6) wherein $A^1$ represents a nitrogen atom, $R^5$ represents an isopropyl group, and T represents any substituents indicated in Table 1 to Table 6 (hereinafter, referred to as Compound Class $SX_{56}$).

A compound (L-6) wherein $A^1$ represents a nitrogen atom, $R^5$ represents a cyclopropyl group, and T represents any substituents indicated in Table 1 to Table 6 (hereinafter, referred to as Compound Class $SX_{57}$).

A compound represented by formula (L-7):

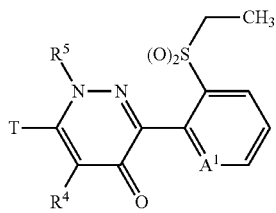

(L-7)

(hereinafter, referred to as Compound (L-7)) wherein $A^1$ represents CH, $R^4$ represents a hydrogen atom, $R^5$ represents a methyl group, and T represents any substituents indicated in Table 1 to Table 6 (hereinafter, referred to as Compound Class $SX_{58}$).

A compound (L-7) wherein $A^1$ represents CH, $R^4$ represents a hydrogen atom, $R^5$ represents an ethyl group, and T represents any substituents indicated in Table 1 to Table 6 (hereinafter, referred to as Compound Class $SX_{59}$).

A compound (L-7) wherein $A^1$ represents a nitrogen atom, $R^4$ represents a hydrogen atom, $R^5$ represents a methyl group, and T represents any substituents indicated in Table 1 to Table 6 (hereinafter, referred to as Compound Class $SX_{60}$).

A compound (L-7) wherein $A^1$ represents a nitrogen atom, $R^4$ represents a hydrogen atom, $R^5$ represents an ethyl group, and T represents any substituents indicated in Table 1 to Table 6 (hereinafter, referred to as Compound Class $SX_{61}$).

A compound (L-7) wherein $A^1$ represents a nitrogen atom, $R^4$ represents a hydrogen atom, $R^5$ represents a propyl group, and T represents any substituents indicated in Table 1 to Table 6 (hereinafter, referred to as Compound Class $SX_{62}$).

A compound (L-7) wherein $A^1$ represents a nitrogen atom, $R^4$ represents a hydrogen atom, $R^5$ represents an isopropyl group, and T represents any substituents indicated in Table 1 to Table 6 (hereinafter, referred to as Compound Class $SX_{63}$).

A compound (L-7) wherein $A^1$ represents a nitrogen atom, $R^4$ represents a hydrogen atom, $R^5$ represents a cyclopropyl group, and T represents any substituents indicated in Table 1 to Table 6 (hereinafter, referred to as Compound Class $SX_{64}$).

A compound (L-7) wherein $A^1$ represents a nitrogen atom, $R^4$ represents a chlorine atom, $R^5$ represents a methyl group, and T represents any substituents indicated in Table 1 to Table 6 (hereinafter, referred to as Compound Class $SX_{65}$).

A compound (L-7) wherein $A^1$ represents a nitrogen atom, $R^4$ represents a chlorine atom, $R^5$ represents an ethyl group, and T represents any substituents indicated in Table 1 to Table 6 (hereinafter, referred to as Compound Class $SX_{66}$).

A compound (L-7) wherein $A^1$ represents a nitrogen atom, $R^4$ represents a chlorine atom, $R^5$ represents a propyl group, and T represents any substituents indicated in Table 1 to Table 6 (hereinafter, referred to as Compound Class $SX_{67}$).

A compound (L-7) wherein $A^1$ represents a nitrogen atom, $R^4$ represents a chlorine atom, $R^5$ represents an isopropyl group, and T represents any substituents indicated in Table 1 to Table 6 (hereinafter, referred to as Compound Class $SX_{68}$).

A compound (L-7) wherein $A^1$ represents a nitrogen atom, $R^4$ represents a chlorine atom, $R^5$ represents a cyclopropyl group, and T represents any substituents indicated in Table 1 to Table 6 (hereinafter, referred to as Compound Class $SX_{69}$).

A compound represented by formula (L-8):

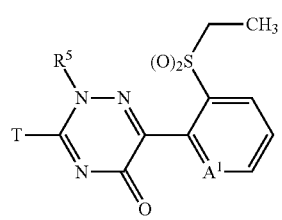

(L-8)

(hereinafter, referred to as Compound (L-8)) wherein $A^1$ represents CH, $R^5$ represents a methyl group, and T represents any substituents indicated in Table 1 to Table 6 (hereinafter, referred to as Compound Class $SX_{70}$).

A compound (L-8) wherein $A^1$ represents CH, $R^5$ represents an ethyl group, and T represents any substituents indicated in Table 1 to Table 6 (hereinafter, referred to as Compound Class $SX_{71}$).

A compound (L-8) wherein $A^1$ represents a nitrogen atom, $R^5$ represents a methyl group, and T represents any substituents indicated in Table 1 to Table 6 (hereinafter, referred to as Compound Class $SX_{72}$).

A compound (L-8) wherein $A^1$ represents a nitrogen atom, $R^5$ represents an ethyl group, and T represents any substituents indicated in Table 1 to Table 6 (hereinafter, referred to as Compound Class $SX_{73}$).

A compound (L-8) wherein $A^1$ represents a nitrogen atom, $R^5$ represents a propyl group, and T represents any substituents indicated in Table 1 to Table 6 (hereinafter, referred to as Compound Class $SX_{74}$).

A compound (L-8) wherein $A^1$ represents a nitrogen atom, $R^5$ represents an isopropyl group, and T represents any substituents indicated in Table 1 to Table 6 (hereinafter, referred to as Compound Class $SX_{75}$).

A compound (L-8) wherein $A^1$ represents a nitrogen atom, $R^5$ represents a cyclopropyl group, and T represents any substituents indicated in Table 1 to Table 6 (hereinafter, referred to as Compound Class $SX_{76}$).

A compound represented by formula (L-9):

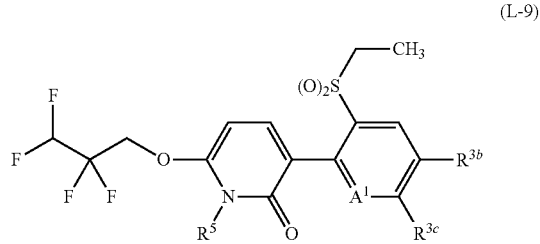

(L-9)

(hereinafter, referred to as Compound (L-9)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{77}$).

TABLE 7
F
Cl
Br
Me
Et
Pr
i-Pr
c-Pr
1-CN-c-Pr
OMe
OEt
OPr
Oi-Pr
CF₃
NH₂
NHCH₂CF₃
CN
C(O)OEt
NHC(O)c-Pr
NMeC(O)c-Pr
CH=N—OH
CH=N—OMe
TABLE 8
Ph
3-F—Ph
4-F—Ph
3-Cl—Ph
4-Cl—Ph
3-CF₃—Ph
4-CF₃—Ph
3-NMe₂—Ph
4-NMe₂—Ph
3-CN—Ph
4-CN—Ph
4-C(O)NMe₂—Ph
4-NHC(O)Me—Ph
3,4-F₂—Ph
3,5-F₂—Ph
2,4-F₂—Ph
3,4,5-F₃—Ph
3,4-Cl₂—Ph
3,5-Cl₂—Ph
3,5-Cl₂-4-F—Ph
OPh
O-2-F—Ph
TABLE 9
Py2
4-F-Py2
5-F-Py2
4-Cl-Py2
5-Cl-Py2
4-CF₃-Py2
5-CF₃-Py2
3-Me-Py2
4-Me-Py2
5-Me-Py2
6-Me-Py2
5-CN-Py2
5-OCH₂CF₂CF₃-Py2
3,5-F₂-Py2
Py3
6-CF₃-Py3
5-CF₃-Py3
6-F-Py3
6-Cl-Py3
Py4
OPy2
OPy3
TABLE 10
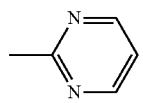
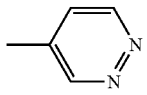
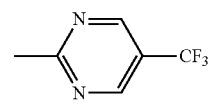
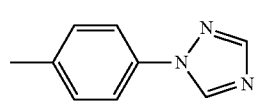
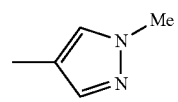
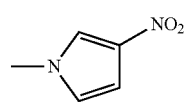
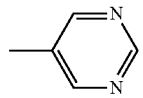
TABLE 11
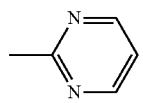
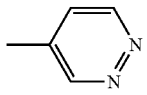
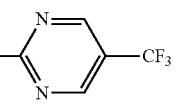
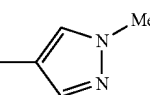
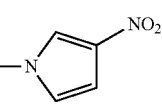
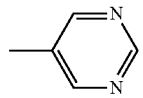
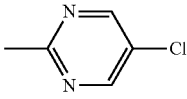

TABLE 12
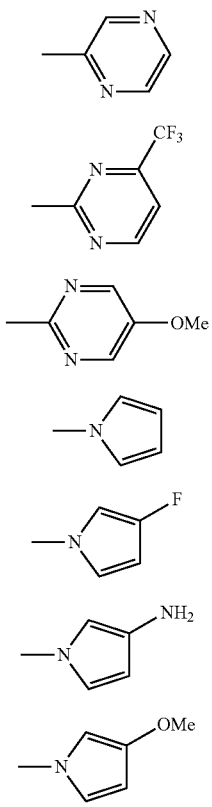
TABLE 13
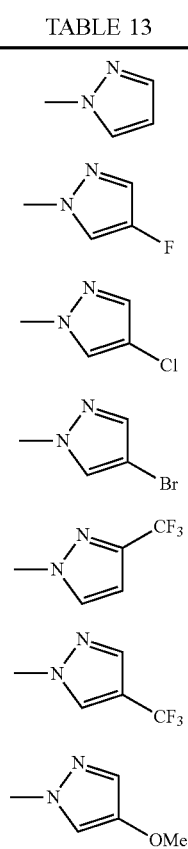
TABLE 13-continued
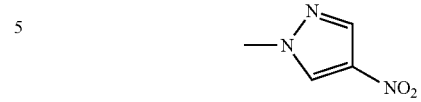
TABLE 14
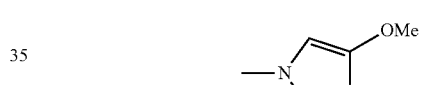
TABLE 15

TABLE 15-continued

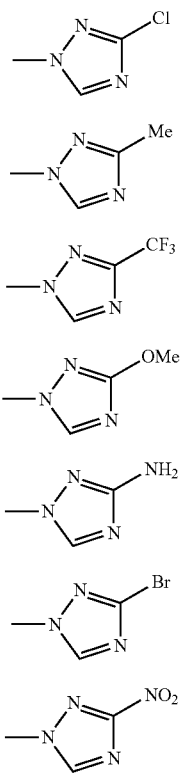

A compound (L-9) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{78}$).

A compound (L-9) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{79}$).

A compound (L-9) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{80}$).

A compound (L-9) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{81}$).

A compound (L-9) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{82}$).

A compound (L-9) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{83}$).

A compound (L-9) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{84}$).

A compound (L-9) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{85}$), A compound (L-9) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{86}$).

A compound (L-9) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{87}$).

A compound (L-9) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{88}$).

A compound (L-9) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{89}$).

A compound (L-9) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{90}$).

A compound represented by formula (L-10):

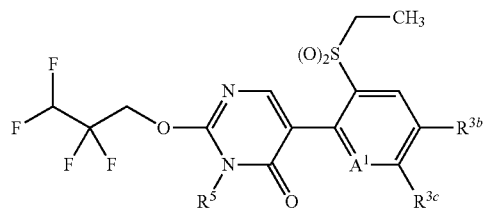

(L-10)

(hereinafter, referred to as Compound (L-10)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{91}$).

A compound (L-10) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{92}$).

A compound (L-10) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{93}$).

A compound (L-10) wherein $A^1$ represents a nitrogen atom, $R^5$ represents an ethyl group, $R^{3b}$ represents a hydrogen atom, and $R^{3c}$ represents any substituents indicated in Table 7 to Table 15 thereinafter, referred to as Compound Class $SX_{94}$).

A compound (L-10) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{95}$).

A compound (L-10) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as compound Class $SX_{96}$).

A compound (L-10) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{97}$).

A compound (L-10) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{98}$).

A compound (L-10) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{99}$).

A compound (L-10) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{100}$).

A compound (L-10) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{101}$).

A compound (L-10) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{102}$).

A compound (L-10) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{103}$).

A compound (L-10) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{104}$).

A compound represented by formula (L-11):

(L-11)

(hereinafter, referred to as Compound (L-11)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{105}$).

A compound (L-11) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{106}$).

A compound (L-11) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{107}$).

A compound (L-11) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{108}$).

A compound (L-11) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{109}$).

A compound (L-11) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{110}$).

A compound (L-11) wherein $A^1$ represents a nitrogen atom, $R^5$ represents a cyclopropyl group, $R^{3c}$ represents a hydrogen atom, and $R^{3b}$ represents any substituent, indicated in Table 7 to Table 15 (hereinafter, referred to as Compound Class $SX_{111}$).

A compound (L-11) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{112}$).

A compound (L-11) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{113}$).

A compound (L-11) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{114}$).

A compound (L-11) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{115}$).

A compound (L-11) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{116}$).

A compound (L-11) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{117}$).

A compound (L-11) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX^{118}$).

A compound represented by formula (L-12):

(L-12)

(hereinafter, referred to as Compound (L-12)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{119}$).

A compound (L-12) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{120}$).

A compound (L-12) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{121}$).

A compound (L-12) wherein $A^1$ represents a nitrogen atom, $R^5$ represents ethyl group, $R^{3b}$ represents a hydrogen atom, and $R^{3c}$ represents any substituents indicated in Table 7 to Table 15 (hereinafter, referred to as Compound Class $SX_{122}$).

A compound (L-12) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{123}$).

A compound (L-12) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{124}$).

A compound (L-12) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{125}$).

A compound (L-12) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{126}$).

A compound (L-12) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{127}$).

A compound (L-12) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{128}$).

A compound (L-12) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{129}$).

A compound (L-12) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{130}$).

A compound (L-12) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{131}$).

A compound (L-12) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{132}$).

A compound represented by formula L-13:

(L-13)

(hereinafter, referred to as Compound (L-13)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{133}$).

A compound (L-13) wherein $A^1$ represents CH, $R^5$ represents an ethyl group, $R^{3b}$ represents a hydrogen atom, and $R^{3c}$ represents any substituents indicated in Table 7 Table 15 (hereinafter, referred to as Compound Class $SX_{134}$).

A compound (L-13) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{135}$).

A compound (L-13) wherein, $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{136}$).

A compound (L-13) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{137}$).

A compound (L-13) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX^{138}$).

A compound (L-13) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{139}$).

A compound (L-13) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{140}$).

A compound (L-13) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX^{141}$).

A compound (L-13) wherein $A^1$ represents a nitrogen atom, and $R^5$ represents a methyl group, $R^{3c}$ represents a hydrogen atom, and $R^{3b}$ represents any substituents indicated in Table 7 to Table 15 (hereinafter, referred to as Compound Class $SX^{142}$).

A compound (L-13) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{143}$).

A compound (L-13) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{144}$).

A compound (L-13) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{145}$).

A compound (L-13) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{146}$).

A compound represented by formula (L-14):

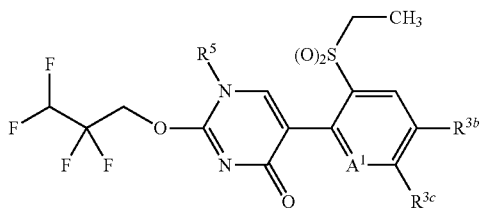

(L-14)

(hereinafter, referred to as Compound (L-14)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{147}$).

A compound (L-14) wherein $A^1$ represents CH, $R^5$ represents an ethyl group $R^{3b}$ represents a hydrogen atom, and $R^{3c}$ represents any substituents indicated in Table 7 to Table 15 (hereinafter, referred to as Compound Class $SX_{148}$).

A compound (L-14) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{149}$).

A compound (L-14) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{150}$).

A compound (L-14) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{151}$).

A compound (L-14) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{152}$).

A compound (L-14) wherein $A^1$ represents a nitrogen atom, $R^5$ represents a cyclopropyl group, $R^{3b}$ represents a hydrogen atom, and $R^{3c}$ represent any substituents indicated in Table 7 to Table 15 (hereinafter, referred to as Compound Class $SX_{153}$).

A compound (L-14) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{154}$).

A compound (L-14) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{155}$).

A compound (L-14) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{156}$).

A compound (L-14) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{157}$).

A compound (L-14) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{158}$).

A compound (L-14) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{159}$).

A compound (L-14) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{160}$).

A compound represented by formula (L-15):

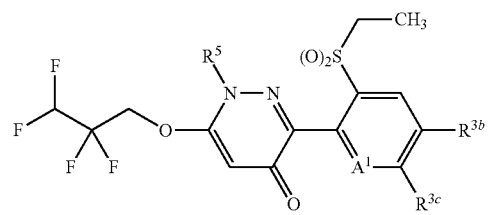

(L-15)

(hereinafter, referred to as Compound (L-15)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{161}$).

A compound (L-15) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{162}$).

A compound (L-15) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{163}$).

A compound (L-15) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{164}$).

A compound (L-15) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{165}$).

A compound (L-15) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{166}$).

A compound (L-15) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{167}$).

A compound (L-15) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{168}$).

A compound (L-15) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{169}$).

A compound (L-15) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{170}$).

A compound (L-15) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{171}$).

A compound (L-15) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{172}$).

A compound (L-15) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{173}$).

A compound (L-15) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{174}$).

A compound represented by formula (L-16):

(L-16)

(hereinafter, referred to as Compound (L-16)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{175}$).

A compound (L-16) wherein $A^1$ represent CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{176}$).

A compound (L-16) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{177}$).

A compound (L-15) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{178}$).

A compound (L-16) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{179}$).

A compound (L-16) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{180}$).

A compound (L-16) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{181}$).

A compound (L-16) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{182}$).

A compound (L-16) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{183}$).

A compound (L-15) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{184}$).

A compound (L-16) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{185}$).

A compound (L-6) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{186}$).

A compound (L-16) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{187}$).

A compound (L-16) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{188}$).

A compound represented by formula (L-17):

(L-17)

(hereinafter, referred Compound (L-17)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{189}$).

A compound (L-17) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{190}$).

A compound (L-17) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{191}$).

A compound (L-17) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{192}$).

A compound (L-17) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{193}$).

A compound (L-17) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{194}$).

A compound (L-17) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{195}$).

A compound (L-17) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{196}$).

A compound (L-17) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{197}$).

A compound (L-17) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{198}$).

A compound (L-17) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{199}$).

A compound (L-17) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{200}$).

A compound (L-17) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{201}$).

A compound (L-17) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{202}$).

A compound represented by formula (L-18):

(L-18)

(hereinafter, referred to as Compound (L-18)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{203}$).

A compound (L-18) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{204}$).

A compound (L-18) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{205}$).

A compound (L-18) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{206}$).

A compound (L-18) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{207}$).

A compound (L-18) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{208}$).

A compound (L-18) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{209}$).

A compound (L-18) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{210}$).

A compound (L-18) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{211}$).

A compound (L-18) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{212}$).

A compound (L-18) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{213}$).

A compound (L-18) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{214}$).

A compound (L-18) wherein $A^1$ represents a nitrogen atom, $R^5$ represents an isopropyl group, $R^{3c}$ represents a hydrogen atom, and $R^{3b}$ represent any substituents indicated in Table 7 to Table 15 (hereinafter, referred to as Compound Class $SX_{215}$).

A compound (L-18) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{216}$).

A compound represented by formula (L-19):

(L-19)

(hereinafter, referred to as Compound (L-19)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{217}$).

A compound (L-19) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{218}$).

A compound (L-19) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{219}$).

A compound (L-19) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{220}$).

A compound (L-19) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{221}$).

A compound (L-19) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{222}$).

A compound (L-19) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{223}$).

A compound (L-19) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{224}$).

A compound (L-19) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{225}$).

A compound (L-19) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{226}$).

A compound (L-19) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{227}$).

A compound (L-19) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{228}$).

A compound (L-19) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{229}$).

A compound (L-19) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{230}$).

A compound represented by formula (L-20):

(L-20)

(hereinafter, referred to as Compound (L-20)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{231}$).

A compound (L-20) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{232}$).

A compound (L-20) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{233}$).

A compound (L-20) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{234}$).

A compound (L-20) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{235}$).

A compound (L-20) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{236}$).

A compound (L-20) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{237}$).

A compound (L-20) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{238}$).

A compound (L-20) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{239}$).

A compound (L-20) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{240}$).

A compound (L-20) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{241}$).

A compound (L-20) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{242}$).

A compound (L-20) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{243}$).

A compound (L-20) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{244}$).

A compound represented by formula (L-21):

(L-21)

(hereinafter, referred to as Compound (L-21)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{245}$).

A compound (L-21) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{246}$).

A compound (L-21) wherein $A^1$ represents a nitrogen atom, $R^5$ represents a methyl group, $R^{3b}$ represent a hydrogen atom, and $R^{3c}$ represents any substituents indicated in Table 7 to Table 15 (hereinafter, referred to as Compound Class $SX_{247}$).

A compound (L-21) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{248}$).

A compound (L-21) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{249}$).

A compound (L-21) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{250}$).

A compound (L-21) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{251}$).

A compound (L-21) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{252}$).

A compound (L-21) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{253}$).

A compound (L-21) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{254}$).

A compound (L-21) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{255}$).

A compound (L-21) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{256}$).

A compound (L-21) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{257}$).

A compound (L-21) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{258}$).

A compound represented by formula (L-22):

(hereinafter, referred to as Compound (L-22)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{259}$).

A compound (L-22) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{260}$).

A compound (L-22) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{261}$).

A compound (L-22) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{262}$).

A compound (L-22) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{263}$).

A compound (L-22) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{264}$).

A compound (L-22) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{265}$).

A compound (L-22) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{266}$).

A compound (L-22) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{267}$).

A compound (L-22) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{268}$).

A compound (L-22) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{269}$).

A compound (L-22) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{270}$).

A compound (L-22) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{271}$).

A compound (L-22) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{272}$).

A compound represented by formula (L-23):

(hereinafter, referred to as Compound (L-23)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{273}$).

A compound (L-23) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{274}$).

A compound (L-23) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{275}$).

A compound (L-23) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{276}$).

A compound (L-23) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{277}$).

A compound (L-23) wherein $A^1$ represents a nitrogen atom, $R^5$ represents an isopropyl group, $R^{3b}$ represents a hydrogen at and $R^{3c}$ represents any substituents indicated in Table 7 to Table 15 (hereinafter, referred to as Compound Class $SX_{278}$).

A compound (L-23) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{279}$).

A compound (L-23) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{280}$).

A compound (L-23) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{281}$).

A compound (L-23) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{282}$).

A compound (L-23) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{283}$).

A compound (L-23) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{284}$).

A compound (L-23) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{285}$).

A compound (L-23) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{286}$).

A compound represented by formula (L-24):

(L-24)

(hereinafter, referred to as Compound (L-24)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{287}$).

A compound (L-24) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{288}$).

A compound (L-24) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{289}$).

A compound (L-24) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{290}$).

A compound (L-24) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{291}$).

A compound (L-24) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{292}$).

A compound (L-24) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{293}$).

A compound (L-24) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{294}$).

A compound (L-24) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{295}$).

A compound (L-24) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{296}$).

A compound (L-24) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{297}$).

A compound (L-24) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{298}$).

A compound (L-24) wherein $A^1$ represents a nitrogen atom, $R^5$ represents an isopropyl group, $R^{3c}$ represents a hydrogen atom, and $R^{3b}$ represents any substituents indicated in Table 7 to Table 1 (hereinafter, referred to as Compound Class $SX_{299}$).

A compound (L-24) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{300}$).

A compound represented by formula (L-25):

(L-25)

(hereinafter, referred to as Compound (L-24)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{301}$).

A compound (L-25) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{302}$).

A compound (L-25) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{303}$).

A compound (L-25) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{304}$).

A compound (L-25) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{305}$).

A compound (L-25) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{306}$).

A compound (L-25) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{307}$).

A compound (L-25) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{308}$).

A compound (L-25) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{309}$).

A compound (L-25) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{310}$).

A compound (L-25) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{311}$).

A compound (L-25) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{312}$).

A compound (L-25) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{313}$).

A compound (L-25) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{314}$).

A compound represented by formula (L-26):

(L-26)

(hereinafter, referred to as Compound (L-26)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{315}$).

A compound (L-26) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{316}$).

A compound (L-26) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{317}$).

A compound (L-26) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{318}$).

A compound (L-26) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{319}$).

A compound (L-26) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{320}$).

A compound (L-26) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{321}$).

A compound (L-26) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{322}$).

A compound (L-26) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{323}$).

A compound (L-26) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{324}$).

A compound (L-26) wherein $A^1$ represents a nitrogen atom, $R^5$ represents an ethyl group, $R^{3c}$ represents a hydrogen atom, Table 15 (hereinafter, referred to as Compound class $SX_{325}$).

A compound (L-26) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{326}$).

A compound (L-26) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{327}$).

A compound (L-26) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{328}$).

A compound represented by formula (L-27):

(L-27)

(hereinafter, referred to as Compound (L-27)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{329}$).

A compound (L-27) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{330}$).

A compound (L-27) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{331}$).

A compound (L-27) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{332}$).

A compound (L-27) wherein $A^1$ represents a nitrogen atom, $R^5$ represents a propel group, $R^{3b}$ represents a hydrogen atom, and $R^{3c}$ represents any substituents indicated in Table 7 to Table 15 (hereinafter, referred to as Compound Class $SX_{333}$).

A compound (L-27) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{134}$).

A compound (L-27) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{335}$).

A compound (L-27) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{336}$).

A compound (L-27) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{337}$).

A compound (L-27) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{338}$).

A compound (L-27) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{339}$).

A compound (L-27) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{340}$).

A compound (L-27) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{341}$).

A compound (L-27) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{342}$).

A compound represented by formula (L-28):

(L-28)

(hereinafter, referred to as Compound (L-28)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{343}$).

A compound (L-28) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{344}$).

A compound (L-28) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred Compound Class $SX_{345}$).

A compound (L-28) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{346}$).

A compound (L-28) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{347}$).

A compound (L-28) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{348}$).

A compound (L-28) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{349}$).

A compound (L-28) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{350}$).

A compound (L-28) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{351}$).

A compound (L-28) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{352}$).

A compound (L-28) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{353}$).

A compound (L-28) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{354}$).

A compound (L-28) wherein $A^1$ represents nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{355}$).

A compound (L-28) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{356}$).

A compound represented by formula (L-29):

(hereinafter, referred to as Compound (L-29)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{357}$).

A compound (L-29) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{358}$).

A compound (L-29) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{359}$).

A compound (L-29) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{360}$).

A compound (L-29) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{361}$).

A compound (L-29) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{362}$).

A compound (L-29) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{363}$).

A compound (L-29) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{364}$).

A compound (L-29) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{365}$).

A compound (L-29) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{366}$).

A compound (L-29) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{367}$).

A compound (L-29) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{368}$).

A compound (L-29) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{369}$).

A compound (L-29) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{370}$).

A compound represented by formula (L-30):

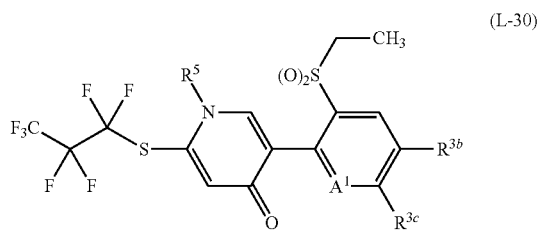

(L-30)

(hereinafter, referred to as Compound (L-30)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{371}$).

A compound (L-30) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{372}$).

A compound (L-30) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{373}$).

A compound (L-30) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{374}$).

A compound (L-30) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{375}$).

A compound (L-30) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{376}$).

A compound (L-30) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{377}$).

A compound (L-30) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{378}$).

A compound (L-30) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{379}$).

A compound (L-30) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{380}$).

A compound (L-30) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{381}$).

A compound (L-30) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{382}$).

A compound (L-30) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{383}$).

A compound (L-30) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{384}$).

A compound represented by formula (L-31):

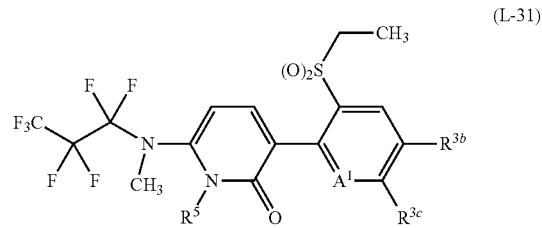

(L-31)

(hereinafter, referred to as Compound (L-31)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{385}$).

A compound (L-31 wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{386}$).

A compound (L-31) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{387}$).

A compound (L-31) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{388}$).

A compound (L-31) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{389}$).

A compound (L-31) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{390}$).

A compound (L-31) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{391}$).

A compound (L-31) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{392}$).

A compound (L-31) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{393}$).

A compound (L-31) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{394}$).

A compound (L-31) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{395}$).

A compound (L-31) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{396}$).

A compound (L-31) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{397}$).

A compound (L-31) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{398}$).

A compound represented by formula (L-32):

(L-32)

(hereinafter, referred to as Compound (L-32)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{399}$).

A compound (L-32) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{400}$).

A compound (L-32) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{401}$).

A compound (L-32) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{402}$).

A compound (L-32) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{403}$).

A compound (L-32) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{404}$).

A compound (L-32) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{405}$).

A compound (L-32) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{406}$).

A compound (L-32) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{407}$).

A compound (L-32) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{408}$).

A compound (L-32) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{409}$).

A compound (L-32) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{410}$).

A compound (L-32) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{411}$).

A compound (L-32) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{412}$).

A compound represented by formula (L-33):

(L-33)

(hereinafter, referred to as Compound (L-33)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{413}$).

A compound (L-33) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{414}$)

A compound (L-33) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{415}$).

A compound (L-33) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{416}$).

A compound (L-33) wherein $A^1$ represents a nitrogen atom, $R^5$ represents propyl group, $R^{3b}$ represents a hydrogen atom, and $R^{3c}$ represents any substituents indicated in Table 7 to Table 15 (hereinafter, referred to as Compound Class $SX_{417}$).

A compound (L-33) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{418}$).

A compound (L-33) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{119}$).

A compound (L-33) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{420}$).

A compound (L-33) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{421}$).

A compound (L-33) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{422}$).

A compound (L-33) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{423}$).

A compound (L-33) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{424}$).

A compound (L-33) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{425}$).

A compound (L-33) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{426}$).

A compound represented by formula (L-34):

(L-34)

(hereinafter, referred to as Compound (L-34)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{427}$).

A compound (L-34) wherein $A^1$ represents CH, $R^5$ represents an ethyl group, $R^{3b}$ represents a hydrogen atom, and $R^{3c}$ represents any substituents indicated in Table 7 to Table 1 (hereinafter, referred to as Compound Class $SX_{428}$).

A compound (L-34) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{429}$).

A compound (L-34) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{430}$).

A compound (L-34) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{431}$).

A compound (L-34) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{432}$).

A compound (L-34) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{433}$).

A compound (L-34) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{434}$).

A compound (L-34) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{435}$).

A compound (L-34) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{436}$).

A compound (L-34) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{437}$).

A compound (L-34) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{438}$).

A compound (L-34) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{439}$).

A compound (L-34) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{440}$).

A compound represented by formula (L-35):

(hereinafter, referred to as Compound (L-35)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{441}$).

A compound (L-35) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{442}$).

A compound (L-35) wherein $A^1$ represents a nitrogen atom, $R^5$ represents a methyl group, $R^{3b}$ represents a hydrogen atom, and $R^{3c}$ represents any substituents indicated it Table 7 to Table 15 (hereinafter, referred to as Compound Class $SX_{443}$).

A compound (L-35) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{444}$).

A compound (L-35) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{445}$).

A compound (L-35) wherein $A^2$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{446}$).

A compound (L-35) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{447}$).

A compound (L-35) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{448}$).

A compound (L-35) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{449}$).

A compound (L-35) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{450}$).

A compound (L-35) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{451}$).

A compound (L-35) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{452}$).

A compound (L-35) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{453}$).

A compound (L-35) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{454}$).

A compound represented by formula (L-36):

(hereinafter, referred to as Compound (L-36)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{455}$).

A compound (L-36) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{456}$).

A compound (L-36) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{457}$).

A compound (L-36) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{458}$).

A compound (L-36) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{459}$).

A compound (L-36) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{460}$).

A compound (L-36) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{461}$).

A compound (L-36) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{462}$).

A compound (L-36) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{463}$).

A compound (L-36) wherein $A^1$ represents a nitrogen atom, $R^5$ represents a methyl group, $R^{3c}$ represents a hydrogen atom, and $R^{3b}$ represents any substituents indicated, in Table 7 to Table 15 (hereinafter, referred to as Compound Class $SX_{464}$).

A compound (L-36) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{465}$).

A compound (L-36) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{466}$).

A compound (L-36) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{467}$).

A compound (L-36) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{468}$).

A compound represented by formula (L-37):

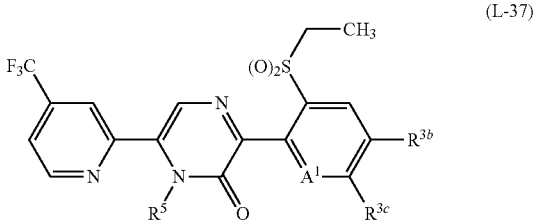

(L-37)

(hereinafter, referred to as Compound (L-37)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{469}$).

A compound (L-37) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{470}$).

A compound (L-37) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{471}$).

A compound (L-37) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{472}$).

A compound (L-37) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{473}$).

A compound (L-37) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{474}$).

A compound (L-37) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{475}$).

A compound (L 37) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{476}$).

A compound (L-37) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{477}$).

A compound (L-37) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{478}$).

A compound (L-37) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{479}$).

A compound (L-37) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{480}$).

A compound (L-37) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{481}$).

A compound (L-37) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{482}$).

A compound represented by formula (L-38):

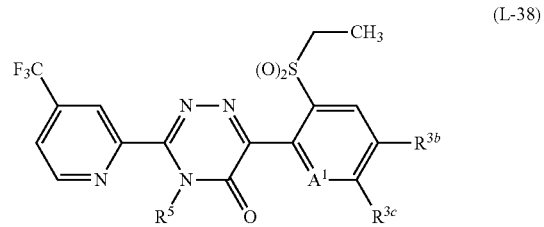

(L-38)

(hereinafter, referred to as Compound (L-38)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{483}$).

A compound (L-38) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{484}$).

A compound (L-38) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{485}$).

A compound (L-38) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{486}$).

A compound (L-38) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{487}$).

A compound (L-38) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{488}$).

A compound (L-38) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{489}$).

A compound (L-38) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{490}$).

A compound (L-38) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{491}$).

A compound (L-38) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{492}$).

A compound (L-38) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{493}$).

A compound (L-38) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{494}$).

A compound (L-38) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{495}$).

A compound (L-38) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{496}$).

A compound represented by formula (L-39):

(hereinafter, referred to as Compound (L-39)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{497}$).

A compound (L-39) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{498}$).

A compound (L-39) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{499}$).

A compound (L-39) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{500}$).

A compound (L-39) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{501}$).

A compound (L-39) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{502}$).

A compound (L-39) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{503}$).

A compound (L-39) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{504}$).

A compound (L-39) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{505}$).

A compound (L-39) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{506}$).

A compound (L-39) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{507}$).

A compound (L-39) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{508}$).

A compound (L-39) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{509}$).

A compound (L-39) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{510}$).

A compound represented by formula (L-40):

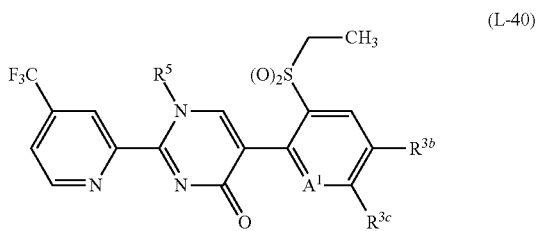

(L-40)

(hereinafter, referred to as Compound (L-40)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{511}$).

A compound (L-40) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{512}$).

A compound (L-40) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{513}$).

A compound (L-40) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{534}$).

A compound (L-40) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{515}$).

A compound (L-40) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{516}$).

A compound (L-40) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{517}$).

A compound (L-40) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{518}$).

A compound (L-40) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{519}$).

A compound (L-40) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{520}$).

A compound (L-40) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{521}$).

A compound (L-40) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{522}$).

A compound (L-40) wherein $A^1$ represents a nitrogen atom, $R^5$ represents an isopropyl group $R^{3c}$ represents a hydrogen atom, and $R^{3b}$ represents any substituents indicated in Table 7 to Table 15 (hereinafter, referred to as Compound Class $SX_{523}$).

A compound (L-40) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{524}$).

A compound represented by formula (L-41):

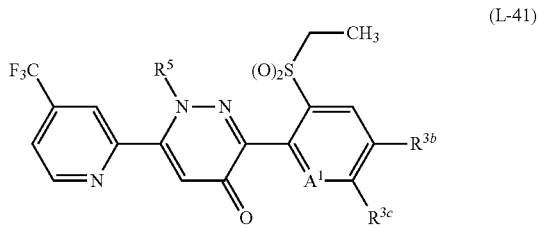

(L-41)

(hereinafter, referred to as Compound (L-41)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{525}$).

A compound (L-41) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{526}$).

A compound (L-41) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{527}$).

A compound (L-41) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{528}$).

A compound (L-41) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{529}$).

A compound (L-41) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{530}$).

A compound (L-41) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{531}$).

A compound (L-41) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{532}$).

A compound (L-41) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{533}$).

A compound (L-41) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{534}$).

A compound (L-41) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{535}$)

A compound (L-41) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{536}$).

A compound (L-41) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{537}$).

A compound (L-41) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{538}$).

A compound represented by formula (L-42):

(L-42)

(hereinafter, referred to as Compound (L-42)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{539}$).

A compound (L-42) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{540}$).

A compound (L-42) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{541}$).

A compound (L-42) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{542}$).

A compound (L-42) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{543}$).

A compound (L-42) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{544}$).

A compound (L-42) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{545}$).

A compound (L-42) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{546}$).

A compound (L-42) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{547}$).

A compound (L-42) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{548}$).

A compound (L-42) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{549}$).

A compound (L-42) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{550}$).

A compound (L-42) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{551}$).

A compound (L-42) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{552}$).

A compound represented by formula (L-43):

(L-43)

[Chemical structure: F₃C-pyridine-pyridinone(R⁵ on N, =O)-phenyl ring with (O)₂S-CH₃, R³ᵇ, A¹, R³ᶜ substituents]

(hereinafter, referred to as Compound (L-43)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{553}$).

A compound (L-43) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{554}$).

A compound (L-43) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{555}$).

A compound (L-43) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{556}$).

A compound (L-43) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{557}$).

A compound (L-43) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{558}$).

A compound (L-43) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{559}$).

A compound (L-43) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{560}$).

A compound (L-43) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{561}$).

A compound (L-43) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{562}$).

A compound (L-43) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{563}$).

A compound (L-43) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{564}$).

A compound (L-43) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{565}$).

A compound (L-43) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{566}$).

A compound represented by formula (L-44):

(L-44)

[Chemical structure similar to L-43 with R⁵ on pyridine, =O on ring, (O)₂S-CH₃, R³ᵇ, A¹, R³ᶜ substituents]

(hereinafter, referred to as Compound (L-44)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{567}$).

A compound (L-44) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{568}$).

A compound (L-44) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{569}$).

A compound (L-44) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{570}$).

A compound (L-44) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{571}$).

A compound (L-44) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{572}$).

A compound (L-44) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{573}$).

A compound (L-44) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{574}$).

A compound (L-44) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{575}$).

A compound (L-44) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{576}$).

A compound (L-44) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{577}$).

A compound (L-44) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{578}$).

A compound (L-44) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{579}$).

A compound (L-44) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{580}$).

A compound represented by formula (L-45):

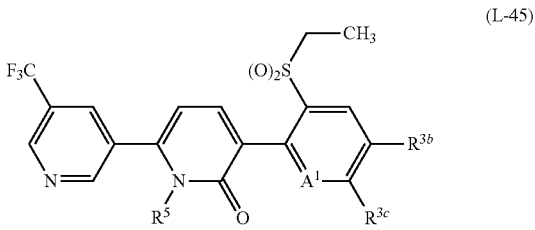

(L-45)

(hereinafter, referred to as Compound (L-45)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{581}$).

A compound (L-45) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{582}$).

A compound (L-45) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{583}$).

A compound (L-45) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{584}$).

A compound (L-45) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{585}$).

A compound (L-45) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{586}$).

A compound (L-45) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{587}$).

A compound (L-45) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{588}$).

A compound (L-45) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{589}$).

A compound (L-45) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{590}$).

A compound (L-45) wherein $A^1$ represents a nitrogen atom, $R^5$ represents n ethyl group, $R^{3c}$ represents a hydrogen atom, and $R^{3b}$ represents any substituents indicated in Table 7 to Table 15 (hereinafter, referred to as Compound Class $SX_{591}$).

A compound (L-45) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{592}$).

A compound (L-45) wherein $A^1$ represents a nitrogen atom, $R^5$ represents an isopropyl group, $R^{3c}$ represent a hydrogen atom, and $R^{3b}$ represents any substituents indicated in Table 7 to Table 15 (hereinafter, referred to as Compound Class $SX_{593}$).

A compound (L-45) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{594}$).

A compound represented by formula (L-46):

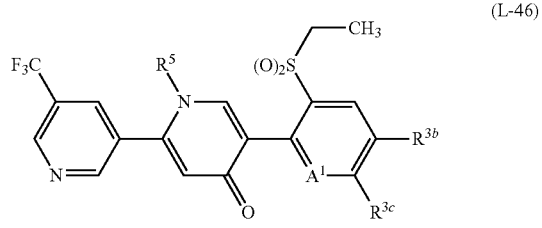

(L-46)

(hereinafter, referred to as Compound (L-46)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{595}$).

A compound (L-46) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{596}$).

A compound (L-46) wherein $A^1$ represents a nitrogen atom, $R^5$ represents a methyl group, $R^{3b}$ represents a hydrogen atom, and R$^{3c}$ represents any substituents indicated in Table 7 to Table 15 (hereinafter, referred to as Compound Class SX$_{597}$).

A compound (L-46) wherein A$^1$ represents a nitrogen atom, R$^5$ represents an ethyl group, R$^{3b}$ represents a hydrogen atom, and R$^{3c}$ represents any substituents indicated in Table 7 to Table 15 (hereinafter, referred to as Compound Class SX$_{598}$).

A compound (L-46) wherein A$^1$ represents a nitrogen atom, R$^5$ represents a propyl group, R$^{3b}$ represents a hydrogen atom, and R$^{3c}$ represents any substituents indicated in Table 7 to Table 15 (hereinafter, referred to as Compound Class SX$_{599}$).

A compound (L-46) wherein A$^1$ represents a nitrogen atom, R$^5$ represents an isopropyl group, R$^{3b}$ represents a hydrogen atom, and R$^{3c}$ represents any substituents indicated in Table 7 to Table 15 (hereinafter, referred to as Compound Class SX$_{600}$).

A compound (L-46) wherein A$^1$ represents a nitrogen atom, R$^5$ represents a cyclopropyl group, R$^{3b}$ represents a hydrogen atom, and R$^{3c}$ represents any substituents indicated in Table 7 to Table 15 (hereinafter, referred to as Compound Class SX$_{601}$).

A compound (L-46) wherein A$^1$ represents CH, R$^5$ represents a methyl group, R$^{3c}$ represents a hydrogen atom, and R$^{3b}$ represents any substituents indicated in Table 7 to Table 15 (hereinafter, referred to as Compound Class SX$_{602}$).

A compound (L-46) wherein A$^1$ represents CH, R$^5$ represents an ethyl group, R$^{3c}$ represents a hydrogen atom, and R$^{3b}$ represents any substituents indicated in Table 7 to Table 15 (hereinafter, referred to as Compound Class SX$_{603}$).

A compound (L-46) wherein A$^1$ represents a nitrogen atom, R$^5$ represents a methyl group, R$^{3c}$ represents a hydrogen atom, and R$^{3b}$ represents any substituents indicated in Table 7 to Table 15 (hereinafter, referred to as Compound Class SX$_{604}$).

A compound (L-46) wherein A$^1$ represents a nitrogen atom, R$^5$ represents an ethyl group, R$^{3c}$ represents a hydrogen atom, and R$^{3b}$ represents any substituents indicated in Table 7 to Table 15 (hereinafter, referred to as Compound Class SX$_{605}$).

A compound (L-46) wherein A$^1$ represents a nitrogen atom, R$^5$ represents a propyl group, R$^{3c}$ represents a hydrogen atom, and R$^{3b}$ represents any substituents indicated in Table 7 to Table 15 (hereinafter, referred to as Compound Class SX$_{606}$).

A compound (L-46) wherein A$^1$ represents a nitrogen atom, R$^5$ represents an isopropyl group, R$^{3c}$ represents a hydrogen atom, and R$^{3b}$ represents any substituents indicated in Table 7 to Table 15 (hereinafter, referred to as Compound Class SX$_{607}$).

A compound (L-46) wherein A$^1$ represents a nitrogen atom, R$^5$ represents a cyclopropyl group, R$^{3c}$ represents a hydrogen atom, and R$^{3b}$ represents any substituents indicated in Table 7 to Table 15 (hereinafter, referred to as Compound Class SX$_{608}$).

A compound represented by formula (L-47):

(L-47)

(hereinafter, referred to as Compound (L-47)) wherein A$^1$ represents CH, R$^5$ represents a methyl group, R$^{3b}$ represents a hydrogen atom, and R$^{3c}$ represents any substituents indicated in Table 7 to Table 15 (hereinafter, referred to as Compound Class SX$_{609}$).

A compound (L-47) wherein A$^1$ represents CH, R$^5$ represents an ethyl group, R$^{3b}$ represents a hydrogen atom, and R$^{3c}$ represents any substituents indicated in Table 7 to Table 15 (hereinafter, referred to as Compound Class SX$_{610}$).

A compound (L-47) wherein A$^1$ represents a nitrogen atom, R$^5$ represents a methyl group, R$^{3b}$ represents a hydrogen atom, and R$^{3c}$ represents any substituents indicated in Table 7 to Table 15 (hereinafter, referred to as Compound Class SX$_{611}$).

A compound (L-47) wherein A$^1$ represents a nitrogen atom, R$^5$ represents an ethyl group, R$^{3b}$ represents a hydrogen atom, and R$^{3c}$ represents any substituents indicated in Table 7 to Table 15 (hereinafter, referred to as Compound Class SX$_{612}$).

A compound (L-47) wherein A$^1$ represents a nitrogen atom, R$^5$ represents a propyl group, R$^{3b}$ represents a hydrogen atom, and R$^{3c}$ represents any substituents indicated in Table 7 to Table 15 (hereinafter, referred to as Compound Class SX$_{613}$).

A compound (L-47) wherein A$^1$ represents a nitrogen atom, R$^5$ represents an isopropyl group, R$^{3b}$ represents a hydrogen atom, and R$^{3c}$ represents any substituents indicated in Table 7 to Table 15 (hereinafter, referred to as Compound Class SX$_{614}$).

A compound (L-47) wherein A$^1$ represents a nitrogen atom, R$^5$ represents a cyclopropyl group, R$^{3b}$ represents a hydrogen atom, and R$^{3c}$ represents any substituents indicated in Table 7 to Table 15 (hereinafter, referred to as Compound Class SX$_{615}$).

A compound (L-47) wherein A$^1$ represents CH, R$^5$ represents a methyl group, R$^{3c}$ represents a hydrogen atom, and R$^{3b}$ represents any substituents indicated in Table 7 to Table 15 (hereinafter, referred to as Compound Class SX$_{616}$).

A compound (L-47) wherein A$^1$ represents CH, R$^5$ represents an ethyl group, R$^{3c}$ represents a hydrogen atom, and R$^{3b}$ represents any substituents indicated in Table 7 to Table 15 (hereinafter, referred to as Compound Class SX$_{617}$).

A compound (L-47) wherein A$^1$ represents a nitrogen atom, R$^5$ represents a methyl group, R$^{3c}$ represents a hydrogen atom, and R$^{3b}$ represents any substituents indicated in Table 7 to Table 15 (hereinafter, referred to as Compound Class SX$_{618}$).

A compound (L-47) wherein A$^1$ represents a nitrogen atom, R$^5$ represents an ethyl group, R$^{3c}$ represents a hydrogen atom, and R$^{3b}$ represents any substituents indicated in Table 7 to Table 15 (hereinafter, referred to as Compound Class SX$_{619}$).

A compound (L-47) wherein A$^1$ represents a nitrogen atom, R$^5$ represents a propyl group, R$^{3c}$ represents a hydrogen atom, and $R^{3b}$ represents any substituents indicated in Table 7 to Table 15 (hereinafter, referred to as Compound Class $SX_{620}$).

A compound (L-47) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{621}$).

A compound (L-47) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{622}$).

A compound represented by formula (L-48):

(L-48)

(hereinafter, referred to as Compound (L-48)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{623}$).

A compound (L-48) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{624}$).

A compound (L-48) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{625}$).

A compound (L-48) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{626}$).

A compound (L-48) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{627}$).

A compound (L-48) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{628}$).

A compound (L-48) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{629}$).

A compound (L-48) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{630}$).

A compound (L-48) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{631}$).

A compound (L-48) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{632}$).

A compound (L-48) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{633}$).

A compound (L-48) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{634}$).

A compound (L-48) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{635}$).

A compound (L-48) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{536}$).

A compound represented by formula (L-49):

(L-49)

(hereinafter, referred to as Compound (L-49)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{637}$).

A compound (L-49) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{638}$).

A compound (L-49) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{639}$).

A compound (L-49) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{640}$).

A compound (L-49) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{641}$).

A compound (L-49) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{642}$).

A compound (L-49) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{643}$).

A compound (L-49) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{644}$).

A compound (L-49) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{645}$).

A compound (L-49) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{646}$).

A compound (L-49) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{647}$).

A compound (L-49) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{648}$).

A compound (L-49) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{649}$).

A compound (L-49) wherein represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{650}$).

A compound represented by formula (L-50):

(L-50)

(hereinafter, referred to as Compound (L-50)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{651}$).

A compound (L-50) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{652}$).

A compound (L-50) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{653}$).

A compound (L-50) wherein $A^1$ represents a nitrogen atom, $R^5$ represents an ethyl group, $R^{3b}$ represents a hydrogen at and $R^{3c}$ represents any substituents indicated in Table 7 to Table 15 (hereinafter, referred to as Compound Class $SX_{654}$).

A compound (L-50) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{655}$).

A compound L-50) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{656}$).

A compound (L-50) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{657}$).

A compound (L-50) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{658}$).

A compound (L-50) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{659}$).

A compound (L-50) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{660}$).

A compound (L-50) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{661}$).

A compound (L-50) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{662}$).

A compound (L-50) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{663}$).

A compound (L-50) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{664}$).

A compound represented by formula (L-51):

(L-51)

(hereinafter, referred to as Compound (L-51)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{665}$).

A compound (L-51) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{666}$).

A compound (L-51) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{667}$).

A compound (L-51) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{669}$).

A compound (L-51) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{669}$).

A compound (L-51) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{670}$).

A compound (L-51) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{671}$).

A compound (L-51) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{672}$).

A compound (L-51) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{673}$).

A compound (L-51) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{674}$).

A compound (L-51) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{675}$).

A compound (L-51) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{676}$).

A compound (L-51) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{677}$).

A compound (L-51) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{678}$).

A compound represented by formula (L-52):

(L-52)

(hereinafter, referred to as Compound (L-52)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{679}$).

A compound (L-52) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{680}$).

A compound (L-52) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{681}$).

A compound (L-52) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{682}$).

A compound (L-52) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{683}$).

A compound (L-52) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{684}$).

A compound (L-52) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{685}$).

A compound (L-52) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{686}$).

A compound (L-52) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{687}$).

A compound (L-52) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{688}$).

A compound (L-52) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{689}$).

A compound (L-52) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{690}$).

A compound (L-52) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{691}$).

A compound (L-52) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{692}$).

A compound represented by formula (L-53):

(L-53)

(hereinafter, referred to as Compound (L-53)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{693}$).

A compound (L-53) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{694}$).

A compound (L-53) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{695}$).

A compound (L-53) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{696}$).

A compound (L-53) wherein $A^1$ represents a nitrogen atom, $R^5$ represents a propyl group, $R^{3b}$ represents a hydrogen atom, and $R^{3c}$ represents any substituents indicated in Table 7 Table 15 (hereinafter, referred to as Compound Class $SX_{697}$).

A compound (L-53) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{698}$).

A compound (L-53) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{699}$).

A compound (L-53) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{700}$).

A compound (L-53) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{701}$).

A compound (L-53) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{702}$).

A compound (L-53) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{703}$).

A compound (L-53) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{704}$).

A compound (L-53) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{705}$).

A compound (L-53) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{706}$).

A compound represented by formula (L-54):

(L-54)

(hereinafter, referred to as Compound (L-54)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{707}$).

A compound (L-54) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{708}$).

A compound (L-54) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{709}$).

A compound (L-54) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{710}$).

A compound (L-54) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{711}$).

A compound (L-54) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{712}$).

A compound (L-54) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{713}$).

A compound (L-54) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{714}$).

A compound (L-54) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{715}$).

A compound (L-54) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{716}$).

A compound (L-54) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{717}$).

A compound (L-54) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{718}$).

A compound (L-54) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{719}$).

A compound (L-54) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{720}$).

A compound represented by formula (L-55):

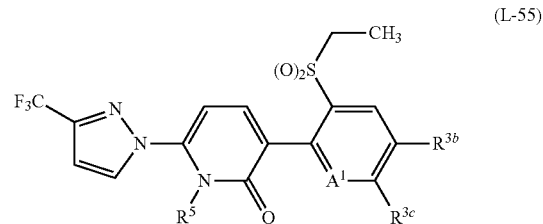

(hereinafter, referred to as Compound (L-55)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{721}$).

A compound (L-55) wherein $A^1$ represents CH, $R^5$ represents an ethyl group, $R^{3b}$ represents a hydrogen atom, and $R^{3c}$ represents n substituents indicated in Table 7 to Table 15 (hereinafter, referred to as Compound Class $SX_{722}$).

A compound (L-55) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{723}$).

A compound (L-55) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{724}$).

A compound (L-55) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{725}$).

A compound (L-55) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{726}$).

A compound (L-55) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{727}$).

A compound (L-55) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{728}$).

A compound (L-55) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{729}$).

A compound (L-55) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{730}$).

A compound (L-55) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{731}$).

A compound (L-55) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{732}$).

A compound (L-55) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{733}$).

A compound (L-55) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{734}$).

A compound represented by formula (L-56):

(L-56)

(hereinafter, referred to as Compound (L-56)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{735}$).

A compound (L-56) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{736}$).

A compound (L-56) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{737}$).

A compound (L-56) wherein $A^2$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{738}$).

A compound (L-56) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{739}$).

A compound (L-56) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{740}$).

A compound (L-56) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{741}$).

A compound (L-56) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{742}$).

A compound (L-56) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{743}$).

A compound (L-56) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{744}$).

A compound (L-56) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{745}$).

A compound (L-56) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{746}$).

A compound (L-56) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{747}$).

A compound (L-56) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{748}$).

A compound represented by formula (L-57):

(L-57)

(hereinafter, referred to as Compound (L-57)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{749}$).

A compound (L-57) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{750}$).

A compound (L-57) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{751}$).

A compound (L-57) wherein $A^1$ presents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{752}$).

A compound (L-57) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{753}$).

A compound (L-57) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{254}$).

A compound (L-57) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{755}$).

A compound (L-57) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{756}$).

A compound (L-57) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{757}$).

A compound (L-57) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{758}$).

A compound (L-57) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{759}$).

A compound (L-57) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{760}$).

A compound (L-57) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{761}$).

A compound (L-57) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{762}$).

A compound represented by formula (L-58):

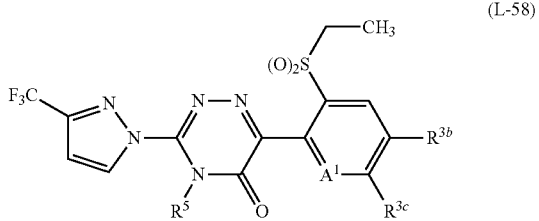

(L-58)

(hereinafter, referred to as Compound (L-58)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{763}$).

A compound (L-58) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{764}$).

A compound (L-58) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{765}$).

A compound (L-58) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{766}$).

A compound (L-58) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{767}$).

A compound (L-58) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{768}$).

A compound (L-58) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{769}$).

A compound (L-58) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{770}$).

A compound (L-58) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{771}$).

A compound (L-58) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{772}$).

A compound (L-58) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{773}$).

A compound (L-56) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{774}$).

A compound (L-56) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{775}$).

A compound (L-58) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{776}$).

A compound represented by formula (L-59):

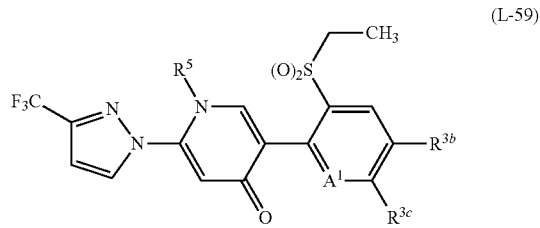

(L-59)

(hereinafter, referred to as Compound (L-59)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{777}$).

A compound (L-59) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{778}$).

A compound (L-59) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{779}$).

A compound (L-59) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{780}$).

A compound (L-59) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{781}$).

A compound (L-59) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{782}$).

A compound (L-59) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{783}$).

A compound (L-59) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{784}$).

A compound (L-59) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{785}$).

A compound (L-59) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{786}$).

A compound (L-59) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{787}$).

A compound (L-59) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{788}$).

A compound (L-59) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{789}$).

A compound (L-59) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{790}$).

A compound represented by formula (L-60):

(L-60)

(hereinafter, referred to as Compound (L-60)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{791}$).

A compound (L-60) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{792}$).

A compound (L-60) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{793}$).

A compound (L-60) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{794}$).

A compound (L-60) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{795}$).

A compound (L-60) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{796}$).

A compound (L-60) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{797}$).

A compound (L-60) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{798}$).

A compound (L-60) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{799}$).

A compound (L-60) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{800}$).

A compound (L-60) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{801}$).

A compound (L-60) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{802}$).

A compound (L-60) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{803}$).

A compound (L-60) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{804}$).

A compound represented by formula (L-61):

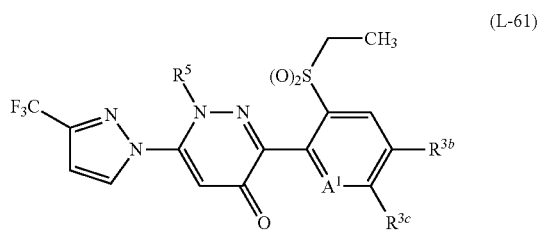

(hereinafter, referred to as Compound (L-61)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{805}$).

A compound (L-61) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{806}$).

A compound (L-61) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{807}$).

A compound (L-61) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{808}$).

A compound (L-61) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{809}$).

A compound (L-61) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{810}$).

A compound (L-61) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{811}$).

A compound (L-61) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{812}$).

A compound (L-61) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{813}$).

A compound (L-61) wherein $A^1$ represents a nitrogen atom, $R^5$ represents methyl group, $R^{3c}$ represents a hydrogen atom, and $R^{3b}$ represents any substituents indicated in Table 7 to Table 15 (hereinafter, referred to as Compound Class $SX_{814}$).

A compound (L-61) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{815}$).

A compound (L-61) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{816}$).

A compound (L-61) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{817}$).

A compound (L-61) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{818}$).

A compound represented by formula (62):

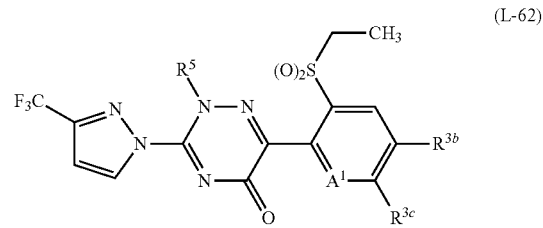

(hereinafter, referred to as Compound (L-62)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{819}$).

A compound (L-62) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{820}$).

A compound (L-62) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{821}$).

A compound (L-62) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{822}$).

A compound (L-62) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{823}$).

A compound (L-62) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{824}$).

A compound (L-62) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{825}$).

A compound (L-62) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{826}$).

A compound (L-62) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{827}$).

A compound (L-62) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{828}$).

A compound (L-62) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{829}$).

A compound (L-62) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{830}$).

A compound (L-62) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{831}$).

A compound (L-62) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{832}$).

A compound represented by formula (L-63):

(L-63)

(hereinafter, referred to as Compound (L-63)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{833}$).

A compound (L-63) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{834}$).

A compound (L-63) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{835}$).

A compound (L-63) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{836}$).

A compound (L-63) wherein $A^1$ represents a nitrogen atom, $P^5$ represents a propyl group, $R^{3b}$ represents a hydrogen atom, and $R^{3c}$ represents any substituents indicated in Table 7 to Table 15 (hereinafter, referred to as Compound Class $SX_{837}$).

A compound (L-63) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, refer to as Compound Class $SX_{838}$).

A compound (L-63) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{839}$).

A compound (L-63) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{840}$).

A compound (L-63) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{841}$).

A compound (L-63) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{842}$).

A compound (L-63) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{843}$).

A compound (L-63) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{844}$).

A compound (L-63) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{845}$).

A compound (L-63) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{846}$).

A compound represented by formula (L-64):

(L-64)

(hereinafter, referred to as Compound (L-64)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{847}$).

A compound (L-64) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{848}$).

A compound (L-64) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{849}$).

A compound (L-64) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{850}$).

A compound (L-64) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{851}$).

A compound (L-64) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{852}$).

A compound (L-64) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{853}$).

A compound (L-64) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{854}$).

A compound (L-64) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{855}$).

A compound (L-64) wherein $A^1$ represents a nitrogen atom, represents a methyl group, $R^{3c}$ represents a hydrogen atom, and $R^{3b}$ represents any substituents indicated in Table 7 to Table 15 (hereinafter, referred to as Compound Class $SX_{856}$).

A compound (L-64) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{857}$).

A compound (L-64) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{858}$).

A compound (L-64) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{859}$).

A compound (L-64) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{860}$).

A compound represented by formula (L-65):

(hereinafter, referred to as Compound (L-65)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{861}$).

A compound (L-65) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{862}$).

A compound (L-65) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{863}$).

A compound (L-65) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{864}$).

A compound (L-65) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{865}$).

A compound (L-65) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{866}$).

A compound (L-65) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{867}$).

A compound (L-65) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{868}$).

A compound (L-65) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{869}$).

A compound (L-65) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{870}$).

A compound (L-65) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{871}$).

A compound (L-65) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{872}$).

A compound (L-65) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{873}$).

A compound (L-65) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{874}$).

A compound represented by formula (L-66):

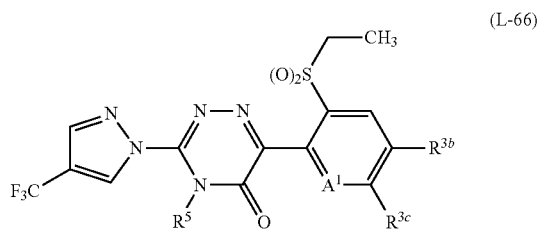

(L-66)

(hereinafter, referred to as Compound (L-66)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{875}$).

A compound (L-66) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{876}$).

A compound (L-66) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{877}$).

A compound (L-66) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{878}$).

A compound (L-66) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{879}$).

A compound (L-66) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{880}$).

A compound (L-66) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{881}$).

A compound (L-66) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{882}$).

A compound (L-66) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{883}$).

A compound (L-66) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{884}$).

A compound (L-66) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{885}$).

A compound (L-66) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{886}$).

A compound (L-66) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{887}$).

A compound (L-66) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{888}$).

A compound represented by formula (L-67):

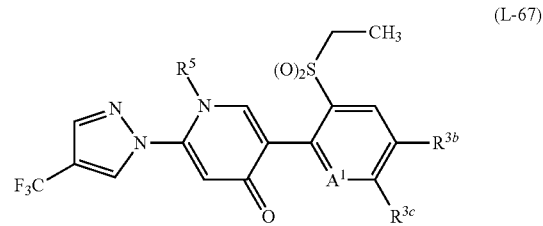

(L-67)

(hereinafter, referred to as Compound (L-67)) wherein $A^1$ represents CH, $R^5$ represents a methyl group, $R^{3b}$ represents a hydrogen atom, and $R^{3c}$ represents any substituents indicated in Table 7 to Table 15 thereinafter, referred to as Compound Class $SX_{889}$).

A compound (L-67) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{890}$).

A compound (L-67) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{891}$).

A compound (L-67) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{892}$).

A compound (L-67) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{893}$).

A compound (L-67) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{894}$).

A compound (L-67) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{895}$).

A compound (L-67) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{896}$).

A compound (L-67) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{897}$).

A compound (L-67) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{898}$).

A compound (L-67) wherein $A^1$ represents a nitrogen atom, $R^5$ represents an ethyl group, $R^{3c}$ represents a hydrogen atom, and $R^{3c}$ represents any substituents indicated in Table 7 to Table 15 (hereinafter, referred to as Compound Class $SX_{899}$).

A compound (L-67) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{900}$).

A compound (L-67) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{901}$).

A compound (L-67) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{902}$).

A compound represented by formula (L-68):

(L-68)

(hereinafter, referred to as Compound (L-68)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{903}$).

A compound (L-68) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{904}$).

A compound (L-68) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{905}$).

A compound (L-68) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{906}$).

A compound (L-68) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{907}$).

A compound (L-69) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{908}$).

A compound (L-68) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{909}$).

A compound (L-68) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{910}$).

A compound (L-68) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{911}$).

A compound (L-68) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{912}$).

A compound (L-68) wherein $A^1$ represents a nitrogen atom, $R^5$ represents an ethyl group, $R^{3c}$ represents a hydrogen atom, and $R^{3b}$ represents any substituents indicated in Table 7 to Table 15 (hereinafter, referred to as Compound Class $SX_{913}$).

A compound (L-68) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{914}$).

A compound (L-68) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{915}$).

A compound (L-68) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{916}$).

A compound represented by formula (L-69):

(L-69)

(hereinafter, referred to as Compound (L-69)) wherein $A^1$ represents CH, $R^5$ represents a methyl group, $R^{3b}$ represents a hydrogen atom, and $R^{3c}$ represents any substituents indicated in Table 7 to Table 15 (hereinafter, referred to as Compound Class $SX_{917}$).

A compound (L-69) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{918}$).

A compound (L-69) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{919}$).

A compound (L-69) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{920}$).

A compound (L-69) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{921}$).

A compound (L-69) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{922}$).

A compound (L-69) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{923}$).

A compound (L-69) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{924}$).

A compound (L-69) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{925}$).

A compound (L-69) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{926}$).

A compound (L-69) wherein $A^1$ represents a nitrogen atom, $R^5$ represents an ethyl group $R^{3c}$ represents a hydrogen atom, and $R^{3b}$ represents any substituents indicated in Table 7 to Table 15 (hereinafter, referred to as Compound Class $SX_{927}$).

A compound (L-69) wherein $A^1$ represents a nitrogen atom, $R^5$ represents a propyl group, $R^{3c}$ represents a hydrogen atom, and $R^{3b}$ represents any substituents indicated in Table 7 to Table 15 (hereinafter, referred to as Compound Class $SX_{928}$).

A compound (L-69) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{929}$).

A compound (L-69) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{930}$).

A compound represented by formula L-70):

$$\text{(L-70)}$$

(hereinafter, referred to as Compound L-7.0)) wherein $A^1$ represents CH, $R^5$ represents a methyl group, $R^{3b}$ represents hydrogen atom, and $R^{3c}$ represents any substituents indicated in Table 7 to Table 15 (hereinafter, referred to as Compound Class $SX_{931}$).

A compound (L-70) wherein $A^1$ represents CH, $R^5$ represents an ethyl group, $R^{3b}$ represents a hydrogen atom, and $R^{3c}$ represents any substituents indicated in Table 7 to Table 15 (hereinafter, referred to as Compound Class $SX_{932}$).

A compound (L-70) wherein $A^1$ represents a nitrogen atom, $R^5$ represents a methyl group, $R^{3b}$ represents a hydrogen atom, and $R^{3c}$ represents any substituents indicated in Table 7 to Table 15 (hereinafter, referred to as Compound Class $SX_{933}$).

A compound (L-70) wherein $A^1$ represents a nitrogen atom, $R^5$ represents an ethyl group, $R^{3b}$ represents a hydrogen atom, and $R^{3c}$ represents any substituents indicated in Table 7 to Table 15 (hereinafter, referred to as Compound Class $SX_{934}$).

A compound (L-70) wherein $A^1$ represents a nitrogen atom, $R^5$ represents a propyl group, $R^{3b}$ represents a hydrogen atom, and $R^{3c}$ represents any substituents indicated in Table 7 to Table 15 (hereinafter, referred to as Compound Class $SX_{935}$).

A compound (L-70) wherein $A^1$ represents a nitrogen atom, $R^5$ represents an isopropyl group, $R^{3b}$ represents a hydrogen atom, and $R^{3c}$ represents any substituents indicated in Table 7 to Table 15 (hereinafter, referred to as Compound Class $SX_{936}$).

A compound (L-70) wherein $A^1$ represents a nitrogen atom, $R^5$ represents a cyclopropyl group, $R^{3b}$ represents a hydrogen atom, and $R^{3c}$ represents any substituents indicated in Table 7 to Table 15 (hereinafter, referred to as Compound Class $SX_{937}$).

A compound (L-70) wherein $A^1$ represents CH, $R^5$ represents a methyl group, $R^{3c}$ represents a hydrogen atom, and $R^{3b}$ represents any substituents indicated in Table 7 to Table 15 (hereinafter, referred to as Compound Class $SX_{938}$).

A compound (L-70) wherein $A^1$ represents CH, $R^5$ represents an ethyl group, $R^{3c}$ represents a hydrogen atom, and $R^{3b}$ represents any substituents indicated in Table 7 to Table 15 (hereinafter, referred to as Compound Class $SX_{939}$).

A compound (L-70) wherein $A^1$ represents a nitrogen atom, $R^5$ represents a methyl group, $R^{3c}$ represents a hydrogen atom, and $R^{3b}$ represents any substituents indicated in Table 7 to Table 15 (hereinafter, referred to as Compound Class $SX_{940}$).

A compound (L-70) wherein $A^1$ represents a nitrogen atom, $R^5$ represents an ethyl group, $R^{3c}$ represents a hydrogen atom, and $R^{3b}$ represents substituents indicated in Table 7 to Table 15 (hereinafter, referred to as Compound Class $SX_{941}$).

A compound (L-70) wherein $A^1$ represents a nitrogen atom, represents a propyl group, $R^{3c}$ represents a hydrogen atom, and $R^{3b}$ represents any substituents indicated in Table 7 to Table 15 (hereinafter, referred to as Compound Class $SX_{942}$).

A compound (L-70) wherein $A^1$ represents a nitrogen atom, $R^5$ represents an isopropyl group, $R^{3c}$ represents a hydrogen atom, and $R^{3b}$ represents any substituents indicated in Table 7 to Table 15 (hereinafter, referred to as Compound Class $SX_{943}$).

A compound (L-70) wherein $A^1$ represents a nitrogen atom, $R^5$ represents a cyclopropyl group, $R^{3c}$ represents a hydrogen atom, and $R^{3b}$ represents any substituents indicated in Table 7 to Table 15 (hereinafter, referred to as Compound Class $SX_{944}$).

A compound represented by formula (L-71):

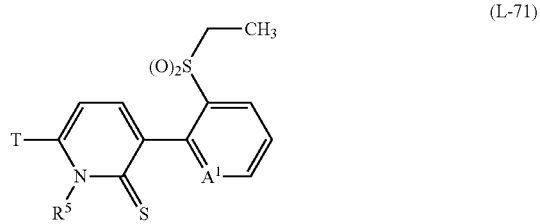

(hereinafter, referred to as Compound (L-71)) wherein $A^1$ represents CH, $R^5$ represents a methyl group, and T represents any substituents indicated in Table 1 to Table 6 (hereinafter, referred to as Compound Class $SX_{945}$).

A compound (L-71) wherein $A^1$ represents CH, $R^5$ represents an ethyl group, and T represents any substituents indicated in Table 1 to Table 6 (hereinafter, referred to as Compound Class $SX_{946}$).

A compound (L-71) wherein $A^1$ represents a nitrogen atom, $R^5$ represents a methyl group, and T represents any substituents indicated in Table 1 to Table 6 (hereinafter, referred to as Compound Class $SX_{947}$).

A compound (L-71) wherein $A^1$ represents a nitrogen atom, $R^5$ represents an ethyl group, and T represents any substituents indicated in Table 1 to Table 6 (hereinafter, referred to as Compound Class $SX_{948}$).

A compound (L-71) wherein $A^1$ represents a nitrogen atom, $R^5$ represents a propyl group, and T represents any substituents indicated in Table 1 to Table 6 (hereinafter, referred to as Compound Class $SX_{949}$).

A compound (L-71) wherein $A^1$ represents a nitrogen atom, $R^5$ represents an isopropyl group, and T represents any substituents indicated in Table 1 to Table 6 (hereinafter, referred to as Compound Class $SX_{950}$).

A compound (L-71) wherein $A^1$ represents a nitrogen atom, $R^5$ represents a cyclopropyl group, and T represents any substituents indicated in Table 1 to Table 6 (hereinafter, referred to as Compound Class $SX_{951}$).

A compound represented by formula (L-72):

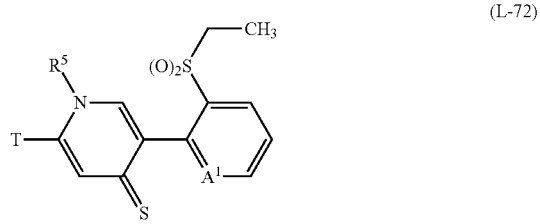

(hereinafter, referred to as Compound (L-72)) wherein $A^1$ represents CH, $R^5$ represents a methyl group, and T represents any substituents indicated in Table 1 to Table 6 (hereinafter, referred to as Compound Class $SX_{952}$).

A compound (L-72) wherein $A^1$ represents CH, $R^5$ represents an ethyl group, and T represents any substituents indicated in Table 1 to Table 6 (hereinafter, referred to as Compound Class $SX_{953}$).

A compound (L-72) wherein $A^1$ represents a nitrogen atom, $R^5$ represents a methyl group, and T represents any substituents indicated in Table 1 to Table 6 (hereinafter, referred to as Compound Class $SX_{954}$).

A compound (L-72) wherein $A^1$ represents a nitrogen atom, $R^5$ represents an ethyl group, and T represents any substituents indicated in Table 1 to Table 6 (hereinafter, referred to as Compound Class $SX_{955}$).

A compound (L-72) wherein $A^1$ represents a nitrogen atom, $R^5$ represents a propyl group, and T represents any substituents indicated in Table 1 to Table 6 (hereinafter, referred to as Compound Class $SX_{956}$).

A compound (L-72) wherein $A^1$ represents a nitrogen atom, $R^5$ represents an isopropyl group, and T represents any substituents indicated in Table 1 to Table 6 (hereinafter, referred to as Compound Class $SX_{957}$).

A compound L-72) wherein $A^1$ represents a nitrogen atom, $R^5$ represents a cyclopropyl group, and T represents any substituents indicated in Table 1 to Table 6 (hereinafter, referred to as Compound Class $SX_{958}$).

A compound represented by formula (L-73):

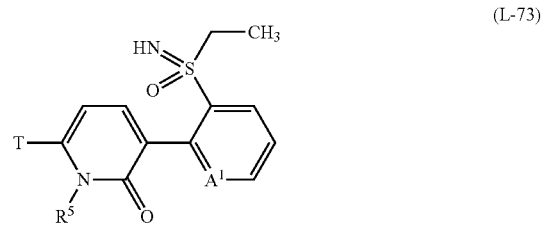

(hereinafter, referred to as Compound (L-73)) wherein $A^1$ represents CH, $R^5$ represents a methyl group, and T represents any substituents indicated in Table 1 to Table 6 (hereinafter, referred to as Compound Class $SX_{959}$).

A compound (L-73) wherein $A^1$ represents CH, $R^5$ represents an ethyl group, and T represents any substituents indicated in Table 1 to Table 6 (hereinafter, referred to as Compound Class $SX_{960}$).

A compound (L-73) wherein $A^1$ represents a nitrogen atom, $R^5$ represents a methyl group, and T represents any substituents indicated in Table 1 to Table 6 (hereinafter, referred to as Compound Class $SX_{961}$).

A compound (L-73) wherein $A^1$ represents a nitrogen atom, $R^5$ represents an ethyl group, and T represents any substituents indicated in Table 1 to Table 6 (hereinafter, referred to as Compound Class $SX_{962}$).

A compound (L-73) wherein $A^1$ represents a nitrogen atom, $R^5$ represents a propyl group, and T represents any substituents indicated in Table 1 to Table 6 (hereinafter, referred to as Compound Class $SX_{963}$).

A compound (L-73) wherein $A^1$ represents a nitrogen atom, $R^5$ represents an isopropyl group, and T represents any substituents indicated in Table 1 to Table 6 (hereinafter, referred to as Compound Class $SX_{964}$).

A compound (L-73) wherein $A^1$ represents a nitrogen atom, $R^5$ represents a cyclopropyl group, and T represents any substituents indicated in Table 1 to Table 6 (hereinafter, referred to as Compound Class SX$_{965}$).

A compound represented by formula (L-74):

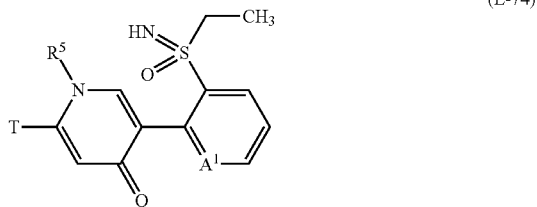

(L-74)

(hereinafter, referred to as Compound (L-74)) wherein A$^1$ represents CH, R$^5$ represents a methyl group, and T represents any substituents indicated in Table 1 to Table 6 (hereinafter, referred to as Compound Class SX$_{966}$).

A compound (L-74) wherein A$^1$ represents CH, R$^5$ represents an ethyl group, and T represents any substituents indicated in Table 1 to Table 6 (hereinafter, referred to as compound Class SX$_{967}$).

A compound (L-74) wherein A$^1$ represents a nitrogen atom, R$^5$ represents a methyl group, and T represents any substituents indicated in Table 1 to Table 6 (hereinafter, referred to as Compound Class SX$_{968}$).

A compound (L-74) wherein A$^1$ represents a nitrogen atom, R$^5$ represents an ethyl group, and T represents any substituents indicated in Table 1 to Table 6 (hereinafter, referred to as Compound Class SX$_{969}$).

A compound (L-74) wherein A$^1$ represents a nitrogen atom, R$^5$ represents propyl group, and T represents any substituents indicated in Table 1 to Table 6 (hereinafter, referred to as Compound Class SX$_{970}$).

A compound (L-74) wherein A$^1$ represents a nitrogen atom, R$^1$ represents an isopropyl group, and T represents any substituents indicated in Table 1 to Table 6 (hereinafter, referred to as Compound Class SX$_{971}$).

A compound (L-74) wherein A$^1$ represents a nitrogen atom, R$^5$ represents a cyclopropyl group, and T represents any substituents indicated in Table 1 to Table 6 (hereinafter, referred to as Compound Class SX$_{972}$).

A compound represented by formula (L-75):

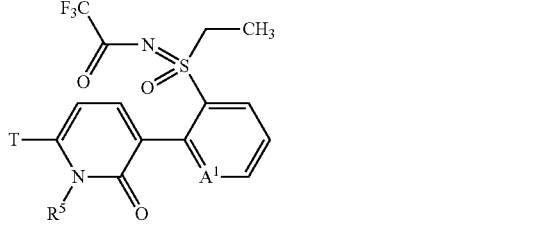

(L-75)

(hereinafter, referred to Compound (L-75)) wherein A$^1$ represents CH, R$^5$ represents a methyl group, and T represents any substituents indicated in Table 1 to Table 6 (hereinafter, referred to as Compound Class SX$_{973}$).

A compound (L-75) wherein A$^1$ represents CH, R$^5$ represents an ethyl group, and T represents any substituents indicated in Table 1 to Table 6 (hereinafter, referred to as Compound Class SX$_{974}$).

A compound (L-75) wherein A$^1$ represents a nitrogen atom, R$^5$ represents a methyl group, and T represents any substituents indicated in Table 1 to Table 6 (hereinafter, referred to as Compound Class SX$_{975}$).

A compound (L-75) wherein A$^1$ represents a nitrogen atom, R$^5$ represents an ethyl group, and T represents any substituents indicated in Table 1 to Table 6 (hereinafter, referred to as Compound Class SX$_{976}$).

A compound (L-75) wherein A$^1$ represents a nitrogen atom, R$^5$ represents a propyl group, and T represents any substituents indicated in Table 1 to Table 6 (hereinafter, referred to as Compound Class SX$_{977}$).

A compound (L-75) wherein A$^1$ represents a nitrogen atom, R$^5$ represents an isopropyl group, and T represents any substituents indicated in Table 1 to Table 6 (hereinafter, referred to as Compound Class SX$_{978}$).

A compound (L-75) wherein A$^1$ represents a nitrogen atom, R$^5$ represents a cyclopropyl group, and T represents any substituents indicated in Table 1 to Table 6 (hereinafter, referred to as Compound Class SX$_{979}$).

A compound represented by formula (L-76):

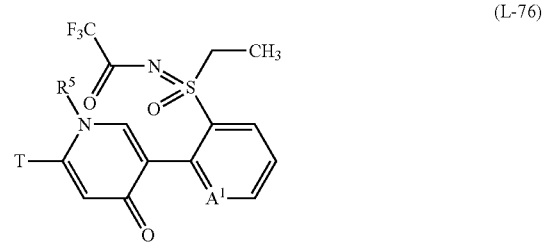

(L-76)

(hereinafter, referred to as Compound (L-76)) wherein A$^1$ represents CH, R$^5$ represents a methyl group, and T represents any substituents indicated in Table 1 to Table 6 (hereinafter, referred to as Compound Class SX$_{980}$).

A compound (L-76) wherein A$^1$ represents CH, R$^5$ represents an ethyl group, and T represents any substituents indicated in Table 1 to Table 6 (hereinafter, referred to as Compound Class SX$_{981}$).

A compound (L-76) wherein A$^1$ represents a nitrogen atom, R$^5$ represents a methyl group, and T represents any substituents indicated in Table 1 to Table 6 (hereinafter, referred to as Compound Class SX$_{982}$).

A compound (L-76) wherein A$^1$ represents a nitrogen atom, R$^5$ represents an ethyl group, and T represents any substituents indicated in Table 1 to Table 6 (hereinafter, referred to as Compound Class SX$_{983}$).

A compound (L-76) wherein A$^1$ represents a nitrogen atom, R$^5$ represents a propyl group, and T represents any substituents indicated in Table 1 to Table 6 (hereinafter, referred to as Compound Class SX$_{984}$).

A compound (L-76) wherein A$^1$ represents a nitrogen atom, R$^5$ represents an isopropyl group, and T represents any substituents indicated in Table 1 to Table 6 (hereinafter, referred to as Compound Class SX$_{985}$).

A compound (L-76) wherein A$^1$ represents a nitrogen atom, R$^5$ represents a cyclopropyl group, and T represents any substituents indicated in Table 1 to Table 6 (hereinafter, referred to as Compound Class SX$_{986}$).

A compound represented by formula (L-77):

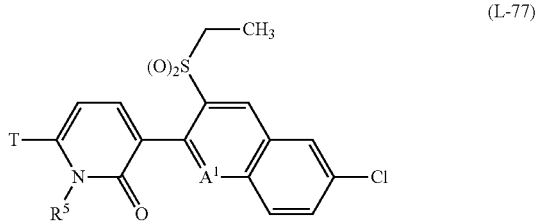

(hereinafter, referred to as Compound (L-77)) wherein $A^1$ represents CH, $R^5$ represents a methyl group, and T represents any substituents indicated in Table 1 to Table 6 (hereinafter, referred to as Compound Class $SX_{987}$).

A compound (L-77) wherein $A^1$ represents CH, $R^5$ represents an ethyl group, and T represents any substituents indicated in Table 1 to Table 6 (hereinafter, referred to as Compound Class $SX_{988}$).

A compound (L-77) wherein $A^1$ represents a nitrogen atom, $R^5$ represents a methyl group, and T represents any substituents indicated in Table 1 to Table 6 (hereinafter, referred to as Compound Class $SX_{989}$).

A compound (L-77) wherein $A^1$ represents a nitrogen atom, $R^5$ represents an ethyl group, and T represents any substituents indicated in Table 1 to Table 6 (hereinafter, referred to as Compound Class $SX_{990}$).

A compound (L-77) wherein $A^1$ represents a nitrogen atom, $R^5$ represents propyl group, and T represents any substituents indicated in Table 1 to Table 6 (hereinafter, referred to as Compound Class $SX_{991}$).

A compound (L-77) wherein $A^1$ represents a nitrogen atom, $R^5$ represents an isopropyl group, and T represents any substituents indicated in Table 1 to Table 6 (hereinafter, referred to as Compound Class $SX_{992}$).

A compound (L-77) wherein $A^1$ represents a nitrogen atom, $R^5$ represents a cyclopropyl group, and T represents any substituents indicated in Table 1 to Table 6 (hereinafter, referred to as Compound Class $SX_{993}$).

A compound represented by formula (L-78):

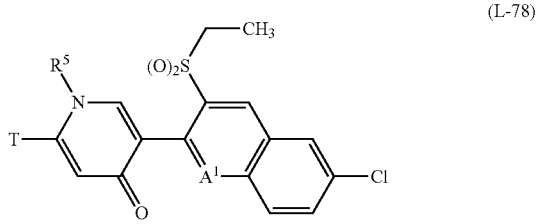

(hereinafter, referred to as Compound (L-78)) wherein $A^1$ represents CH, $R^5$ represents a methyl group, and T represents any substituents indicated in Table 1 to Table 6 (hereinafter, referred to as Compound Class $SX_{994}$).

A compound (L-78) wherein $A^1$ represents CH, $R^5$ represents an ethyl group, and T represents any substituents indicated in Table 1 to Table 6 (hereinafter, referred to as Compound Class $SX_{995}$).

A compound (L-78) wherein $A^1$ represents a nitrogen atom, $R^5$ represents a methyl group, and T represents any substituents indicated in Table 1 to Table 6 (hereinafter, referred to as Compound Class $SX_{996}$).

A compound (L-78) wherein $A^1$ represents a nitrogen atom, $R^5$ represents an ethyl group, and T represents any substituents indicated in Table 1 to Table 6 (hereinafter, referred to as Compound Class $SX_{997}$).

A compound (L-78) wherein $A^1$ represents a nitrogen atom, $R^5$ represents a propyl group, and b represents any substituents indicated in Table 1 to Table 6 (hereinafter, referred to as Compound Class $SX_{998}$).

A compound (L-78) wherein $A^1$ represents a nitrogen atom, $R^5$ represents an isopropyl group, and T represents any substituents indicated in Table 1 to Table 6 (hereinafter, referred to as Compound Class $SX_{999}$).

A compound (L-78) wherein $A^1$ represents a nitrogen atom, $R^5$ represents a cyclopropyl group, and T represents any substituents indicated in Table 1 to Table 6 (hereinafter, referred to as Compound Class $SX_{1000}$).

A compound represented by formula (L-79):

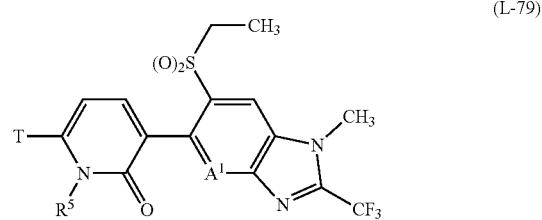

(hereinafter, referred to as Compound (L-79)) wherein $A^1$ represents CH, $R^5$ represents a methyl group, and T represents any substituents indicated in Table 1 to Table 6 (hereinafter, referred to as Compound Class $SX_{1001}$).

A compound (L-79) wherein $A^1$ represents CH, $R^5$ represents an ethyl group, and T represents any substituents indicated in Table 1 to Table 6 (hereinafter, referred to as Compound Class $SX_{1002}$).

A compound (L-79) wherein $A^1$ represents a nitrogen atom, $R^5$ represents a methyl group, and T represents any substituents indicated in Table 1 to Table 6 (hereinafter, referred to as Compound Class $SX_{1003}$).

A compound (L-79) wherein $A^1$ represents a nitrogen atom, $R^5$ represents an ethyl group, and T represents any substituents indicated in Table 1 to Table 6 (hereinafter, referred to as Compound Class $SX_{1004}$).

A compound (L-79) wherein $A^1$ represents a nitrogen atom, $R^5$ represents a propyl group, and T represents any substituents indicated in Table 1 to Table 6 (hereinafter, referred to as Compound Class $SX_{1005}$).

A compound (L-79) wherein $A^1$ represents a nitrogen atom, $R^5$ represents an isopropyl group, and T represents any substituents indicated in Table 1 to Table 6 (hereinafter, referred to as Compound Class $SX_{1006}$).

A compound (L-79) wherein $A^1$ represents a nitrogen atom, $R^5$ represents a cyclopropyl group, and T represents any substituents indicated in Table 1 to Table 6 (hereinafter, referred to as Compound Class $SX_{1007}$).

A compound represented by formula (L-80):

(L-80)

(hereinafter, referred to as Compound (L-80)) wherein $A^1$ represents CH, $R^5$ represents a methyl group, and T represents any substituents indicated in Table 1 to Table 6 (hereinafter, referred to as Compound Class $SX_{1008}$).

A compound (L-80) wherein $A^1$ represents CH, $R^5$ represents an ethyl group, and T represents any substituents indicated in Table 1 to Table 6 (hereinafter, referred to as Compound Class $SX_{1009}$).

A compound (L-80) wherein $A^1$ represents a nitrogen atom, $R^5$ represents a methyl group, and T represents any substituents indicated in Table 1 to Table 6 (hereinafter, referred to as Compound Class $SX_{1010}$).

A compound (L-80) wherein $A^1$ represents a nitrogen atom, $R^5$ represents an ethyl group, and T represents any substituents indicated in Table 1 to Table 6 (hereinafter, referred to as Compound Class $SX_{1011}$).

A compound (L-80) wherein $A^1$ represents a nitrogen atom, $R^5$ represents a propyl group, and T represents any substituents indicated in Table 1 to Table 6 (hereinafter, referred to as Compound Class $SX_{1012}$).

A compound (L-80) wherein $A^1$ represents a nitrogen atom, $R^5$ represents an isopropyl group, and T represents any substituents indicated in Table 1 to Table 6 (hereinafter, referred to as Compound Class $SX_{1013}$).

A compound (L-80) wherein $A^1$ represents a nitrogen atom, $R^5$ represents a cyclopropyl group, and T represents any substituents indicated in Table 1 to Table 6 (hereinafter, referred to as Compound Class $SX_{1014}$).

A compound (L-1) wherein $A^1$ represents a nitrogen atom, $R^4$ represents a methyl group, $R^5$ represents a methyl group, and T represents any substituents indicated in Table 1 to Table 6 (hereinafter, referred to as Compound Class $SX_{1015}$).

A compound (L-1) wherein $A^1$ represents a nitrogen atom, $R^4$ represents a methyl group, $R^5$ represents an ethyl group, and T represents any substituents indicated in Table 1 to Table 6 (hereinafter, referred to as Compound Class $SX_{1016}$).

A compound (L-1) wherein $A^1$ represents a nitrogen atom, $R^4$ represents a methyl group, $R^5$ represents a propyl group, and T represents any substituents indicated in Table 1 to Table 6 (hereinafter, referred to as Compound Class $SX_{1017}$).

A compound (L-1) wherein $A^1$ represents a nitrogen atom, $R^4$ represents a methyl group, $R^5$ represents an isopropyl group, and T represents any substituents indicated in Table 1 to Table 6 (hereinafter, referred to as Compound Class $SX_{1018}$).

A compound (L-1) wherein $A^1$ represents a nitrogen atom, $R^4$ represents a methyl group, $R^5$ represents a cyclopropyl group, and T represents any substituents indicated in Table 1 to Table 6 (hereinafter, referred to as Compound Class $SX_{1019}$).

A compound (L-3) wherein $A^1$ represents a nitrogen atom, $R^4$ represents a methyl group, $R^5$ represents a methyl group, and T represents any substituents indicated in Table 1 to Table 6 (hereinafter, referred to as Compound Class $SX_{1020}$).

A compound (L-3) wherein $A^1$ represents a nitrogen atom, $R^4$ represents a methyl group, $R^5$ represents an ethyl group, and T represents any substituents indicated in Table 1 to Table 6 (hereinafter, referred to as Compound Class $SX_{1021}$).

A compound (L-3) wherein $A^1$ represents a nitrogen atom, $R^4$ represents a methyl group, $R^5$ represents a propyl group, and T represents any substituents indicated in Table 1 to Table 6 (hereinafter, referred to as Compound Class $SX_{1022}$).

A compound (L-3) wherein $A^1$ represents a nitrogen atom, $R^4$ represents a methyl group, $R^5$ represents an isopropyl group, and T represents any substituents indicated in Table 1 to Table 6 (hereinafter, referred to as Compound Class $SX_{1023}$).

A compound (L-3) wherein $A^1$ represents a nitrogen atom, $R^4$ represents a methyl group, $R^5$ represents a cyclopropyl group, and T represents any substituents indicated in Table 1 to Table 6 (hereinafter, referred to as Compound Class $SX_{1024}$).

A compound (L-5) wherein $A^1$ represents a nitrogen atom, $R^4$ represents a methyl group, $R^5$ represents a methyl group, and T represents any substituents indicated in Table 1 to Table 6 (hereinafter, referred to as Compound Class $SX_{1025}$).

A compound (L-5) wherein $A^1$ represents a nitrogen atom, $R^4$ represents a methyl group, $R^5$ represents an ethyl group, and T represents any substituents indicated in Table 1 to Table 6 (hereinafter, referred to as Compound Class $SX_{1026}$).

A compound (L-5) wherein $A^1$ represents a nitrogen atom, $R^4$ represents a methyl group, $R^5$ represents a propyl group, and T represents any substituents indicated in Table 1 to Table 6 (hereinafter, referred to as Compound Class $SX_{1027}$).

A compound (L-5) wherein $A^1$ represents a nitrogen atom, $R^4$ represents a methyl group, $R^5$ represents an isopropyl group, and T represents any substituents indicated in Table 1 to Table 6 (hereinafter, referred to as Compound Class $SX_{1028}$).

A compound (L-5) wherein $A^1$ represents a nitrogen atom, represents a methyl group, $R^5$ represents a cyclopropyl group, and T represents any substituents indicated in Table 1 to Table 6 (hereinafter, referred to as Compound Class $SX_{1029}$).

A compound (L-7) wherein $A^1$ represents a nitrogen atom, $R^4$ represents a methyl group, $R^5$ represents a methyl group, and T represents any substituents indicated in Table 1 to Table 6 (hereinafter, referred to as Compound Class $SX_{1030}$).

A compound (L-7) wherein $A^1$ represents a nitrogen atom, $R^4$ represents a methyl group, $R^5$ represents an ethyl group, and T represents any substituents indicated in Table 1 to Table 6 (hereinafter, referred to as Compound Class $SX_{1031}$).

A compound (L-7) wherein $A^1$ represents a nitrogen atom, $R^4$ represents a methyl group, $R^5$ represents a propyl group, and T represents any substituents indicated in Table 1 to Table 6 (hereinafter, referred to as Compound Class $SX_{1032}$).

A compound (L-7) wherein $A^1$ represents a nitrogen atom, $R^4$ represents a methyl group, $R^5$ represents an isopropyl group, and T represents any substituents indicated in Table 1 to Table 6 (hereinafter, referred to as Compound Class $SX_{1033}$).

A compound (L-7) wherein $A^1$ represents a nitrogen atom, $R^4$ represents a methyl group, $R^5$ represents an cyclopropyl group, and T represents any substituents indicated in Table 1 to Table 6 (hereinafter, referred to as Compound Class $SX_{1034}$).

A compound represented by formula (L-81):

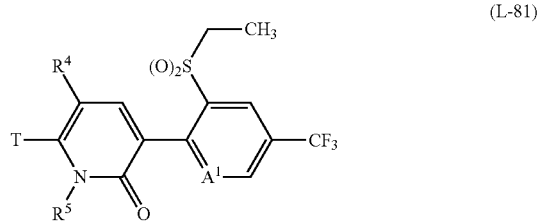

(hereinafter, referred to as Compound (L-81)) wherein $A^1$ represents CH, $R^4$ represents a hydrogen atom, $R^5$ represents a methyl group, and T represents any substituents indicated in Table 1 to Table 6 (hereinafter, referred to as Compound Class $SX_{1035}$).

A compound (L-81) wherein $A^1$ represents CH, $R^4$ represents a hydrogen atom, $R^5$ represents an ethyl group, and T represents any substituents indicated in Table 1 to Table 6 (hereinafter, referred to as Compound Class $SX_{1036}$).

A compound (L-81) wherein $A^1$ represents a nitrogen atom, $R^4$ represents a hydrogen atom, $R^5$ represents a methyl group, and T represents any substituents indicated in Table 1 to Table 6 (hereinafter, referred to as Compound Class $SX_{1037}$).

A compound (L-81) wherein $A^1$ represents a nitrogen atom, $R^4$ represents a hydrogen atom, $R^5$ represents an ethyl group, and T represents any substituents indicated in Table 1 to Table 6 (hereinafter, referred to as Compound Class $SX_{1038}$).

A compound (L-81) wherein $A^1$ represents a nitrogen atom, $R^4$ represents a hydrogen atom, $R^5$ represents a propyl group, and T represents any substituents indicated in Table 1 to Table 6 (hereinafter, referred to as Compound Class $SX_{1039}$).

A compound (L-81) wherein $A^1$ represents a nitrogen atom, $R^4$ represents a hydrogen atom, $R^5$ represents an isopropyl group, and T represents any substituents indicated in Table 1 to Table 6 (hereinafter, referred to as Compound Class $SX_{1040}$).

A compound (L-81) wherein $A^1$ represents a nitrogen atom, $R^4$ represents a hydrogen atom, $R^5$ represents a cyclopropyl group, and T represents any substituents indicated in Table 1 to Table 6 (hereinafter, referred to as Compound Class $SX_{1041}$).

A compound (L-81) wherein $A^1$ represents a nitrogen atom, $R^4$ represents a chlorine atom, $R^5$ represents a methyl group, and T represents any substituents indicated in Table 1 to Table 6 (hereinafter, referred to as Compound Class $SX_{1042}$).

A compound (L-81) wherein $A^1$ represents a nitrogen atom, $R^4$ represents a chlorine atom, $R^5$ represents an ethyl group, and T represents any substituents indicated in Table 1 to Table 6 (hereinafter, referred to as Compound Class $SX_{1043}$).

A compound (L-81) wherein $A^1$ represents a nitrogen atom, $R^4$ represents a chlorine atom, $R^5$ represents a propyl group, and T represents any substituents indicated in Table 1 to Table 6 (hereinafter, referred to as Compound Class $SX_{1044}$).

A compound (L-81) wherein $A^1$ represents a nitrogen atom, $R^4$ represents a chlorine atom, $R^5$ represents an isopropyl group, and T represents any substituents indicated in Table 1 to Table 6 (hereinafter, referred to as Compound Class $SX_{1045}$).

A compound (L-81) wherein $A^1$ represents a nitrogen atom, $R^4$ represents a chlorine atom, $R^5$ represents a cyclopropyl group, and T represents any substituents indicated in Table 1 to Table 6 (hereinafter, referred to as Compound Class $SX_{1046}$).

A compound (L-81) wherein $A^1$ represents a nitrogen atom, $R^4$ represents a methyl group, $R^5$ represents a methyl group, and T represents any substituents indicated in Table 1 to Table 6 (hereinafter, referred to as Compound Class $SX_{1047}$).

A compound (L-81) wherein $A^1$ represents a nitrogen atom, $R^4$ represents a methyl group, $R^5$ represents an ethyl group, and T represents any substituents indicated in Table 1 to Table 6 (hereinafter, referred to as Compound Class $SX_{1048}$).

A compound (L-81) wherein $A^1$ represents a nitrogen atom, $R^4$ represents a methyl group, $R^5$ represents a propyl group, and T represents any substituents indicated in Table 1 to Table 6 (hereinafter, referred to as Compound Class $SX_{1049}$).

A compound (L-81) wherein $A^1$ represents a nitrogen atom, $R^4$ represents a methyl group, $R^5$ represents an isopropyl group, and T represents any substituents indicated in Table 1 to Table 6 (hereinafter, referred to as Compound Class $SX_{1050}$).

A compound (L-81) wherein $A^1$ represents a nitrogen atom, $R^4$ represents a methyl group, $R^5$ represents a cyclopropyl group, and T represents any substituents indicated in Table 1 to Table 6 (hereinafter, referred to as Compound Class $SX_{1051}$).

A compound represented by formula (L-82):

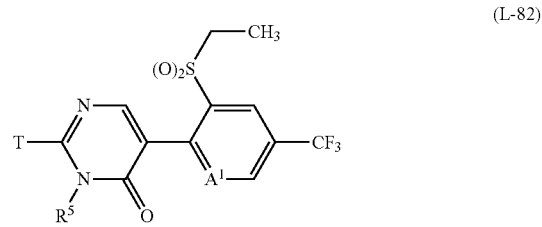

(hereinafter, referred to as Compound (L-82)) wherein $A^1$ represents CH, $R^5$ represents a methyl group, and T represents any substituents indicated in Table 1 to Table 6 (hereinafter, referred to as Compound Class $SX_{1052}$).

A compound (L-82) wherein $A^1$ represents CH, $R^5$ represents an ethyl group, and T represents any substituents indicated in Table 1 to Table 6 (hereinafter, referred to as Compound Class $SX_{1053}$).

A compound (L-82) wherein $A^1$ represents a nitrogen atom, $R^5$ represents a methyl group, and T represents any substituents indicated in Table 1 to Table 6 (hereinafter, referred to as Compound Class $SX_{1054}$).

A compound (L-82) wherein $A^1$ represents a nitrogen atom, $R^5$ represents an ethyl group, and T represents any substituents indicated in Table 1 to Table 6 (hereinafter, referred to as Compound Class $SX_{1055}$).

A compound (L-82) wherein $A^1$ represents a nitrogen atom, $R^5$ represents a propyl group, and T represents any substituents indicated in Table 1 to Table 6 (hereinafter, referred to as Compound Class $SX_{1056}$).

A compound (L-82) wherein $A^1$ represents a nitrogen atom, $R^5$ represents an isopropyl group, and T represents any substituents indicated in Table 1 to Table 6 (hereinafter, referred to as Compound Class $SX_{1057}$).

A compound (L-82) wherein $A^1$ represents a nitrogen atom, $R^5$ represents a cyclopropyl group, and T represents any substituents indicated in Table 1 to Table 6 (hereinafter, referred to as Compound Class $SX_{1058}$).

A compound represented by formula (L-83):

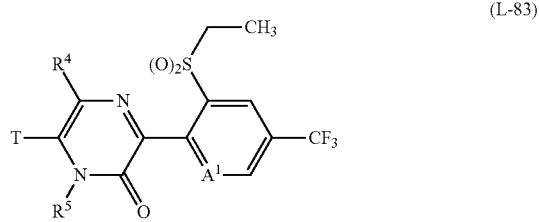

(L-83)

(hereinafter, referred to as Compound (L-83)) wherein $A^1$ represents CH, $R^4$ represents a hydrogen atom, $R^5$ represents a methyl group, and T represents any substituents indicated in Table 1 to Table 6 (hereinafter, referred to as Compound Class $SX_{1059}$).

A compound (L-83) wherein $A^1$ represents CH, $R^4$ represents a hydrogen atom, $R^5$ represents a methyl group, and T represents any substituents indicated in Table 1 to Table 6 (hereinafter, referred to as Compound Class $SX_{1060}$).

A compound (L-83) wherein $A^1$ represents a nitrogen atom, $R^4$ represents a hydrogen atom, $R^5$ represents a methyl group, and T represents any substituents indicated in Table 1 to Table 6 (hereinafter, referred to as Compound Class $SX_{1061}$).

A compound (L-83) wherein $A^1$ represents a nitrogen atom, $R^4$ represents a hydrogen atom, $R^5$ represents an ethyl group, and T represents any substituents indicated in Table 1 to Table 6 (hereinafter, referred to as Compound Class $SX_{1062}$).

A compound (L-83) wherein $A^1$ represents a nitrogen atom, $R^4$ represents a hydrogen atom, $R^5$ represents propyl group, and T represents any substituents indicated in Table 1 to Table 6 (hereinafter, referred to as Compound Class $SX_{1063}$).

A compound (L-83) wherein $A^1$ represents a nitrogen atom, $R^4$ represents a hydrogen atom, $R^5$ represents an isopropyl group, and T represents any substituents indicated in Table 1 to Table 6 (hereinafter, referred to as Compound Class $SX_{1064}$).

A compound (L-83) wherein $A^1$ represents a nitrogen atom, $R^4$ represents a hydrogen atom, $R^5$ represents a cyclopropyl group, and T represents any substituents indicated in Table 1 to Table 6 (hereinafter, referred to as Compound Class $SX_{1065}$).

A compound (L-83) wherein $A^1$ represents a nitrogen atom, $R^4$ represents a chlorine atom, $R^5$ represents a methyl group, and T represents any substituents indicated in Table 1 to Table 6 (hereinafter, referred to as Compound Class $SX_{1066}$).

A compound (L-83) wherein $A^1$ represents a nitrogen atom, $R^4$ represents a chlorine atom, $R^5$ represents an ethyl group, and T represents any substituents indicated in Table 1 to Table 6 (hereinafter, referred to as Compound Class $SX_{1067}$).

A compound (L-83) wherein $A^1$ represents a nitrogen atom, $R^4$ represents a chlorine atom, $R^5$ represents a propyl group, and T represents any substituents indicated in Table 1 to Table 6 (hereinafter, referred to as Compound Class $SX_{1068}$).

A compound (L-83) wherein $A^1$ represents a nitrogen atom, $R^4$ represents a chlorine atom, $R^5$ represents an isopropyl group, and T represents any substituents indicated in Table 1 to Table 6 (hereinafter, referred to as Compound Class $SX_{1069}$).

A compound (L-83) wherein $A^1$ represents a nitrogen atom, $R^4$ represents a chlorine atom, $R^5$ represents a cyclopropyl group, and T represents any substituents indicated in Table 1 to Table 6 (hereinafter, referred to as Compound Class $SX_{1070}$).

A compound (L-83) wherein $A^1$ represents a nitrogen atom, $R^4$ represents a methyl group, $R^5$ represents a methyl group, and T represents any substituents indicated in Table 1 to Table 6 (hereinafter, referred to as Compound Class $SX_{1071}$).

A compound (L-83) wherein $A^1$ represents a nitrogen atom, $R^4$ represents a methyl group, $R^5$ represents an ethyl group, and T represents any substituents indicated in Table 1 to Table 6 (hereinafter, referred to as Compound Class $SX_{1072}$).

A compound (L-83) wherein $A^1$ represents a nitrogen atom, $R^4$ represents a methyl group, $R^5$ represents a propyl group, and T represents any substituents indicated in Table 1 to Table 6 (hereinafter, referred to as Compound Class $SX_{1073}$).

A compound (L-83) wherein $A^1$ represents a nitrogen atom, $R^4$ represents a methyl group, $R^5$ represents an isopropyl group, and T represents any substituents indicated in Table 1 to Table 6 (hereinafter, referred to as Compound Class $SX_{1074}$).

A compound (L-83) wherein $A^1$ represents a nitrogen atom, $R^4$ represents a methyl group, $R^5$ represents a cyclopropyl group, and T represents any substituents indicated in Table 1 to Table 6 (hereinafter, referred to as Compound Class $SX_{1075}$).

A compound represented by formula (L-64):

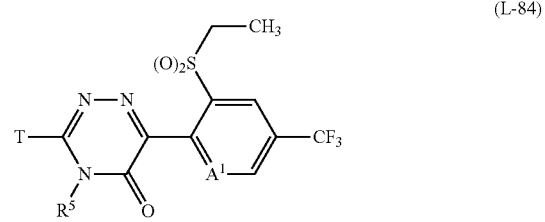

(L-84)

(hereinafter, referred to as Compound (L-84)) wherein $A^1$ represents CH, $R^5$ represents a methyl group, and T represents any substituents indicated in Table 1 to Table 6 (hereinafter, referred to as Compound Class $SX_{1076}$).

A compound (L-84) wherein $A^1$ represents CH, $R^5$ represents an ethyl group, and T represents any substituents indicated in Table 1 to Table 6 (hereinafter, referred to as Compound Class $SX_{1077}$).

A compound (L-84) wherein $A^1$ represents a nitrogen atom, $R^5$ represents a methyl group, and T represents any substituents indicated in Table 1 to Table 6 (hereinafter, referred to as Compound Class $SX_{1078}$).

A compound (L-84) wherein $A^1$ represents a nitrogen atom, $R^5$ represents an ethyl group, and T represents any substituents indicated in Table 1 to Table 6 (hereinafter, referred to as Compound Class $SX_{1079}$).

A compound (L-84) wherein $A^1$ represents a nitrogen atom, $R^5$ represents a propyl group, and T represents any substituents indicated in Table 1 to Table 6 (hereinafter, referred to as Compound Class $SX_{1080}$).

A compound (L-84) wherein $A^1$ represents a nitrogen atom, $R^5$ represents an isopropyl group, and T represents any substituents indicated in Table 1 to Table 6 (hereinafter, referred to as Compound Class $SX_{1081}$).

A compound (L-84) wherein $A^1$ represents a nitrogen atom, $R^5$ represents a cyclopropyl group, and T represents any substituents indicated in Table 1 to Table 6 (hereinafter, referred to as Compound Class $SX_{1082}$).

A compound represented by formula (L-85):

(L-85)

(hereinafter, referred to as Compound (L-85)) wherein $A^1$ represents CH, $R^4$ represents a hydrogen atom, $R^5$ represents a methyl group, and T represents any substituents indicated in Table 1 to Table 6 (hereinafter, referred to as Compound Class $SX_{1083}$).

A compound (L-85) wherein $A^1$ represents CH, $R^4$ represents a hydrogen atom, $R^5$ represents an ethyl group, and T represents any substituents indicated in Table 1 to Table 6 (hereinafter, referred to as Compound Class $SX_{1084}$).

A compound (L-85) wherein $A^1$ represents a nitrogen atom, $R^4$ represents a hydrogen atom, $R^5$ represents a methyl group, and T represents any substituents indicated in Table 1 to Table 6 (hereinafter, referred to as Compound Class $SX_{1085}$).

A compound (L-85) wherein $A^1$ represents a nitrogen atom, $R^4$ represents a hydrogen atom, $R^5$ represents an ethyl group, and T represents any substituents indicated in Table 1 to Table 6 (hereinafter, referred to as Compound Class $SX_{1086}$).

A compound (L-85) wherein $A^1$ represents a nitrogen atom, $R^4$ represents a hydrogen atom, $R^5$ represents a propyl group, and T represents any substituents indicated in Table 1 to Table 6 (hereinafter, referred to as Compound Class $SX_{1087}$).

A compound (L-85) wherein $A^1$ represents a nitrogen atom, $R^4$ represents a hydrogen atom, $R^5$ represents an isopropyl group, and T represents any substituents indicated in Table 1 to Table 6 (hereinafter, referred to as Compound Class $SX_{1088}$).

A compound (L-85) wherein $A^1$ represents a nitrogen atom, $R^4$ represents a hydrogen atom, $R^5$ represents a cyclopropyl group, and T represents any substituents indicated in Table 1 to Table 6 (hereinafter, referred to as Compound Class $SX_{1089}$).

A compound (L-85) wherein $A^1$ represents a nitrogen atom, $R^4$ represents a chlorine atom, $R^5$ represents a methyl group, and T represents any substituents indicated in Table 1 to Table 6 (hereinafter, referred to as Compound Class $SX_{1090}$).

A compound (L-85) wherein $A^1$ represents a nitrogen atom, $R^4$ represents a chlorine atom, $R^5$ represents an ethyl group, and T represents any substituents indicated in Table 1 to Table 6 (hereinafter, referred to as Compound Class $SX_{1091}$).

A compound (L-85) wherein $A^1$ represents a nitrogen atom, $R^4$ represents a chlorine atom, $R^5$ represents a propyl group, and T represents any substituents indicated in Table 1 to Table 6 (hereinafter, referred to as Compound Class $SX_{1092}$).

A compound (L-85) wherein $A^1$ represents a nitrogen atom, $R^4$ represents a chlorine atom, $R^5$ represents an isopropyl group, and T represents any substituents indicated in Table 1 to Table 6 (hereinafter, referred to as Compound Class $SX_{1093}$).

A compound (L-8 wherein $A^1$ represents a nitrogen atom, $R^4$ represents a chlorine atom, $R^5$ represents a cyclopropyl group, and T represents any substituents indicated in Table 1 to Table 6 (hereinafter, referred to as Compound Class $SX_{1094}$).

A compound (L-85) wherein $A^1$ represents a nitrogen atom, $R^4$ represents a methyl group, $R^5$ represents a methyl group, and T represents any substituents indicated in Table 1 to Table 6 (hereinafter, referred to as Compound Class $SX_{1095}$).

A compound (L-85) wherein $A^1$ represents a nitrogen atom, $R^4$ represents a methyl group, $R^5$ represents an ethyl group, and T represents any substituents indicated in Table 1 to Table 6 (hereinafter, referred to as Compound Class $SX_{1096}$).

A compound (L-85) wherein $A^1$ represents a nitrogen atom, $R^4$ represents a methyl group, $R^5$ represents a propyl group, and T represents any substituents indicated in Table 1 to Table 6 (hereinafter, referred to as Compound Class $SX_{1097}$).

A compound (L-85) wherein $A^1$ represents a nitrogen atom, $R^4$ represents a methyl group, $R^5$ represents an isopropyl group, and T represents any substituents indicated in Table 1 to Table 6 (hereinafter, referred to as Compound Class $SX_{1098}$).

A compound (L-85) wherein $A^1$ represents a nitrogen atom, $R^4$ represents a methyl group, $R^5$ represents a cyclopropyl group, and T represents any substituents indicated in Table 1 to Table 6 (hereinafter, referred to as Compound Class $SX_{1099}$).

A compound represented by formula (L-86):

(L-86)

(hereinafter, referred to as Compound (L-86)) wherein $A^1$ represents CH, $R^5$ represents a methyl group, and T represents any substituents indicated in Table 1 to Table 6 (hereinafter, referred to as Compound Class $SX_{1100}$).

A compound (L-86) wherein $A^1$ represents CH, $R^5$ represents an ethyl group, and T represents any substituents indicated in Table 1 to Table 6 (hereinafter, referred to as Compound Class $SX_{1101}$).

A compound (L-86) wherein $A^1$ represents a nitrogen atom, $R^5$ represents a methyl group, and T represents any substituents indicated in Table 1 to Table 6 (hereinafter, referred to as Compound Class $SX_{1102}$).

A compound (L-86) wherein $A^1$ represents a nitrogen atom, $R^5$ represents an ethyl group, and T represents any substituents indicated in Table 1 to Table 6 (hereinafter, referred to as Compound Class $SX_{1103}$).

A compound (L-86) wherein $A^1$ represents a nitrogen atom, $R^5$ represents a propyl group, and T represents any substituents indicated in Table 1 to Table 6 (hereinafter, referred to as Compound Class $SX_{1104}$).

A compound (L-86) wherein $A^1$ represents a nitrogen atom, $R^5$ represents an isopropyl group, and T represents any substituents indicated in Table 1 to Table 6 (hereinafter, referred to as Compound Class $SX_{1105}$).

A compound (L-86) wherein $A^1$ represents a nitrogen atom, $R^5$ represents a cyclopropyl group, and T represents any substituents indicated in Table 1 to Table 6 (hereinafter, referred to as Compound Class $SX_{1106}$).

A compound represented by formula (L-87):

(L-87)

(hereinafter, referred to as Compound (L-87)) wherein $A^1$ represents CH, $R^4$ represents a hydrogen atom, $R^5$ represents a methyl group, and T represents any substituents indicated in Table 1 to Table 6 (hereinafter, referred to as Compound Class $SX_{1107}$).

A compound (L-87) wherein $A^1$ represents CH, $R^4$ represents a hydrogen atom, $R^5$ represents an ethyl group, and T represents any substituents indicated in Table 1 to Table 6 (hereinafter, referred to as Compound Class $SX_{1108}$).

A compound (L-87) wherein $A^1$ represents a nitrogen atom, $R^4$ represents a hydrogen atom, $R^5$ represents a methyl group, and T represents any substituents indicated in Table 1 to Table 6 (hereinafter, referred to as Compound Class $SX_{1109}$).

A compound (L-87) wherein $A^1$ represents a nitrogen atom, $R^4$ represents a hydrogen atom, $R^5$ represents an ethyl group, and T represents any substituents indicated in Table 1 to Table 6 (hereinafter, referred to as Compound Class $SX_{1110}$).

A compound (L-87) wherein $A^1$ represents a nitrogen atom, $R^4$ represents a hydrogen atom, $R^5$ represents a propyl group, and T represents any substituents indicated in Table 1 to Table 6 (hereinafter, referred to as Compound Class $SX_{1111}$).

A compound (L-87) wherein $A^1$ represents a nitrogen atom, $R^4$ represents a hydrogen atom, $R^5$ represents an isopropyl group, and T represents any substituents indicated in Table 1 to Table 6 (hereinafter, referred to as Compound Class $SX_{1112}$).

A compound (L-87) wherein $A^1$ represents a nitrogen atom, $R^4$ represents a hydrogen atom, $R^5$ represents a cyclopropyl group, and T represents any substituents indicated in Table 1 to Table 6 (hereinafter, referred to as Compound Class $SX_{1113}$).

A compound (L-87) wherein $A^1$ represents a nitrogen atom, $R^4$ represents a chlorine atom, $R^5$ represents a methyl group, and T represents any substituents indicated in Table 1 to Table 6 (hereinafter, referred to as Compound Class $SX_{1114}$).

A compound (L-87) wherein $A^1$ represents a nitrogen atom, $R^4$ represents a chlorine atom, $R^5$ represents an ethyl group, and T represents any substituents indicated in Table 1 to Table 6 (hereinafter, referred to as Compound Class $SX_{1115}$).

A compound (L-87) wherein $A^1$ represents a nitrogen atom, $R^4$ represents a chlorine atom, $R^5$ represents a propyl group, and T represents any substituents indicated in Table 1 to Table 6 (hereinafter, referred to as Compound Class $SX_{1116}$).

A compound (L-87) wherein $A^1$ represents a nitrogen atom, $R^4$ represents a chlorine atom, $R^5$ represents an isopropyl group, and T represents any substituents indicated in Table 1 to Table 6 (hereinafter, referred to as Compound Class $SX_{1117}$).

A compound (L-87) wherein $A^1$ represents a nitrogen atom, $R^4$ represents a chlorine atom, $R^5$ represents a cyclopropyl group, and T represents any substituents indicated in Table 1 to Table 6 (hereinafter, referred to as Compound Class $SX_{1118}$).

A compound (L-87) wherein $A^1$ represents a nitrogen atom, $R^4$ represents a chlorine atom, $R^5$ represents a methyl group, and T represents any substituents indicated in Table 1 to Table 6 (hereinafter, referred to as Compound Class $SX_{1119}$).

A compound (L-87) wherein $A^1$ represents a nitrogen atom, $R^4$ represents a chlorine atom, $R^5$ represents an ethyl group, and T represents any substituents indicated in Table 1 to Table 6 (hereinafter, referred to, Compound Class $SX_{1120}$).

A compound (L-87) wherein $A^1$ represents a nitrogen atom, $R^4$ represents a chlorine atom, $R^5$ represents a propyl group, and T represents any substituents indicated in Table 1 to Table 6 (hereinafter, referred to as Compound Class $SX_{1121}$).

A compound (L-87) wherein $A^1$ represents a nitrogen atom, $R^4$ represents a chlorine atom, $R^5$ represents an isopropyl group, and T represents any substituents indicated in Table 1 to Table 6 (hereinafter, referred to as Compound Class $SX_{1122}$).

A compound (L-67) wherein $A^1$ represents a nitrogen atom, $R^4$ represents a chlorine atom, $R^5$ represents a cyclopropyl group, and T represents any substituents indicated in Table 1 to Table 6 (hereinafter, referred to as Compound Class $SX_{1123}$).

A compound represented by formula (L-88):

(L-88)

(hereinafter, referred to as Compound (L-88)) wherein $A^1$ represents CH, $R^5$ represents a methyl group, and T represents any substituents indicated in Table 1 to Table 6 (hereinafter, referred to as Compound Class $SX_{1124}$).

A compound (L-88) wherein $A^1$ represents CH, $R^5$ represents an ethyl group, and T represents any substituents indicated in Table 1 to Table 6 (hereinafter, referred to as Compound Class $SX_{1125}$).

A compound (L-88) wherein $A^1$ represents a nitrogen atom, $R^5$ represents a methyl group, and T represents any substituents indicated in Table 1 to Table 6 (hereinafter, referred to as Compound Class $SX_{1126}$).

A compound (L-88) wherein $A^1$ represents a nitrogen atom, $R^5$ represents an ethyl group, and T represents any substituents indicated in Table 1 to Table 6 (hereinafter, referred to as Compound Class $SX_{1127}$).

A compound (L-88) wherein $A^1$ represents a nitrogen atom, $R^5$ represents a propyl group, and T represents any substituents indicated in Table 1 to Table 6 (hereinafter, referred to as Compound Class $SX_{1128}$).

A compound (L-88) wherein $A^1$ represents a nitrogen atom, $R^5$ represents an isopropyl group, and T represents any substituents indicated in Table 1 to Table 6 (hereinafter, referred to as Compound Class $SX_{1129}$).

A compound (L-88) wherein $A^1$ represents a nitrogen atom, $R^5$ represents a cyclopropyl group, and T represents any substituents indicated in Table 1 to Table 6 (hereinafter, referred to as Compound Class $SX_{1130}$).

Next, specific examples of an intermediate compound for preparing the compound Z of the present invention are indicated below.

A compound represented by formula (LL-1):

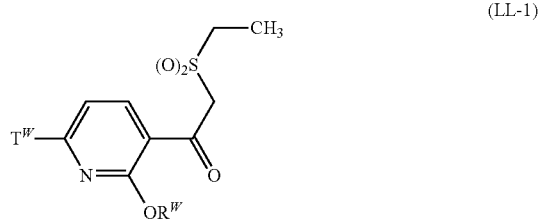

(LL-1)

(hereinafter, referred to as Compound (LL-1)) wherein $R^w$ represents a hydrogen atom, and $T^W$ represents any substituents indicated in Table 1 to Table 6 and Table 16.

TABLE 16

| SMe |
| SEt |
| SPr |
| S(i-Pr) |
| S(O)Me |
| S(O)Et |
| S(O)Pr |
| S(O)i-Pr |
| S(O)$_2$Me |
| S(O)$_2$Et |
| S(O)$_2$Pr |
| S(O)$_2$i-Pr |
| OS(O)$_2$Me |
| OS(O)$_2$Et |
| OS(O)$_2$Pr |
| OMe |
| Oi-Pr |
| OCH$_2$OMe |
| OBn |
| OCH$_2$(4-OMe—Ph) |
| OC(O)Me |
| OC(O)Et |
| OC(O)CMe$_3$ |
| OH |
| F |
| Cl |
| Br |
| I |

A compound (LL-1) wherein $R^w$ represents a methyl group, and $T^W$ represents any substituents indicated in Table 1 to Table 6 and Table 16.

A compound (LL-1) wherein $R^w$ represents a benzyl group, and $T^W$ represents any substituents indicated in Table 1 to Table 6 and Table 16.

A compound represented by formula (LL-2):

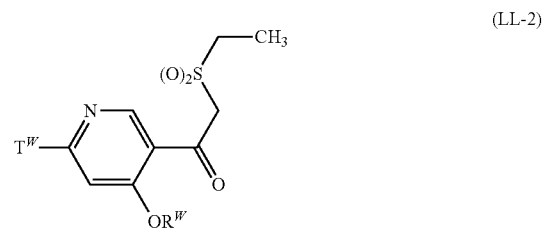

(LL-2)

(hereinafter, referred to as Compound (LL-2)) wherein $R^w$ represents a hydrogen atom, and $T^W$ represents any substituents indicated in Table 1 to Table 6 and Table 16.

A compound (LL-2) wherein $R^w$ represents a methyl group, and $T^W$ represents any substituents indicated in Table 1 to Table 6 and Table 16.

A compound (LL-2) wherein $R^w$ represents a benzyl group, and $T^W$ represents any substituents indicated in Table 1 to Table 6 and Table 16.

A compound represented by formula (LL-3):

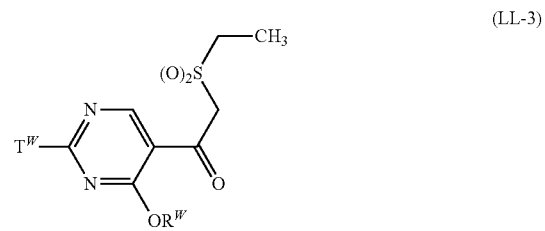

(LL-3)

(hereinafter, referred to as Compound (LL-3)) wherein $R^w$ represents a hydrogen atom, and $T^W$ represents any substituents indicated in Table 1 to Table 6 and Table 16.

A compound (LL-3) wherein $R^w$ represents a methyl group, and $T^W$ represents any substituents indicated in Table 1 to Table 6 and Table 16.

A compound (LL-3) wherein $R^{ow}$ represents a benzyl group, and $T^W$ represents any substituents indicated in Table 1 to Table 6 and Table 16.

A compound represented by formula (LL-4):

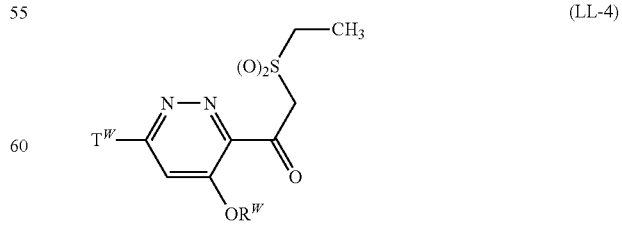

(LL-4)

(hereinafter, referred to as Compound (LL-4)) wherein $R^{ow}$ represents a hydrogen atom, and $T^W$ represents any substituents indicated in Table 1 to Table 6 and Table 16.

A compound (LL-4) wherein $R^w$ represents a methyl group, and $T^W$ represents any substituents indicated in Table 1 to Table 6 and Table 16.

A compound (LL-4) wherein $R^w$ represents a benzyl group, and $T^W$ represents any substituents indicated in Table 1 to Table 6 and Table 16.

A compound represented by formula (LL-5):

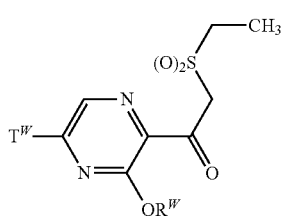

(LL-5)

(hereinafter, referred to as Compound (LL-5)) wherein $R^w$ represents a hydrogen atom, and $T^w$ represents any substituents indicated in Table 1 to Table 6 and Table 16.

A compound (LL-5) wherein $R^w$ represents a methyl group, and $T^W$ represents any substituents indicated in Table 1 Table 6 and Table 16.

A compound (LL-5) wherein $R^w$ represents a benzyl group, and $T^W$ represents any substituents indicated in Table 1 to Table 6 and Table 16.

A compound represented by formula (LL-6):

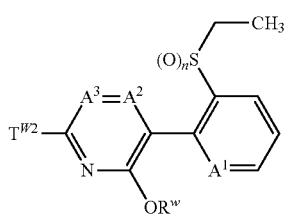

(LL-6)

(hereinafter, referred to as Compound (LL-6)) wherein $A^1$ represents CH, $A^2$ and $A^3$ represent CH, $R^w$ represents a hydrogen atom, n is 0, and $T^{W2}$ represents any substituents indicated in Table 1 to Table 6 and Table 16.

A compound (LL-6) wherein $A^1$ represents CH, $A^2$ and $A^3$ represent CH, $R^w$ represents a hydrogen atom, n is 2, and $T^{W2}$ represents any substituents indicated in Table 1 to Table 6 and Table 16.

A compound (LL-6) wherein $A^1$ represents a nitrogen atom, $A^2$ and $A^3$ represent CH, $R^w$ represents a hydrogen atom, n is 0, and $T^{W2}$ represents any substituents indicated in Table 1 to Table 6 and Table 16.

A compound (LL-6) wherein $A^1$ represents a nitrogen atom, $A^2$ and $A^3$ represent CH, $R^w$ represents a hydrogen atom, n is 2, and $T^{W2}$ represents any substituents indicated in Table 1 to Table 6 and Table 16.

A compound (LL-6) wherein $A^1$ represents a nitrogen atom, $A^2$ and $A^3$ represent CH, $R^w$ represents a methyl group, n is 0, and $T^{W2}$ represents any substituents indicated in Table 1 to Table 6 and Table 16.

A compound (LL-6) wherein $A^1$ represents a nitrogen atom, $A^2$ and $A^3$ represent CH, $R^w$ represents a methyl group, n is 2, and $T^{W2}$ represents any substituents indicated in Table 1 to Table 6 and Table 16.

A compound (LL-6) wherein $A^1$ represents a nitrogen atom, $A^2$ and $A^3$ represent CH, $R^w$ represents a benzyl group, n is 0, and $T^{W2}$ represents any substituents indicated in Table 1 to Table 6 and Table 16.

A compound (LL-6) wherein $A^1$ represents a nitrogen atom, $A^2$ and $A^3$ represent CH, $R^w$ represents a benzyl group, n is 2, and $T^{W2}$ represents any substituents indicated in Table 1 to Table 6 and Table 16.

A compound (LL-6) wherein $A^1$ represents a nitrogen atom, $A^2$ represents CH, $A^3$ represents a nitrogen atom, $R^w$ represents a hydrogen atom, n is 0, and $T^{W2}$ represents any substituents indicated in Table 1 to Table 6 and Table 16.

A compound (LL-6) wherein $A^1$ represents a nitrogen atom, $A^2$ represents CH, $A^3$ represents a nitrogen atom, $R^w$ represents a hydrogen atom, n is 2, and $T^{W2}$ represents any substituents indicated in Table 1 to Table 6 and Table 16.

A compound (LL-6) wherein $A^1$ represents a nitrogen atom, represents CH, $A^3$ represents a nitrogen atom, $R^w$ represents a methyl group, n is 0, and $T^{W2}$ represents any substituents indicated in Table 1 to Table 6 and Table 16.

A compound (LL-6) wherein $A^1$ represents a nitrogen atom, $A^2$ represents CH, $A^3$ represents a nitrogen atom, $R^w$ represents a methyl group, n is 2, and $T^{W2}$ represents any substituents indicated in Table 1 to Table 6 and Table 16.

A compound (LL-6) wherein $A^1$ represents a nitrogen atom, $A^2$ represents CH, $A^3$ represents a nitrogen atom, $R^w$ represents a benzyl group, n is 0, and $T^{W2}$ represents any substituents indicated in Table 1 to Table 6 and Table 16.

A compound (LL-6) wherein $A^1$ represents a nitrogen atom, $A^2$ represents CH, $A^3$ represents a nitrogen atom, $R^w$ represents a benzyl group, n is 2, and $T^{W2}$ represents any substituents indicated in Table 1 to Table 6 and Table 16.

A compound represented by formula (LL-7):

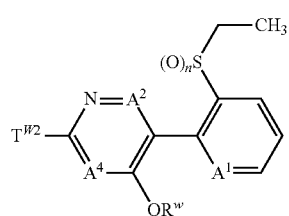

(LL-7)

(hereinafter, referred to as Compound (LL-1)) wherein $A^1$ represents CH, $A^2$ and $A^4$ represent CH, $R^w$ represents a hydrogen atom, n is 0, and $T^{W2}$ represents any substituents indicated in Table 1 to Table 6 and Table 16.

A compound (LL-7) wherein $A^1$ represents CH, $A^2$ and $A^4$ represent CH, $R^w$ represents a hydrogen atom, n is 2, and $T^{W2}$ represents any substituents indicated in Table 1 to Table 6 and Table 16.

A compound (LL-7) wherein $A^1$ represents a nitrogen atom, $A^2$ and $A^4$ represent CH, $R^w$ represents a hydrogen atom, n is 0, and $T^{W2}$ represents any substituents indicated in Table 1 to Table 6 and Table 16.

A compound (LL-7) wherein $A^1$ represents a nitrogen atom, $A^2$ and $A^4$ represent CH, $R^w$ represents a hydrogen atom, n is 2, and $T^{W2}$ represents any substituents indicated in Table 1 to Table 6 and Table 16.

A compound (LL-7) wherein $A^1$ represents a nitrogen atom, $A^2$ and $A^4$ represent CH, $R^w$ represents a methyl group, n is 0, and $T^{W2}$ represents any substituents indicated in Table 1 to Table 6 and Table 16.

A compound (LL-7) wherein $A^1$ represents a nitrogen atom, $A^2$ and $A^4$ represent CH, $R^w$ represents a methyl group, n and $T^{W2}$ represents any substituents indicated in Table 1 to Table 6 and Table 16.

A compound (LL-7) wherein $A^1$ represents a nitrogen atom, $A^2$ and $A^4$ represent CH, $R^w$ represents a benzyl group, n is 0, and $T^{W2}$ represents any substituents indicated in Table 1 to Table 6 and Table 16.

A compound (LL-7) wherein $A^1$ represents a nitrogen atom, $A^2$ and $A^4$ represent CH, $R^w$ represents a benzyl group, n is 2, and $T^{W2}$ represents any substituents indicated in Table 1 to Table 6 and Table 16.

A compound (LL-7) wherein $A^1$ represents a nitrogen atom, $A^2$ represents CH, $A^4$ represents a nitrogen atom, $R^w$ represents a hydrogen atom, n is 0, and $T^{W2}$ represents any substituents indicated in Table 1 to Table 6 and Table 16.

A compound (LL-7) wherein $A^1$ represents a nitrogen atom, $A^2$ represents CH, $A^4$ represents a nitrogen atom, $R^w$ represents a hydrogen atom, n is 2, and $T^{W2}$ represents any substituents indicated in Table 1 to Table 6 and Table 16.

A compound (LL-7) wherein $A^1$ represents a nitrogen atom, $A^2$ represents CH, $A^4$ represents a nitrogen atom, $R^w$ represents a methyl group, n is 0, and $T^{W2}$ represents any substituents indicated in Table 1 to Table 6 and Table 16.

A compound (LL-7) wherein $A^1$ represents a nitrogen atom, $A^2$ represents CH, $A^4$ represents a nitrogen atom, $R^w$ represents a methyl group, n is 2, and $T^{W2}$ represents any substituents indicated in Table 1 to Table 6 and Table 16.

A compound (LL-7) wherein $A^1$ represents a nitrogen atom, $A^2$ represents CH, $A^4$ represents a nitrogen atom, $R^w$ represents a benzyl group, n is 0, and $T^{W2}$ represents any substituents indicated in Table 1 to Table 6 and Table 16.

A compound (LL-7) wherein $A^1$ represents a nitrogen atom, $A^2$ represents CH, $A^4$ represents a nitrogen atom, $R^w$ represents a benzyl group, n is 2, and $T^{W2}$ represents any substituents indicated in Table 1 to Table 6 and Table 16.

A compound represented by formula (LL-8):

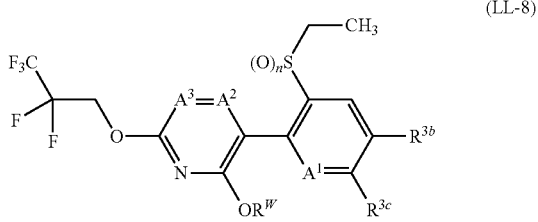

(hereinafter, referred to as Compound (LL-8)) wherein $A^1$ represents CH, $A^2$ and $A^3$ represent CH, $R^w$ represents a hydrogen atom, n is 0, $R^{3b}$ represents a hydrogen atom, and $R^{3c}$ represents any substituents indicated in Table 7 to Table 15.

A compound (LL-8) wherein $A^1$ represents CH, $A^2$ and $A^3$ represent CH, $R^w$ represents a hydrogen atom, n is 2, $R^{3b}$ represents a hydrogen atom, and $R^{3c}$ represents any substituents indicated in Table 7 to Table 15.

A compound (LL-8) wherein $A^1$ represents CH, $A^2$ and $A^3$ represent CH, $R^w$ represents a hydrogen atom, n is 0, $R^{3c}$ represents a hydrogen atom, and $R^{3b}$ represents any substituents indicated in Table 7 to Table 15.

A compound (LL-8) wherein $A^1$ represents CH, $A^2$ and $A^3$ represent CH, $R^w$ represents a hydrogen atom, n is 2, $R^{3c}$ represents a hydrogen atom, and $R^{3b}$ represents any substituents indicated in Table 7 to Table 15.

A compound (LL-8) wherein $A^1$ represents a nitrogen atom, $A^2$ and $A^3$ represent CH, $R^w$ represents a hydrogen atom, n is 0, $R^{3c}$ represents a hydrogen atom, and $R^{3b}$ represents any substituents indicated in Table 7 to Table 15.

A compound (LL-8) wherein $A^1$ represents a nitrogen atom, $A^2$ and $A^3$ represent CH, $R^w$ represents a hydrogen atom, n is 2, $R^{3c}$ represents a hydrogen atom, and $R^{3b}$ represents any substituents indicated in Table 7 to Table 15.

A compound (LL-8) wherein $A^1$ represents a nitrogen atom, $A^2$ and $A^3$ represent CH, $R^w$ represents a hydrogen atom, n is 0, $R^{3c}$ represents a hydrogen atom, and $R^{3b}$ represents any substituents indicated in Table 7 to Table 15.

A compound (LL-8) wherein $A^1$ represents a nitrogen atom, $A^1$ and $A^3$ represent CH, $R^w$ represents a hydrogen atom, n is 2, $R^{3c}$ represents a hydrogen atom, and $R^{3b}$ represents any substituents indicated in Table 7 to Table 15.

A compound (LL-8) wherein $A^1$ represents a nitrogen atom, $A^2$ and $A^3$ represent CH, $R^w$ represents a methyl group, n is 0, $R^{3b}$ represents a hydrogen atom, and $R^{3c}$ represents any substituents indicated in Table 7 to Table 15.

A compound (LL-8) wherein $A^1$ represents a nitrogen atom, $A^2$ and $A^3$ represent CH, $R^w$ represents a methyl group, n is 2, $R^{3b}$ represents a hydrogen atom, and $R^{3c}$ represents any substituents indicated in Table 7 to Table 15.

A compound (LL-8) wherein $A^1$ represents a nitrogen atom, $A^2$ and $A^3$ represent CH, $R^w$ represents a methyl group, n is 0, $R^{3c}$ represents a hydrogen atom, and $R^{3b}$ represents any substituents indicated in Table 7 to Table 15.

A compound (LL-8) wherein $A^1$ represents a nitrogen atom, $A^2$ and $A^3$ represent CH, $R^w$ represents a methyl group, n is 2, $R^{3c}$ represents a hydrogen atom, and $R^{3b}$ represents any substituents indicated in Table 7 to Table 15.

A compound (LL-8) wherein $A^1$ represents a nitrogen atom, $A^2$ represents CH, $A^3$ represents a nitrogen atom, $R^w$ represents a hydrogen atom, is 0, $R^{3b}$ represents a hydrogen atom, and $R^{3c}$ represents any substituents indicated in Table 7 to Table 15.

A compound (LL-8) wherein $A^1$ represents a nitrogen atom, $A^2$ represents CH, $A^3$ represents a nitrogen atom, $R^w$ represents a hydrogen atom, n is 2, $R^{3b}$ represents a hydrogen atom, and $R^{3c}$ represents any substituents indicated in Table 7 to Table 15.

A compound (LL-8) wherein $A^1$ represents a nitrogen atom, $A^2$ represents CH, $R^w$ represents a hydrogen atom, n is 0, $R^{3c}$ represents a hydrogen atom, and $R^{3b}$ represents any substituents indicated in Table 7 to Table 15.

A compound (LL-8) wherein $A^1$ represents a nitrogen atom, $A^2$ represents CH, $A^3$ represents a nitrogen atom, $R^w$ represents a hydrogen atom, n is 2, $R^{3c}$ represents a hydrogen atom, and $R^{3b}$ represents any substituents indicated in Table 7 to Table 15.

A compound (LL-8) wherein $A^1$ represents a nitrogen atom, $A^2$ represents CH, $A^3$ represents a nitrogen atom, $R^w$ represents a methyl group, n is 0, $R^{3b}$ represents a hydrogen atom, and $R^{3c}$ represents any substituents indicated in Table 7 to Table 15.

A compound (LL-8) wherein $A^1$ represents a nitrogen atom, $A^2$ represents CH, $A^3$ represents a nitrogen atom, $R^w$ represents a methyl group, n is 2, $R^{3b}$ represents a hydrogen atom, and $R^{3c}$ represents any substituents indicated in Table 7 to Table 15.

A compound (LL-8) wherein $A^1$ represents a nitrogen atom, $A^2$ represents CH, $A^3$ represents a nitrogen atom, $R^w$ represents a methyl group, n is 0, $R^{3c}$ represents a hydrogen atom, and $R^{3b}$ represents any substituents indicated in Table 7 to Table 15.

A compound (LL-8) wherein $A^1$ represents a nitrogen atom, $A^2$ represents CH, $A^3$ represents a nitrogen atom, $R^w$ represents a methyl group, n is 2, $R^{3c}$ represents a hydrogen atom, and $R^{3b}$ represents any substituents indicated in Table 7 to Table 15.

211

A compound represented by formula (LL-9):

(LL-9)

[Chemical structure diagram showing a compound with F₃C-CF-CH₂-O- group attached to a ring system with A², A⁴, A¹ positions, OR^W, R^3b, R^3c substituents, and (O)ₙS-CH₃ group]

(hereinafter, referred to as Compound (LL-9)) wherein $A^1$ represents CH, $A^2$ and $A^4$ represent CH, $R^w$ represents a hydrogen atom, n is 0, $R^{3b}$ represents a hydrogen atom, and $R^{3c}$ represents any substituents indicated in Table 7 to Table 15.

A compound (LL-9) wherein $A^1$ represents CH, $A^2$ and $A^4$ represent CH, $R^w$ represents a hydrogen atom, a is 2, $R^{3b}$ represents a hydrogen atom, and $R^{3c}$ represents any substituents indicated in Table 7 to Table 15.

A compound (LL-9) wherein $A^1$ represents CH, $A^2$ and $A^4$ represent CH, $R^w$ represents a hydrogen atom, n is 0, $R^{3c}$ represents a hydrogen atom, and $R^{3b}$ represents any substituents indicated in Table 7 to Table 15.

A compound (LL-9) wherein $A^1$ represents CH, $A^2$ and $A^4$ represent CH, $R^w$ represents a hydrogen atom, n is 2, $R^{3c}$ represents a hydrogen atom, and $R^{3b}$ represents any substituents indicated in Table 7 to Table 15.

A compound (LL-9) wherein $A^1$ represents a nitrogen atom, $A^2$ and $A^4$ represent CH, $R^w$ represents a hydrogen atom, n is 0, $R^{3b}$ represents a hydrogen atom, and $R^{3c}$ represents any substituents indicated in Table 7 to Table 15.

A compound (LL-9) wherein $A^1$ represents a nitrogen atom, $A^2$ and $A^4$ represent CH, $R^w$ represents a hydrogen atom, n is 0, $R^{3b}$ represents a hydrogen atom, and $R^{3c}$ represents any substituents indicated in Table 7 to Table 15.

A compound (LL-9) wherein $A^1$ represents a nitrogen atom, $A^2$ and $A^4$ represent CH, $R^w$ represents a hydrogen atom, n is 0, $R^{3c}$ represents a hydrogen atom, and $R^{3b}$ represents any substituents indicated in Table 7 to Table 15.

A compound (LL-9) wherein $A^1$ represents a nitrogen atom, $A^2$ and $A^4$ represent CH, $R^w$ represents a hydrogen atom, n is 2, $R^{3c}$ represents a hydrogen atom, and $R^{3b}$ represents any substituents indicated in Table 7 to Table 15.

A compound (LL-9) wherein $A^1$ represents a nitrogen atom, $A^2$ and $A^4$ represent CH, $R^w$ represents a methyl group, n is 0, $R^{3b}$ represents a hydrogen atom, and $R^{3c}$ represents any substituents indicated in Table 7 to Table 15.

A compound (LL-9) wherein $A^1$ represents a nitrogen atom, $A^2$ and $A^4$ represent CH, $R^w$ represents a methyl group, n is 2, $R^{3b}$ represents a hydrogen atom, and $R^{3c}$ represents any substituents indicated in Table 7 to Table 15.

A compound (LL-9) wherein $A^1$ represents a nitrogen atom, $A^2$ and $A^4$ represent CH, $R^w$ represents a methyl group, n is 0, $R^{3c}$ represents a hydrogen atom, and $R^{3b}$ represents any substituents indicated in Table 7 to Table 15.

A compound (LL-9) wherein $A^1$ represents a nitrogen atom, $A^2$ and $A^4$ represent CH, $R^w$ represents a methyl group, n is 2, $R^{3c}$ represents a hydrogen atom, and $R^{3b}$ represents any substituents indicated in Table 7 to Table 15.

A compound (LL-9) wherein $A^1$ represents a nitrogen atom, $A^2$ represents CH, $A^4$ represents a nitrogen atom, $R^w$ represents a hydrogen atom, n is 0, $R^{3b}$ represents a hydrogen atom, and $R^{3c}$ represents any substituents indicated in Table 7 to Table 15.

212

A compound (LL-9) wherein $A^1$ represents a nitrogen atom, $A^2$ represents CH, $A^4$ represents a nitrogen atom, $R^w$ represents a hydrogen atom, n is 2, $R^{3b}$ represents a hydrogen atom, and $R^{3c}$ represents any substituents indicated in Table 7 to Table 15.

A compound (LL-9) wherein $A^1$ represents a nitrogen atom, $A^2$ represents CH, $A^4$ represents a nitrogen atom, $R^w$ represents a hydrogen atom, n is 0, $R^{3c}$ represents a hydrogen atom, and $R^{3b}$ represents any substituents indicated in Table 7 to Table 15.

A compound (LL-9) wherein $A^1$ represents a nitrogen atom, $A^2$ represents CH, $A^4$ represents a nitrogen atom, $R^w$ represents a hydrogen atom, n is 2, $R^{3c}$ represents a hydrogen atom, and $R^{3b}$ represents any substituents indicated in Table 7 to Table 15.

A compound (LL-9) wherein $A^1$ represents a nitrogen atom, $A^2$ represents CH, $A^4$ represents a nitrogen atom, $R^w$ represents a methyl group, n is 0, $R^{3b}$ represents a hydrogen atom, and $R^{3c}$ represents any substituents indicated in Table 7 to Table 15.

A compound (LL-9) wherein $A^1$ represents a nitrogen atom, $A^2$ represents CH, $A^4$ represents a nitrogen atom, $R^w$ represents a methyl group, n is 2, $R^{3b}$ represents a hydrogen atom, and $R^{3c}$ represents any substituents indicated in Table 7 to Table 15.

A compound (LL-9) wherein $A^1$ represents a nitrogen atom, $A^2$ represents CH, $A^4$ represents a nitrogen atom, $R^w$ represents a methyl group, n is 0, $R^{3c}$ represents a hydrogen atom, and $R^{3b}$ represents any substituents indicated in Table 7 to Table 15.

A compound (LL-9) wherein $A^1$ represents a nitrogen atom, $A^2$ represents CH, $A^4$ represents a nitrogen atom, $R^w$ represents a methyl group, n is 2, $R^{3c}$ represents a hydrogen atom, and $R^{3b}$ represents any substituents indicated, in Table 7 to Table 15.

A compound represented by formula (LL-10):

(LL-10)

[Chemical structure diagram showing a compound with Cl-, A³-A², A¹, N-R⁵, O, R^3b, R^3c substituents, and (O)ₙS-CH₃ group]

(hereinafter, referred to as Compound (LL-10)) wherein $A^1$ represents CH, $A^2$ and $A^3$ represent CH, $R^5$ represents a methyl group, n is 0, $R^{3b}$ represents a hydrogen atom, and $R^{3c}$ represents any substituents indicated in Table 7 to Table 15.

A compound (LL-10) wherein $A^1$ represents CH, $A^2$ and $A^3$ represent CH, $R^5$ represents a methyl group, n is 2, $R^{3b}$ represents a hydrogen atom, and $R^{3c}$ represents any substituents indicated in Table 7 to Table 1.5

A compound (LL-10) wherein $A^1$ represents CH, $A^2$ and $A^3$ represent CH, $R^5$ represents a methyl group, n is 0, $R^{3c}$ represents a hydrogen atom, and $R^{3b}$ represents any substituents indicated in Table 7 to Table 15.

A compound (LL-10) wherein $A^1$ represents CH, $A^2$ and $A^3$ represent CH, $R^5$ represents a methyl group, n is 2, $R^{3c}$ represents a hydrogen atom, and $R^{3b}$ represents any substituents indicated in Table 7 to Table 15.

A compound (LL-10) wherein $A^1$ represents a nitrogen atom, $A^2$ and $A^3$ represent CH, $R^5$ represents a methyl group, n is 0, $R^{3b}$ represents a hydrogen atom, and $R^{3c}$ represents any substituents indicated in Table 7 to Table 15.

A compound (LL-10) wherein $A^1$ represents a nitrogen atom, $A^2$ and $A^3$ represent CH, $R^5$ represents a methyl group, n is 2, $R^{3b}$ represents a hydrogen atom, and $R^{3c}$ represents any substituents indicated in Table 7 to Table 15.

A compound (LL-10) wherein $A^1$ represents a nitrogen atom, $A^2$ and $A^3$ represent CH, $R^5$ represents a methyl group, n is 0, $R^{3b}$ represents a hydrogen atom, and $R^{3c}$ represents any substituents indicated in Table 7 to Table 15.

A compound (LL-10) wherein $A^1$ represents a nitrogen atom, $A^2$ and $A^3$ represent CH, $R^5$ represents a methyl group, n is 2, $R^{3c}$ represents a hydrogen atom, and $R^{3b}$ represents any substituents indicated in Table 7 to Table 15.

A compound (LL-10) wherein $A^1$ represents a nitrogen atom, $A^2$ represents CH, $A^3$ represents a nitrogen atom, $R^5$ represents a methyl group, n is 0, $R^{3b}$ represents a hydrogen atom, and $R^{3c}$ represents any substituents indicated in Table 7 to Table 15.

A compound (LL-10) wherein $A^1$ represents a nitrogen atom, $A^2$ represents CH, $A^3$ represents a nitrogen atom, $R^5$ represents a methyl group, n is 2, $R^{3b}$ represents a hydrogen atom, and $R^{3c}$ represents any substituents indicated in Table 7 to Table 15.

A compound (LL-10) wherein $A^1$ represents a nitrogen atom, $A^2$ represents CH, $A^3$ represents a nitrogen atom, $R^5$ represents a methyl group, n is 0, $R^{3c}$ represents a hydrogen atom, and $R^{3b}$ represents any substituents indicated in Table 7 to Table 15.

A compound (LL-10) wherein $A^1$ represents a nitrogen atom, $A^2$ represents CH, $A^3$ represents a nitrogen atom, $R^5$ represents a methyl group, n is 2, $R^{3c}$ represents a hydrogen atom, and $R^{3b}$ represents any substituents indicated in Table 7 to Table 15.

A compound represented by formula (LL-11):

(LL-11)

(hereinafter, referred to as Compound (LL-11)) wherein $A^1$ represents CH, $A^2$ and $A^3$ represent CH, $R^5$ represents a methyl group, $R^{3b}$ represents a hydrogen atom, and $R^{3c}$ represents any substituents indicated in Table 7 to Table 15.

A compound (LL-11) wherein $A^1$ represents CH, $A^2$ and $A^3$ represent CH, $R^5$ represents a methyl group, $R^{3c}$ represents a hydrogen atom, and $R^{3b}$ represents any substituents indicated in Table 7 to Table 15.

A compound (LL-11) wherein $A^1$ represents a nitrogen atom, $A^2$ and $A^3$ represent CH, $R^5$ represents a methyl group, $R^{3b}$ represents a hydrogen atom, and $R^{3c}$ represents any substituents indicated in Table 7 to Table 15.

A compound (LL-11) wherein $A^1$ represents a nitrogen atom, $A^2$ and $A^3$ represent CH, $R^5$ represents a methyl group, $R^{3c}$ represents a hydrogen atom, and $R^{3b}$ represents any substituents indicated in Table 7 to Table 15.

A compound (LL-11) wherein $A^1$ represents a nitrogen atom, $A^2$ represents CH, $A^3$ represents a nitrogen atom, $R^5$ represents a methyl group, $R^{3b}$ represents a hydrogen atom, and $R^{3c}$ represents any substituents indicated in Table 7 to Table 15.

A compound (LL-11) wherein $A^1$ represents a nitrogen atom, $A^2$ represents CH, $A^3$ represents a nitrogen atom, $R^5$ represents a methyl group, $R^{3c}$ represents a hydrogen atom, and $R^{3b}$ represents any substituents indicated in Table 7 to Table 15.

A compound represented by formula (LL-12):

(LL-12)

(hereinafter, referred to as Compound (LL-12)) wherein $A^1$ represents CH, $A^2$ and $A^3$ represent CH, $R^5$ represents a methyl group, n is 0, $R^{3b}$ represents a hydrogen atom, and $R^{3c}$ represents any substituents indicated in Table 7 to Table 15.

A compound (LL-12) wherein $A^1$ represents CH, $A^2$ and $A^3$ represent CH, $R^5$ represents a methyl group, n is 2, $R^{3b}$ represents a hydrogen atom, and $R^{3c}$ represents any substituents indicated in Table 7 to Table 15.

A compound (LL-12) wherein $A^1$ represents CH, $A^2$ and $A^3$ represent CH, $R^5$ represents a methyl group, n is 0, $R^{3c}$ represents a hydrogen atom, and $R^{3b}$ represents any substituents indicated in Table 7 to Table 15.

A compound (LL-12) wherein $A^1$ represents CH, $A^2$ and $A^3$ represent CH, $R^5$ represents a methyl group, n is 2, $R^{3c}$ represents a hydrogen atom, and $R^{3b}$ represents any substituents indicated in Table 7 to Table 15.

A compound (LL-12) wherein $A^1$ represents a nitrogen atom, $A^2$ and $A^3$ represent CH, $R^5$ represents a methyl group, n is 0, $R^{3b}$ represents a hydrogen atom, and $R^{3c}$ represents any substituents indicated in Table 7 to Table 15.

A compound (LL-12) wherein $A^1$ represents a nitrogen atom, $A^2$ and $A^3$ represent CH, $R^5$ represents a methyl group, n is 2, $R^{3b}$ represents a hydrogen atom, and $R^{3c}$ represents any substituents indicated in Table 7 to Table 15.

A compound (LL-12) wherein $A^1$ represents a nitrogen atom, $A^2$ and $A^3$ represent CH, $R^5$ represents a methyl group, n is 0, $R^{3c}$ represents a hydrogen atom, and $R^{3b}$ represents any substituents indicated in Table 7 to Table 15.

A compound (LL-12) wherein $A^1$ represents a nitrogen atom, $A^2$ and $A^3$ represent CH, $R^5$ represents a methyl group, n is 2, $R^{3c}$ represents a hydrogen atom, and $R^{3b}$ represents any substituents indicated in Table 7 to Table 15.

A compound (LL-12) wherein $A^1$ represents a nitrogen atom, $A^2$ represents CH, $A^3$ represents a nitrogen atom, $R^5$ represents a methyl group, n is 0, $R^{3b}$ represents a hydrogen atom, and $R^{3c}$ represents any substituents indicated in Table 7 to Table 15.

A compound (LL-12) wherein $A^1$ represents a nitrogen atom, $A^2$ represents CH, $A^3$ represents a nitrogen atom, $R^5$ represents a methyl group, n is 2, $R^{3b}$ represents a hydrogen atom, and $R^{3c}$ represents any substituents indicated in Table 7 to Table 15.

A compound (LL-12) wherein $A^1$ represents a nitrogen atom, $A^2$ represents CH, $A^3$ represents a nitrogen atom, $R^5$ represents a methyl group, n is 0, $R^{3c}$ represents a hydrogen atom, and $R^{3b}$ represents any substituents indicated in Table 7 to Table 15.

A compound (LL-12) wherein $A^1$ represents a nitrogen atom, $A^2$ represents CH, $A^3$ represents a nitrogen atom, $R^5$ represents a methyl group, n is 2, $R^{3c}$ represents a hydrogen atom, and $R^{3b}$ represents any substituents indicated in Table 7 to Table 15.

A compound represented by formula (LL-13):

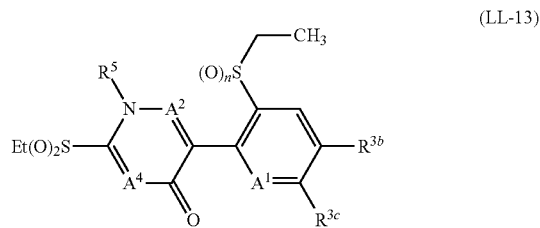

(LL-13)

(hereinafter, referred to as Compound (LL-13)) wherein $A^1$ represents CH, $A^2$ and $A^3$ represent CH, $R^5$ represents a methyl group, $R^{3b}$ represents a hydrogen atom, and $R^{3c}$ represents any substituents indicated in Table 7 to Table 15.

A compound (LL-13) wherein $A^1$ represents CH, $A^2$ and $A^3$ represent CH, $R^5$ represents a methyl group, $R^{3c}$ represents a hydrogen atom, and $R^{3b}$ represents any substituents indicated in Table 7 to Table 15.

A compound (LL-13) wherein $A^1$ represents a nitrogen atom, $A^2$ and $A^3$ represent CH, $R^5$ represents a methyl group, $R^{3b}$ represents a hydrogen atom, and $R^{3c}$ represents any substituents indicated in Table 7 to Table 15.

A compound (LL-13) wherein $A^1$ represents a nitrogen atom, $A^2$ and $A^3$ represent CH, $R^5$ represents a methyl group, $R^{3c}$ represents a hydrogen atom, and $R^{3b}$ represents any substituents indicated in Table 7 to Table 15.

A compound (LL-13) wherein $A^1$ represents a nitrogen atom, $A^2$ represents CH, $A^3$ represents a nitrogen atom, $R^5$ represents a methyl group, $R^{3b}$ represents a hydrogen atom, and $R^{3c}$ represents any substituents indicated in Table 7 to Table 15.

A compound (LL-13) wherein $A^1$ represents a nitrogen atom, $A^2$ represents CH, $A^3$ represents a nitrogen atom, $R^5$ represents a methyl group, $R^{3c}$ represents a hydrogen atom, and $R^{3b}$ represents any substituents indicated in Table 7 to Table 15.

All the compounds classes $SX_1$ to $SX_{1130}$ may be prepared according to the method described in the Example or the Process described herein.

The Present compound Z may be mixed or combined with one or more ingredients selected from a group consisting of the following Group (a), Group (b), Group (c), Group (d), and Group (e).

The Present compound may be mixed or combined with one or more ingredients selected from a group consisting of the following Group (a), Group (b), Group (c), Group (d), Group (e), Group (f), Group (g), and group (h) (hereinafter, referred to as Present ingredient).

The above-mentioned mixing or combining represents a use of Present compound Z and the Present ingredient at same time, separately or at certain intervals.

When the Present compound Z and the present ingredient are used at the same time, the Present compound Z and the Present ingredient may be contained in separate formulations respectively or may be contained in the same one formulation.

One aspect of the present invention is a composition comprising one or more ingredients selected from Group (a) or Group (b) as well as the Present compound Z.

Group (a) is a group consisting of Acetylcholinesterase inhibitors (for example, carbamate insecticides, or organophosphorus insecticides), ABA-gated chloride channel blockers (for example, phenylpyrazole insecticides), Sodium channel modulators (for example, pyrethroid insecticides), Nicotinic acetylcholine receptor competitive modulators (for example, neonicotinoid insecticides), Nicotinic acetylcholine receptor allosteric modulators, Glutamatergic chlorine ion channel allosteric modulators (for example, macrolide insecticides), Juvenile hormone mimic, Multisite inhibitors, chordotonal organ TRPV channel modulators, Mites growth inhibitors, Mitochondria ATP biosynthetic enzyme inhibitors, Uncouplers of oxidative phosphorylation, Nicotinic acetylcholine receptor channel blocker (for example, Nereistoxin insecticides), Chitin synthesis inhibitors, Molting inhibitors, Ecdysone receptor agonist, Octopamine receptor agonist, Inhibitors of Mitochondrial electron transport system complex I, II, III and IV, Voltage-dependent sodium channel blockers, Acetyl CoA carboxylase inhibitor, Ryanodine receptor modulator (for example, Diamide insecticides), Chordtonal organ modulators, Microbial pesticides, and the other insecticidal, miticidal or nematicidal active ingredients. These ingredients are classified as a class based on the action mechanism of IRAC.

Group (b) is a group consisting of Nucleic acid synthesis inhibitors (for example, Phenylamide fungicides, or Acylamino acid fungicides), Cell division and cytoskeleton inhibitors (for example, MBC fungicides), Respiratory inhibitors (for example, QoI fungicides or Qil fulgicides), Amino acid synthesis and protein synthesis inhibitors (for example, anilinopyridine fungicides), Signal transduction inhibitors, Lipid synthesis and membrane synthesis inhibitors, sterol biosynthesis inhibitors (for example, DMI fungicides such as triazole), Cell wall synthesis inhibitors, Melanin synthesis inhibitors, Plant defense inducers, Other action point contact active fungicides, Microbial fungicides, and the other fungicidal ingredients. These are classified as a class based on the action mechanism of FRAC.

Group (c) is a plant growth modulating ingredients group consisting of Plant growth modulating ingredients, Mycorrhizal fungi, and Root nodule bacteria.

Group (d) is a phytotoxicity-reducing ingredient group which reduces the phytotoxicity against the crop when it is used in combination with the other chemicals.

Group (e) is a synergist group which enhances the effectiveness of the other chemicals when it is used in combination with the other chemicals.

Group (f) is a group consisting of repellent components consisting of bird repellant components, insect repallant components, and animal repallant components.

Group is a molluscicidal component group.

Group (h) is an insect pheromone group.

Examples of the combination of the Present ingredient and the Present compound Z are described below. For example, alanycarb+SX represents a combination of alanycarb and SX The symbol of "SX" represents any one of the Present compound Z selected from the Compound Class $SX_1$ to the Compound Class $SX_{1130}$. Also, all of the below-mentioned present ingredient are known ingredients, and are commercially available or may be produced by the known method. If the present ingredient is a bacterium, it is available also from the bacterial authority depository. The numerical number in bracket represents a CAS RN (Register Trademark).

Combination of the Present ingredient of the above group (a) and the Present compound Z:

abamectin+SX, acephate+SX, acequinocyl+SX, acetamiprid+SX, acrinathrin+SX, acynonapyr+SX, afidopyropen+SX, afoxolaner+SX, alanycarb+SX, aldicarb+SX, allethrin+SX, alpha-cypermethrin+SX, alpha-endoaulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium cyanide+SX, calcium phosphide+SX, carbaryl+SX, carbofuran+EX, carbosulfan+SX, cartap hydrochloride+SX, cartap+SX, chinomethionat+SX, chlorantraniliprole+SX, chlordane+SX, chloethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dichloromezotiaz+SX, dicofol+SX, dicrotophos+SX, diflovidazin+SX, diflubenzuron+SX, dimefluthrin+SX, dimethoate+SX, dimethylvinphos+SX, dinotefuran+SX, disodium octaborate+SX, disulfoton+SX, DNOC (2-methyl-4,6-dinitrophenol)+SX, dorametin+SX, dried leaves of Dryopteris filix-mas+SX, emamectin-benzoate+SX, empenthrin+SX, endosulfan+SX, EPN (O-ethyl O-(4-nitrophenyl) phenylphosphonothioate)+SX, epsilon-etofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of *Clitoria ternatea*+SX, extract of *Symphytum officinale*+SX, extracts or simulated blend of *Chenopodium ambrosioides*+SX, extract of *Tanacetum vulgare*+SX, extract of *Urtica dioica*+SX, extract of *Viscum album*+SX, famphur+SX, fenamlphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+fluazuron+SX, flubendiamide+SX, flucycloxuron+SX, flucythrinate+SX, fluensulfone+SX, flufenoprox+SX, flufenoxuron+SX, flufiprole+SX, flumethrin+SX, fluopyram+SX, flupyradifurone+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SK, hydroprene+SX, imicyafos+SX, imidacloprid+SX, imiprothrin+SX, indoxacarb+SX, isofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lepimectin+SX, lime sulfur+SX, lufenuron+SX, machine oil+SX, malathion+SX, mecarbam+SX, meperfluthrin+SX, metafiumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novalurori+SX, noviflumuron+SX, oil of the seeds of *Chenopodium anthelminticum*+SX, omethoate+SX, oxamyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon SX, phosphine+SX, phoxim+SX, pirimicarb+SX, pirimiphos-methyl+SX, potassium cyanide+SX, prallethrin+SX, profenofos+SX, profluthr+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, selamactin+SX, sigma-cypermethrin+SX, silafluofen+SX, sodium borate+SX, sodium cyanide+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate SX, tebufenozide+SX, tebufenpyrad+SX, tebupirimfos+SX, teflubenzuron+SX, tefluthrin+SX, temephos SX, terbufos+SX, terpene constituents of the extract of *Chenopodium ambrosioides* near *ambrosioides*, Brand name: Terpenoid blend QRD 460+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, vamidothion+SX, XMC (3,5-dimethylphenya N-methylcarbamate)+SX, xylylcarb+SX, zeta-cypermethrin+SX, zinc phosphide+SX, (E)-N-{1-[(6-chloropyridin-3-yl)methyl]pyridin-2(1H)-ylidene}-2,2, trifluoroacetamide (1689566-03-7)+SX, 3-bromo-N-[2,4-dichloro-6-(methylcarbamoyl)phenyl]-1-(3,5-dichloropyridin-2-yl)-1H-pyrazole-5-carboxamide (1104384-14-6)+SX, N-[3-chloro-1-(pyridin-3-yl)-1H-pyrazol-4-yl]-N-ethyl-3-(3,3,3-trifluoropropylsulfanyl)propanamide (1477919-27-9)+SX, N-[3-chloro-1-(pyridin-3-yl)-1H-pyrazol-4-yl]-N-ethyl-3-(3,3,3-trifluorapropanesulfinyl)propanamide (1477923-37-7)+SX, 2-[(ethanesulfonyl)pyridin-2-yl]-5-(trifluoromethanesulfonyl)benzoxazole (1616678-32-0)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl) propanamide (1118626-57-5)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-difluoromethoxy-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazole-5-amine (885026-50-6)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, *Adoxophyes orana granulosis* virus+SX, *Anticarsia gemmatalis* mNPV+SX, *Autographa californica* mNPV FV#11+SX, *Cydia pomonella* GV V15+SX, *Cydia pomonella* GV V22+SX, *Cryptophlebia leucotreta* GV+SX, *Dendrolimus punctatus* cypovirus+SX *Helicorerpa armigera* NPV BV-0003+SX, *Helicoverpa zea* NPV+SX, *Lymantria dispar* NPV+SX, *Mamestra brassicae* NPV+SX, *Mamestra configurator* NPV+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* GB-126+SX, *Bacillus firmus* I-1582+SX, *Bacillus megaterium*+SX, *Bacillus* sp. AQ175+SX, *Bacillus* sp. AQ177+SX, *Bacillus* sp. AQ178+SX, *Bacillus sphaericus* 2362+SX, *Bacillus sphaericus* ABTS1743+SX, *Bacillus sphaericus* Serotype H-5a5b+SX, *Bacillus thuringiensis* AQ52+SX, *Bacillus thuringiensis* BD#32+SX, *Bacillus thuringiensis* CR-371+SX, *Bacillus thuringiensis* subsp. *Aizawai* BTS-1857+SX, *Bacillus thuringiensis* subsp. *Aizawai* AM65-52+SX, *Bacillus thuringiensis* subsp. *Aizawai* GC-91+SX, *Bacillus thuringiensis* subsp. *Aizawai* Serotype H-7+SX, *Bacillus thuringiensis* subsp. *Kurstaki* ABTS351+SX, *Bacillus thuringiensis* subsp. *Kurstaki* BMP123+SX, *Bacillus thuringiensis* subsp. *Kurstaki* EG234+SX, *Bacillus thuringiensis* subsp. *Kurstaki* EG7841+SX, *Bacillus thuringiensis* subsp. *Kurstaki* EVB113-19+SX, *Bacillus thuringiensis* subsp. *Kurstaki* F10+SX, *Bacillus thuringiensis* subsp. *Kurstaki* HD-1+SX, *Bacillus thuringiensis* subsp. *Kurstaki* PB54+SX, *Bacillus thuringiensis* subsp. *Kurstaki* SA-11+SX, *Bacillus thuringiensis* subsp. *Kurstaki* SA-12+SX, *Bacillus thuringiensis* subsp. *Tenebriosis* NB176+SX, *Bacillus thuringiensis* subsp. *Thuringiensis* MPPL002+SX, *Bacillus thuringiensis* subsp. *morrisoni*+SX, *Bacillus thuringiensis* var. *colmeri*+SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *israelensis* BMP144+SX, *Bacillus thuringiensis* var. *israelensis* serotype H-11+SX, *Bacillus thuringiensis* var. *japonensis* buibui+SX, *Bacillus thuringiensis* var. san diego M-7+SX, *Bacillus thuringiensis* var. 7216+SX, *Bacillus thuringiensis* var. *aegypti*+SX, *Bacillus thuringiensis* var. T36+SX, *Beauveria bassiana* ANT-03+SX, *Beauveria bassiana* ATCC74040+SX, *Beauveria bassisana* GHA+SX, *Beauveria brongniartii*+SX, *Burkholderia rinojensis* A396+SX, *Chromobacterium subtsugae* PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX, *Lagenidium giganteum*+SX, *Lecanicillium lecanii* KV01+SX, *Lecanicillium lecanii conidia* of strain DAOM198499+SX, *Lecanicillium lecanii conidia* of strain DAOM216596+SX, *Metarhizium anisopliae* F52+SX, *Metarhizium anisopliae* var. *acridum*+SX, *Metarhizium flavoviride*+SX, *Monacrosporium phymatopagum*+SX, *Paecilomyces fumosoroseus* Apopka97+SX, *Paecilomyces lilacinus* 251+SX, *Paecilomyces tenuipes* T1+SX, *Paenibacillus popilliae*+SX, *Pasteuria nishizawae* Pn1+SX, *Pasteuria penetrans*+SX, *Pasteuria usgae*+SX, *Pasteuria thoynei*+SX, *Serratia entomophila*+SX, *Verticillium chlamydosporium*+SX, *Verticillium lecani* NCIM1312+SX, lenoremycin+SX, concanamycin A+SX Combination of the Present ingredient of the above Group (b) and the Present compound Z:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chioroneb+SX, chlorothalonil+SX, chlozolinate+SX, colletochlorin B+SX, copper(II) acetate+SX, copper(II) hydroxide+SX, copper oxychloride SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, imethachlone+SX, dimethirimol+SX, dimethomorph+SX, dimoxystrobin+SX, diniconazole+SX, diniconazole-M+SX, dinocap SX, dipotassium hydrogenphosphite+SX, dipymetitrone+SX, dithianon+SX, dodecylbenzenesulphonic acid bisethylenediamine copper(II) salt+SX, dodemorph+SX, iodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets ("BLAD")+SX, extract of *Allium sativum*+SX, extract of *Eauisetum arvense*+SX, extract of *Tropaeolum majus*+SX, famoxadone+SX, fenamidone+SX, fenaminstrobin+SX, fenarimol+SX, fenbuconazole+SX, fenfuram SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopimomide+SX, fluoroimide+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hyinexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, sofiucypram+SX, isoprothiolane+SX, isopyrazam+SX, isotianil+SX, kasugamycin+SX, kresoxim-methyl+SX, laminarin+SX, leaves and bark of Quercus+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyrifenox+SX, pyrimethanil+SX, pyrimorph+SX, pyriofenone+SX, pyrisoxazole+SX, pyroquilon+SX, Quillaja extract+SX, guinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadirnenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, 3-difluoromethyl-N-methoxy-1-methyl-N-[(1R)-1-methyl-2-(2,4,6-trichlorophenyl)ethyl]pyrazol-4-carboxamide (1639015-48-7)+SX, 3-difluoromethyl-N-methoxy-1-methyl-N-[(1S)-1-methyl-2-(2,4,6-trichlorophenyl)ethyl]pyrazol-4-carboxamide (1639015-49-8)+SX, 3-difluoromethyl-1-methyl-N-(1,1,3-trimethylindan-4-yl)pyrazole-4-carboxamide (141573-94-6)+SX, 3-difluoromethyl-N-[(3R)-7-fluoro-1,1,3-trimethylindan-4-yl]-1-methylpyrazole-4-carboxamide (1513466-73-3)+SX, 3-chloro-5-phenyl-6-methyl-4-(2,6-difluorophenyl) pyridazine (1358061-55-8)+SX, N'-[4-({3-[(4-chlorophenyl)methyl]-1,2,4-thiadiazol-5-yl}oxy-2,5-dimethylphenyl]-N-ethyl-N-methylmethaneimidamide (1202781-91-6+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazole-5-amine (1362477-26-6)+SX, 2,2-dimethyl-9-fluoro-5-(quinolin-3-yl)-2,3-dihydrobenzo[f] [1,4]oxazepine (1207749-50-5+SX, 2-[6-(3-fluoro-4-methoxyphenyl)-5-methylpyridin-2-yl] quinazoline (1257056-97-5)+SX, 5-fluoro-2-[(4-methylphenyl)methoxy]-4-pyrimidineamine (1174376-25-0)+SX, 5-fluoro-4-imino-3-methyl-1-tosyl-3,4-dihydropyrimidine-2(1H)-one (1616664-98-2)+SX, N'-(2,5-dimethyl-4-phenoxyphenyl)-N-ethyl-N-methyl-methaneimidamide (1052688-31-9)+SX, N'-{4-[(4,5-dichlorothiazol-2-yl)oxy]-2,5-dimethylphenyl}-N-ethyl-N-methyl-methaneimidamide (929908-57-6)+SX, ethyl (2Z)-3-amino-2-cyano-3-phenylacrylate (39491-78-6)+SX, N-{(2-chlorothiazol-5-yl)methyl}-N-ethyl-6-methoxy-3-nitropyridine-2-amine (1446247-98-8)+SX, 1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX, α-[3-(4-chloro-2-fluorophenyl)-5-(2,4-difluorophenyl)-4-isoxazolyl]-3-pyridine methanol (1229605-96-2)+SX, (αS)-[3-(4-chloro-2-fluorophenyl)-5-(2,4-difluorophenyl)-4-isoxazolyl]-3-pyridine methanol (1229606-46-5)+SX, (αR)-[3-(4-chloro-2-fluorophenyl)-5-(2,4-difluorophenyl)-4-isoxazolyl]-3-pyridine methanol (1229606-46-5)+SX, (αR)-[3-(4-chloro-2-f luorophenyl)-5-(2,4-difluorophenyl)-4-isoxazolyl]-3-pyridine methanol (1229606-02-3)+SX, 2-{[3-(2-chlorophenyl)-2-(2,4-difluorophenyl)oxiran-2-yl]methyl}-2,4-dihydro-3H-1,2,4-triazole-3-thione (1342260-19-8)+SX, 2-{[(2R,3S)-3-(2-chlorophenyl)-2-(2,4-difluorophenyl)oxiran-2-yl]methyl}-2,4-dihydro-3H-1,2,4-triazole-3-thione (1638897-70-7)+SX, 2-{[(2S,3R)-3-(2-chlorophenyl)-2-(2,4-difluorophenyl)oxiran-2-yl]methyl}-2,4-dihydro-3H-1,2,4-triazole-3-thione (1638897-71-8)+SX, 2-{[(2R,3R)-3-(2-chlorophenyl)-2-(2,4-difluorophenyl)oxiran-2-yl]methyl}-2,4-dihydro-3H-1,2,4-triazole-3-thione (1638897-72-9)+SX, 2-{[(2S,3S)-3-(2-chlorophenyl)-2-(2,4-difluorophenyl)oxiran-2-yl]methyl}-2,4-dihydro-3H-1,2,4-triazole-3-thione (1638897-73-0)+SX, 1-{[3-(2-chlorophenyl)-2-(2,4-difluorophenyl)oxiran-2-yl]methyl}-1H-1,2,4-triazol-5-yl thiocyanate (1342260-26-7)+SX, 1-{[(2R,3S)-3-(2-chlorophenyl)-2-(2,4-difluorophenyl)oxiran-2-yl]methyl}-1H-1,2,4-triazol-5-yl thiocyanate (1638897-82-1)+SX, 1-{[(2S,3R)-3-(2-chlorophenyl)-2-(2,4-difluorophenyl)oxiran-2-yl]methyl}-1H-1,2,4-triazol-5-yl thiocyanate (1638897-84-3)+SX, 1-{[(2R,3R)-3-(2-chlorophenyl)-2-(2,4-difluorophenyl)oxian-2-yl]methyl}-1H-1,2,4-triazol-5-yl thiocyanate (1638897-86-5)+SX, 1-{[(2S,3S)-3-(2-chlorophenyl)-2-(2,4-difluorophenyl)oxiran-2-yl]methyl}-1H-1,2,4-triazol-5-yl thiocyanate (1638897-89-8)+SX, 5-(4-chlorobenzyl)-2-chloromethyl-2-methyl-1-(1H-1,2,4-triazol-1-ylmethyl)cyclopentanol (1394057-11-4)+SX, (1R,2S,5S)-5-(4-chlorobenzyl)-2-chloromethyl-2-methyl-1-(1H-1,2,4-triazol-1-ylmethyl)cyclopenotanol (1801930-06-2)+SX, (1S,2R,5R)-(4-chlorobenzyl)-2-chloromethyl-2-methyl-1-(1H-1,2,4-triazol-1-ylmethyl)cyclopentanol (1801930-07-3)+SX, (1R,2R,5R)-5-(4-chlorobenzyl)-2-chloromethyl-2-methyl-1-(1H-1,2,4-triazol-1-ylmethyl)cyclopentanol (1801919-53-8)+SX, (1S,2S,5S)-5-(4-chlorobenzyl)-2-chloromethyl-2-methyl-1-(1H-1,2,4-triazol-1-ylmethyl)cyclopentanol (1801919-54-9)+SX, (1R,2R,5S)-(4-chlorobenzyl)-2-chloromethyl-2-methyl-1-(1H-1,2,4-triazol-1-ylmethyl)cyclopentanol (1801919-55-0)+SX, (1S,2R,5R)-5-(4-chlorobenzyl)-2-chloromethyl-2-methyl-1-(1H-1,2,4-triazol-1-ylmethyl)cyclopentanol (1801919-56-1)+SX, (1R,2S,5R)-5-(4-chlorobenzyl)-2-chloromethyl-2-methyl-1-(1H-1,2,4-triazol-1-ylmethyl)cyclopentanol (1801919-57-2)+SX, (1S,2R,5S)-5-(4-chlorobenzyl)-2-chloromethyl-2-methyl-1-(1H-1,2,4-triazol-1-ylmethyl)cyclopentanol (1801919-58-3)+SX, Methyl=3-[4-(chlorophenyl)methyl]-2-hydroxy-1-methyl-2-(1H-1,2,4,-triazol-1-ylmethyl)cyclopentane carboxylate (1791398-02-1)+SX, Methyl=(1R,2S,3S)-3-[(4-chlorophenyl)methyl]-2-hydroxy-1-methyl-2-(1H-1,2,4-triazol-1-yl ethyl)cyclopentane carboxylate+SX, Methyl=(1S,2R,3R)-3-[(4-chlorophenyl)methyl]-2-hydroxy-1-methyl-2-(1H-1,2,4-triazol-1-ylmethyl)cyclopentane carboxylate+SX, Methyl=(1R,2R,3R)-3-[(4-chlorophenyl)methyl]-2-hydroxy-1-methyl-2-(1H-1,2,4-triazol-1-ylmethyl)cyclopentane carboxylate+SX, Methyl=(1S,2S,3S)-3-[(4-chlorophehyl)methyl]-2-hydroxy-1-methyl-2-(1H-1,2,4-triazol-1-ylmethyl)cyclopentane carboxylate+SX, Methyl=(1R,2R,3S)-3-[(4-chlorophenyl)methyl]-2-hydroxy-1-methyl-2-(1H-1,2,4-triazol-1-ylmethyl) cyclopentane carboxylate+SX, Methyl=(1S,2S,3R)-3-[(4-chlorophenyl)methyl]-2-hydroxy-1-methyl-2-(1H-1,2,4-triazol-1-ylmethyl)cyclopentane carboxylate+SX, Methyl=(1R,2S,3R)-3-[(4-chlorophenyl)methyl]-2-hydroxy-1-methyl-2-(1H-1,2,4-triazol-1-ylmethyl)cyclopentane carboxylate+SX, Methyl=(1S,2R,3S)-3-[(4-chlorophenyl)methyl]-2-hydroxy-1-methyl-2-(1H-1,2,4-triazol-1-ylmethyl)cyclopentane carboxylate+SX, 2-chloromethyl-5-(4- fluorobenzyl)-2-methyl-1-(1H-1,2,4-triazol-1-ylmethyl) cyclopentanol (1394057-13-6)+SX, (1R,2S,5S)-2-chloromethyl-5-(4-fluorobenzyl)-2-methyl-1-(1H-1,2,4-triazol-1-ylmethyl)cyclopentanol (1301930-08-4)+SX, (1S,2R,5R)-2-chloromethyl-5-(4-fluorobenzyl)-2-methyl-1-(1H-1,2,4-triazol-1-ylmethyl)cyclopentanol (1801930-09-5)+SX, (1R,2R,5R)-2-chloromethyl-5-(4-fluorobenzyl)-2-methyl-1-(1H-1,2,4-triazol-1-ylmethyl)cyclopentanol (1638898-08-4)+SX, (1S,2S,5S)-2-chloromethyl-5-(4-fluorobenzyl)-2-methyl-1-(1H-1,2,4-triazol-1-ylmethyl)cyclopentanol (1638898-10-8)+SX, (1R,2R,5S)-2-chloromethyl-5-(4-fluorobenzyl)-2-methyl-1-(1H-1,2,4-triazol-1-ylmethyl)cyclopentanol (1638898-13-1)+SX, (1S,2S,5R)-2-chloromethyl-5-(4-fluorobenzyl)-2-methyl-1-(1H-1,2,4-triazol-1-ylmethyl)cyclopentanol (1638898-16-4)+SX, (1R, 2S, 5R)-2-chloromethyl-5-(4-fluorobenzyl)-2-methyl-1-(1H-1,2,4-triazol-1-ylmethyl)cyclopentanol (1638898-20-0)+SX, (1S,2R,5S)-2-chloromethyl-5-(4-fluorobenzyl)-2-methyl-1-(1H-1,2,4-triazol-1-ylmethyl)cyclopentanol (1638898-24-4)+SX, (R)-2-[2-chloro-4-(4-chlorophenoxy) phenyl]-1-(1,2,4-triazol-1-yl)pent-3-yne-2-ol (1801919-59-4)+SX, (R)-2-[4-(4-chlorophenoxy)-2-(trifluoromethyl)phenyl]-1-(1,2,4-triazol-1-yl)propane-2-ol (1616236-94-2)+SX, (R)-1-[4-(4-chlorophenoxy)-2-(trifluoromethyl) phenyl]-1-cyclopropyl-2-(1,2,4-triazol-1-yl)ethanol (1801919-60-7)+SX, (R)-2-[4-(4-chlorophenoxy)-2-(trifluoromethyl)phenyl]-3-methyl-1-(1,2,4-triazol-1-yl)butane-2-ol (1801919-61-8)+SX, 3-[5-(4-chlorophenyl)-2,3-dimethyl-1,2-oxazolydin-3-yl]pyridine (847749-37-5)+SX, *Agrobacterium radiobactor* K1025+SX, *Agrobacterium radiobactor* K84+SX, *Bacillus amyloliquefaciens* AT332+SX, *Bacillus amyloliquefaciens* B3+SX, *Bacillus amyloliquefaciens* D747+SX, *Bacillus amyloliquefaciens* DB101+SX, *Bacillus amyloliquefaciens* DB102+SX, *Bacillus amyloliquefaciens* GB03+SX, *Bacillus amyloliquefaciens* FZB24+SX, *Bacillus amyloliquefaciens* FZB42+SX, *Bacillus amyloliquefaciens* IN937a+SX, *Bacillus amyloliquefaciens* MBI600+SX, *Bacillus amyloliquefaciens* QST713+SX, *Bacillus amyloliquefaciens* isolate B246+SX, *Bacillus amyloliquefaciens* F727+SX, *Bacillus licheniformis* HB-2+SX, *Bacillus licheniformis* SD3086+SX, *Bacillus pumilus* AQ717+SX, *Bacillus pumulis* BUF-33+SX, *Bacillus pumulis* GB34+SX, *Bacillus pumulis* QST2808+SX, *Bacillus simplex* CGF2856+SX, *Bacillus subtilis* AQ153+SX, *Bacillus subtilis* AQ743+SX, *Bacillus subtilis* BU1814+SX, *Bacillus subtilis* D747+SX, *Bacillus subtilis* DB101+SX, *Bacillus subtilis* FZB24+SX, *Bacillus subtilis* GB03+SX, *Bacillus subtilis* HAI0404+SX, *Bacillus subtilis* IAB/BS03+SX, *Bacillus subtilis* MBI600 SX, *Bacillus subtilis* QST30002/AQ30002+SX, *Bacillus subtilis* QST30004/AQ30004+SX, *Bacillus subtilis* QST713+SX, *Bacillus subtilis* QST714+SX, *Bacillus subtilis* var. *Amyloliquefaciens* FZB24+SX, *Bacillus subtilis* Y1336+SX, *Burkholderia cepacia*+SX, *Burkholderia cepacia* type Wisconsin J82+SX, *Burkholderia cepacia* type Wisconsin M54+SX, *Candida oleophila*O+SX, *Candida saitoana*+SX, *Chaetomium cupreum*+SX, *Clonostayhys rosea*+SX, *Coniothyrium minitans* CGMCC8325+SX, *Coniothyrium minitans* CON/M/91-8+SX, *Cryptococcus albidus*+SX, *Erwinia carotovora* subsp. *carotovora* CGE234M403+SX, *Fusarium oxysporum* Fo47+SX, *Gliocladium catenulatum* J1446+SX, *Paenibacillus polymyxa* AC-1+SX, *Paenibacillus polymyxa* BS-0105+SX, *Pantoea agglomerans* E325+SX, *Phlebiopsis gigantea* VRA1992+SX, *Pseudomonas aureofaciens* TX-1+SX, *Pseudomonas chlororaphis* 63-28+SX, *Pseudomonas chlororaphis* MA342+SX, *Pseudomonas fluorescens* 1629RS+SX, *Pseudomonas fluorescens* A506+SX, *Pseudomonas fluorescens* CL145A+SX, *Pseudomonas fluorescens* G7090+SX, *Pseudomonas* sp. CAB-02+SX, *Pseudomonas syringae* 742RS+SX, *Pseudomonas syringae* MA-4+SX, *Pseudozyma flocculosa* PF-A22UL+SX, *Pseudomonas rhodesiae* HAI-0604+SX, *Pythium oligandrum* DV74+SX, *Streptomyces griseoviridis* K61+SX, *Streptomyces lydicus* WYCD108US+SX, *Streptomyces lydicus* WYEC108+SX, *Talaromyces flavus* SAY-Y-94-01+SX, *Talaromyces flavus* V117b+SX, *Trichoderma asperellum* ICC012+SX, *Trichoderma asperellum* SKT-1+SX, *Trichoderma asperellum* T34+SX, *Trichoderma atroviride* CNCM 1-1237+SX, *Trichoderma atroviride* LC52+SX, *Trichoderma atroviride* SCI+SX, *Trichoderma atroviride* SKT-1+SX, *Trichoderma gamsii* ICC080+SX, *Trichoderma harzianum* 21+SX, *Trichoderma harzianum* DB104+SX, *Trichoderma harzianum* DSM 14944+SX, *Trichoderma harzianum* ESALQ-1303+SX, *Trichoderma harzianum* ESALQ-1306+SX, *Trichoderma harzianum* IIHR-Th-2+SX, *Trichoderma harzianum*+SX, *Trichoderma harzianum* MO1+SX, *Trichoderma harzianum* SF+SX, *Trichoderma harzianum* T22+SX, *Trichoderma harzianum* T39+SX, *Trichoderma harzianum* TEM908+SX, *Trichoderma harzianum* TH35+SX, *Trichoderma polysporm* IM1206039+SX, *Trichoderma stromaticum*+SX, *Trichoderma virens* G-41+SX, *Trichoderma virens* GL-21+SX, *Trichoderma viride*+SX, *Variovorax paradoxus* CGF4526+SX, and Harpin protein+SX.

Combination of the Present ingredient of the above Group (c) and the Present compound Z:

1-methylcyclopropene+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, Gibberellin A+SX, Gibberellin A3+SX, inabenfide+SX, Kinetin+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tributos+SX, trinexapac-ethyl+SX, uniconazole-P+SX, 2-(naphthalene-1-yl)acetamide+SX, [4-oxo-4-(2-phenyethyl) amino]butyric acid+SX, Methyl 5-(trifluoromethyl)benzo [b]thiophen-2-carboxylate+SX, 3-[(6-chloro-4-phenylquinazolin-2-yl)amino]-1-propanol+SX, formononetin+SX, *Glomus* spp.+SX, *Glomus intraradices*+SX, *Glomus mosseae*+SX, *Glomus aggregatum*+SX, *Glomus etunicatum*+SX, *Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, *Rhizobium* spp.+SX, *Rhizobium fredii*+SX, *Rhizobium loti*+SX, *Rhizobium trifolii*+SX, *Rhizobium tropici*+SX, 1,3-diphenylurea+SX, *Claroideoglomus etunicatum*+SX, *Funneliformis mosseae*+

SX, *Gigaspora margarita*+SX, *Gigaspora rosea*+SX, *Glomus aggregatum*+SX, *Glomus deserticola*+SX, *Glomus monosporum*+SX, *Paraglomus brasillianum*+SX, *Rhizophagus clarus*+SX, *Rhizophagus intraradices* RTI-801+SX, *Rhizophagus irregularis* DACM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Bradyrhizobium lupini*+SX, *Delftia acidovorans* RAY209+SX, *Mesorhizobium ciceri*+SX, *Mesorhizobium huakii*+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium tropici*+SX, *Sinorhizobium fredii*+SX, and *Sinorhizobium meliloti*+SX Combination of the Present ingredient of the above Group (d) and the Present compound Z:

allidochlor+SX, benoxacor+SX, cloquintocet+SX, cloquintocet-mexyl+SX, cyometrinil+SX, cyprosulfamide+SX, dichlormid+SX, dicyclonone+SX, dimepiperate+SX, disulfoton+SX, dymron+SX, fenchlorazole+SX, fenchlorazole-ethyl+SX, fenclorim+SX, flurazole+SX, furilazole+SX, fluxofenim+SX, Hexim+SX, isoxadifen+SX, isoxadifen-ethyl+SX, mecoprop+SX, mefenpyr+SX, mefenpyr-ethyl+SX, mefenpyr-diethyl+SX, mephenate+SX, metcamifen+SX, oxabetrinil+SX, 1,8-naphthalic anhydride+SX, 1,8-octamethylene diamine+SX, AD-67 (4-(dicloroacetyl)-1-oxa-4-azaspiro[4.5]decane)+SX, CL-304415 (4-carboxy-3,4-dihydro-2H-1-benzopyran-4-acetic acid)+SX, CSB (1-bromo-4-[(chloromethyl)sulfonyl]benzene)+SX, DKA-24 (2,2-dichloro-N-[2-oxo-2-(2-propenylamino)ethyl]-N-(2-propenyl)acetamide)+SX, MG191 (2-(dichloromethyl)-2-methyl-1,3-dioxolane)+SX, MG-838 (2-propenyl 1-oxa-4-azaspiro[4,5]decane-4-carbodithioate)+SX, PPG-1292 (2,2-dichloro-N-(1,3-dioxan-2-ylmethyl)-N-(2-propenyl)acetamide)+SX, R-28725 (3-(dichloroacetyl)-2,2-dimethyl-1,3-oxazolidine)+SX, R-29148 (3-(dichloroacetyl)-2,2,5-trimethyl-1,3-oxazolidine)+SX, and TI-35 (1-(dichloroacetyl)azepane)+SX.

Combination of the Present ingredient of the above Group (e) and the Present compound Z:

1-dodecyl-1H-imidazole+SX, N-(2-ethylhexyl)-8,9,10-trinorborn-5-ene-2,3-dicarboximide+SX, bucarpolate+SX, N,N-dibutyl-4-chlorobenzenesulfonamide+SX, diethotate+SX, diethylmaleate+SX, piperonyl butoxide+SX, piperonyl cyclonene+SX, piprotal+SX, propyl isome+SX, safroxan+SX, sesamex+SX, sesamolin+SX, sulfoxide+SX, Verbutin+SX, DMC (1,1-bis(4-chlorophenyl)ethanol)+SX, FDMC (1,1-bis(4-chlorophenyl)-2,2,2-trifluoroethanol)+SX, ETN (1,2-epoxy-1,2,3,4-tetrahydronaphthalene)+SX, ETP (1,1,1-trichloro-2,3-expoxypropane)+SX, PSCP (phenylsaligenin cyclic phosphate)+SX, TBPT (S,S,S-tributyl phosphorotrithioate)+SX, and TPP (triphenyl phosphate)+SX.

Combination of the Present ingredient of the above Group (f) and the Present compound Z:

anthraquinone+SX, chloralose+SX, acrep+SX, butopyronoxyl+SX, camphor+SX, d-camphor+SX, arboxide+SX, dibutyl phthalate+SX, deet+SX, dimethyl carbate+SX, dimethyl phthalate+SX, dibutyl succinate+SX, dibutyl adipate+SX, ethohexadiol+SX, hexamide+SX, icaridin+SX, methoquin-butyl+SX, methylneodecanamide+SX, 2-(octylthio) ethanol+SX, butoxypolypropylene glycol+SX, oxamate+SX, quwenzhi+SX, quyingding+SX, zengxiaon+SX, rebemide+SX, copper naphthenate+SX, and zinc naphthenate+SX.

Combination of the Present ingredient of the above Group (g) and the Present compound Z bis(tributyltin) oxide+SX, allicin+SX, bromoacetamide+SX, cloethocarb+SX, copper sulfate+SX, fentin+SX, ferric phosphate+SX, metaldehyde+SX, niclosamide+SX, pentachlorophenol+SX, sodium pentachlorophenoxide+SX, tazimcarb+SX, tralopyril+SX, and trifenmorph+SX.

Combination of the Present ingredient of the above Group (h) and the Present compound Z:

(E)-2-hexenal+SX, (E)-2-octadecenal+SX, (E)-4-tridecen-1-yl acetate+SX, (E)-5-decen-1-yl acetate+SX, (E)-5-decen-1-ol+SX, (E)-3,3-dimethylcyclohexylideneacetaldehyde+SX, (E)-7-dodecen-1-yl acetate+SX, (E)-8-dodecen-1-yl acetate+SX, (E)-9-dodecen-1-yl acetate+SX, (E)-10-hexadecenal+SX, (E)-11-hexadecen-1-yl acetate+SX, (E)-11-tetradecen-1-yl acetate+SX, (E)-11-tetradecen-1-ol+SX, (E)-4-tridecen-1-yl acetate+SX, (E)-6-methylhept-2-en-4-ol+SX, (Z)-2-(3,3-dimethylcyclohexylidene)ethanol+SX, (Z)-4-decen-1-yl acetate+SX, (Z)-4-tridecen-1-yl acetate+SX, (Z)-5-decen-1-yl acetate+SX, (Z)-5-decen-1-ol+SX, (Z)-7-tetradecenal+SX, (Z)-7-dodecen 1-yl acetate+SX, (Z)-8-dodecen-1-yl acetate+SX, (Z)-9-dodecen-1-yl acetate+SX, (Z)-8-dodecen-1-ol+SX, (Z)-9-hexadecenal+SX, (Z)-10-hexadecen-1-yl acetate+SX, (Z)-11-hexadecen-1-ol+SX, (Z)-11-hexadecenal+SX, (Z)-11-hexadecen-1-yl acetate+SX, (Z)-11-octadecenal+SX, (Z)-13-octadecenal+SX, (Z)-hexadec-13-en-11-yn-1-yl acetate+SX, (Z)-13-octadecenal+SX, icos13-en-10-one+SX, (Z)-7-tetradecenal+SX, (Z)-tetradec-9-en-1-ol+SX, (Z)-9-tetradecen-1-yl acetate+SX, (Z)-11-tetradecen-1-yl acetate+SX, (Z)-13-icosen-10-one+SX, (Z,E)-7,11-hexadecadien-1-yl acetate+SX, (Z,E)-9,12-tetradecadien-1-yl acetate)+SX, (E,Z)-4,10-tetradecadien-1-yl acetate+SX, (E,E)-10-dodecadien-1-ol+SX, (E,E)-10,12-hexadecadienal+SX, (E,E)-9,11-tetradecadien-1-yl acetate+SX, (E,Z)-2,13-octadecadien-1-ol+SX, (E,Z)-3,13-octadecadien-1-ol+SX, (E,Z)-2,13-octadecadien-1-yl acetate+SX, (E,Z)-3,13-octadecadien-1-yl acetate+SX, (E,Z)-7,9-dodecadien-1-yl acetate+SX, (E,E)-7,8-dodecadien-1-yl acetate+SX, (Z,E)-9,12-tetradecadien-1-yl acetate+SX, (Z,E)-9,11-tetradecadien-1-yl acetate+SX, (Z,E)-7,11-hexadecadien-1-yl acetate+SX, (Z,Z)-3,13-octadecadien-1-ol+SX, (Z,Z)-4,7-decadien-1-yl acetate+SX, (Z,Z)-3,13-octadecadien-1-yl acetate+SX, (Z,Z)-7,11-hexadecadien-1-yl acetate+SX, (Z,Z,E)-7,11,13-hexadecatrienal+SX, (5R)-5-[(1Z)-1-decen-1-yl]dihydro-2(3H)-furanone+SX, (2R,5R)-ethyl-1,6-dioxaspiro[4,4]nonane+SX, (2R,5S)-ethyl-1,6-dioxaspiro[4,4]nonane+SX, (4R,8R)-4,8-dimethyldecanal+SX, (4R,8S)-4,8-dimethyldecanal+SX, 2,4-dimethyl-5-ethyl-6,8-dioxabicyclo[3,2,1]octane+SX, (−)-4-methyl-3-heptanol+SX, 1,7-dioxaspiro[5,5]undecane+SX, 3-carene+SX, methylcyclohex-2-en-1-one+SX, 14-methyloctadec-1-ene+SX, 4-methylnonan-5-ol+SX, 4-methylnonan-5-one+SX, 4-(3-oxobutyl)phenyl acetate+SX, dodecyl acetate+SX, dodeca-8,10-dien-1-yl acetate+SX, ethyl (2E,4Z)-decadienoate+SX, ethyl 4-methyloctanoate+SX, methyl 2,6,10-trimethyldodecanoate+SX, tetradecan-1-ol+SX, tetradec-11-en-1-ol+SX, tetradec-11-en-1-yl acetate+SX, tridec-4-en-1-yl acetate+SX, (3S,6R)-3-methyl-6-isopropyl-9-decen-1-yl acetate+SX, (3S,6S)-3-methyl-6-isopropyl-9-decen-1-yl acetate+SX, alpha-multistriatin+SX, alpha-pinine+SX, endo-brevicomin+SX, exo-brevicomin+SX, camphene+SX, codlelure+SX, codlemone+SX, cuelure+SX, disparlure+SX, dominicalure+SX, eugenol+SX, farnesol+SX, ferrolure+SX, frontalin+SX, gossyplure+SX, grandlure+SX, grandlure I+SX, grandlure II+SX, grandlure III+SX, grandlure IV+SX, hexalure+SX, ipsdienol+SX, ipsenol+SX, japonilure+SX, lineatin+SX, litlue+SX, looplure+SX, medlure+SX, megatomoic acid+SX, methyl eugenol+SX, muscalure+SX, nerolidol+SX, orfralure+SX, oryctalure+SX, ostramone+SX, rhyncolure+SX, siglure+SX, sordidin+SX, sulcatol+SX, trimedlure+SX, trimedlure A+SX, trimedlure B1+SX, trimedlure B2+SX, trimedlure C+SX, trunc-call+SX, (E)-verbenol+SX, (Z)-verbenol+SX, trans-verbenol+SX, and (S)-verbenone+SX.

The ratio of the Present compound Z to the Present ingredient includes, but not limited thereto, as a ration by weight (the Present compound Z: the Present ingredient) 1,000:1 to 1:1,000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, or 1:1 to 1:10, abd the others.

Examples of the pests on which the present compound Z or the present composition has efficacies include harmful arthropods such as harmful insects and harmful mites, harmful nematodes, and harmful molluscs, and specific examples of the harmful arthropods include the followings, but which are not limited thereto.

Hemiptera Pests:

Delphacidae (for example, *Laodelphax striatellus*, *Nilaparvata lugens*, *Sogatella furcifera*, *Peregrinus maidis*, *Javesella pellucida*, *Perkinsiella saccharicida*, or *Tagosodes orizicolus*);

Cicadellidae (for example, *Nephotettix cincticeps*, *Nephotettix virescens*, *Nephotettix nigropictus*, *Recilia dorsalis*, *Empoasca onukii*, *Empoasca fabae*, *Dalbulus maidis*, or *Cofana spectra*);

Cercopidae (for example, *Mahanarva posticata*, or *Makanarva fimbriolata*);

Aphididae (for example, *Aphis fabae*, *Aphis glycines*, *Aphis gossypii*, *Aphis pomi*, *Aphis spiraecola*, *Myzus persicae*, *Brachycaudus helichrysi*, *Brevicoryne brassicae*, Rosy apple aphid (*Dysaphis plantaginea*), *Lipaphis erysimi*, *Macrosiphum euphozbiae*, *Aulacorthum solani*, *Nasonovia ribisnigri*, *Rhopalosiphum padi*, *Rhopalosiphum maidis*, *Toxopteza citricidus*, *Hyalopterus pruni*, *Melanaphis sacchari*, *Tetraneura nigriabdominalis*, *Ceratovacuna lanigera*, or *Eriosoma lanigerum*);

Phylioxeridae (for example, *Daktulosphaira vitifoliae*, Pecan *phylloxera* (*Phylloxera devastatrix*), Pecan leaf *Phylloxera* (*Phylloxera notabilis*), or Southern pecan leaf *Phylloxera* (*Phylloxera russellae*));

Adelgidae (for example, *Adelges tsugae*, *Adelgas piceae*, or *Aphrastatsia pectinatae*);

Pentatomidae (for example, *Scotinophara lurida*, Malayan rice black bug (*Scotinophara coarctate*) *Nezara antennata*, *Eysarcoris aeneus*, *Eysarcoris lewisis*, *Eysarcaris ventralis*, *Eysarcoris annamita*, *Halyomorpha halys*, *Nezara viridula*, Brown stink bug (*Euschistus heros*), Red banded stink bug (*Piezodorus guildinii*), *Oebalus pugnax*, *Dichelops melacanthus*);

Cydnidae (for example, Burrower brown bug (*Scaptocoris castanea*));

Alydidae (for example, *Rilotortus pedestris*, *Leptocorisa chinensis*, or *Leptocorisa acuta*);

Coreidae (for example, *Cletus punctiger*, or *Leptoglossus australis*);

Lygaeidae (for example, *Caverelius saccharivorus*, *Togo hemipterus*, or *Blissus leucopterus*);

Miridae (for example, *Trigonotylus caelestialium*, *Stenotus rubrovittatus*, *Stenodema calcarata*, or *Lygus lineolaris*);

Aleyrodidae (for example, *Trialeurodes vaporariorum*, *Bemisia tabaci*, *Dialeurodes citri*, *Aleuaocanthus spiniferus*, *Aleurocanthus camelliae*, or *Pealius euryae*);

Diaspididae (for example, *Abgrallaspis cyanophylli*, *Aonidiella aurantii*, *Diaspidiotus perniciosus*, *Pseudaulacaspis pentagona*, *Unaspis yanonensis*, or *Unaspis citri*);

Coccidae (for example, *Ceroplastes rubens*);

Margarodidae (for example, *Icerya purchasi*, or *Icerya seychellarum*);

Pseudococcidae (for example, *Phenacoccus solani*, *Phenacoccus solenopsis*, *Planococcus kraunhiae*, *Planococcus comstocki*, *Planococcus citri*, *Pseudococcus calceolariae*, *Pseudococcus longispinus*, or *Brevennia rehi*);

Psyllidae (for example, *Diaphorina citri*, *Trioza erytreae*, *Cacopsylla pyrisuga*, *Cacopsylla chinensis*, *Bactericera cockerelli*, or Pear *psylla* (*Cacopsylla pyricole*));

Tingidae (for example, *Corythucha ciliata*, *Corythucha marmorata*, *Stephanitis nashi*, or *Stephanitis pyrioides*);

Cimicidae (for example, *Cimex lectulerius*);

Cicadidae (for example, Giant *Cicada* (*Quesada gigas*)); and

*Triatoma* spp. (for example, *Triatoma infestans*).

Lepidoptera

Crambidae (for example, *Chilo suppressalis*, Darkheaded stem borer (*Chilo polychrysus*), White stem borer (*Scirpophaga innotata*), *Scirpophaga incertulas*, *Rupela albina*, *Cnaphalocrocis medinalis*, *Marasmia patnalis*, *Marasmia exigua*, *Notarcha derogata*, *Ostrinia furnacalis*, European corn borer (*Ostrinia nubilalis*), *Hellula undalis*, *Herpetogramma luctuosale*, *Pediasia teterrellus*, *Nymphua depunctalis*, or Sugarcane borer (*Diatraea saccharalis*));

Pyralidae (for example, *Elasmpalpus lignosellus* or *Plodia interpunctella*);

Noctuidae (for example, *Spodoptera litura*, *Spodoptera exigua*, *Mythimna separata*, *Memestra brassicae*, *Sesamia inferens*, *Spodoptera mauritia*, *Narang aenescens*, *Spodoptera frugiperda*, *Spodoptera exempta*, *Agrotis ipsilon*, *Autographa nigrisigna*, *Plusia festucae*, Soybean looper (*Chrysodeixis includens*), *Trichoplusia* spp., *Heliothis* spp. (for example, *Heliothis virescens*), *Helicoverpa armigera*, *Helicoverpa* spp. (for example, *Helicoverpa zea*), Velvetbean caterpillar (*Antiarsia gemmatalis*), Cotton leafworm (*Alabama argillacea*), or Hop vine borer (*Hydraecia immanis*));

Pieridae (for example, *Pieris rapae*);

Tortricidae (for example, *Grapholita molesta*, *Grapholita dimorphs*, *Leguminivora glycinivorella*, *Matsumuraeses azukivora*, *Adoxophyes orana fasciata*, *Adoxophyes honmai*, *Homona magnanima*, *Archips fuscocupreanus*, *Cydia pomonella*, *Tetramoera schistaceana*, Bean Shoot Borer (*Epinotia aporema*), or Citrus fruit borer (*Ecdytolopha aurantiana*));

Gracillariidae (for example, *Caloptilia theivora*, or *Phyllonorycter ringoniella*);

Carposinidae (for example, *Carposina sasakii*);

Lyonetiidae (for example, Coffee Leaf miner (*Leucoptera coffeela*), *Lyonetia clerkella*, or *Lyonetia prunifoliella*);

Lymantriidae (for example, *Lymantria* spp. (for example, *Lymantria dispar*), or *Euproctis* spp. (for example, *Euproctis pseudoconspersa*);

Pluteliidae (for example, *Plutella xylostella*);

Gelechiidae (for example, *Anarsia lineatella*, *Helcystogramma triannulellum*, *Pectinophora gossypiella*, *Phthorimaea operculella*, or *Tuta absolut*);

Arctiidae (for example, *Hyphantria cunea*);

Castniidae (for example, Giant Sugarcane borer (*Telchin licus*));

Cossidae (for example, *Cosus insularis*);
Geometridae (for example, *Ascotis selenaria*);
Limacodidae (for example, *Parasa lepida*);
Stathmopodidae (for example, *Stathmopoda masinissa*);
Sphingidae (for example, *Acherontic lachesis*);
Sesiidae (for example, *Nokona feralis*);
Hesperiidae (for example, *Parnara guttate*); and
Tinedae (for example, *Tinea translucens* or *Tineola bisselliella*).

Thysanoptera

Thripidae (for example, *Frankliniella occidentalis*, *Thrips palmi*, *Scirtothrips dorsalis*, *Thrips tabaci*, *Frankliniella intonsa*, *Stenchaetothrips biformis*, or *Echinothrips americanus*); and
Phlaeothripidae (for example, *Haplothrips aculeatus*).

Diptera

Anthomyiidae (for example, *Delia platura* or *Delia antigua*);
Ulidiidae (for example, *Tetanops myopaeformis*);
Agromyzidae (for example, *Agromyza oryzae*, *Liriomyza sativae*, *Liriomyza trifolii*, or *Chromatomyi horticola*);
Chloropidae (for example, *Chlorops oryzae*);
Tephritidae (for example, *Bactrocera cucurbitae*, *Bactrocera dorsalis*, *Bactrocera latifrons*, *Bactrocera oleae*, *Bactrocera tryoni*, or *Ceratitis capitata*);
Ephydridae (for example, *Hydrellia griseala*, *Hydrellia philippina*, or *Hydrellia sasakii*);
Drosophilidae (for example, *Drosophila suzukii*);
Phoridae (for example, *Megaselia spiracularis*);
Psychodidae (for example, *Clogmia albipunctata*);
Salaridae (for example, *Bradysia difformis*);
Cecidomyiidae (for example, *Mayetiola destructor*, or *Orseolia oryzae*);
Diopsidae (for example, *Diopsis macrophthalma*);
Tipulidae (for example, *Tipula aino*, Common cranefly (*Tipula oleracea*), or European cranefly (*Tipula paludosa*)).
Culicidae (for example, *Culex pipiens pallens*, *Aedes aegypti*, *Aedes albopicutus*, *Anopheles hyracanus sinesis*, *Culex quinquefasciatus*, *Culex pipiens molestus Forskal*, or *Culex quinquefasciatus*);
Simulidae (for example, *Prosimulium yezoensis*, or *Simulium ornatum*);
Tabanidae (for example, *Tabanus trigonus*);
Muscidae (for example, *Musca domestica*, *Muscina stabulans*, *Stomoxys calcitrans*, or *Haematobia irritans*);
Calliphoridae;
Sarcophagidae;
Chironomidae (for example, *Chironomus plumosus*, *Chironomus yoshimatsui*, or *Glyptotendipes tokunagai*); and
Fannidae.

Coleoptera

Chrysomelidae (for example, *Diabrotica virgifera virgifera*, *Diabrotica undecimpuictata howardi*, *Diabrotica barberi*, *Diabrotica virgifera zeae*, *Diabrotica balteata*, Cucurbit Beetle (*Diabrotica speciosa*), *Cerotoma trifurcate*, *Oulema melanopus*, *Aulacophora femoralis*, *Phyllotreta striolata*, Cabbage flea beetle (*Phyllotreta cruciferae*), Western black flea beetle (*Phyllotreta pusilla*), Cabbage stem flea beetle (*Psylliodes chrysocephala*), *Leptinotarsa deceralineata*, *Qulema oryzae*, *Colaspis brunnea*, *Chaetocnema pulicaria*, *Chaetocnema confinis*, *Epitrix cucumeris*, *Dicladispa armigera*, Grape *colaspis* (*Colaspis brunnea*), southern corn leaf beetle (*Myochrous denticollis*), *Laccoptera quadrimacu*, or *Epitrix hirtipennis*);
Carabidae (for example, Seedcorn beetle (*Stenolophus lecontei*), or Slender seedcorn beetle (*Clivina impressifros*));
Scarabaeidae (for example, *Anomala cuprea*, *Anomala rufocuprea*, *Anomala albopilosa*, *Popillia japonica*, *Heptophylla picea*, European Chafer (*Rhizotrogus majalis*), *Tomarus gibbosus*, *Holotrichia* spp., *Phyllophaga* spp. (for example, *Phyllophaga crinita*), or *Diloboderus* spp. (for example, *Diloboderus abderus*);
Curculionidae (for example, *Araecerus coffeae*, *Cylas formicarius*, *Euscepes post fasciatus*, *Hypera postica*, *Sitophilus zeamais*, *Echinocmemus squameus*, *Lissorhoptrus oryzophilus*, *Rhabdoscelus lineatocollis*, *Anthonomus grandis*, *Sphenophorus latus*, Southern Corn Bilibug (*Sphenophorus callosus*), Soybean stalk weevil (*Sternechus subsignatus*), Sgarcane wiivil (*Sphenophorus levis*), *Scepticus griseus*, *Scepticus uniformis*, *Zabrotes subfasciatus*, *Tomicus piniperda*, Coffee Berry Borer (*Hypothenemus hampei*), *Aracanthus* spp. (for example, *Aracanthus mourei*), or Curculionidae (for example, cottox root borer (*Eutinobothrus brasiliensis*)
Tenebrionidae (for example, *Tribolium castaneum*, or *Tribolium confusum*);
Coccinellidae (for example, *Epilachna vigintioctopunctata*);
Bostrychidae (for example, *Lyctus brunneus*);
Ptinidae;
Cerambycidae (for example, *Anoplophora malasiaca*, or *Migdolus fryanus*);
Elateridae (for example, *Melanotus okinawensis*, *Agriotes fuscicollis*, *Melanotus legatus*, *Anchastus* spp., *Conoderus* spp., *Ctenicera* spp., *Limonius* spp., or *Aeolus* spp.);
Staphylinidae (for example, *Paederus fuscipes*);
Dermestidae (for example, *Anthrenus verbasci*, or *Dermestes maculate*);
Anobidae (for example, *Lasioderma serricorne*, or *Stegobium paniceum*).

Orthoptera

Acrididae (for example, *Locusta migratoria*, *Dociostaurus marcccanus*, *Chortoicetes terminifera*, *Nomadacris septemfasciata*, Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), *Schistocerca gregaria*, Yellow-winged locust (*Gastrimargus musicus*), Spur-throated locust (*Austracris guttulosa*), *Oxya yezoensis*, *Oxya japonica*, or *Patanga succincta*);
Grvilotalpidae (for example, *Gryllotalpa orientalis*);
Gryllidae (for example, *Acheta domestica*, or *Teleogryllus emma*); and
Tettigoniidae (for example, Mormon cricket (*Anabrus simplex*)).

Hymenoptera

Tenthredinidae (for example, *Athalia rosae*, or *Athalia japonica*);
Formicidae (for example, *Solenopsis* spp. (for example, *Solenopsis invicta*, or *Solenop geminata*), *Atta* spp. (for example, Brown leaf-cutting ant (*Atta capiquara*)), *Acromyrmex* spp., *Camponotus* spp. (for example, *Paraponera clavata*, *Ochetellus glaber*, *Monomorium phareonis*, *Linepithema humile*, *Formica fusca japonica*, *Pristomyrmex punctutus*), *Pheidole node*, *Pheidole megacephala*, *Camponotus japonicus*, or *Camponotus obscuripes*), *Pogonomyrmex* spp. (for example, *Pogonomyrmex occidentalis*), *Wasmania* spp. (for example, *Wasmania auropunctata*), or *Anopiolepis gracilipes*)

Vespidae (for example, *Vespa mandarinia japonica, Vespa simillima, Vespa analis Fabriciusi, Vespa velutina, Polistes jokahamae*);

Siricidae (for example, *Urooerus gigas*); and Bethylidae.

Blattodea

Blattellidae (for example, *Blattella germanica*);

Blattidae (for example, *Periplaneta fuliginosa, Periplaneta americana, Periplaneta brunnea,* or *Blatta orientalis*);

Termitidae (for example, *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guanqzhouensis, Reticulitermes amamianus, Reticulitermes miyatakei, Reticulitermes kanmonensis, Nasutitermes takasagoensis, Pericapritermes nitobei, Sinocapritermes mushae,* or *Cornitermes cumulans*).

Siphonaptera

*Ctenocephalides felis, Ctenocephalides canis, Pulex irritans, Xenopsylla cheopis, Tunga penetrans, Echidnophaga gallinacea,* and *Nosopsyllus fasciatus.*

Anoplura

*Haematopinus suis, Haematopinus eurysternus, Dalmalinia ovis, Linognathus seypsus, Pediculus humanis, Pediculuc humanus corporis, Pediculus humanus humanus,* and *Phthirus pubis.*

Mallophagida

Menoponidae such as *Bovicola* spp. (for example, *Dalmalinia bovis,* or *Dalmalinia avis*), *Trichodectes* spp. (for example, *Trichodectes canis*), *Felocola* spp. (for example, *Felicola subrostrata*), *Lipeurus* spp, (for example, *Lipeurus caponis*), *Trimenopon* spp., and *Menopon* spp.

Acari

Tetranychidae (for example, *Tetranychus urticae, Tetranychus kanzawai, Tetranychus evansi, Panonychus citri, Panonychus ulmi,* or *Oligonychus* spp.);

Eriophyidae (for example, *Aculops pelekassi, Phyllocoptruta citri, Aculops lycopersici, Calacarus carinatus, Acaphylla theavagrans, Eriophyes chibaensi Aculus schlechtendali, Aceria diospyri, Aceria tosicheila,* or *Shevtchenkella* sp.);

Tarsonemidae (for example, *Polyphagot sonemus latus*);

Tenuipalpidae (for example, *Brevipalpus phoenicis*);

Tuckerellidae;

Ixodidae (for example, *Haemaphysalis longicornis, Haemaphysalis flava, Dermacentor taiwanensis, Dermacentor variabilis, Dermacentor andersoni, Ixodes ovatus, Ixodes persulcatus, Ixodes ricinus, Ixodes scapularis, Amblyomma americanum, Ambryomma maculatum, Boophilus microplus, Boophilus annulatus,* or *Rhipicephalus sanguineus*);

Acaridae (for example, *Tyrophagus putrescentiae,* or *Tyrophagus similius*);

Pyroglyphidae (for example, *Dermatophagoides farinae,* or *Dermatophagoides pteronyssinus*);

Cheyletidae (for example, *Cheyletus eruditus, Cheyletus malaccensis, Cheyletus moorei,* or *Cheyletiella yasguri*);

Sarcoptidae (for example, *Otodectes cynotis,* or *Sarcoptes scabiei*);

Demodicidae (for example, *Demodex canis*);

Listrophoridae;

Haplochthoniidae;

Macronyssidae (for example, *Ornithonyssus bacoti,* or *Ornithonyssus sylviarum*);

Dermanyssidae (for example, *Dermanyssus gallinae*); and

Trombiculidae (for example, *Leptotrombidium akamushi*).

Araneae

Eutichuridae (for example, *Cheiracanthium japonicum*); and Theridiidae (for example, *Latrodectus hasseltii*).

Polydesmida

Paradoxosomatidae (for example, *Oxidus gracilis* and *Nedyopus tambanus*);

Isopoda

Armadillidiidae (for example, *Armadillidium vulgare*).

Chilopoda

Scutigeridae (for example, *Thereuonema hilgendorfi*); Scolopendridae (for example, *Scolopendra subspinipes*) and Ethopolidae (for example, *Bohropolys rugosus*).

Gastropoda

Limacidae (for example, *Limax marginatus,* or *Limax flavus*); Philomycidae (for example, *Meghimatium bilineatum*); Ampullariidae (for example, *Pomacea canaliculata*); and Lymnaeidae (for example, *Austropeplea ollula*).

Nematoda

Aphelenchoididae (for example, *Aphelenchoides besseyi*); Pratylenchidae (for example, *Pratylenchus coffeae, Pratylenchus brachyurus, Pratylenchus neglectus,* or *Radopholus similis*); Heteroderidae (for example, *Meloidogyne javanica, Meloidogyne incognita, Meloidogyne hapla, Heterodera glycines, Globodera rostochiensis,* or *Globodera pallida*): Hoplolaimidae (for example, *Rotydenchulus reniformis*); Anguinidae (for example, *Nothotylenchus auris,* or *Ditydenchus dipsaci*); Tylenchulidae (for example, *Tylenchulus semipenetrans*); Longidoridae (for example, *Xiphinema index*); Trichodoridae; and Parasitaphelenchidae (for example, *Bursaphelenehus xylophilus*).

The harmful insects and harmful mites to be targeted may be insects and mites whose sensitivity to the insecticides and miticides. However, when the sensitivity to chemicals is largely reduced or the resistance against chemicals is largely developed, it is desirable to use the position of the present invention comprising any insecticides and miticides other than the insecticides and the miticides to be targeted.

The present compound Z or the present composition may be used to protect plants from the plant diseases csused by insect-mediated viruses or insect-mediated bacteria.

Examples of the insect-mediated viruses are included the followings.

Rice tungro spherical virus, Rice tungro bacilliform virus, Rice grassy stunt virus, Rice ragged stunt virus, Rice stripe virus, Rice black streaked dwarf virus, Southern rice black-streaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean, mild mosaic virus, Cycas necrotic stunt, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, Capsicum chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, plum pox virus, Chrysanthemum stem necrosis virus, Impatiens necrotic spot virus, Iris yellow spot virus, Lily mottle cirus, Lilly symptomless virus, Tulip mosaic virus, and the like.

Examples of the insect-mediated bacetria are included the followings.

Candidatus Phytoplasma oryzae, Candidatus Phytoplasma asteris, Maize bushy stunt phytoplasma, Candidatus Liberbacter asiaticus, Candidatus Liberbacter africanus, Candidatus Liberbacter amer canus, and the like.

When the present ingredient is a fungicide active ingredient, the composition of the present invention can be used to control plant diseases. Examples of the plant disease include the following. Here the descriptions in a parenthesis indicates an academic name of phytopathogenic microorganism that causes the disease.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Erysiphe graminis*), fusarium blight (*Fusarium graminearum, F. avenaceum, F. culmorum, Microdochium nivale*), stem rust (*Puccinia striiforruis, P. graminis, P. recondita*), snow mould (*Microdochium nivale, M. majus*), typhulasnow snow blight (*Typhula* sp.), loose smut (*Ustilago tritici*), stinking smut (*Tilletia caries, T. controversa*), eyespot (*Pseudocercosporella herpotrichoides*), septoria leaf blotch (*Septoria tritici*), glume blotch (*Stagonospora nodorum*), tan spot (*Pyrenophora tritici-repentis*), Rhizoctonia seeding blight (*Rhizoctonia solani*), and take-all disease (*Gaeumannomyces graminis*);

Barley diseases: owdery mildew (*Erysiphe graminis*), Fusarium blight (*Fusarium graminearum, F. avenaceum, F. culmorum, Microdochium nivale*), stem rust (*Puccinia striiformis, P. graminis, P. hordei*), loose smut (*Ustilago nuda*), scald (*Rhynchosporium secalis*), scald (*Rhynchosporium secalis*), net blotch (*Pyrenophora teres*), spot blotch (*Cochliobolus sativus*), stripe (*Pyrenophora graminea*), Ramularia disease (*Ramularia collo-cygni*), stripe rust. (*Puccinia striiformis*), stun rust (*Puccinia graminis*), dwarf leaf rust (*Puccinia hordei*), loose smut (*Ustilago nuda*), scald (*Rhynchosporium secalis*), net blotch (*Pyrenophora teres*), spot blotch (*Cochliobolus sativus*), stripe (*Pyrenophora graminea*), Ramularia disease (*Ramularia colllo-cygni*), and Rrhizoctonia seeding blight (*Rhizoctonia solani*);

Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), phaeosphaeria leaf spot (*Phaeosphaeria maydis*), diplodia rot (*Stenocarpella maydis, Stenocarpella macrospora*), stalk rot (*Fusarlum graminearum, Fusarium verticilioides, Colletotrichum graminicola*), smut (*Ustilgo maydis*);

Cotton diseases: anthracnose (*Colletotrichum gossypii*), grey mildew (*Ramularia areola*), alternaria leaf spot (*Alternaria macrospore, A. gossypii*), and black root rot (*Thielaviopsis brasicola*);

Coffee diseases: rust (*Hemileia vastatrix*), and leaf spot (*Cercospora coffeicola*);

Rape seed diseases: *Sclerotinia* rot (*Sclerotinia sclerotiorum*), gray leaf spot (*Alternaria brassicae*), and root rot (*Phoma lingam*);

Sugar cane diseases: rust (*Puccinia melanocephela, Puccinia kuehnii*), and smut (*Ustilago scitaminea*);

Sunflower diseases; rust (*Puccinia heliathi*), and downy mildew (*Plasmopara halstedii*);

Citrus diseases: melanose (*Diaporthe citri*), scab (*Elsinoe fawcetti*), mold (*Penicillium digitatum, Penicillium italicum*), and *Phytophthora* rot (*Phytophthora parasitica, Phytophthora citrophthora*);

Apple diseases: blossom blight (*Monilinia mali*), valsa canker (*Valsa ceratosperma*), powdery mildew (*Podosphaera leucotricha*), alternaria leaf spot (*Alternaria alternata* apple pathotype), scab (*Venturia inaequalis*), bitter rot (*Glomerella cingulata*), blotch (*Diplocarpon mali*), ring rut (*Botryosphaeria berengeriana*), crown rot (*Phytophtora cactorum*);

Pear diseases: scab (*Venturia nashicola, V. pirina*), black spot (*Alternaria alternata* Japanese pear pathotype), rust (*Gymnosporangium haraeanum*);

Peach diseases: brown rot (*Monilinia fructicola*), scab (*Cladosporium carpophilum*), Phomopsis rot (*Phomopsis* sp.), and leaf curl (*Taphriria deformans*);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Japanese persimmon diseases: anthracnose (*Gloeosporium kaki, Colletotrichum acutatum*), and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), Corynespora leaf spot (*Corynespora cassiicola*), Fusarium wilt (*Fusarium oxysporum*), downy mildew (*Pseudoperonospora cubensis*), Phytophthora rot (*Phytophthora* sp.), and damping-off (*Pythium* sp.);

Tomato diseases: early blight (*Alternaria solani*), leaf mold (*Cladosporium fulvum*), CercosPora leaf mold (*Pseudocercospora fuligena*), late blight (*Phytophthora infestans*), and powdery mildew (*Leveillula taurica*);

Eggplant diseases: brown spot (*Phomopsis vexans*), and powdery mildew (*Erysiphe cichoracearum*);

Cruciferous vegetables diseases: *Alternaria* leaf spot (*Alternaria japonica*), white spot (*Cercosporelia brassicae*), clubroot (*Plasmodiophora brassicae*), downy mildew (*Peronospora parasitica*);

Welsh onion disease: rust (*Puccinia allii*);

Soybean diseases: purple stain (*Cercospora kikuchii*), sphaceloma scab (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), Rhizoctonia rot (*Rhizoctonia solani*), Septoria brown spot (*Septoria glycines*), Cercospora leaf spot (*Cercospora sojina*), stem rot (*Sclerotinia sclerotiorum*), powdery mildew (*Microsphaera diffusa*), Phytophthora stem and root rot (*Phytophthora* sojae), downy mildew (*Peronospora manshurica*), sudden death syndrome (*Fusarium virguliforme*), Kidney bean diseases: stem rot (*Sclerotinia sclerotiorum*), rust (*Uromyces appendiculatus*), angular leaf spot (*Phaeoisariopsis griseola*), and anthracnose (*Colletotrichum lindemuthianum*);

Peanut diseases: leaf spot (*Cercospora personata*), brown leaf spot (*Cercospora arachidicola*), and southern blight (*Sclerotium rolfsii*);

Garden pea disease: powdery mildew (*Erysaphe pisi*);

Potato diseases: early blight (*Alternaria solani*), late blight (*Phytophthora infestans*), Pink rot (*Phytophthora erythroseptica*), powdery scab (*Spongospora subterranea*f. sp. *subterranea*), and *Verticillium* wilt (*Verticillium altoatzum, Verticillium dahliae, Verticillium nigrescens;*

Strawberry disease: powdery mildew (*Sphaerotheca humuli*);

Tea diseases: net blister blight (*Exobasidium reticulatum*), white scab (*Elsinoe leucospila*), gray blight (*Pestalotiopsis* sp.), and anthracnose (*Colletotrichum theae-sinensis*);

Tobacco diseases: brown spot (*Alternaria longipes*), anthracnose (*Collectotrichum tabacum*), blue mold (*Peronospora tabacina*), and black shank (*Phytophthora nicotianae*);

Sugar beet diseases: *Cercospora* leaf spot (*Cercospora beticola*), leaf blight (*Thanatephorus cucumeris*), root rot (*Thanatephorus cucumeris*), and *Aphanomyces* root rot (*Aphanomyces cochlioides*), and rust (*Uromyces betae*);

Rose diseases: black spot (*Diplocarpon rosae*), and powdery mildew (*Sphaerotheca pannosa*);

Chrysanthemum diseases: leaf blight (*Septoria chrysanthemi-indici*), and white rust (*Puccinia horiana*);

Onion diseases: *Botrytis* leaf blight (*Botrytis cinerea, B. byssoidea, B. squamosa*), gray-mold neck rot (*Botrytis allii*), and small sclerotial neck rot (*Botrytis squamosa*);

Various crops diseases: *Botrytis* rot (*Botrytis cinerea*), and *Sclerotinia* rot (*Sclerotinia sclerotiorum*);

Japanese radish disease: *Alternaria* leaf spot (*Alternaria brassicicola*);

Turfgrass diseases: dollar spot (*Sclerotinia homoeocarpa*), and brown pate and large patch (*Rhizoctonia solani*); as well as Banana disease: Sigatoka disease (*Mycosphaerella fijiensis, Myrosphaerella musicola*).

Seed diseases or diseases in the early stages of the growth of various plants caused by *Aspergillus* spp., *Penicillium* spp, *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp. or *Diplodia* spp.; and the like;

Viral diseases: viral diseases of several crops transmitted by *Polymixa* spp. or *Olpidium* spp.

Bacterial seedling blight of rice (*Burkholderia plantarii*), bacterial spot cucumber (*Pseudomonas syringae* pv. *Lachrymans*), bacterial wilt of eggplant (*Ralstonia solanacearum*), canker of *citrus* (*Xanthomonas citri*), and bacterial soft rot of Chinese cabbage (*Erwinia carotovora*).

The harmful arthropods, harmful nematodes and phytopathogenic fungus may be harmful arthropods, harmful nematodes or phytopathogenic fungus whose the sensitivity to any of the present ingredient is lowered or whose the resistance against the present ingredient is developed.

The composition for controlling harmful arthropods of the present invention comprises the compound Z of the present invention or the composition of the present invention and an inert carrier. The composition for controlling harmful arthropods of the present invention is usually prepared by mixing the compound Z of the present invention or the composition of the present invention with an inert carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations, and tablets and the others. Such formulations may be processed into mosquito repellent coils, electric mosquito repellent mats, liquid mosquito formulations, smoking agents, fumigants, sheet formulations, spot-on formulations or formulations for oral treatment. Also, the composition for controlling harmful arthropods of the present invention comprises usually 0.0001 to 95% by weight of the compound Z of the present invention or the composition of the present invention.

Examples of the solid carrier to be used in the formulation include fine powders or granules of clays (for example, kaolin clay, diatomaceous earth, bentonite, Fubasami clay, or acid white clay), dry silica, wet silica talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chlor propylene copolymers, and the others).

Examples of the liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalere); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl ether, 1,4-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, DMF, or N,N-dimethylacetamide); sulfoxides (for example, dimethyl sulfoxide); propylene carbonate; and vegetable oils (for example, soybean oil or cottonseedoil).

Examples of gaseous carrier include fluorocarbon, butane gas, liquefied petroleum was (LPG), dimethyl ether, and carbon dioxide gas.

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling harmful arthropods of the present invention is carried out by applying an effective amount of the compound Z of the present invention or the composition of the present invention to a harmful arthropod directly and/or a habitat thereof (for example, plant bodies, soil, an interior of a house, animal bodies). Also, the method for controlling harmful arthropods of the present invention may be applied to seeds. In the method for controlling harmful arthropods of the present invention, the Present compound is usually used in the form of a harmful arthropod controlling composition.

When a composition for controlling harmful arthropods of the present invention is used for controlling harmful arthropods in an agricultural field, the application dose as an amount sf the compound Z of the present invention is usually within a range from 1 to 10,000 g per 10,000 $m^2$. In the case of being applied to seeds, the application dose as an amount of the compound of the present invention is usually within a range of 0.001 to 100 g per 1 Kg seeds. When the composition for controlling harmful arthropods of the present invention is formulated into emulsifiable concentrate, wettable powder, or flowable formulation, the composition of the present invention is usually applied by diluting it with water in such a way that a concentration of the concentration of the active ingredient is within a range from 0.01 to 10,000 ppm. The granular formulation, or the dust formulation etc., is usually applied as itself without diluting it.

These formulations or an aqueous dilution thereof may be sparged directly to harmful arthropods or plants (such as crops) to be protected from harmful arthropods, and also may be applied to the soil of crop land in order to control harmful arthropods which live there.

Also, the resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the composition for controlling harmful arthropods of the present invention is used to control harmful arthropods that live inside a house, the application dose as an amount of the Present compound Z is usually within a range from 0.01 to 1,000 mg per 1 $m^2$ of an area to be treated, in the case of using it on a planar area. In the case of using it spatially, the application dose as an amount of the Present compound Z is usually within a range from 0.01 to 500 mg per 1 $m^3$ of the space to be treated. When the composition for controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the composition for controlling harmful arthropods of the present invention is used for controlling external parasites of livestock such as cows, horses, pigs, sheep, goats and chickens and small animals such as dogs, cats, rats and mice, the agent of the present invention may be applied to the animals by a known method in the veterinary field. Specifically, when systemic control is intended, the agent of the present invention is administered to the animals as a tablet, a mixture with feed or a suppository, or by injection (including intramuscular, subcutaneous, intravenous and intraperitoneal injections). On the other hand, when non-systemic control is intended, the agent of the present invention is applied to the animals by means of spraying of the oil solution or aqueous solution, pour-on or spot-on treatment, or washing of the animal with a shampoo formulation, or by putting a collar or tag made of the resin formulations to the animal. In the case of being administered to an animal body, the dose of rhe Present compound usually within a range from 0.1 to 1,000 mg per 1 kg of an animal body weight.

Also, the Present compound Z or the Present composition may be used as an agent for controlling harmful arthropods in agricultural lands such as paddy fields, fields, turfs, and orchards. The Present compound Z or the Present composition may be controlled the harmful arthropods where lives in agricultural lands where the following plants etc., are grown.

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper, or potato), cucurbitaceous vegetables (for example, cucumber, pumpkin, zucchini, water melon, or melon), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, green onion, onion, garlic, or asparagus), ammiaceous vegetables (for example, carrot, parsley, celery, or parsnip), chenopoddaceous vegetables (for example, spinach, or Swiss chard), lamiaceous vegetables (for example, *Perilla frutescens*, mint, or basil), strawberry, sweet potato, *Dioscorea japonica*, colocasia, or the others;

Flowers:
Ornamental Foliage Plants:
Lawn:
Fruits:
pomaceous fruits (for example, apple, pear, Japanese pear, Chinese quince, or quince),
stone fleshy fruits (for example, peach, plum, nectarine, *Prunus mume*, cherry fruit, apricot, or prune)
*citrus* fruits (for example, *Citrus unshiu*, orange, lemon, lime, or grapefruit),
nuts (for example, chestnut, walnuts, hazelnuts, almond, pistachio, cashew nuts, or macadamia nuts), berry fruits (for example, blueberry, cranberry, blackberry or raspberry),
grape, kaki persimmon, olive, Japanese plum, banana, coffee, date palm, coconuts, and the others;
Trees Other than Fruit Trees:
tea, mulberry, flowering plant, roadside trees (for example, ash, birch, dogwood, Eucalyptus, *Ginkgo biloba*, lilac, maple, Quercus, poplar, Judas tree, *Liquidambar formosana*, plane tree, zelkova, Japanese arborvitae, fir wood, hemlock, juniper, Pinus, Picea, and *Taxus cuspidate*); and the others.

The above plants also include a plant that can be generated by a natural crossbreeding, a plant that can be generated by mutations, an F1 hybrid plant, and a genetically modified crop. Examples of the genetically modified crop include a plant modified to have the resistance to HPPD (4-hydroxyphenylpyruvate dioxygenase) inhibitors such as isoxaflutole, ALS (acetolactate synthase) inhibitors such as imazethapyr and thifensulfuron-methyl, EPSP (5-enolpyruvoylshikimate-3-phosphate synthase) inhibitors, glutamine synthetase inhibitors, PPO (protoporphyrinogen oxidase) inhibitors, or herbicides such as bromoxynil and dicamba; a plant modified to synthesize a selective toxin known to be produced in *Bacillus* such as *Bacillus thuringiensis*; and a plant modified to have a specific insecticidal activity by synthesizing a gene fragment partially corresponding to an endogenous gene derived from a harmful insect to induce the gene silencing (RNAi; RNA inerference) in the target harmful insect.

Examples of applying an effective amount of the compound Z of the present invention or the composition of the present invention to plant or soils for cultivating plants include a method of applying an effective amount of the compound Z of the present invention or the composition of the present invention to a stem and leaf, a flower, a seedling, an ear of a plant; a method of applying an effective amount of the compound Z of the present invention or the composition of the present invention to a seed or a bulb such as seed tuber (for example, a seed disinfection, a seed soaking, or a seed coating), or a method of applying an effective amount of the compound Z of the present invention or the composition of the present invention to soils before planting plants or soils after planting plants.

Specific examples of applying an effective amount of the compound Z of the present invention or the composition of the present invention to a stem and leaf, a flower, fruit, an ear of a plant include a method for applying an effective amount of the compound Z of the present invention or the composition of the present invention to a surface of plant (for example, foliage application, and trunk application), a method for applying an effective amount of the compound Z of the present invention or the composition of the present invention to a flower or a whole plant at flowering times including before flowering, during flowering, and after flowering, and a method for applying an effective amount of the compound Z of the present invention or the composition of the present invention to an ear or a whole grain at sprouting season of grain.

Also, examples a method of controlling harmful arthropods by applying an effective amount of the compound. Z of the present invention or the composition of the present invention soils before planting plants or after planting plants include a method of applying an effective amount of the compound Z of the present invention or the composition of the present invention to a root part of a crop to be protected from damage such as ingestion by harmful arthropods, and a method controlling harmful arthropods that ingest a plant by permeating and transferring an effective amount of the compound Z of the present invention or the composition of the present invention from a root into the interior of the plant body. More specifically, examples of the method of applying an effective amount of the compound of the present invention or the composition of the present invention to soils before planting plants or after planting plants include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of soaring (planting row spraying at the time of sowing, soil mixing after planting row treatment at the time of sowing), broadcast treatment (overall soil surface spraying, soil mixing after broadcast t eatment), side-article treatment, treatment of water surface (application to water surface, application to water surface after flooding), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at seedling raising stage, drug solution injection treatment, irrigation of a plant part just above the ground, drug solution drip irrigation, chemigation), seedling raising box treatment (spraying into a seedling raising box, irrigation of a seedling raising box, flooding into a seedling raising box with drug solution), seedling raising tray treatment (spraying on a seedling raising tray, irrigation of a seedling raising tray, flooding into a seedling raising tray with drug solution), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing, spraying at sowing before covering with soils, spraying at sowing after covering with soils, mixing with covering soil, and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

A bulb described herein represents discoid stems, corms, rhizomes, tubers, tuberous, seed tubers, and tuberous roots. A method for controlling harmful arthropods by applying an effective amount of the compound Z of the present invention or the composition of the present invention into a seed or a bulb include a method of applying an effective amount of the compound Z of the present invention or the composition of the present invention directly into a seed or a bulb a plant to be protected from damage such as ingestion by harmful arthropods; and a method for controlling harmful arthropods that ingest a seed by applying an effective amount of the compound Z of the present invention or the composition of the present invention in the vicinity of a seed or a bulb; and a method for controlling harmful arthropods that ingest a plant by permeating and transferring an effective amount of the compound Z of the present invention or the composition of the present invention from a seed or a bulb into the interior of the plant body. More specifically, spraying treatment, spray coating treatment, immersion treatment, impregnation treatment, coating treatment, film coating treatment, and pellet coating treatment are included. These methods can provide a preparation of a seed or a bulb that retain an effective amount of the compound. Z of the present invention or the composition of the present invention on the surface and/or into the interior thereof.

When the compound Z of the present invention or the composition of the present invention are applied to a seed or a bulb, an effective amount of the compound Z of the present invention is usually within a range of 0.001 to 100 g, preferably within a range of 0.02 to 20 g, based on 1 kg of the seed or the bulb. Also an effective amount of the composition of the present invention is usually within a range of 0.000001 to 50 g, preferably within a range of 0.0001 to 30 g of a total amount of the compound Z of the present invention and the active ingredient of the present invention, based on 1 kg of the seed or the bulb.

The plants described above are not limited specifically, as long as they are breeds that are usually cultivated.

EXAMPLES

Hereinafter, the present invention is explained in more detail by using Preparation Example, Formulation Example, and Test Example and the like, however, the present invention should not be limited to these examples.

In the below-mentioned Examples, when "present compound" is described, the term encompasses the "Present compound" and the "Present compound Z". First, the Preparation Examples of the present compound Z are shown.

Reference Preparation Example 1-1

The mixture of 6-chloro-2-fluoropyridin-3-yl boronic acid 3.75 g, 2-bromo-3-(ethylsulfanyl)pyridine 4.66 g, [1,1-bis(diphenylphosphino)ferrocene]palladium dichloride 0.77 g, tripotassium phosphate 13.5 g, DMF 20 mL, and water 2 mL were stirred at 80° C. under argon atmosphere for 9 hours. The reaction mixtures were cooled to room temperature, and water was added to the mixtures, and the mixtures were extracted with ethyl acetate. The resulting organic layers were dried over anhydrous sodium sulfate, and concentrated under reduced pressure. The resulting residue was subjected to a silica gel column chromatography to obtain the intermediate compound A-1 shown below 2.9 g.

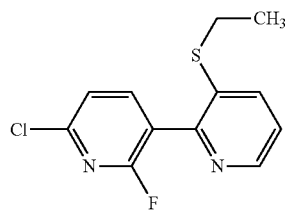 [SMILES: CCSc1cccnc1-c1ccc(Cl)nc1F]

Intermediate compound A-1: $^1$H-NMR (CDCl$_2$) δ: 8.50 (1H, dd), 7.85 (1H, dd), 7.75 (1H, dd), 7.35-7.31 (2H, m), 2.88 (2H, q), 1.26 (3H, t).

Reference Preparation Example 1-2

The process was carried out by using 6-chloro-4-fluoropyridin-3-yl boronic acid pinacol ester in place of 6-chloro-2-fluoropyridin-3-yl boronic acid according to the method described in Reference Preparation obtain the intermediate compound B-1 shown below.

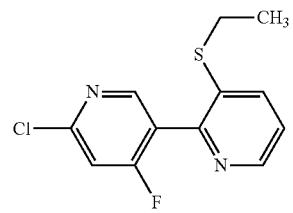

Intermediate compound B-1: $^1$H-NMR (CDCl$_3$) δ: 8.53 (1H, dd), 8.46 (1H, d), 7.76 (1H, dd), 7.34 (1H, dd), 7.20 (1H, d), 2.87 (2H, q), 1.25 (3H, t).

Reference Preparation Example 2-1

To the mixtures of the intermediate compound A-1 2.9 g, sodium hydride (60% in oil) 0.43 g and DMF 10 mL were added dropwise benzyl alcohol 1.1 mL under ice-cooling, and the reaction mixtures were stirred at 0° C. for 5 h. Water was added to the mixtures, and the mixtures were extracted with ethyl acetate. The resulting organic layers were dried over anhydrous sodium sulfate, and concentrated under reduced pressure. The resulting residue was subjected to a silica gel column chromatography to obtain the intermediate compound A-2 shown below 3.31 g.

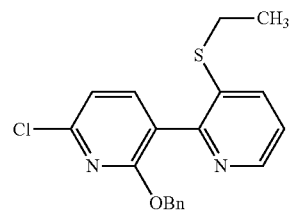 [SMILES: CCSc1cccnc1-c1ccc(Cl)nc1OCc1ccccc1]

Intermediate compound A-2: $^1$H-NMR (CDCl$_3$) δ: 8.47 (1H, dd), 7.69 (1H, dd), 7.59 (1H, d), 7.31-7.26 (6H, m), 7.04 (1H, d), 5.42 (2H, s), 2.78 (2H, q), 1.17 (3H, t).

Reference Preparation Example 2-2

The compound which was prepared according to the method described in Reference Preparation Example 2-1 and its physical property value are shown below.

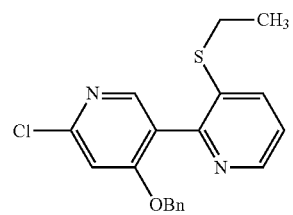 [SMILES: CCSc1cccnc1-c1cnc(Cl)cc1OCc1ccccc1]

Intermediate compound B-2: ¹H-NMR. (CDCl₃) δ: 8.50 (1H, dd), 8.22 (1H, s), 7.71 (1H, dd), 7.31-7.29 (6H, m), 6.96 (1H, s), 5.14 (2H, s), 2.81 (2H, q), 1.20 (3H, t).

Reference Preparation Example 2-3

To the mixtures of the intermediate compound B-2 0.53 g and chloroform 15 mL was added mCPBA (purity 70%) 0.8 g under ice-cooling, and the mixtures were stirred at 0° C. to room temperature for 5 hours. To the mixtures was added aqueous sodium thiosulfate solution, and the mixtures were extracted with chloroform. The resulting organic layers were washed with saturated aqueous sodium bicarbonate solution, dried over anhydrous sodium sulfate, and concentrated under reduced pressure. The resulting residue was subjected to a silica gel column chromatography to obtain the intermediate compound B-3 shown below 0.35 g.

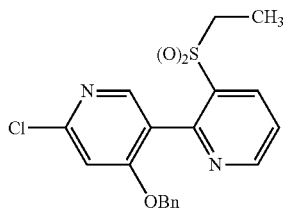

Intermediate compound B-3: ¹H-NMR (CDCl₃) δ: 8.92 (1H, dd), 8.42 (1H, dd), 8.19 (1H, s), 7.57 (1H, dd), 7.31-7.29 (3H, m), 7.23-7.21 (2H, m), 7.01 (1H, s), 5.10 (2H, s), 2.90 (2H, q), 1.10 (3H, t).

Reference Preparation Example 2-4

The compound which was prepared according to the method described in Reference Preparation Example 2-3 and its physical property value are shown below.

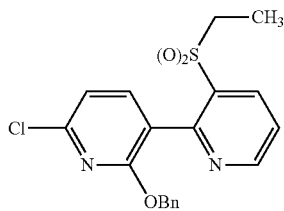

Intermediate compound A-6: ¹H-NMR (CDCl₃) δ: 8.91 (1H, dd), 8.40 (1H, dd), 7.63 (1H, d), 7.55 (1H, dd), 7.30-7.24 (5H, m), 7.08 (1H, d), 5.50-5.28 (2H, m), 2.78-2.71 (2H, m), 0.92 (3H, t).

Reference Preparation Example 3-1

The mixtures of the intermediate compound A-2 3.31 g and concentrated hydrochloric acid 10 mL was stirred at 80° C. for 1.5 hours. The mixtures were cooled to room temperature, and then to the mixtures was added 2M aqueous sodium hydroxide solution to adjust the pH 4. The precipitated solids were collected by filtration to obtain the intermediate compound A-3 shown below 2.03 g.

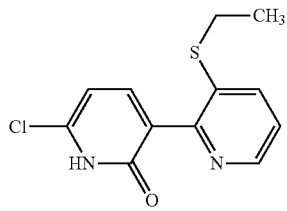 [SMILES: CCSc1cccnc1-c1ccc(Cl)[nH]c1=O]

Intermediate compound A-3: ¹H-NMR (CDCl₃) δ: 8.44 (1H, d), 8.39 (1H, dd), 7.85 (1H, dd, J=8.1, 1.5 Hz), 7.30 (1H, dd), 6.94 (1H, d), 2.94 (2H, q), 1.29 (3H, t).

Reference Preparation Example 3-1 A

The compounds which were prepared according to the method described in Reference Preparation Example 3-1 and their physical property values are shown below.

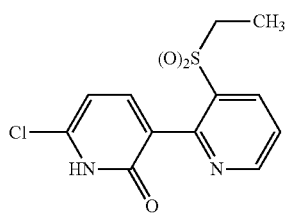

Intermediate compound A-7: ¹H-NMR (CDCl₃) δ: 8.91 (1H, dd), 8.41 (1H, dd), 7.64 (1H, d), 7.58 (1H, dd), 6.68 (1H, d), 3.37 (2H, q), 1.30 (3H, t).

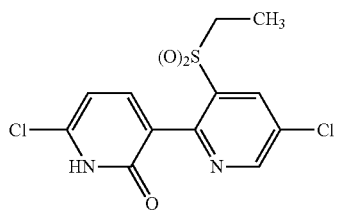

Intermediate compound A-21: ¹H-NMR (CDCl₃) δ: 8.84 (1H, d), 8.37 (1H, d), 7.59 (1H, d), 6.64 (1H, d), 3.40 (2H, q), 1.33 (3H, t).

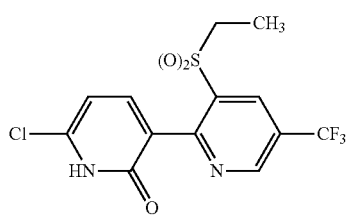

Intermediate compound A-25: ¹H-NMR (CDCl₃) δ: 9.13 (1H, s), 8.61 (1H, s), 7.62 (1H, d), 6.64 (1H, d), 3.46-3.43 (2H, m), 1.35 (3H, t).

Reference Preparation Example 3-2

A mixture of the intermediate compound A-38 10 g and concentrated hydrochloric acid 30 mL was stirred under reflux for 16 hours. The mixture was cooled to room temperature, and thereto was added toluene, and the mixture was concentrated under reduced pressure. The resulting solids were washed with hexane to obtain the intermediate compound A-39 shown below 8 g.

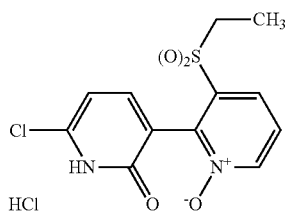

Intermediate compound A-39: ¹H-NMR (CDCl₃) δ: 8.63 (1H, d), 7.87-7.85 (1H, m), 7.73-7.68 (2H, m), 7.04 (1H, d), 3.18-3.02 (2H, m), 1.07 (3H, t).

Reference Preparation Example 3-2A

The compounds which were prepared according to the method described in Reference Preparation Example 3-2 and their physical property values are shown below.

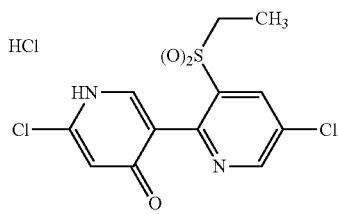

Intermediate compound B-16: ¹H-NMR (CDCl₃) δ: 8.87 (1H, s), 8.34 (1H, s), 8.26 (1H, s), 7.89 (1H, s), 3.24-3.18 (2H, m), 1.30 (3H, t).

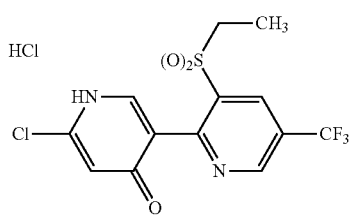

Intermediate compound B-20: ¹H-NMR (CDCl₃) δ: 9.16 (1H, s), 8.60 (1H, s), 8.29 (1H, s), 7.66 (1H, s), 3.25-3.19 (2H, m), 1.32-1.26

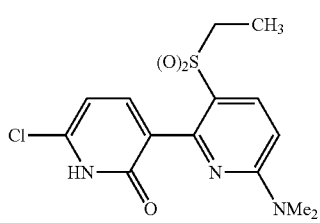

Intermediate Compound A-44

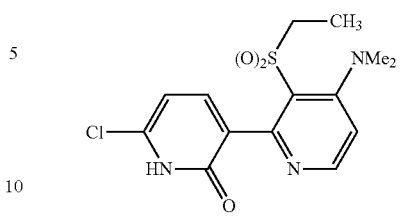

Intermediate Compound A-47

Reference Preparation Example B-3

The mixtures of the intermediate compound B-3 0.35 g, 10% palladium-carbon 100 mg, and ethyl acetate 5 mL were stirred under hydrogen atmosphere for 3 hours. The reaction mixtures were filtered through Celite (Registered Trademark), concentrated under reduced pressure to obtain the intermediate compound B-4 shown below 0.11 g.

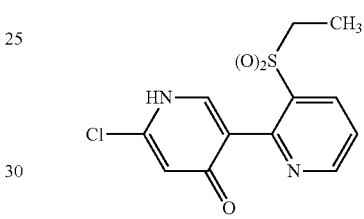

Intermediate compound B-4: ¹H-NMR (CDCl₃) δ: 8.87 (1H, dd), 8.61 (1H, d), 8.54 (1H, s), 7.62 (1H, dd), 6.94 (1H, s), 3.08 (2H, q), 1.18 (3H, t).

Reference Preparation Example 4-1

The mixtures of the intermediate compound A-3 1.0 g, methyl iodide 0.28 mL, cesium carbonate 1.82 g, and DMF 10 mL were stirred at 0° C. for 3.5 hours. Water was added to the mixtures, and the mixtures were extracted with ethyl acetate. The resulting organic layers were dried over anhydrous sodium sulfate, and concentrated under reduced pressure. The resulting residue was subjected to a silica gel column chromatography to obtain the intermediate compound A-4 shown below 0.55 g.

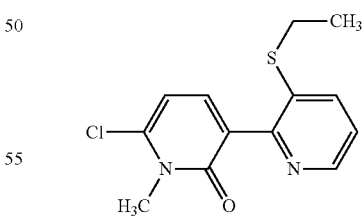

Intermediate compound A-4: ¹H-NMR (CDCl₃) δ: 8.45 (1H, dd), 7.69 (1H, dd), 7.42 (1H, d, J=7.5 Hz), 7.24 (1H, dd), 6.43 (1H, d), 3.76 (3H, s), 2.88 (2H, q), 1.26 (3H, t).

Reference Preparation Example 4-2

The compounds which were prepared according to the method described in Reference Preparation Example 4-1 and their physical property values are shown below.

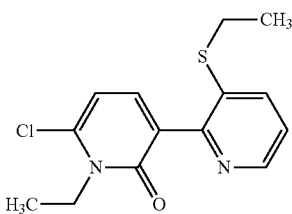 [SMILES: CCSc1cccnc1-c1ccc(Cl)n(CC)c1=O]

Intermediate compound A-5: $^1$H-NMR (CDCl$_3$) δ: 8.45 (1H, d), 7.70 (1H, d), 7.40 (1H, d), 7.23 (1H, dd), 6.40 (1H, d), 4.39-4.38 (2H, m), 2.91-2.85 (2H, m), 1.37 (3H, t), 1.25 (3H, t)

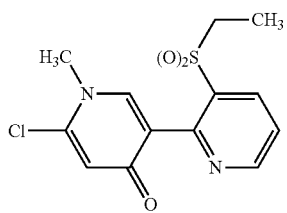

Intermediate compound B-5: $^1$H-NMR (CDCl$_3$) δ: 8.93 (1H, dd), 8.45 (1H, dd), 8.16 (1H, 7.60 (1H, dd), 6.95 (1H, s), 3.83 (3H, s), 2.93 (2H, q), 1.19 (3H, t).

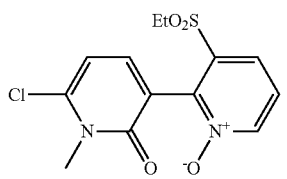

Intermediate Compound A-40

The compounds represented by formula (MA-1):

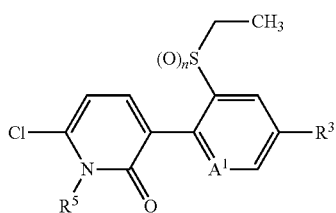

(MA-1)

wherein the combination of R$^5$, A$^1$, R$^3$ and n represents any combinations indicated in Table 17.

TABLE 17

| Intermediate compound | R$^5$ | A$^1$ | R$^3$ | n |
|---|---|---|---|---|
| A-8 | Pr | N | H | 2 |
| A-9 | i-Pr | N | H | 2 |
| A-10 | Bu | N | H | 2 |
| A-11 | CH$_2$CH=CH$_2$ | N | H | 2 |
| A-12 | CH$_2$C≡CH | N | H | 2 |
| A-13 | CH$_2$c-Pr | N | H | 2 |
| A-14 | CH$_2$CF$_2$CF$_3$ | N | H | 2 |
| A-15 | Bn | N | H | 2 |

TABLE 17-continued

| Intermediate compound | R$^5$ | A$^1$ | R$^3$ | n |
|---|---|---|---|---|
| A-16 | ethyl-thiazole-Cl (see structure) | N | H | 2 |
| A-22 | Me | N | Cl | 2 |
| A-26 | Me | N | CF$_3$ | 2 |
| A-37 | Me | N | H | 2 |
| A-42 | Et | N | CF$_3$ | 2 |

Intermediate compound A-8: $^1$H-NMR (CDCl$_3$) δ: 8.87 (1H, dd), 8.34 (1H, dd), 7.52 (1H, dd), 7.39 (1H, d), 6.46 (1H, d), 4.25 (2H, m), 3.53-3.42 (2H, m), 1.85-1.74 (2H, 1.33 (3H, t), 1.01 (3H, t).

Intermediate compound A-9: $^1$H-NMR (CDCl$_3$) δ: 8.86 (1H, dd), 8.33 (1H, dd), 7.51 (1H, dd), 7.33 (1H, t), 6.42 (1H, q), 5.18-5.14 (1H, m), 3.55-3.41 (2H, m), 1.65-1.61 (6H, m), 1.33 (3H, t).

Intermediate compound A-10: $^1$H-NMR (CDCl$_3$) δ: 8.87 (1H, dd), 8.34 (1H, dd), 7.52 (1H, dd), 7.39 (1H, d), 6.46 (1H, d), 4.28 (2H, t), 3.48 (2H, q), 1.78-1.69 (2H, m), 1.45-1.42 (2H, m), 1.33 (3H, t), 0.97 (3H, t).

Intermediate compound A-11: $^1$H-NMR (CDCl$_3$) δ: 8.87 (1H, dd), 8.33 (1H, dd), 7.52 (1H, dd), 7.43 (1H, d), 6.49 (1H, d), 5.98-5.89 (1H, m), 5.27-5.20 (2H, m), 4.95-4.89 (2H, m), 3.47 (2H, q), 1.32 (3H, t).

Intermediate compound A-12: $^1$H-NMR (CDCl$_3$) δ: 8.87 (1H, dd), 8.35 (1H, dd), 7.53 (1H, dd), 7.45 (1H, d), 6.51 (1H, d), 5.11-5.00 (2H, m), 3.47 (2H, q), 2.27 (1H, t), 1.33 (3H, t).

Intermediate compound A-13: $^1$H-NMR (CDCl$_3$) δ: 8.87 (1H, dd), 8.35 (1H, dd), 7.52 (1H, dd), 7.40 (1H, d), 6.47 (1H, d), 4.23-4.20 (2H, m), 3.48-3.44 (2H, m), 1.33 (4H, t), 0.56-0.52 (4H, m).

Intermediate compound A-14: $^1$H-NMR (CDCl$_3$) δ: 8.88 (1H, dd), 8.35 (1H, dd), 7.55 (1H, dd), 7.47 (1H, d), 6.56 (1H, d), 5.03 (2H, br s), 3.40 (2H, q), 1.32 (3H, t).

Intermediate compound A-15: $^1$H-NMR (CDCl$_3$) δ: 8.87 (1H, dd), 8.33 (1H, dd), 7.52 (1H, dd), 7.45 (1H, d), 7.33-7.27 (5H, m), 6.51 (1H, d), 5.64-5.42 (2H, m), 3.40-3.37 (2H, m), 1.25 (3H, t).

Intermediate compound A-16: $^1$H-NMR (CDCl$_3$) δ: 8.88 (1H, dd), 8.36 (1H, dd), 7.66 (1H, s), 7.55 (1H, dd), 7.44 (1H, d), 6.52 (1H, d), 5.57-5.47 (2H, m), 3.54-3.37 (2H, m), 1.36 (3H, t).

Intermediate compound A-22: $^1$H-NMR (CDCl$_3$) δ: 8.81 (1H, d), 8.33 (1H, d), 7.41 (1H, d), 6.50 (1H, d), 3.74 (3H, s), 3.50-3.46 (2H, m), 1.35 (3H, t).

Intermediate compound A-26: $^1$H-NMR (CDCl$_3$) δ: 9.10 (1H, s), 8.57 (1H, s), 7.46 (1H, d), 6.53 (1H, d), 3.75 (3H, s), 3.52 (2H, q), 1.36 (3H, t).

Intermediate compound A-37: $^1$H-NMR (CDCl$_3$) δ: 8.86 (1H, d), 8.34 (1H, d), 7.52-7.4 (1H, m), 7.40 (1H, d), 6.48 (1H, d), 3.72 (3H, s), 3.43 (2H, q), 1.31 (3H, t).

Intermediate compound. A-42: $^1$H-NMR (CDCl$_3$) δ: 9.10 (1H, d), 8.55 (1H, d), 7.44 (1H, d), 6.50 (1H, d), 4.38 (2H, q), 3.61-3.54 (2H, m), 1.38 (3H, t), 1.37 (3H, t).

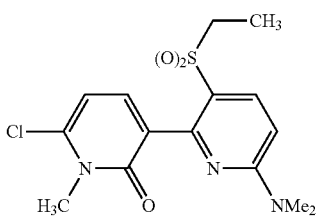

Intermediate compound A-45: ¹H-NMR (CDCl₃) δ: 7.93 (1H, d), 7.30 (1H, d), 6.52-6.40 (2H, m), 3.70 (3H, s), 3.37-3.30 (2H, m), 3.13 (6H, s), 1.27 (3H, t).

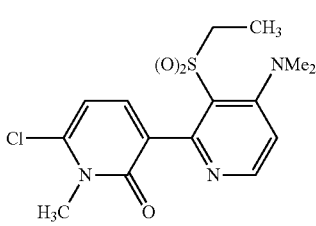

Intermediate compound A-48

The compounds represented by formula (MB-1):

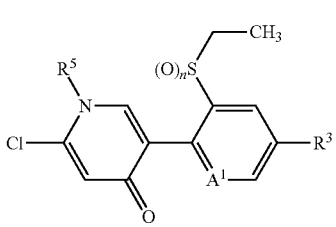

(MB-1)

wherein the combination of $R^5$, $A^1$, $R^3$ and n represents any combinations indicated in Table 18.

TABLE 18

| Intermediate compound | $R^5$ | $A^1$ | $R^3$ | n |
|---|---|---|---|---|
| B-9 | Et | N | H | 2 |
| B-10 | Pr | N | H | 2 |
| B-11 | Bu | N | H | 2 |
| B-12 | CH₂CH=CH₂ | N | H | 2 |
| B-13 | CH₂c-Pr | N | H | 2 |
| B-17 | Me | N | Cl | 2 |
| B-21 | Me | N | CF₃ | 2 |
| B-22 | i-Pr | N | H | 2 |
| B-23 | Bn | N | H | 2 |
| B-24 | CH₂CH₂CF₃ | N | H | 2 |

Intermediate compound B-9: ¹H-NMR (CDCl₃) δ: 8.88 (1H, dd), 8.38 (1H, dd), 7.56 (1H, s), 7.53 (1H, dd), 6.62 (1H, s), 4.15-4.09 (2H, m), 3.49-3.39 (2H, m), 1.48 (3H, t), 1.30 (3H, t).

Intermediate compound B-10: ¹H-NMR (CDCl₃) δ: 8.88 (1H, dd), 8.38 (1H, dd), 7.53 (1H, s), 7.52 (1H, dd), 6.61 (1H, s), 4.10-3.92 (2H, m), 3.51-3.36 (2H, m), 1.93-1.84 (2H, m), 1.30 (3H, t), 1.01 (3H, t).

Intermediate compound B-11: ¹H-NMR (CDCl₃) δ: 8.88 (1H, dd), 8.38 (1H, dd), 7.52 (2H, dd), 6.62 (1H, s), 4.07 (2H, s), 3.44 (2H, s), 1.84-1.81 (2H, m), 1.43-1.40 (2H, m), 1.30 (3H, t), 0.98 (3H, t).

Intermediate compound B-12: ¹H-NMR (CDCl₃) δ: 8.88 (1H, dd), 8.37 (1H, dd), 7.54-7.52 (2H, m), 6.63 (1H, s), 6.00-5.90 (1H, m), 5.39 (1H, d), 5.27 (1H, d), 4.70-4.64 (2H, m), 3.49-3.44 (2H, m), 1.31 (3H, t).

Intermediate compound B-13: ¹H-NMR (CDCl₃) δ: 8.89 (1H, dd), 8.39 (1H, dd), 7.63 (1H, s), 7.53 (1H, dd), 6.63 (1H, s), 4.01-3.88 (2H, m), 3.50-3.37 (2H, m), 1.33-1.28 (4H, m), 0.74-0.70 (2H, m), 0.45 (2H, m).

Intermediate compound B-17: ¹H-NMR (CDCl₃) δ: 8.80 (1H, d), 8.34 (1H, d), 7.53 (1H, s), 6.63 (1H, s), 3.77 (3H, s), 3.57-3.49 (2H, m), 1.35 (3H, t).

Intermediate compound B-21: ¹H-NMR (CDCl₃) δ: 9.16 (1H, d), 8.68 (1H, d), 8.17 (1H, s), 6.98 (1H, s), 3.85 (3H, 2.96 (2H, q), 1.22 (3H, t).

Intermediate compound B-21: ¹H-NMR (CDCl₃) δ: 8.90 (1H, dd), 8.41 (1H, dd), 7.64 (1H, s), 7.53 (1H, dd), 6.62 (1H, s), 5.02-4.96 (1H, m), 3.41-3.29 (2H, m), 1.49 (6H, d), 1.29-1.25 (3H, m).

Intermediate compound B-23: ¹H-NMR (CDCl₃) δ: 8.87 (1H, dd), 8.37 (1H, dd), 7.62 (1H, s), 7.52 (1H, dd), 7.43-7.33 (3H, m), 7.26-7.22 (2H, m), 6.65 (1H, s), 5.27-5.23 (2H, m), 3.52-3.41 (2H, m), 1.32 (3H, t).

Intermediate compound B-24: ¹H-NMR (CDCl₃) δ: 8.89 (1H, dd), 8.38 (1H, dd), 7.54 (1H, dd), 7.53 (1H, s), 6.64 (1H, s), 4.41-4.22 (2H, m), 3.44-3.37 (2H, m), 2.77-2.63 (2H, m), 1.30 (3H, t).

Reference Preparation Example 5

The mixtures of the intermediate compound A-7 0.4 g, copper(II) acetate 0.48 g, cesium carbonate 0.43 g, cyclopropyl boronic acid 0.23 g, pyridine 0.3 mL, and xylene 2.7 mL were stirred at 110° C. for 20 hours. The resulting mitures were cooled to room temperature, and the mixtures were filtered through Celite (Registered trademark) and the filtrates were concentrated under reduced pressure. The resulting residue was subjected to a silica gel column chromatography to obtain the intermediate compound A-17 shown below 37 mg.

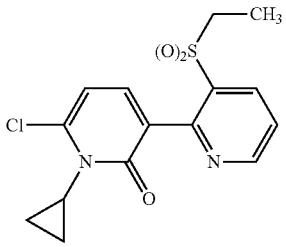

Intermediate compound A-17: ¹H-NMR (CDCl₃) δ: 8.86 (1H, dd), 8.32 (1H, dd), 7.51 (1H, dd), 7.38 (1H, d), 6.43 (1H, d), 3.52 (2H, q), 2.99-2.95 (1H, m), 1.36 (3H, t), 1.32-1.31 (2H, m), 1.03-1.00 (2H, m).

Reference Preparation Example 6-1

To the mixtures of methyl 6-chloro-2-methoxy nicotinic acid 0.5 g, ethyl methyl sulfone 5 mL and THF 12 mL was added dropwise lithium hexamethyl disilazide (1.1 M THF solution) 5 mL at −10° C. The resulting mixtures were stirred for 20 minutes, and thereto was added 6N hydrochloric acid 1 mL.

Water was added to the resulting mixtures, and the mixtures were extracted with ethyl acetate. The resulting organic layers were dried over anhydrous sodium sulfate, and concentrated under reduced pressure. The resulting residue was subjected to a silica gel column chromatography to obtain the intermediate compound A-18 shown below 0.6 cf.

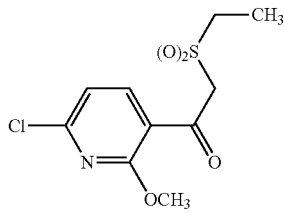

Intermediate compound A-18: $^1$H-NMR (CDCl$_3$) δ: 8.14 (1H, d), 7.06 (1H, d), 4.74 (2H, s), 4.13 (3H, s), 3.28 (2H, q), 1.44 (3H, t).

Reference Preparation Example 6-2

The compound which was prepared according to the method described in Reference Preparation Example 6-1 and its physical property value are shown below.

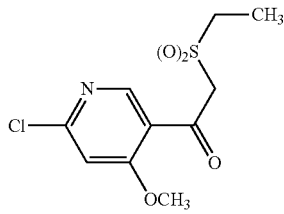

Intermediate compound B-6: $^1$H-NMR (CDCl$_3$) δ: 8.69 (1H, s), 6.98 (1H, s), 4.67 (2H, s), 4.06 (3H, s), 3.26 (2H, q), 1.44 (3H, t).

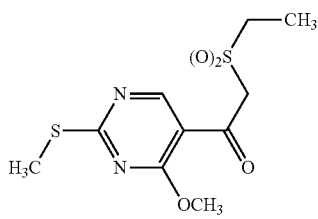

Intermediate compound C-2: $^1$H-NMR (CDCl$_3$) δ: 8.81 (1H, s), 4.68 (2H, s), 4.17 (3H, s), 3.26 (2H, q), 2.61 (3H, s), 1.44 (5H, t).

Reference Preparation Example 7-1

The mixtures of the intermediate compound A-18 2.96 g, ammonium acetate 5.0 g, acetic acid 0.15 mL, and methanol 13 mL were stirred at 65° C. for 6 hours. The resulting mixtures were cooled to room temperature, and thereto was added aqueous sodium hydroxide solution. The precipitated solids were filtered, and the obtained solids were washed with water, concentrated under reduced pressure to obtain the intermediate compound A-19 shown below 2.7 g.

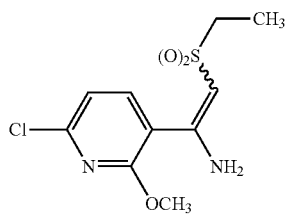

Intermediate compound A-19: $^1$H-NMR (CDCl$_3$) δ: 7.67 (1H, d), 6.98 (1H, d), 6.11 (2H, br s), 4.83 (1H, s), 4.02 (3H s), 3.07 (2H, q), 1.41 (3H, t).

Reference Preparation Example 7-2

The compound which was prepared according to the method described in Reference Preparation Example 7-1 and its physical property value are shown below.

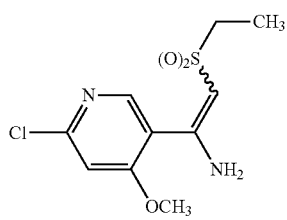

Intermediate compound B-14: $^1$H-NMR (CDCl$_3$) δ: 8.28 (1H, s), 6.91 (1H, s), 5.95 (2H, 4.81 (1H, s), 3.95 (3H, s), 3.08 (2H, q), 1.42 (3H, t).

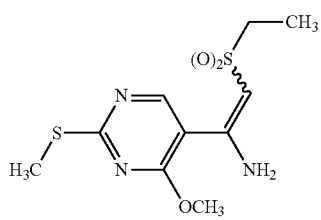

Intermediate compound C-3: $^1$H-NMR (CDCl$_3$) δ: 8.38 (1H, s), 6.08 (2H, br), 4.87 (1H, s), 4.06 (3H, s), 3.08 (2H, q), 2.58 (3H, s), 1.41 (3H, t).

Reference Preparation Example 8-1

The mixtures of sodium hydride (60% in oil) 0.90 g and DMF 25 mL were cooled to 0° C., and thereto was added dropwise the intermediate compound A-19 2.71 g that was dissolved in DMF 5 mL. The resulting mixtures were stirred at 0° C. for 30 minutes, and thereto was then added 2-chloro-1,3-bis(dimethylamino)trimethinium hexafluorophoshate 6.60 g, and the mixtures were stirred at 60° C. for 2 hours. The resulting mixtures were cooled to room temperature, and, water was added thereto, and the mixtures were extracted with ethyl acetate. The resulting organic layers were dried over anhydrous sodium sulfate and concentrated under reduced pressure. The esulting residue was subjected to a silica gel column chromatography to obtain the intermediate compound A-20 shown below 2.48 g Here 2-chloro-1,3-bis(dimethylamino)trimethinium hexafluo ophosphate was prepared according to the method described in *J. Org. chem.*, 2000, 65, 4571.

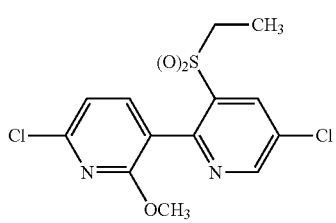

Intermediate compound A-20: ¹H-NMR (CDCl₃) δ: 8.84 (1H, d), 8.43 (1H, d), 7.60 (1H, d), 7.06 (1H, d), 3.91 (3H, s), 2.97-2.87 (2H, m), 1.21 (3H, t).

Reference Preparation Example 8-2

The compound which was prepared according to the method described in Reference Preparation Example 8-1 and its physical property value are shown below.

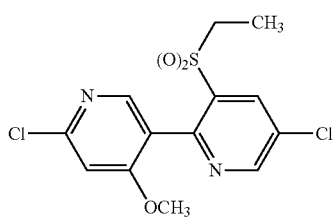

Intermediate compound B-15: ¹H-NMR (CDCl₃) δ: 8.86 (1H, d), 8.43 (1H, d), 8.14 (1H, s), 6.95 (1H, s), 3.83 (3H, s), 2.93 (2H, q), 1.21 (3H, t).

Reference Preparation Example 8-3

The compounds which were prepared by using 2-trifluoromethyl-1,3-bis(dimethylamino)trimethinium hexafluorophosphate in place of 2-chloro-1,3-bis(dimethylamino)trimethinium hexafluorophosphate according to the method described in Reference Preparation Example 8-1 and their physical property values are shown below.

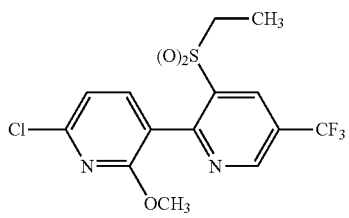

Intermediate compound A-24: ¹H-NMR (CDCl₃) δ: 9.14 (1H, d), 8.69 (1H, d), 7.62 (1H, d), 7.09 (1H, d), 3.92 (3H, s), 2.98-2.93 (2H, m), 1.22 (3H, t).

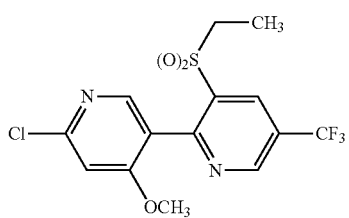

Intermediate compound B-19: ¹H-NMR (CDCl₃) δ: 9.16 (1H, d), 8.68 (1H, d), 8.17 (1H, s), 6.98 (1H, s), 3.85 (3H, s), 2.96 (2H, q), 1.22 (3H, t).

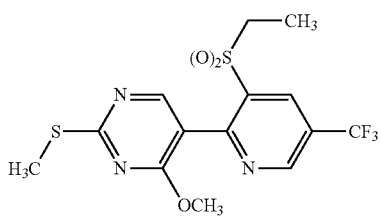

Intermediate compound C-4: ¹H-NMR (CDCl₃) δ: 9.15 (1H, 8.67 (1H, d), 8.29 (1H, s), 3.97 (3H, s), 3.02-2.99 (2H, m), 2.62 (3H, s), 1.23 (3H, t).

Reference Preparation Example 9-1

To the mixtures of DMF 0.84 mL and chloroform 24 mL was added dropwise oxalyl chloride 0.92 mL under ice-cooling. The resulting mixtures were stirred for 15 minutes under ice-cooling, and then stirred at room temperature for 2 hours. The resulting mixtures were cooled again under ice-cooling, and thereto was added butyl vinyl ether 2.8 mL, and the mixtures were stirred for 1 hour. The resulting mixtures were warmed to room temperature, and stirred for 2 hours. To the resulting mixtures were added the intermediate compound B-6 1.00 g and triethyl amine 3.5 mL successively under ice-cooling. The resulting mixtures were stirred at room temperature for 3 hours, and thereto was added saturated aqueous ammonium chloride solution, and the mixtures were extracted with chloroform. The resulting organic layers were dried over sodium sulfate, filtered and concentrated under reduced pressure. To the resulting residues were added ethanol 13 mL and 30% ammonia water 1.4 mL successively. The resulting mixtures were stirred at 60° C. for 9 hours, and concentrated under reduced pressure. Water was added to the resulting residues, and the mixtures were extracted with ethyl acetate. The resulting organic layers were washed with saturated brine, dried over anhydrous sodium sulfate, filtered, and concentrated under reduced pressure. To resulting residue were added to ethanol 13 mL and 30 aqueous ammonia 1.4 mL successively. The resulting mixture was stirred at 60° C. for 9 hours, and concentrated under reduced pressure. Water was added to the resulting residue, and the mixture was extracted with ethyl acetate. The resulting organic layer was washed with saturated brine, dried over anhydrous sodium sulfate, filtered, and concentrated under reduced pressure. The resulting residue was subjected to a silica gel column chromatography to obtain the intermediate compound B-7 shown below 0.87 g.

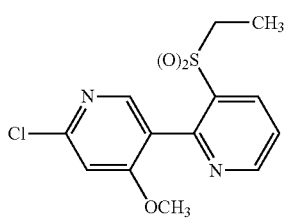

Intermediate compound B-7: ¹H-NMR (CDCl₃) δ: 8.93 (1H, dd), 8.45 (1H, dd), 8.16 (1H, s), 7.59 (1H, dd), 6.95 (1H, s), 3.83 (3H, s), 2.93 (2H, q), 1.19 (3H, t).

Reference Preparation Example 9-2

The compound which was prepared according to the method described in Reference Preparation Example 9-1 and its physical property value are shown below,

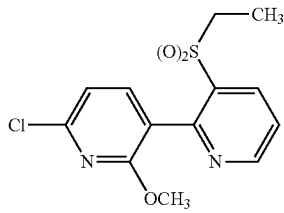

Intermediate compound A-27: ¹H-NMR (CDCl₃) δ: 8.91 (1H, dd), 8.45 (1H, dd), 7.61 (1H, d), 7.57 (1H, dd), 7.06 (1H, d), 3.91 (3H, s), 2.96-2.88 (2H, m), 1.19 (3H, t).

Reference Preparation Example 10-1

The mixtures of the Present compound A-18 (described in Preparation Example 1) 0.45 g, bis(pinacolato)diboron 0.37 g, tris(dibenzylideneacetone)dipalladium(0) 0.09 g, 2-dicyclohpxylphosphino-2',4',6'-triisopropylbiphenyl 0.14 g, potassium acetate 0.29 g, and 1,2-dimethoxyethane 9 mL were stirred at 70° C. under nitrogen atmosphere for 30 minutes. Water was added to the resulting mixtures at room temperature, and the mixtures were extracted with ethyl acetate. The resulting organic layers were washed with saturated brine, dried over anhydrous sodium sulfate, and concentrated under reduced pressure. The resulting solids were washed with hexane to obtain the intermediate compound A-23 shown below 0.52 g.

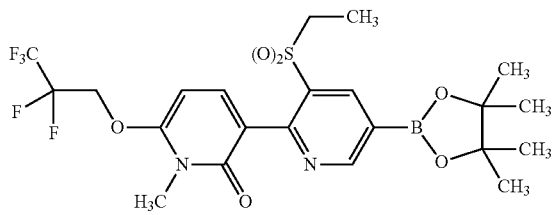

Intermediate compound A-23: ¹H-NMR (CDCl₃) δ: 9.13 (1H, d), 8.69 (1H, d), 7.51 (1H, d), 5.67 (1H, d), 4.51 (2H, t), 3.52 (3H, s), 3.49-3.43 (2H, m), 1.37 (12H, s), 1.34 (3H, t).

Reference Preparation Example 10-2

The compound which was prepared according to the method described in Reference Preparation Example 10-1 and its physical property value are shown below.

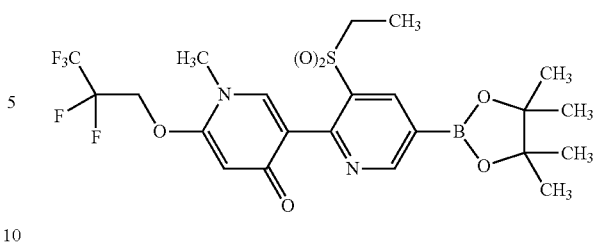

Intermediate compound B-18: ¹H-NMR (CDCl₃) δ: 9.12 (1H, d), 8.69 (1H, d), 7.36 (1H,), 5.86 (1H, s), 4.47 (2H, t), 3.59-3.55 (5H, m), 1.35-1.26 (15H, m).

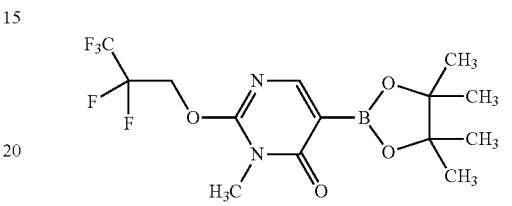

Intermediate Compound A-30

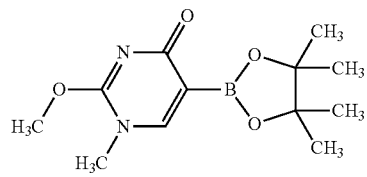

Intermediate compound B-26: ¹H-NMR (CDCl₃) δ: 7.66 (1H, s), 3.42 (3H, s), 3.33 (3H, s), 1.32 (12H, s).

Reference Preparation Example 11-1

To the mixtures of 3-bromo-6-chloro-1-methylpyridin-2 (1H)-one 27.28 g, cesium carbonate 47.94 g, and DMF 100 mL was added dropwise 2,2,3,3,3-pentafluoro-1-propanol 19.32 g under ice-cooling, and the mixtures were stirred at room temperature for 3 hours. Water was added to the resulting mixtures, and the mixtures were extracted with ethyl acetate. The resulting organic layers were dried over anhydrous sodium sulfate, and concentrated under reduced pressure. The resulting residues were washed with water and hexane successively to obtain the intermediate compound A-28 shown below 39.41 g.

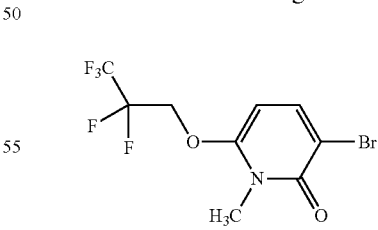

Intermediate compound A-28: ¹H-NMR (CDCl₃) δ: 7.68 (1H, d), 5.46 (1H, d), 4.46 (2H, t), 3.55 (3H, s).

Reference Preparation Example 11-2

The compounds which were prepared according to the method described in Reference Preparation Example 11-1 and their physical property values are shown below.

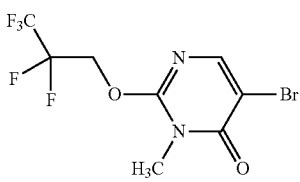 [SMILES: Cn1c(OCC(F)(F)C(F)(F)F)ncc(Br)c1=O]

Intermediate compound A-29: ¹H-NMR (CDCl₃) δ: 7.93 (1H, s), 4.85 (2H, t), 3.52 (3H, s).

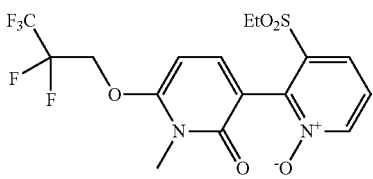

Intermediate compound A-41: ¹H-NMR (CDCl₃) δ: 8.46 (1H, d), 7.91 (1H, d), 7.54 (1H, d), 7.43 (1H, t), 5.72 (1H, d), 4.52 (2H, t), 3.53 (3H, s), 3.11-3.06 (2H, m), 1.23 (3H, t).

Reference Preparation Example 12-1

The mixtures of the intermediate compound A-28 2.0 g, 2-fluoro-4-(trifluoromethyl)phenyl boronic acid 1.24 g, [1,1'-bis(diphenylphosphino)ferrocene]palladium(II) dichloride additive 0.44 g, tripotassium phosphate 3.79 g, 1,2-dimethoxyethane 15 mL and water 1.5 mL were stirred at 80° C. for 3 hours. The resulting mixtures were stood to cool to room temperature, and water was then added thereto, and the mixtures were extracted with ethyl acetate. The resulting organic layers were dried over anhydrous sodium sulfate, and concentrated under reduce pressure. The resulting residue was subjected to a silica gel column chromatography to obtain the intermediate compound A-31 shown below 0.53 g.

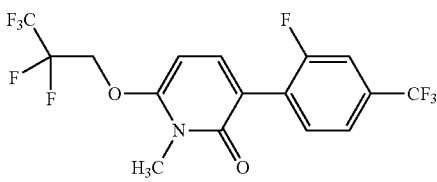 [SMILES: Cn1c(OCC(F)(F)C(F)(F)F)ccc(-c2ccc(C(F)(F)F)cc2F)c1=O]

Intermediate compound A-31: ¹H-NMR (CDCl₃) δ: 7.69 (1H, t), 7.51 (1H, dd), 7.44 (1H, d), 7.38 (1H, d), 5.65 (1H, d), 4.53 (2H, t), (3H, s).

Reference Preparation Example 12-2

The compound which was prepared according to the method described in Reference Preparation Example 12-1 and its physical property value are shown below.

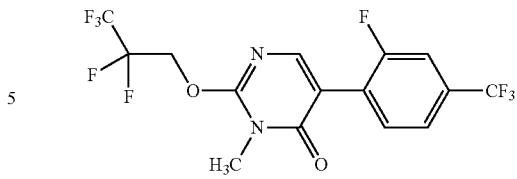

Intermediate compound A-34: ¹H-NMR (CDCl₃) δ: 7.84 (1H, d), 7.64 (1H, t), 7.47 (1H, d), 7.42 (1H, d), 4.93 (2H, t), 3.54 (3H, s).

Reference Preparation Example 13-1

To the mixtures of the intermediate compound A-31 1.13 g, sodium hydride (60%, in oil) 0.23 g, and DMF 10 mL was added dropwise ethanethiol 0.39 mL under ice-cooling, and the mixtures were stirred at 60° C. for 9 hours. Water was added to the resulting mixtures, and the mixtures were extracted with ethyl acetate. The resulting organic layers were dried over anhydrous sodium sulfate, and concentrated under reduced pressure. The resulting residue waw subjected to a silica gel column chromatography to obtain the intermediate compound A-32 shown below 0.65 g.

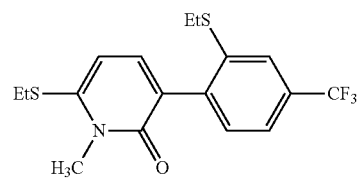

Intermediate compound A-32: ¹H-NMR (CDCl₃) δ: 7.54 (1H, s), 7.41 (1H, dd), 7.36 (1H, d), 7.28 (1H, d), 6.12 (1H, d), 3.69 (3H, s), 3.03 (2H, q), 2.92 (2H, q), 1.46 (3H, t), 1.28 (3H, t).

Reference Preparation Example 13-2

The compound which was prepared according to the method described Ln Reference Preparation Example 13-1 and its physical property value are shown below.

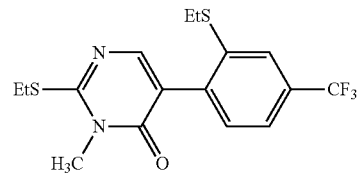

Intermediate compound A-35: ¹H-NMR (CDCl₃) δ: 7.79 (1H, s), 7.57 (1H, s), 7.44 (1H, d), 7.34 (1H, d), 3.53 (3H, s), 3.26 (2H, q), 2.94 (2H, q), 1.44 (3H, t), 1.29 (3H, t).

Reference Preparation Example 14-1

To the mixtures of the intermediate compound A-32 0.61 g and chloroform 30 mL was added mCPBA (purity 70%, containing 30% water) 1.63 g, and the mixtures were stirred at 0° C. room temperature for 25 hours. To the resulting mixtures was added aqueous sodium thiosulfate solution and the mixtures ere extracted with chloroform. The resulting organic layers were washed with saturated aqueous sodium bicarbonate solution, dried over anhydrous sodium sulfate, and concentrated under reduced pressure. The resulting residue was subjected to a silica gel column chromatography to obtain the intermediate compound A-33 shower below 0.65 g.

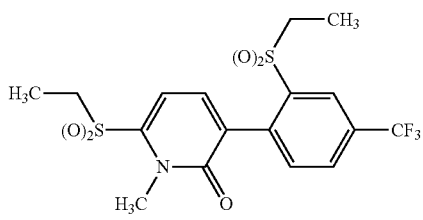

Intermediate compound. A-33: ¹H-NMR (CDCl₃) δ: 8.30 (1H, d), 7.94 (1H, dd), 7.46 (1H, 7.42 (1H, d), 7.24 (1H, d), 3.90 (3H, s), 3.40-3.34 (4H, m), 1.42 (3H, t), 1.34 (3H, t).

Reference Preparation Example 14-2

The compound which was prepared according to the method described in Reference Preparation Example 14-1 and its physical property value are shown below.

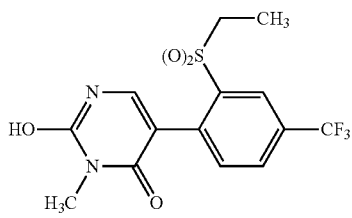

Intermediate compound A-36: ¹H-NMR (CDCl₃) δ: 9.25 (1H, s), 8.36 (1H, d), 7.92 (1H, dd), 7.51 (1H, d), 7.34 (1H, d), 3.40 (3H, s), 3.25 (2H, q), 1.29 (3H, t).

Reference Preparation Example 15

The compound which was prepared by using hydroxylamine in place of 30% ammonia water according to the method described in Reference Preparation Example 9-1 and its physical property value are shown below.

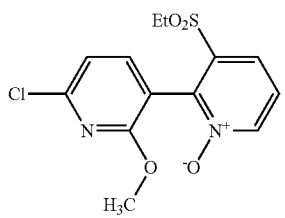

Intermediate compound A-38: ¹H-NMR (CDCl₃) δ: 8.46 (1H, d), 7.96 (1H, d), 7.62 (1H, d), 7.48 (1H, t), 7.10 (1H, d), 3.93 (3H, s), 2.87-2.72 (2H, m), 1.17 (3H, t).

Reference Preparation Example 16

To a mixture of 4-methoxy-2-(methylthio)pyrimidine-5-carboxylic acid 8.38 g and methanol 90 mL was added thionyl chloride 9 mL under ice cooling, and the mixture was stirred at 85° C. for 3 hours. The resulting mixture was cooled to room temperature, and concentrated. To the resulting residue was added aqueous saturated sodium hydrogen cardonate solution, and the mixture was extracted with ethyl acetate. The resulting organic layer was dried over anhydrous sodium sulfate, and concentrated to obtain intermediate compound C-1 shown below 4.18 g.

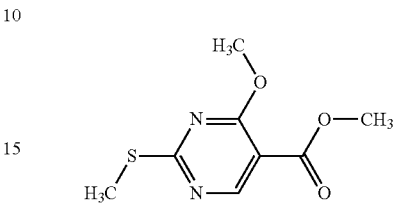

Intermediate compound C-1: ¹H-NMR (CDCl₃) δ: 8.82 (1H, s), 4.10 (3H, s), 3.89 (3H, s), 2.59 (3H, s).

Reference Preparation Example 17

To a mixture of the intermediate compound C-4 0.51 g and acetonitrile 26 mL was added dropwise a mixture of sulfuryl chloride 0.52 mL and chloroform 32 mL over 30 minutes under ice-cooling. The resulting mixture was stirred under ice-cooling for 1 hour, and the mixture was warmed to room temperature and stirred for 6 hours. To the resulting mixture was added aqueous saturated sodium hydrogen carbonate solution, and the mixture was extracted with ethyl acetate. The resulting organic layer was washed with saturated brine, dried over anhydrous sodium sulfate, and concentrated. The resulting residue was subjected to a silica gel column chromatography to obtain the intermediate compound C-5 shown below 0.50 g.

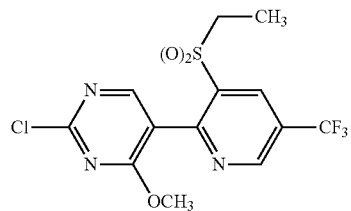

Intermediate compound. C-5: ¹H-NMR (CDCl₃) δ: 9.17 (1H, d), 8.66 (1H, d), 8.34 (1H, s), 4.01 (3H, s), 3.05-2.98 (2H, m), 1.26 (3H, t).

Preparation Example 1

To the mixtures of the intermediate compound A-4 0.65 g, sodium hydride (60% in oil) 0.11 g, and DMF 10 mL y added dropwise 2,3,3,3-pentafluoro-1-propanol 0.28 mL under ice-cooling, and the mixtures were stirred at room temperature for 3.5 hours. Water was added to the mixtures, and the mixtures were extracted with ethyl acetate. The resulting organic layers were dried over anhydrous sodiu 1 sulfate, and concentrated under reduced pressure. The resulting residue was subjected to a silica gel column chromatography (methanol:ethyl acetate=1:19) to obtain the present compound A-2 shown below 0.73 g.

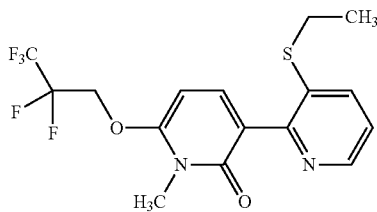

Present compound A-2: ¹H-NMR (CDCl₃) δ: 8.44 (1H, dd), 7.68 (1H, dd), 7.51 (1H, d), 7.22 (1H, dd), 5.63 (1H, d), 4.51 (2H, t), 3.55 (3H, 2.88 (2H, q), 1.26 (3H, t).

Preparation Example A

The compounds which were prepared according to the method described in Preparation Example 1 and their physical property values are shown below.

The compounds represented by formula (A-1)

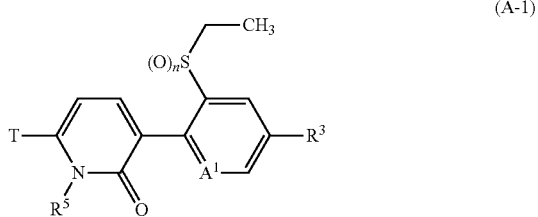

wherein the combination of T, R⁵, A¹, R³ and n represents any combinations indicated in Table 19.

TABLE 19

| Present compound | T | R⁵ | A¹ | R³ | n |
|---|---|---|---|---|---|
| A-4 | OCH₂CF₂CF₃ | Et | N | H | 0 |
| A-6 | OCH₂CF₂CHF₂ | Me | N | H | 2 |
| A-7 | OCH₂CF₂CHFCF₃ | Me | N | H | 2 |
| A-8 | OCH₂CF₂CF₂CF₃ | Me | N | H | 2 |
| A-9 | OCH₂CF₂CF₂CF₂CF₃ | Me | N | H | 2 |
| A-10 | OCH₂CF₃ | Me | N | H | 2 |
| A-11 | OCH(CH₃)CF₃ | Me | N | H | 2 |
| A-17 | ![pyrazole-CF₃] | Me | N | H | 2 |
| A-18 | OCH₂CF₂CF₃ | Me | | N | Cl 2 |
| A-19 | OCH₂CF₂CF₃ | Pr | N | H | 2 |
| A-20 | OCH₂CF₂CF₃ | i-Pr | N | H | 2 |
| A-21 | OCH₂CF₂CF₃ | Bu | N | H | 2 |
| A-22 | OCH₂CF₂CF₃ | CH₂CH=CH₂ | N | H | 2 |
| A-23 | OCH₂CF₂CF₃ | Me | CH | CF₃ | 2 |
| A-24 | OCH₂CF₂CF₃ | CH₂C≡CH | N | H | 2 |
| A-25 | OCH₂CF₂CF₃ | CH₂c-Pr | N | H | 2 |
| A-27 | OCH₂CF₂CF₃ | CH₂CF₂CF₃ | N | H | 2 |
| A-32 | OCH₂CF₂CF₃ | c-Pr | N | H | 2 |
| A-39 | OCH₂CF₂CF₃ | Me | N | CF₃ | 2 |
| A-41 | OCH₂CF₂CF₃ | [ethylthiazolyl-Cl] | N | H | 2 |
| A-42 | OCH₂CF₂CF₃ | Bn | N | H | 2 |
| A-55 | OCH₂CF₂CHF₂ | Me | N | CF₃ | 2 |

TABLE 19-continued

| Present compound | T | R⁵ | A¹ | R³ | n |
|---|---|---|---|---|---|
| A-59 | OCH₂CF₂CF₃ | Et | N | CF₃ | 2 |
| C-1 | OCH₂(1-CN—c-Pr) | Me | N | H | 2 |
| C-2 | OCH₂C(Me)₂CN | Me | N | H | 2 |
| C-7 | OCH₂C(Me)₂CN | Me | N | Cl | 2 |
| C-8 | OCH₂(1-CN—c-Pr) | Me | N | Cl | 2 |

Present compound A-4: ¹H-NMR (CDCl₃) δ: 8.44 (1H, dd), 7.68 (1H, dd), 7.49 (1H, d), 7.22 (1H, dd), 5.60 (1H, d), 4.50 (2H, t), 4.22 (2H, q), 2.88 (2H, q), 1.28 (3H, t), 1.26 (3H, t).

Present compound A-6: ¹H-NMR (CDCl₃) δ: 8.86 (1H, d), 8.35 (1H, d), 7.52-7.47 (2H, m), 6.12-5.85 (1H, m), 5.70 (1H, d), 4.46 (2H, t), 3.52 (3H, m), 3.40 (2H, t), 1.29 (3H, t).

Present compound A-7: ¹H-NMR (CDCl₃) δ: 8.85 (1H, d), 8.34 (1H, d), 7.51-7.47 (2H, m), 5.69 (1H, d), 5.14-4.97 (1H, m), 4.94-4.38 (2H, m), 3.59-3.39 (5H, m), 1.29 (3H, t).

Present compound A-8: ¹H-NMR (CDCl₃) δ: 8.86 (1H, d), 8.34 (1H, d), 7.52-7.47 (2H, m), 5.68 (1H, d), 4.54 (2H, t), 3.52 (3H, s), 3.42 (2H, s), 1.29 (3H, t).

Present compound A-9: ¹H-NMR (CDCl₃) δ: 8.85 (1H, d), 8.34 (1H, d), 7.51-7.47 (2H, m), 5.67 (1H, d), 4.55 (2H, t), 3.52 (3H, s), 3.47-3.39 (2H, m), 1.29 (3H, t).

Present compound A-10: ¹H-NMR (CDCl₃) δ: 8.85 (1H, d), 8.34 (1H, d), 7.49 (2H, d), 5.66 (1H, d), 4.54 (2H, t), 3.52 (3H, s), 3.47-3.39 (2H, m), 1.29 (3H, t).

Present compound A-11: ¹H-NMR (CDCl₃) δ: 8.85 (1H, d), 8.35 (1H, d), 7.49 (2H, t), 5.71 (1H, d), 4.78 (1H, t), 3.51 (3H, s), 3.44 (2H, s), 1.59 (3H, d), 1.29 (3H, t).

Present compound A-17: ¹H-NMR (CDCl₃) δ: 8.88 (1H, d), 8.36 (1H, d), 7.78 (1H, s), 7.56-7.54 (2H, m), 6.78 (1H, s), 6.41 (1H, d), 3.47 (2H, br), 3.35 (3H, s), 1.34 (3H, t).

Present compound A-18: ¹H-NMR (CDCl₃) δ: 8.80 (1H, d), 8.33 (1H, d), 7.50 (1H, d), 5.69 (1H, d), 4.52 (2H, t), 3.53 (3H, s), 3.50-3.44 (2H, m), 1.34 (3H, t).

Present compound A-19: ¹H-NMR (CDCl₃) δ: 8.86 (1H, dd), 8.34 (1H, dd), 7.50 (1H, dd), 7.49 (1H, d), 5.66 (1H, d), 4.50 (2H, dd), 4.09 (2H, t), 3.51-3.44 (2H, m), 1.74-1.65 (2H, m), 1.32 (3H, t), 0.96 (3H, t).

Present compound A-20: ¹H-NMR (CDCl₃) δ: 8.86 (1H, dd), 8.35 (1H, dd), 7.49 (1H, dd), 7.44 (1H, d), 5.62 (2H, d), 4.50 (2H, t), 3.48-3.41 (2H, m), 1.52-1.50 (6H, m), 1.31 (3H, t).

Present compound A-21: ¹H-NMR (CDCl₃) δ: 8.86 (1H, dd), 8.34 (1H, dd), 7.49 (1H, dd), 7.48 (1H, d), 5.65 (1H, d), 4.50 (2H, t), 4.12 (2H, t), 3.47 (2H, ddd), 1.67-1.61 (2H, m), 1.39-1.33 (5H, m), 0.94 (3H, t).

Present compound A-22: ¹H-NMR (CDCl₃) δ: 8.86 (1H, dd), 8.34 (1H, dd), 7.51 (1H, d), 7.50 (1H, dd), 5.88 (1H, dddd), 5.68 (1H, d), 5.21-5.16 (2H, 4.81-4.68 (2H, m), 4.49 (2H, t), 3.50-3.44 (2H, m), 1.30 (3H, t).

Present compound A-23: ¹H-NMR (CDCl₃) δ: 8.35 (1H, d), 7.88 (1H, dd), 7.46 (1H, d), 7.39 (1H, d), 5.67 (1H, d), 4.52 (2H, t), 3.54 (3H, s), 3.30 (2H, q), 1.27 (3H, t).

Present compound A-24: ¹H-NMR (CDCl₃) δ: 6.87 (1H, dd), 8.35 (1H, dd), 7.55-7.50 (2H, m), 5.71 (1H, d), 4.89 (2H, dd), 4.56 (2H, t), 3.49-3.47 (2H, m), 2.17-2.15 (1H, m), 1.32 (3H, t).

Present compound A-25: ¹H-NMR (CDCl₃) δ: 8.87 (1H, dd), 8.35 (1H, dd), 7.52-7.48 (2H, m), 5.67 (1H, d), 4.52 (2H, t), 4.10-3.97 (2H, m), 3.50-3.43 (2H,), 1.32 (3H, t,), 1.26-1.21 (1H, m), 0.53-0.47 (2H, m), 0.44-0.39 (2H, m).

Present compound A-27: $^{1}$H-NMR (CDCl$_3$) δ: 8.87 (1H, dd), 8.36 (1H, dd), 7.57 (1H, d), 7.53 (1H, dd), 5.74 (1H, d), 4.85 (2H, br s), 4.54 (2H, t), 3.40 (2H, q), 1.31 (3H, t).

Present compound A-32: $^{1}$H-NMR (CDCl$_3$) δ: 8.85 (1H, dd), 8.32 (1H, dd), 7.49 (1H, dd), 7.47 (1H, d), 5.60 (1H, d), 4.48 (2H, t), 3.55-3.49 (2H, m), 2.81-2.75 (1H, m), 1.35 (3H, t), 1.24-1.20 (2H, m), 0.94-0.85 (2H, m).

Present compound A-39: $^{1}$H-NMR (CDCl$_3$) δ: 9.09 (1H, s), 8.57 (1H, s), 7.56 (1H, d), 5.72 (1H, d), 4.54 (2H, t), 3.54 (3H, s), 3.53 (2H, q), 1.36 (3H, t).

Present compound A-41: $^{1}$H-NMR (CDCl$_3$) δ: 8.88 (1H, dd), 8.36 (1H, dd), 7.55 (1H, s), 7.55-7.52 (2H, m), 5.71 (1H, d), 5.35 (2H, d), 4.55 (2H, t), 3.45 (2H, dt), 1.35 (3H, t).

Present compound A-42: $^{1}$H-NMR (CDCl$_3$) δ: 8.87 (1H, dd), 8.34 (1H, dd), 7.53 (1H, d), 7.50 (1H, dd), 7.35-7.23 (5H, m), 5.69 (1H, d), 5.43-5.25 (2H, 1), 4.45 (2H, t), 3.41 (2H, q), 1.27 (3H, t).

Present compound A-55: $^{1}$H-NMR (CDCl$_3$) δ: 9.09 (1H, d), 8.57 (1H, d), 7.56 (1H, d), 6.01 (1H, tt), 5.74 (1H, d), 4.50 (2H, t), 3.56-3.50 (2H, m), 3.55 (3H, s), 1.35 (3H, t).

Present compound A-59: $^{1}$H-NMR (CDCl$_3$) δ: 9.09 (1H, d), 8.55 (1H, d), 7.54 (1H, d), 5.70 (1H, d), 4.53 (2H, t), 4.20 (2H, q), 3.58 (2H, q), 1.37 (3H, t), 1.28 (3H, t).

Present compound C-1: $^{1}$H-NMR (CDCl$_3$) δ: 8.84 (1H, d), 8.34 (1H, d), 7.47 (2H, d), 5.57 (1H, d), 4.04 (2H, br), 3.58 (3H, s), 3.42 (2H, br), 1.53 (2H, br), 1.29 (3H, t), 1.17 (2H, br).

Present compound C-2: $^{1}$H-NMR (CDCl$_3$) δ: 8.85 (1H, d), 8.35 (1H, d), 7.50-7.46 (2H, m), 5.65 (1H, d), 4.00 (2H, s), 3.57 (3H, s), 3.43 (2H, br), 1.58 (3H, s), 1.54 (3H, s), 1.29 (3H, t).

Present compound C-7: $^{1}$H-NMR (CDCl$_3$) δ: 8.80 (1H, d), 8.34 (1H, d), 7.50 (1H, d), 5.68 (1H, d), 4.02 (2H, s), 3.58 (3H, s), 3.51-3.44 (2H, m), 1.55 (3H, s), 1.55 (3H, s), 1.34 (3H, t).

Present compound C-8: $^{1}$H-NMR (CDCl$_3$) δ: 8.80 (1H, d), 8.34 (1H, d), 7.48 (1H, d), 5.59 (1H, d), 4.05 (2H, br), 3.59 (3H, s), 3.51-3.43 (2H, m), 1.54 (2H, dd), 1.33 (3H, t), 1.19 (2H, dd).

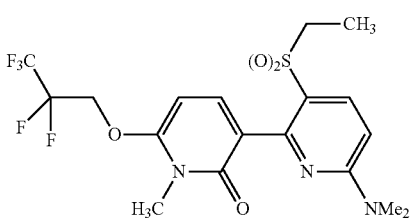

Present compound A-53: $^{1}$H-NMR (CDCl$_3$) δ: 7.94 (1H, d), 7.38 (1H, d), 6.79 (1H, d), 5.60 (1H, d), 4.47 (2H, t), 3.49 (3H, s), 3.47-3.27 (2H, m), 3.17 (6H, s), 1.26 (3H, t).

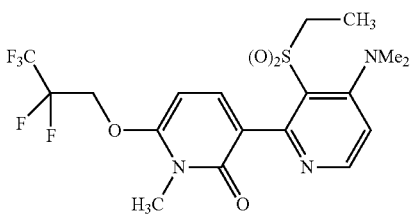

Present compound A-50: $^{1}$H-NMR (CDCl$_3$) δ: 8.42 (1H, d), 7.58 (1H, d), 6.91 (1H, d), 5.60 (1H, d), 4.48 (2H, t), 3.52 (3H, s), 3.27-3.25 (2H, m), 3.05 (6H, s), 1.03 (3H, t).

The compounds represented by formula (B-1):

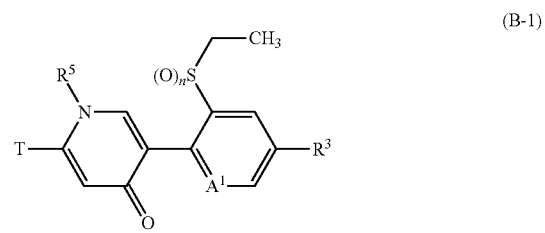

wherein the combination of T, R$^5$, A$_1$, R$^3$ and n represents any combinations indicated in Table 20.

TABLE 20

| Present compound | T | R$^5$ | A$^1$ | R$^3$ | n |
|---|---|---|---|---|---|
| B-1 | OCH$_2$CF$_2$CF$_3$ | Me | N | H | 2 |
| B-2 | OCH$_2$CF$_2$CF$_3$ | Me | N | CF$_3$ | 2 |
| B-4 | OCH$_2$CF$_2$CF$_3$ | Et | N | H | 2 |
| B-5 | OCH$_2$CF$_2$CF$_3$ | Pr | N | H | 2 |
| B-6 | OCH$_2$CF$_2$CF$_3$ | Bu | N | H | 2 |
| B-7 | OCH$_2$CF$_2$CF$_3$ | Me | N | Cl | 2 |
| B-8 | OCH$_2$CF$_2$CF$_3$ | CH$_2$CH=CH$_2$ | N | H | 2 |
| B-9 | OCH$_2$CF$_2$CF$_3$ | CH$_2$c-Pr | N | H | 2 |
| B-10 | OCH$_2$CF$_2$CF$_3$ | i-Pr | N | H | 2 |
| B-11 | OCH$_2$CF$_2$CF$_3$ | Bn | N | H | 2 |
| B-12 | OCH$_2$CF$_2$CF$_3$ | CH$_2$CH$_2$CF$_3$ | N | H | 2 |

Present compound B-1: $^{1}$H-NMR (CDCl$_3$) δ: 8.86 (1H, dd), 8.36 (1H, dd), 7.51 (1H, dd), 7.36 (1H, s), 5.88 (1H, s), 4.49 (2H, t), 3.60-3.48 (5H, m), 1.33 (3H, t).

Present compound B-2: $^{1}$H-NMR (CDCl$_3$) δ: 9.09 (1H, d), 8.57 (1H, d), 7.40 (1H, s), 5.89 (1H, s), 4.50 (2H, t), 3.63-3.58 (2H, m) 3.60 (3H, s), 1.37 (3H, t).

Present compound B-4: $^{1}$H-NMR (CDCl$_3$) δ: 8.88 (1H, dd), 8.38 (1H, dd), 7.51 (1H, dd), 7.38 (1H, s), 5.87 (1H, s), 4.49 (2H, t), 3.94 (2H, q), 3.52-3.42 (2H, m), 1.40 (3H, t), 1.31 (3H, t).

Present compound B-5: $^{1}$H-NMR (CDCl$_3$) δ: 8.87 (1H, dd), 8.37 (1H, dd), 7.51 (1H, dd), 7.36 (1H, s), 5.87 (1H, s), 4.48 (2H, t) 3.91-3.79 (2H, m), 3.54-3.40 (2H, m), 1.83-1.74 (2H, m), 1.31 (3H, t), 0.96 (3H, t).

Present compound B-6: $^{1}$H-NMR (CDCl$_3$) δ: 8.87 (1H, dd), 8.37 (1H, dd), 7.51 (1H, dd), 7.36 (1H, s), 5.87 (1H, s), 4.49 (2H, t), 3.94-3.80 (2H, m), 3.53-3.39 (2H, m), 1.77-1.70 (2H, m), 1.42-1.34 (2H, m), 1.30 (3H, t), 0.95 (3H, t).

Present compound B-7: $^{1}$H-NMR (CDCl$_3$) δ: 8.80 (1H, d), 8.34 (1H, d), 7.35 (1H, s), 5.86 (1H, s), 4.48 (2H, t), 3.57 (3H, s), 3.59-3.52 (2H, m), 1.35 (3H, t).

Present compound B-8: $^{1}$H-NMR (CDCl$_3$) δ: 8.87 (1H, dd), 8.36 (1H, dd), 7.51 (1H, dd), 7.36 (1H,), 5.90 (1H, ddt), 5.88 (1H, s), 5.32 (1H, d), 5.24 (1H, d), 4.48 (2H, t), 4.48 (2H, d), 3.53-3.44 (2H, m), 1.32 (3H, t).

Present compound B-9: $^{1}$H-NMR (CDCl$_3$) δ: 8.88 (1H, dd), 8.38 (1H, dd), 7.51 (1H, dd), 7.46 (1H, s), 5.88 (1H, s), 4.49 (2H, t), 3.81-3.69 (2H, m), 3.52-3.40 (2H, m), 1.31 (3H, t), 1.26-1.16 (1H, m), 0.69-0.64 (2H, m), 0.39-0.35 (2H, m).

Present compound B-10: $^{1}$H-NMR (CDCl$_3$) δ: 8.89 (1H, dd), 8.40 (1H, dd), 7.52 (1H, dd), 7.51 (1H, s), 5.88 (1H, s), 4.81-4.74 (1H, m), 4.50 (2H, t), 3.43-3.35 (2H, m), 1.45 (6H, d), 1.28 (3H, t).

Present compound B-11: $^{1}$H-NMR (CDCl$_3$) δ: 8.87 (1H, dd), 8.37 (1H, dd), 7.51 (1H, dd), 7.48 (1H, s), 7.39-7.32

(3H, m), 7.25-7.22 (2H, m), 5.89 (1H, s), 5.05 (2H, s), 4.42 (2H, t), 3.53-3.41 (2H, m), 1.31 (3H, t).

Present compound B-12: ¹H-NMR (CDCl₃) δ: 8.88 (1H, dd), 8.37 (1H, dd), 7.53 (1H, dd), 7.37 (1H, s), 5.89 (1H, s), 4.51 (2H, 4.21-4.06 (2H, m), 3.46-3.39 (2H, m), 2.66-2.55 (2H, m), 1.30 (3H, t).

Preparation Example 2

The process was carried out by using the Present compound A-2 place of the international compound B-2 according to the method described in Reference Preparation Example 2-3 to obtain the present compound A-1 shown below.

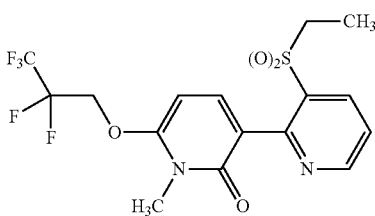

Present compound A-1: ¹H-NMR (CDCl₃) δ: 8.87 (1H, dd), 8.36 (1H, dd), 7.51 (1H, dd), 7.51 (1H, d), 5.69 (1H, d), 4.52 (2H, t), 3.53 (3H, s), 3.47-3.41 (2H, m), 1.31 (3H, t).

Preparation Example 2A

The compounds which were prepared according to the method described in Preparation Example 2 and their physical property values are shown below.

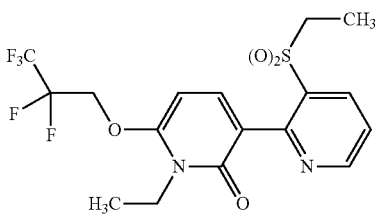

Present compound A-5: ¹H-NMR (CDCl₃) δ: 8.87 (1H, dd), 8.34 (1H, dd), 7.50-7.49 (2H, m), 5.66 (1H, d), 4.51 (2H, t), 4.21-4.18 (2H, m), 3.53-3.45 (2H, m), 1.32 (3H, t), 1.27 (3H, t).

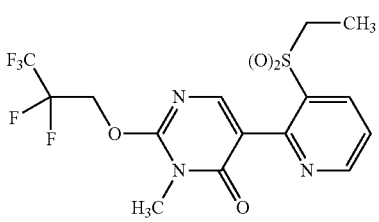

Present compound A-34: ¹H-NMR (CDCl₃) δ: 8.89 (1H, dd), 8.36 (1H, dd), 7.81 (1H, s), 7.55 (1H, dd), 4.92 (2H, d), 3.51 (3H, s), 3.42 (2H, q), 1.33 (3H, t).

Preparation Example 3

To the mixtures of the present compound A-2 0.1 g and chloroform 2 mL was added mCPBA (purity 70%) 0.06 g under ice-cooling, and the mixtures were stirred at 0° C. to room temperature for 3 hours. To the mixtures was added aqueous sodium thiosulfate solution, and the mixtures were extracted with chloroform. The resulting organic layers were washed with aqueous st dium bicarbonate solution, dried over anhydrous sodium sulfate, and concentrated under reduced pressure. The resulting residue was subjected to a silica gel column chromatography (methanol:ethyl acetate=1:19) to obtain the present compound A-3 shown below 0.08 g.

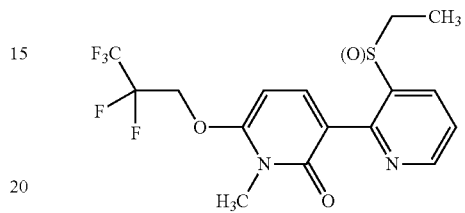

Present compound A-3: ¹H-NMR (CDCl₃) δ: 8.73 (1H, dd), 8.35 (1H, dd), 7.69 (1H, d, J=8.2 Hz), 7.50 (1H, dd), 5.73 (1H, d), 4.55 (2H, t), 3.54 (3H, s), 3.38-3.31 (1H, m), 2.89-2.86 (1H, m), 1.40 (3H, t).

Preparation Example 3A

The compound which was prepared according to the method described in Preparation Example 3 and its physical property value are shown below.

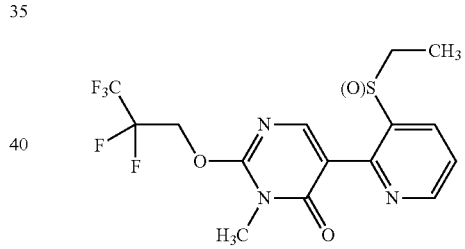

Present compound A-33: ¹H-NMR (CDCl₃) δ: 8.76 (1H, dd), 8.38 (1H, dd), 7.97 (1H, s), 7.55 (1H, dd), 4.99-4.91 (2H, m), 3.52 (3H, s), 3.27-3. (1H, m), 2.87-2.83 (1H, m), 1.37 (3H, t).

Preparation Example 4-1

The mixtures of the Present compound A-18 0.1 q, cyclopropyl boronic acid 56 mg, [1,1'-bis(diphenylphosphino)ferrocene]palladium(II) dichloromethane additive 32 mg, tripotassium phosphate 0.23 g, toluene 1.5 mL and water 0.4 mL were stirred at 100° C. for 2 hours. The resulting mixtures were stood to cool to room temperature, and water was then added thereto, and the mixtures were extracted with ethyl acetate. The resulting organic layers were dried over anhydrous sodium sulfate, and concentrated under reduced pressure. The resulting residue was subjected to a silica gel column chromatography (ethyl acetate: hexane=3:1) to obtain the present compound A-28 shown below 89 mg.

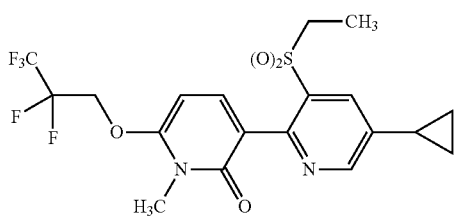

Present compound A-28: ¹H-NMR (CDCl₃) δ: 8.63 (1H, d), 7.94 (1H, d), 7.47 (1H, d), 5.67 (1H, d), 4.54-4.48 (2H, m), 3.52 (3H, s), 3.41-3.35 (2H, m), 2.06-1.99 (1H, m), 1.29 (3H, t), 1.16-1.13 (2H, m), 0.87-0.82 (2H, m).

Preparation Example 4-2

The compounds which were prepared according to the method described in Preparation Example 4-1 and their physical property values are shown below.

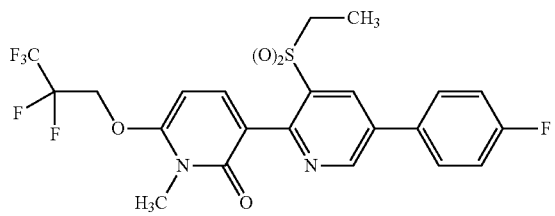

Present compound A-29: ¹H-NMR (CDCl₃) δ: 9.03 (1H, d), 8.48 (1H, d), 7.65-7.61 (2H, m), 7.56 (1H, d), 7.23 (2H, dd), 5.71 (1H, d), 4.53 (2H, t), 3.55 (3H, s), 3.50-3.43 (2H, m), 1.34 (3H, t).

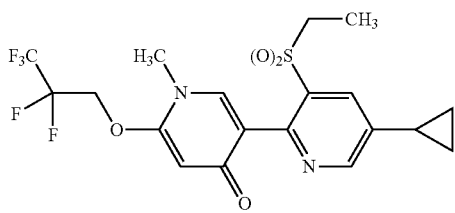

Present compound B-3: ¹H-NMR (CDCl₃) δ: 8.62 (1H, d), 7.94 (1H, d), 7.33 (1H, s), 5.89 (1H, s), 4.48 (2H, t), 3.56 (3H, s), 3.48 (2H, q), 2.04-2.00 (1H, m), 1.31 (3H, t), 1.16-1.14 (2H, m), 0.86-0.81 (2H, m).

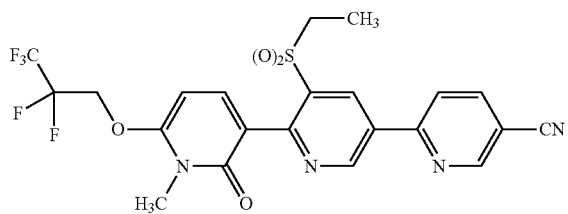

Present compound A-31: ¹H-NMR (CDCl₃) δ: 9.59 (1H, d), 9.02 (1H, dd), 8.99 (1H, d), 8.13 (1H, dd), 7.99 (1H, dd), 7.59 (1H, d), 5.72 (1H, d), 4.54 (2H, t), 3.56-3.50 (2H, m), 3.55 (3H, s), 1.37 (3H, t).

Preparation Example 4-3

The compounds which were prepared by using the present compound A-47 in lace of the present compound A-18 according to the method described in Preparation Example 4-1 and their physical property values are shown below.

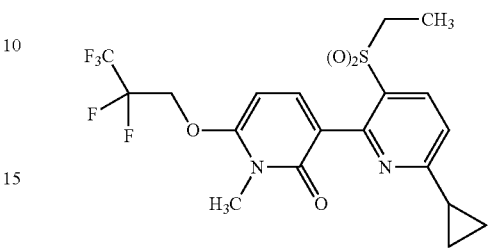

Present compound A-44

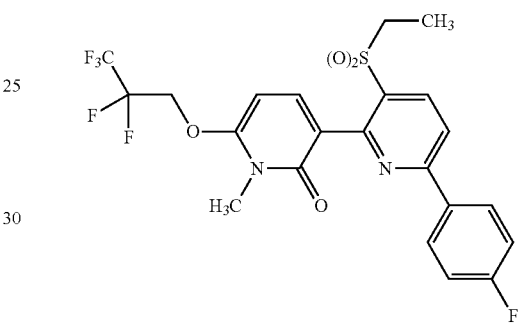

Present compound A-45: ¹H-NMR (CDCl₃) δ: 8.34 (1H, d), 8.06-8.02 (2H, m), 7.82 (1H, d), 7.53 (1H, d), 7.14 (2H, t), 5.68 (1H, d), 4.51 (2H, t), 3.53 (3H, m), 3.48-3.44 (2H, m), 1.19 (3H, t).

Preparation Example 5-1

The mixtures of the intermediate compound A-23 1.68 g, sodium acetate 1.87 g, THF 12 mL and 30% hydrogen peroxide solution 0.4 mL, and water 6 mL was stirred at 0° C. for 1 hour. To the resulting ixtures was added saturated aqueous sodium thiosulfate solution 3 mL, and the mixtures were stirred for 1 hour. To the resulting mixtures was added saturated aqueous ammonium chloride solution at room temperature, and the mixtures were extracted with chloroform. The resulting organic layers were washed with saturated brine, dried over sodium sulfate, and concentrated under reduced pressure. The resulting residue was subjected to a silica gel column chromatography (ethyl acetate) to obtain the present und. A-43 shown below 0.94 g.

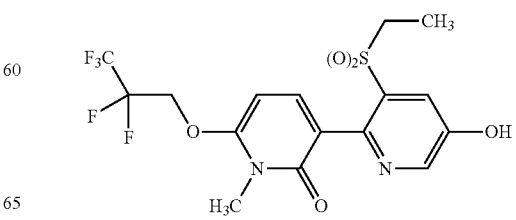

Present compound A-43: ¹H-NMR (CDCl₃) δ: 9.35 (1H, s), 8.10 (1H, d), 7.60 (1H, d), 7.55 (1H, d), 5.79 (1H, d), 4.55 (2H, t), 3.62 (3H, s), 3.24-3.14 (2H, m), 1.32 (3H, t).

Preparation Example 6

The mixtures of the present compound A-43 0.25 q, 2-iodopyridine 0.17 g, copper(II) iodide 0.02 g, 1-butyl imidazole 0.04 g, potassium carbonate 0.16 g, and toluene 3 mL were stirred under reflux for 7 hours. The resulting mixtures were stood to cool to room temperature, and the mixtures were filtered through Celite (Registered Trademark) and the filtrates were concentrated. The resulting residue was subjected to a silica gel column chromatography (ethyl acetate:hexane 1:2) to obtain the present compound. A-40 shown below 0.08 g.

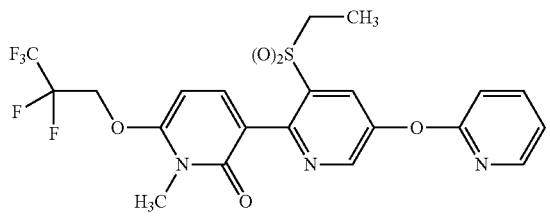

Present compound A-40: ¹H-NMR (CDCl₃) δ: 8.75 (1H, d), 8.20 (1H, dd), 8.17-8.16 (1H, m), 7.81-7.76 (1H, m), 7.53 (1H, d), 7.10 (1H, dd), 7.07 (1H, d), 8.68 (1H, d), 4.52 (2H, t), 3.58-3.36 (2H, m), 3.54 (3H, s), 1.33 (3H, t), Preparation Example 7-1

To the mixtures of the present compound A-43 180 mg, cesium carbonate 199 mg, and DMF 1 mL was added iodo ethane 49 μL at under ice-cooling, and the mixtures were stirred at room temperature for 4 hours. Water was added to the resulting mixtures, and the precipitated solids were filtered, and the obtained solids were washed with wate dried under reduced pressure to obtain the present compound A-35 shown below 150 mg.

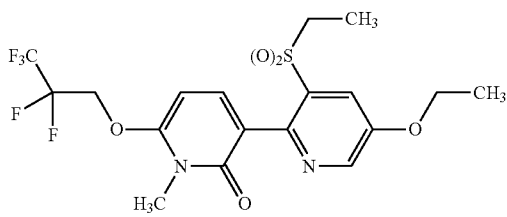

Present compound A-35: ¹H-NMR (CDCl₃) δ: 8.53 (1H, d), 7.81 (1H, d), 7.47 (1H, d), 5.66 (1H, d), 4.50 (2H, t), 4.21-4.15 (2H, m), 3.52 (3H, s), 3.43-3.34 (2H, m), 1.49 (3H, t), 1.30 (3H, t).

Preparation Example 7-2

The compounds which were prepared according to the method described in Preparation Example 7-1 and their physical property values are shown below.

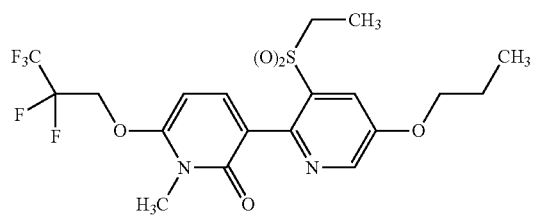

Present compound A-36: ¹H-NMR (CDCl₃) δ: 8.53 (1H, d), 7.81 (1H, d), 7.47 (1H, d), 5.65 (1H, d), 4.50 (2H, t), 4.09-4.04 (2H, m), 3.52 (3H,), 3.43-3.35 (2H, m), 1.92-1.83 (2H, m), 1.31 (3H, t), 1.08 (3H, t).

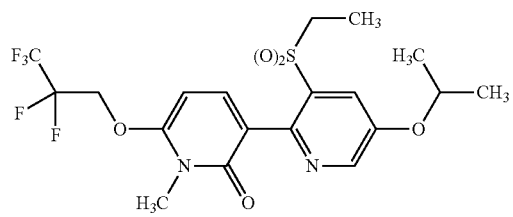

Present compound A-37: ¹H-NMR (CDCl₃) δ: 8.49 (1H, d), 7.79 (1H, d), 7.47 (1H, d), 5.65 (1H, d), 4.72-4.66 (1H, m), 4.50 (2H, t), 3.53 (3H, s), 3.41-3.34 (2H, m), 1.42 (3H, br s), 1.40 (3H, br s), 1.30 (3H, t).

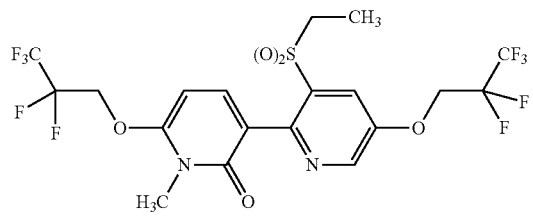

Present compound A-38: ¹H-NMR (CDCl₃) δ: 8.62 (1H, d), 7.90 (1H, d), 7.48 (1H, d), 5.68 (1H, d), 4.59 (2H, t), 4.52 (2H, t), 3.53 (3H, s), 3.42 (2H, q), 1.32 (3H, t).

Preparation Example 8-1

The mixtures of the interuediate compound A-37 700 mg, and copper powder 285 mg, heptafluoropropyl iodide 2.65 g and DMSO 10 mL were stirred at 140° C. for 16 hours and a half hour in a sealed container. The resulting mixtures were cooled to room temperature, and ethyl acetate was added thereto, and the mixtures were filtered through. Celite (Registered Trademark). The resulting filtrates were extracted with ethyl acetate and water. The resulting organic layers were washed with saturated brine and dried over sodium sulfate, and concentrated under reduced pressure. The resulting residue was subjected to a silica gel column chromatography to obtain the present compound A-12 shown below 437 mg.

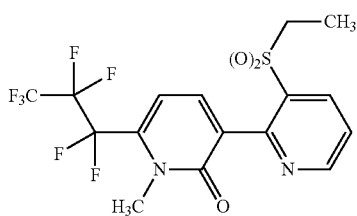

Present compound A-12: ¹H-NMR (CDCl₃) δ: 8.88 (1H, d), 8.34 (1H, d), 7.57-7.50 (2H, m), 6.74 (1H, d), 3.64 (3H, s), 3.46-3.37 (2H, m), 1.29 (3H, t).

Preparation Example 8-2

The compound which was prepared according to the method described in Preparation Example 8-1 and its physical property value are shown below

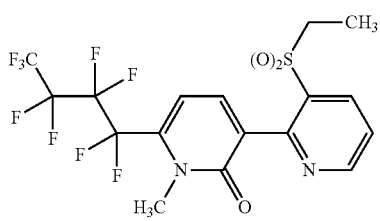

Present compound A-13: ¹H-NMR (CDCl₃) δ: 8.88 (1H, d), 8.34 d), 7.57-7.51 (2H, m), 6.77 (1H, d), 3.64 (3H,$), 3.46-3.42 (2H, m), 1.33 (3H, t).

Preparation Example 9

The compounds which were prepared by using the intermediate compound A-37 in place of the present compound A-18 according to the method described in Preparation Example 4-1 and their physical property values are shown below.

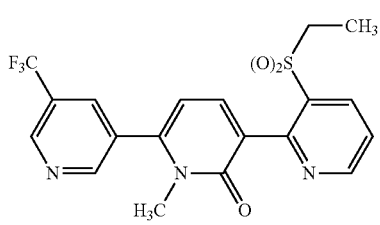

Present compound. A-14: ¹H-NMR (CDCl₃) δ: 8.89-8.83 (2H, m), 8.36 (1H, d), 7.97 (1H, d), 7.85 (1H, d), 7.55-7.54 (2H, m), 6.30 (1H, d), 3.58-3.42 (5H, m) 1.35 (3H, t).

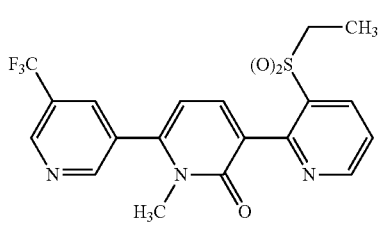

Present compound A-15: ¹H-NMR (CDCl₃) δ: 9.02 (1H, s), 8.90 (2H, 8.36 (1H, d), 8.02 (1H, s) 7.54 (2H, d), 6.31 (1H, d), 3.56-3.48 (2H, m), 3.42 (3H, s), 1.33 (3H, t).

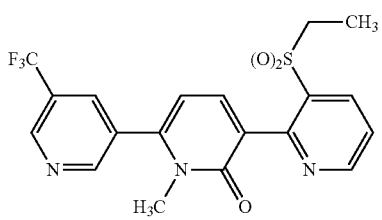

Present compound A-16: ¹H-NMR (CDCl₃) δ: 8.88 (1H, d), 8.37 (1H, d), 7.76 (1H, d), 7.69-7.62 (3H, m), 7.54-7.46 (2H, 6.31 (1H, d), 3.56-3.48 (2H, m), 3.42 (3H, s), 1.33 (3H, t).

Preparation Example 10

The process was carried out by using the intermediate compound A-36 in place of the present compound A-43 and using 2,2,3,3,3-pentafluoropropyl triflate in place of iodo ethane according to the method described in Preparation. Examples 7-1 to obtain the present compound A-30 shown below.

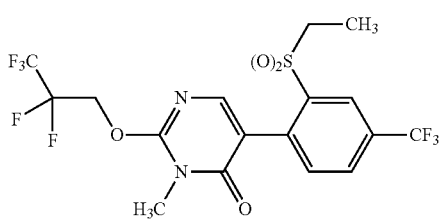

Present compound A-30

Preparation Example 11

The process was carried out by using the intermediate compound A-30 in place of 2-fluoro-4-(trifluoromethyl) phenyl boronic acid and using 2-bromo-3-ethylthiopyridine in place of the intermediate compound A-28 according Lo the method described in Reference Preparation 12-1 to obtain the present compound A-26 shown below.

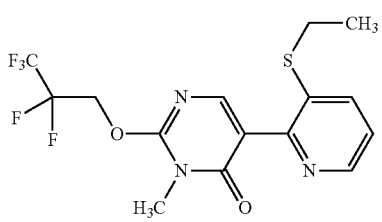 [SMILES: CCSc1cccnc1-c1cnc(OCC(F)(F)C(F)(F)F)n(C)c1=O]

Present compound A-26: ¹H-NMR (CDCl₃) δ: 1H-NMR (CDCl₃) δ: 8.46 (1H, dd), 7.81 (1H, s), 7.70 (1H, dd), 7.26 (1H, dd), 4.92 (2H, t), 3.52 (3H, s), 2.90 (2H, q), 1.27 (3H, t).

Preparation Example 12

The mixtures of the intermediate compound A-41 10 g and acetic anhydride 50 mL were stirred at 150° C. for 16 hours in a sealed container. The resulting mixtures were cooled to room temperature, and acetic anhydride zas removed by concentrating under reduced pressure. To the resulting reaction mixtures were added methanol 70 mL and concentrated hydrochloric acid, and the mixtures were stirred at 60° C. for 16 hours. The resulting mixtures were cooled to room temperature, and methanol was removed by concentrating under reduced pressure. The resulting reaction mixtures wereextracted with water, saturated aqueous sodium bicarbonate solution, and ethyl acetate successively, to obtain the present compound. A-46 shown below 7 g.

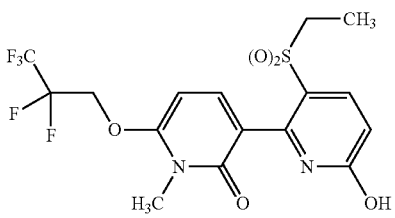

Present compound A-46: $^1$H-NMR (CDCl$_3$) δ: 7.86 (1H, d), 7.63 (1H, d), 6.49 (1H, d), 5.68 (1H, d), 4.53 (2H, t), 3.48 (3H, s), 3.25 (2H, q), 1.24 (3H, t).

Preparation Example 13

To the mixtures of the present compound A-46 4 g, triethylamine 3.7 mL, and dichloromethane 15 ml was added dropwise trifluoromethane sulfonic anhydride 2.5 mL under ice-cooling, and the mixtures were stirred at 0° C. to room temperature for 16 hours. Water was added to the xtures, and the mixtures were extracted with dichloromethane. The resulting organic layers were dried over anhydrous sodium sulfate, and concentrated under reduced pressure to obtain the present compound A-47 4 g.

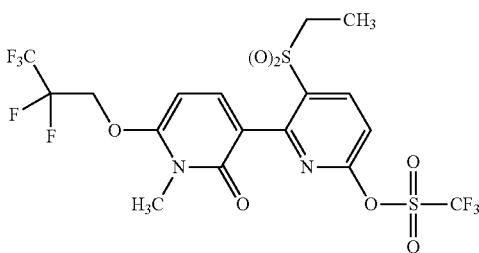

Present compound A-47: $^1$H-NMR (CDCl$_3$) δ: 8.46 (1H, d), 7.52 (1H, d), 7.27 (1H, m), 5.59 (1H, d), 4.51 (2H, t), 3.62 (2H, m), 3.57 (3H, s) 1.36 (3H, t).

Preparation Example 14

The mixtures of the present compound A-18 100 mg, tert-butyl carbamate 31 mg, 2-dicylohexylphoshino-2',4',6'-triisopropyl biphenyl 11 mg, palladium(II) acetate 4 mg, cesium carbonate 99 mg, and dioxane 1.7 mL was stirred at 100° C. for 3 hours under nitrogen atmosphere. Water was added to the resulting mixtures at room temperature, and the mixtures were extracted with ethyl acetate. The resulting organic lavers were washed with saturated brine, dried over anhydrous sodium sulfate, and concentrated under reduced pressure. The resulting residue was subjected to a silica gel column chromatography (ethyl acetate hexane=1:1) to obtain the present compound A-56 shown below 100 mg.

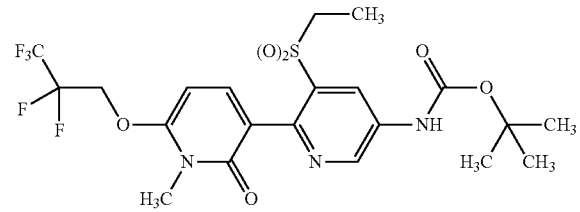

Present compound A-56: $^1$H-NMR (CDCl$_3$) δ: 8.76 (1H, d), 8.51 (1H, d), 7.47 (1H, d), 6.76 (1H, s), 5.65 (1H, d), 4.50 (2H, t), 3.52 (3H, s), 3.47-3.41 (2H, m), 1.54 (9H, 1.33 (3H, t).

Preparation Example 14-1

The compounds which were prepared according to the method described in Preparation Example 14 and their physical property values are shown below.

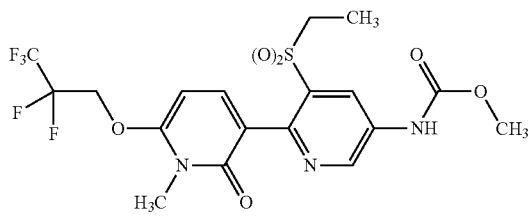

Present compound A-57: $^1$H-NMR (CDCl$_3$) δ: 8.83 (1H, d), 8.49 (1H, d), 7.49 (1H, d), 6.99 (1H, s), 5.67 (1H, d), 4.51 (2H, t), 3.84 (3H,), 3.53 (3H, s), 3.49-3.37 (2H, m), 1.33 (3H, t).

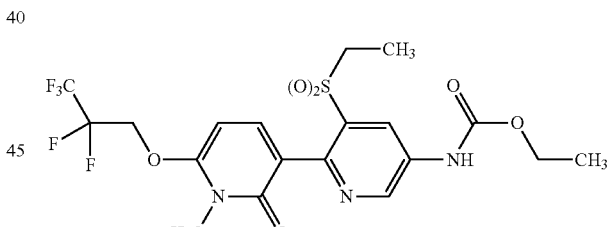

Present compound A-58: $^1$H-NMR (CDCl$_3$) δ: 8.81 (1H, d), 8.50 (1H, d), 7.49 (1H, d), 6.97 (1H, s), 5.66 (1H, d), 4.51 (2H, t), 4.28 (2H, q), 3.53 (3H, s), 3.50-3.37 (2H, m), 1.34 (3H, t), 1.33 (3H, t).

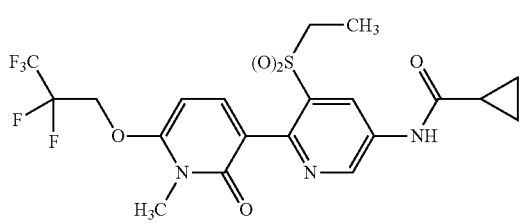

Present compound A-60: $^1$H-NMR (CDCl$_3$) δ: 8.92 (1H, d), 8.59 (1H, d), 8.24 (1H, 7.48 (1H, d), 5.68 (1H, d), 4.51

(2H, t), 3.53 (3H, s), 3.48-3.36 (2H, m), 1.63-1.57 (1H, m), 1.32 (3H, t), 1.15-1.11 (2H, m), 0.94-0.90 (2H, m).

Preparation Exampl 15

The mixtures of the present compound A-56 1.31 g, trifluoroacetic acid 1.8 mL and chloroform 5 mL were stirred at 60° C. for 1 hour. To the resulting mixtures was added 10N aqueous sodium hydroxide solution under ice-cooling, and the mixtures were extracted with chloroform The resulting organic layers were washed with saturated brine, dried over anhydrous sodium sulfate, and concentrated under reduced pressure to obtain the present compound A-62 shown below 1.08 g.

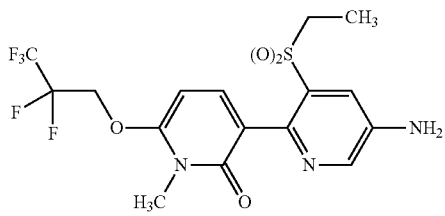

Present compound A-62: $^1$H-NMR (CDCl$_3$) δ: 8.29 (1H, d), 7.60 (1H, d), 7.46 (1H, d), 5.63 (1H, d), 4.50 (2H, t), 4.03 (2H, br), 3.53 (3H, s), 3.39-3.32 (2H, m), 1.30 (3H, t).

Preparation Example 16

To the mixtues of the present compound A-62 200 mg, cupper(II)bromide 152 mg, and acetonitrile 1.1 mL was added dropwise tert-butyl nitrite 0.06 mL, and the mixtures were stirred at room temperature for 1 hour. Water was added to the resulting mixtures, and the mixtures were extracted with ethyl acetate. The resulting organic layers were washed with saturated brine, dried over anhydrous sodium sulfate, and concentrated under reduced pressure. The resulting residue was subjected to a silica gel column chromatography to obtain the present compound A-61 shown below 139 mg.

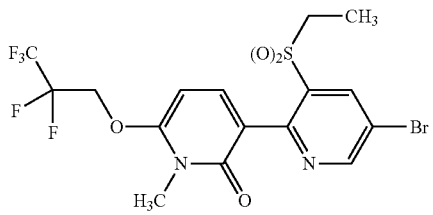

Present compound A-61: $^1$H-NMR (CDCl$_3$) δ: 8.90 (1H, d), 8.47 (1H, d), 7.51 (1H, d), 5.68 (1H, d), 4.52 (2H, t), 3.53 (3H, s), 3.50-3.44 (2H, m), 1.34 (3H, t).

Preparation Example 17

The mixtures of the present compound. A-18 1.00 g, (trimethylsilyl)acetonitrile 0.7 mL, zinc fluoride 0.27 q, 4,5'-bis(diphenylphoshino)-9,9'-dimethylxanthene 0.25 g, and tris(dibenzylideneacetone)dipalladium (0) 0.2 g, and DMF 7 mL were stirred at 140° C. for 3 hours. The resulting mixtures were cooled to room temperature, and water was added thereto, and the mixtures were extracted with ethyl acetate. The resulting organic layers were washed with saturated brine, dried over anhydrous sodium sulfate, and concentrated under reduced pressure. The resulting residue was subjected to a silica gel column chromatography (ethyl acetate:hexane=2:1) to obtain the present compound A-48 shown below 0.34 g.

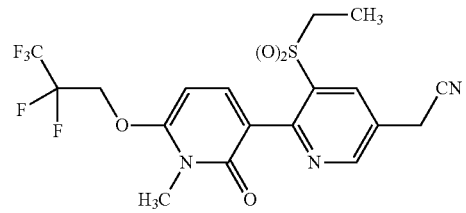

Present compound A-48: $^1$H-NMR (CDCl$_3$) δ: 8.86 (1H, d), 8.33 (1H, d), 7.53 (1H, d), 5.70 (1H, d), 4.52 (2H, t), 3.91 (2H, s), 3.53 (3H, s), 3.47 (2H, q), 1.34 (3H, t).

Preparation Example 18

The mixtures of the present compound A-48 0.24 g, 1,2-dibromoethane 0.13 mL, cesium carbonate 0.50 g, and acetonitrile 4 mL were stirred under reflux for 9 hours. Water was added to the resulting mixtures, and the mixtures were extracted with ethyl acetate. The resulting organic layers were dried over anhydrous sodium sulfate, and concentrated under reduced pressure. The resulting residue was subjected to a silica gel column chromatography (ethyl acetate) to obtain the present compound A-54 shown below 0.13

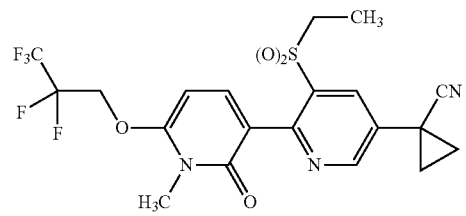

Present compound A-54: $^1$H-NMR (CDCl$_3$) δ: 8.88 (1H, d), 8.14 (1H, d), 7.50 (1H, d), 5.69 (1H, d), 4.52 (2H, t), 3.53 (3H, s), 3.44 (2H, q), 1.32 (3H, t), 1.26 (2H, t), 0.88 (2H, t).

Preparation Example 19

The compound which was prepared according to the method described in Preparation Examples 1 to 28 and its physical property value are shown below.

The compounds represented by formula (C-1):

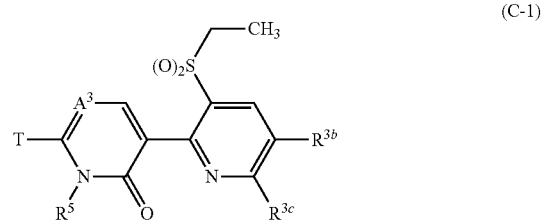

(C-1)

wherein the combination of T, $R^5$, $A^1$, $R^{3B}$ and $R^{3c}$ represents any combinations indicated in Table 21.

TABLE 21

| Present compound | T | $R^5$ | $A^3$ | $R^{3b}$ | $R^{3c}$ |
|---|---|---|---|---|---|
| A-49 | $OCH_2CF_2CF_3$ | Me | CH | H | Me |
| A-51 | $OCH_2CF_2CF_3$ | Me | CH | H | OEt |
| A-52 | $OCH_2CF_2CF_3$ | Me | CH | H | Oi-Pr |
| C-3 | $OCH_2C(Me)_2CN$ | Me | CH | H | c-Pr |
| C-4 | $OCH_2C(Me)_2CN$ | Me | CH | H | 4-F—Ph |
| C-5 | $OCH_2(1\text{-}CN\text{-}c\text{-}Pr)$ | Me | CH | H | c-Pr |
| C-6 | $OCH_2(1\text{-}CN\text{-}c\text{-}Pr)$ | Me | CH | H | 4-F—Ph |
| A-65 | $OCH_2CF_2CF_3$ | Me | N | $CF_3$ | H |
| A-74 | $OCH_2CF_2CF_3$ | $CH_2OCH_3$ | CH | H | H |
| A-75 | $OCH_2CF_2CF_3$ | Me | CH | $CH_3$ | H |
| A-81 | $OCH_2CF_2CF_3$ | Me | CBr | H | H |
| C-9 | $OCH_2C(Me)_2CN$ | Me | CH | $CF_3$ | H |
| C-10 | $OCH_2(1\text{-}CN\text{-}c\text{-}Pr)$ | Me | CH | $CF_3$ | H |

Present compound A-49

Present compound A-51: $^1$H-NMR (CDCl$_3$) δ: 8.12 (1H, d), 7.42 (1H, d), 6.79 (1H, d), 5.63 (1H, d), 4.48 (2H, t), 4.41-4.35 (2H, m), 3.50 (3H, s), 3.22-3.13 (2H, m), 1.36 (3H, t), 1.31-1.24 (3H, m).

Present compound A-52: $^1$H-NMR (CDCl$_3$) δ: 8.10 (1H, d), 7.41 (1H, d), 6.74 (1H, d), 5.63 (1H, d), 5.34-5.30 (1H, m), 4.48 (2H, t), 3.58-3.35 (5H, m), 1.38-1.27 (9H, m).

Present compound C-3: $^1$H-NMR (CDCl$_3$) δ: 8.63 (1H, d), 7.94 (1H, d), 7.47 (1H, d), 5.64 (1H, d), 4.00 (2H, s), 3.58 (3H, s), 3.43-3.34 (2H, m), 2.05-1.99 (1H, m), 1.55 (3H, s), 1.55 (3H, s), 1.29 (3H, t), 1.15-1.13 (2H, m), 0.87-0.82 (2H, m).

Present compound C-4: $^1$H-NMR (CDCl$_3$) δ: 9.03 (1H, d), 8.48 (1H, d), 7.65-7.61 (2H, m), 7.56 (1H, d), 7.25-7.20 (2H, m), 5.69 (1H, d), 4.03 (2H, s), 3.60 (3H, s), 3.51-3.43 (2H, m), 1.56 (3H, s), 1.56 (3H, s), 1.34 (3H, t).

Present compound C-5: $^1$H-NMR (CDCl$_3$) δ: 8.63 (1H, d), 7.94 (1H, d), 7.45 (1H, d), 5.56 (1H, d), 4.04 (2H, d), 3.58 (3H, s), 3.42-3.33 (2H, m), 2.03-2.00 (1H, m) 1.53 (2H, dd), 1.29 (3H, t), 1.18 (2H, dd), 1.15-1.12 (2H, m), 0.87-0.82 (2H, m).

Present compound C-6: $^1$H-NMR (CDCl$_3$) δ: 9.02 (1H, d), 8.48 (1H, d), 7.63 (2H, dd), 7.54 (1H, d), 7.22 (2H, t), 5.61 (1H, d), 4.07 (2H, br), 3.61 (3H, s), 3.50-3.43 (2H, m), 1.55 (2H, dd), 1.34 (3H, t), 1.19 (2H, dd).

Present compound A-65: $^1$H-NMR (CDCl$_3$) δ: 9.13-9.11 (1H, dd), 8.58-8.56 (1H, dd), 7.86 (1H, s), 4.93-4.90 (2H, 3.54-3.48 (2H, m), 3.52 (3H, s), 1.37 (3H, t).

Present compound A-74: $^1$H-NMR (CDCl$_3$) δ: 8.87 (1H, dd), 8.34 (1H, dd), 7.53-7.49 (2H, m), 5.68 (1H, d), 5.57-5.53 (2H, m), 4.53 (2H, t), 3.50-3.44 (5H, m), 1.32 (3H, t).

Present compound A-75: $^1$H-NMR (CDCl$_3$) δ: 8.68 (1H, d), 8.16 (1H, d), 7.49 (1H, d), 5.67 (1H, d), 4.51 (2H, t), 3.52 (3H, s), 3.43-3.39 (2H, m), 2.48 (3H, s), 1.31 (3H, t).

Present compound A-81: $^1$H-NMR (CDCl$_3$) δ: 8.87 (1H, dd), 8.34 (1H, dd), 7.61 (1H, s), 7.55 (1H, dd), 4.76-4.71 (2H, m), 3.60 (3H, s), 3.53-3.48 (2H, m), 1.35 (3H, t).

Present compound C-9: $^1$H-NMR (CDCl$_3$) δ: 9.09 (1H, d), 8.57 (1H, d), 7.56 (1H, d), 5.70 (1H, d), 4.03 (2H, s), 3.60 (3H, s), 3.54 (2H, q), 1.56 (3H, s), 1.55 (3H, s), 1.36 (3H, t).

Present compound C-10: $^1$H-NMR (CDCl$_3$) δ: 9.08 (1H, d), 8.57 (1H, d), 7.53 (1H, d), 5.62 (1H, d), 4.07 (2H, br), 3.61 (3H, s), 3.53 (2H, q), 1.56-1.54 (3H, m), 1.35 (3H, t), 1.21-1.17 (2H, m).

The compounds represented by formula (D-1)

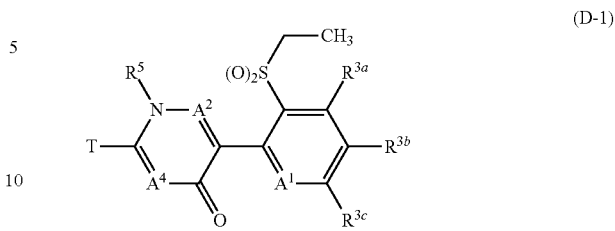

(D-1)

wherein the combination of T, $R^5$, $A^1$, $A^2$, $A^4$, $R^{3a}$, $R^{3b}$ and $R^{3c}$ represents any combinations indicated in Table 22.

TABLE 22

| Present compound | T | $R^5$ | $A^1$ | $A^2$ | $A^4$ | $R^{3a}$ | $R^{3b}$ | $R^{3c}$ |
|---|---|---|---|---|---|---|---|---|
| B-13 | $OCH_2CF_2CF_3$ | Me | N | CH | CH | H | OEt | H |
| B-14 | $OCH_2CF_2CF_3$ | Me | N | CH | CH | H | OH | H |
| B-17 | $OCH_2CF_2CF_3$ | Me | N | N | CH | H | H | H |

Present compound B-13: $^1$H-NMR (CDCl$_3$) δ: 8.52 (1H, 7.81 (1H, d), 7.32 (1H, s), 5.86 (1H, s), 4.47 (2H, t), 4.21-4.14 (2H, m), 3.55 (3H, s), 3.52-3.45 (2H, m), 1.48 (3H, t), 1.32 (3H, t).

Present compound B-14: $^1$H-NMR (CDCl$_3$) δ: 8.08 (1H, d), 7.59 (1H, d), 7.44 (1H, s), 6.08 (1H, s), 4.55 (2H, t), 3.62 (3H, s), 3.31-3.20 (2H, m), 1.34 (3H, t).

Present compound B-17: $^1$H-NMR (CDCl$_3$) δ: 8.94 (1H, dd), 8.33 (1H, dd), 7.61 (1H, dd), 6.04 (1H, s), 4.54 (2H, t), 3.83 (3H, s), 3.49 (2H, q), 1.36 (3H, t).

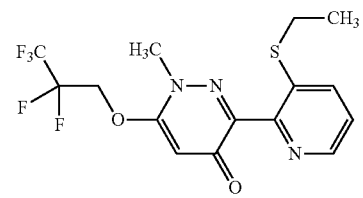 [SMILES: CCSc1cccnc1-c1nn(C)c(OCC(F)(F)C(F)(F)F)cc1=O]

Present compound B-15: $^1$H-NMR (CDCl$_3$) δ: 8.54 (1H, dd), 7.79 (1H, dd), 7.32 (1H, dd), 6.07 (lH, s), 4.53 (2H, t), 3.84 (3H, s), 2.91 (2H, q), 1.26 (3H, t).

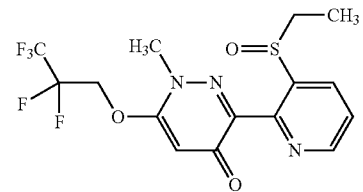 [SMILES: CCS(=O)c1cccnc1-c1nn(C)c(OCC(F)(F)C(F)(F)F)cc1=O]

Present compound B-16: $^1$H-NMR (CDCl$_3$) δ: 8.64 (1H, dd), 8.42 (1H, dd), 7.61 (1H, dd), 6.13 (1H, s), 4.57 (2H, t), 3.87 (3H, s), 3.29-3.21 (1H, m), 2.91-2.87 (1H, m), 1.37 (3H, t).

Reference Process Example 18

A mixture of the intermediate compound A-19 8 g and DMF 50 mL was cooled to 0° C., and thereto was added sodium hydride (60%, in oil) 2.8 g. The resulting mixture was stirred at 0° C. for 30 minutes, and thereto was added the compound of formula (D):

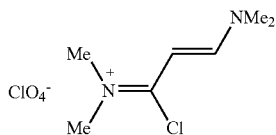

9 g, and the mixture was stirred at 0° C. for 3 hours. Water was added to the resulting mixture, and the mixture was extracted with ethyl acetate. The resulting organic layer was dried over anhydrous sodium sulfate, and Concentrated under reduced pressure. The resulting residue was subjected to a silica gel colUmn chromatography to obtain the intermediate compound A-43 shown below 0.5 g and the intermediate compound A-46 shown below 0.4 g.

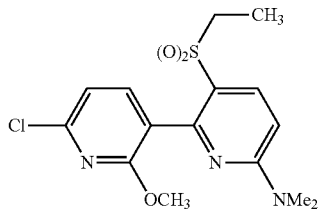

Intermediate compound A-43: $^1$H-NMR (CDCl$_3$) δ: 8.01 (1H, d), 7.50 (1H, d), 6.98 (1H, d), 6.53 (1H, d), 3.89 (3H, s), 3.13 (6H, s), 2.96-2.86 (2H, m), 1.16 (3H, t).

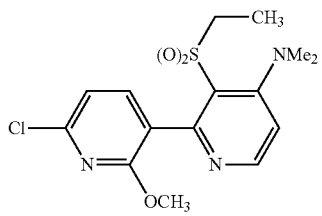

Intermediate compound A-46: $^1$H-NMR (CDCl$_3$) δ: 8.47 (1H, d), 7.69 (1H, d), 7.00-6.98 (2H, m), 3.95 (3H, s), 3.21-3.13 (2H, m), 3.05 (6H, s), 0.99 (3H, t).

Preparation Example 20

To a mixture of the present compound A-18 2.50 g, 4,5-bis(diphenylphosphino)-9,9-dimethylxantene 629 mg, palladium (II) acetate 122 mg, N,N-diisopropylethylamine 2.8 mL, and toluene 19 mL were added dropwise mixture of 2,4,6-trichlorophenyl formate 3.67 g and toluene 17 mL over 6 hours at 100° C. under nitrogen atmosphere. The resulting mixture was stirred at 100° C. for 2 hours, and the mixture was then cooled to room temperature. Water was added to the resulting mixture and the mixture was extracted with ethyl acetate. The resulting organic layer was washed with saturatedbrine, dried over anhydrous sodium sulfate, and concentrated under reduced pressure. The resulting residue was subjected to a silica gel column chromatography (ethyl acetate:hexane=1:1) to obtain the present compound A-63 shown below 1.61 g.

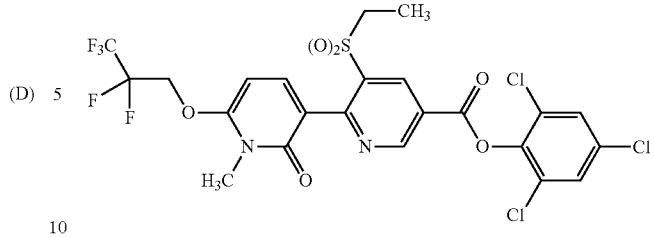

Present compound A-63: $^1$H-NMR (CDCl$_3$) δ: 9.58 (1H, d), 9.07 (1H, d), 7.62 (1H, d), 7.47 (2H, s), 5.74 (1H, d), 4.54 (2H, t), 3.62-3.55 (2H, m), 3.55 (3H, s), 1.40 (3H, t).

Preparation Example 21

To a mixture of the present compound A-63 1.31 g, THF 11 mL and water 5.5 mL was added lithium hydroxide monohydrate 169 mg under ice-cooling, and the mixture was stirred at room temperature for 30 minutes. Water was added to the resulting mixture, and the mixture was extracted with ethyl acetate. The resulting aqueous layer was acidified with 6N hydrochloric acid, and the mixture was extracted with ethyl acetate. The resulting organic layer was dried over anhydrous sodium sulfate, concentrated under reduced pressure to obtain the present compound A-64 shown below 0.5 g

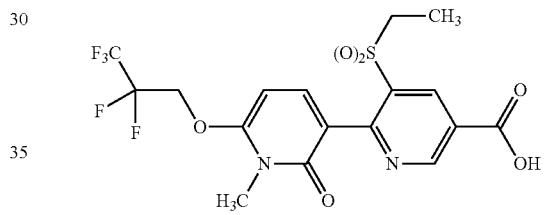

Present compound A-64: $^1$H-NMR (CDCl$_3$) δ: 9.28 (1H, d), 8.83 (1H, d), 7.66 (1H, d), 5.83 (1H, d), 4.57 (2H, t), 3.61 (3H, s), 3.53-3.45 (2H, m), 1.41 (3H, t).

Preparation Example 22

To a mixture of the present compound A-64 126 mg, chloroform 2 mL and DMF 16 µL was added oxalyl chloride 46 µL under ice-cooling, and the mixture was stirred at room temperature for 1 hour. Methanol 0.5 mL was added to the resulting mixture under ice-cooling, and the mixture was stirred at room temperature for 2 hours. Aqueous saturated hydrogen carbonate solution was added to the resulting mixture, and the mixture was extracted with ethyl acetate. The resulting organic layer was dried over anhydrous sodium sulfate, concentrated under reduced pressure to obtain the present compound A-66 shown below 0.12 g.

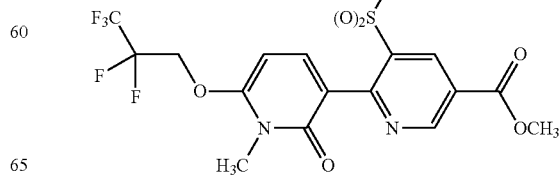

Present comp A-66: ¹H-NMR (CDCl₃) δ: 9.40 (1H, d), 8.89 (1H, d), 7.57 (1H, d), 5.71 (1H, d), 4.52 (2H, t), 4.01 (3H, s), 3.56-3.52 (2H, m), 3.5 (3H, s), 1.36 (3H, t).

Preparation Example 22-1

The compound which was prepared according to the method described in Preparation Example 22 and its physical property value are shown below.

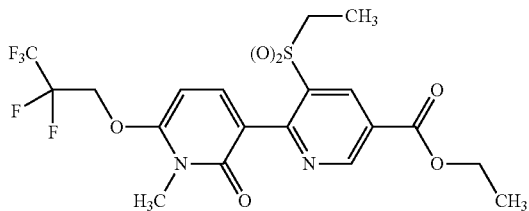

Present compound A-67: 1H-NMR (CDCl₃) δ: 9.40 (1H, d), 8.88 (1H, d), 7.56 (1H, d), 5.71 (1H, d), 4.53 (2H, t), 4.47 (2H, q), 3.54 (2H, q), 3.53 (3H, s), 1.44 (3H, t), 1.36 (3H, t).

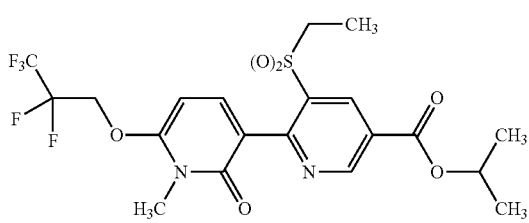

Present compound A-68: ¹H-NMR (CDCl₃) δ: 9.38 (2H, d), 8.86 (1H, d), 7.55 (1H, d), 5.71 (1H, d), 5.37-5.31 (1H, m), 4.53 (2H, t), 3.54-3.52 (5H, m), 1.42 (6H, d), 1.36 (3H, t).

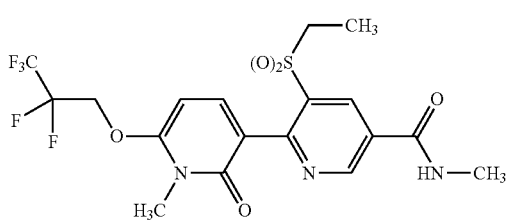

Present compound A-71: ¹H-NMR (CDCl₃) δ: 9.22 (1H, d), 8.64 (1H, d), 7.54 (1H, d), 6.27 (1H, br), 5.70 (1H, d), 4.52 (2H, t), 3.53 (3H, s), 3.50 (2H, q), 3.08 (3H, d), 1.34 (3H, t).

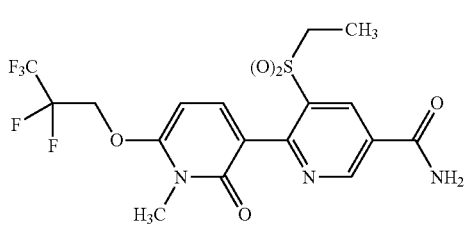

Present compound A-70: ¹H-NMR (CDCl₃) δ: 9.26 (1H, d), 8.71 (1H, d), 7.55 (1H, d), 6.31 (1H, br), 5.84 (1H, br), 5.71 (1H, d), 4.53 (2H, t), 3.51 (2H, q), 3.54 (3H, s), 1.34 (3H, t).

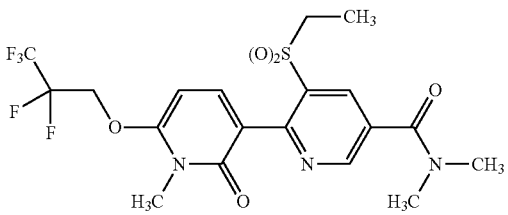

Present compound A-72: ¹H-NMR (CDCl₃) δ: 8.93 (1H, d), 8.39 (1H, d), 7.53 (1H, d), 5.69 (1H, d), 4.52 (2H, t), 3.54-3.45 (2H, m), 3.54 (3H, s), 3.17 (3H, s), 3.08 (3H, s), 1.33 (3H, t).

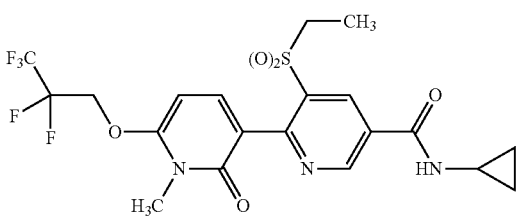

Present compound A-73: ¹H-NMR (CDCl₃) δ: 9.20 (1H, d), 8.58 (1H, d), 7.53 (1H, d), 6.41 (1H, br), 5.70 (1H, d), 4.52 (2H, t), 3.53-3.46 (2H, m), 3.53 (3H, s), 2.98-2.92 (1H, m), 1.33 (3H, t), 0.96-0.91 (2H, m), 0.71-0.67 (2H, m).

Preparation Example 23

A mixture of the present compound A-61 200 mg, sodium iodide 178 mg, copper (i) iodide 15 mg, trans-N,N'-dimethylcyclohexane-1,2-diamine 22 mg, and dioxane 13 was stirred at 130° C. for 2 hours. Water was added to the resulting mixture at room temperature, and the mixture was extracted with ethyl acetate. The resulting organic layer was washed with saturated brine, dried over anhydrous sodium sulfate, and concentrated under reduced pressure. The resulting residue was subjected to a silica gel column chromatography to obtain the present compound A-69 shown below 160 mg.

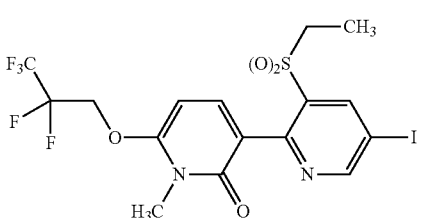

Present compound A-69: ¹H-NMR (CDCl₃) δ: 9.04 (1H, d), 8.63 (1H, d), 7.51 (1H, d), 5.68 (1H, d), 4.51 (2H, t), 3.52 (3H, s), 3.46 (2H, q), 1.33 (3H, t).

Preparation Example 24

To a mixture of the present compound A-61 0.5 g, tert-butyl carbazate 0.2 g, 2-(dicyclohexylphoshino)-3,6- dimethoxy-2',4',6'-triisopropyl-1,1'-biphenyl 54 mg, cesium carbonate 0.97 g, and dioxane 6.6 mL was added tris(dibenzylideneacetone)dipalladium (0) 90 mg, and the mixture was stirred at 100° C. for 1.5 hours. Water was added to the resulting mixture at room temperature, and the mixture was extracted with ethyl acetate. The resulting organic layer was washed with saturated brine, dried over anhydrous sodium sulfate, and concentrated under reduced pressure. The resulting residue was subjected to a silica gel column chromatography (ethyl acetate:hexane=1:1) to obtain the present compound A-76 shown below 0.21 g.

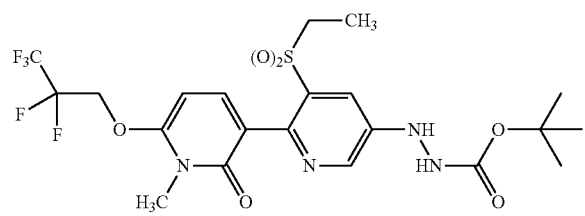

Present compound A-76: $^1$H-NMR (CDCl$_3$) δ: 9.14 (1H, d), 8.58 (1H, d), 7.50 (1H, d), 5.66 (1H, d), 4.50 (2H, t), 4.45 (2H, s), 3.52 (3H, s), 3.45 (2H, q), 1.57 (9H, s), 1.33 (3H, t).

Preparation Example 25

A mixture of the present compound A-76 0.27 g, trifluoro cetic acid 0.18 mL, and chloroform 1.5 mL was stirred at 60° C. for 5 hours. The resulting mixture was cooled to room temper ure, and concentrated under reduced pressure to obtain the present compound A-77 as crude product shown below.

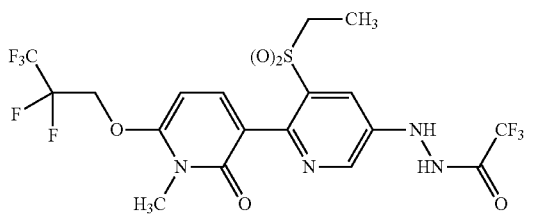

Present compound A-77: $^1$H-NMR (CDCl$_3$) δ: 8.45 (1H, d), 7.92 (1H, d), 7.59 (1H, d), 5.84 (1H, d), 5.39 (2H, br), 4.57 (2H, t), 3.56 (3H, s), 3.25 (2H, q), 1.27 (3H, t).

Preparation Example 26

To the present compound A-77 were added ammonium formate 0.15 g and ethyl orthoformate 1 mL, and the mixture was stirred under reflux for 6 hours. Water was added to the resulting mixture at room temperature, and the mixture was extracted with ethyl acetate. The resulting organic layer was washed with saturated brine, dried over anhydrous sodium sulfate, and concentrated under reduced pressure. The resulting residue was subjected to a silica gel column chromatography (ethyl acetate) to obtain the present compound A-78 shown below 35 mg and the present compound A-79 shown below 0.13 g.

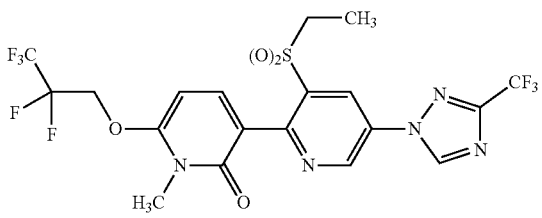

Present compound A-78: $^1$H-NMR (CDCl$_3$) δ: 9.26 (1H, d), 8.78 (1H, s), 8.68 (1H, d), 7.59 (1H, d), 5.73 (1H, d), 4.55 (2H, t), 3.60-3. (5H, m), 1.38 (3H, t).

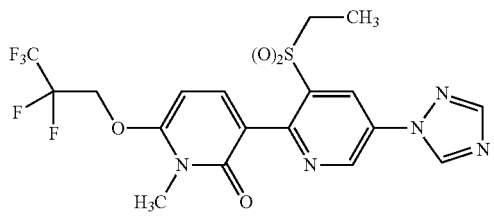

Present compound A-79: $^1$H-NMR (CDCl$_3$) δ: 9.26 (1H, d), 8.74 (1H, s), 8.57 (1H, d), 8.22 (1H, s), 7.57 (1H, d), 5.73 (1H, d), 4.54 (2H, t), 3.58-3.50 (5H, m), 1.37 (3H, t).

Preparation Example 27

A mixture of the present compound A-2 1.0 g, N-bromo-succinimide 0.45 g, and DMF 10 mL was stirred for 2 hours at room temperature. Aqueous saturated hydrogen carbonate solution was added to the resulting mixture, and the mixture was extracted with ethyl acetate. The resulting organic layer was washed with saturated brine, dried over anhydrous sodium sulfate, and concentrated. The resulting residue was subjected to a silica gel column chromatography (methanol:chloroform=1:9) to obtain the present compound A-80 shown below 0.74 g.

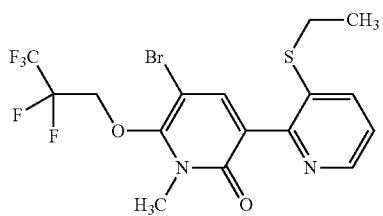 [SMILES: CCSc1cccnc1-c1cc(Br)c(OCC(F)(F)C(F)(F)F)n(C)c1=O]

Present compound A-80: $^1$H-NMR (CDCl$_3$) δ: 8.44 (1H, dd), 7.71 (1H, dd), 7.63 (1H, s), 7.26 (1H, dd), 4.70 (2H, t), 3.62 (3H, s), 2.90 (2H, q), 1.27 (3H, t).

Preparation Example 28

A mixture of the present compound A-2 1.5 g, N-bromo-succinimide 1.02 g, tert-butoxide potassium 0.55 g, and cyanamide 0.21 g, and methanol 30 mL was stirred at room temperature for 5 hours. Water was added to the resulting mixture, and the mixture was extracted with ethyl acetate. The resulting organic layer was concentrated under reduced pressure to obtain the present compound A-83 shown below 0.93 g.

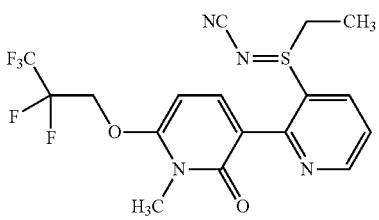 [SMILES: CC/S(=N\C#N)c1cccnc1-c1ccc(OCC(F)(F)C(F)(F)F)n(C)c1=O]

Present compound A-83: $^1$H-NMR (CDCl$_3$) δ: 8.80 (1H, dd), 8.46 (1H, dd), 7.97 (1H, d), 7.52 (1H, dd), 5.86 (1H, d), 4.60 (2H, t), 3.77-3.69 (1H, m), 3.57 (3H, s), 3.44-3.39 (1H, m), 1.61 (3H, t).

Preparation Example 29

Examples of the compounds that can be prepared according to the methods described in the Preparation Examples 1 to 28 are indicated below.

The compounds represented by formula (E-1):

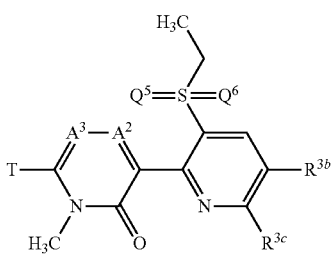

wherein the combination of T, A$^2$, A$^3$, Q$^5$, Q$^6$, R$^{3b}$ and R$^{3c}$ represents any combinations indicated in Table 23.

TABLE 23

| Present compound | T | A$^2$ | A$^3$ | Q$^5$ | Q$^6$ | R$^{3b}$ | R$^{3c}$ |
|---|---|---|---|---|---|---|---|
| A-82 | OCH$_2$CF$_2$CF$_3$ | CH | CMe | O | O | H | H |
| A-84 | OCH$_2$CF$_2$CF$_3$ | CH | CH | O | N—CN | H | H |
| A-85 | OCH$_2$CF$_2$CF$_3$ | CH | CH | O | NH | H | H |
| A-86 | OCH$_2$CF$_2$CF$_3$ | CH | CH | O | NMe | H | H |
| A-87 | OCH$_2$CF$_2$CF$_3$ | N | CH | — | — | H | H |
| A-88 | OCH$_2$CF$_2$CF$_3$ | N | CH | O | — | H | H |
| A-89 | OCH$_2$CF$_2$CF$_3$ | N | CH | O | O | H | H |
| A-90 | OCH$_2$CF$_2$CHF$_2$ | N | CH | O | O | H | H |
| A-91 | OCH$_2$CF$_2$CF$_3$ | N | CH | O | O | CF$_3$ | H |
| A-92 | OCH$_2$CF$_2$CF$_3$ | N | CH | O | O | c-Pr | H |
| A-93 | OCH$_2$CF$_2$CF$_3$ | N | CH | O | O | 4-F—Ph | H |
| A-94 | OCH$_2$CF$_2$CF$_3$ | N | CH | O | O | OEt | H |
| A-95 | OCH$_2$CF$_2$CF$_3$ | N | CH | O | O | H | CF$_3$ |
| A-96 | OCH$_2$CF$_2$CF$_3$ | N | CH | O | O | H | c-Pr |
| A-97 | OCH$_2$CF$_2$CF$_3$ | N | CH | O | O | H | 4-F—Ph |
| A-98 | OCH$_2$CF$_2$CF$_3$ | N | CH | O | O | H | OEt |

The compounds represented by formula (F-1):

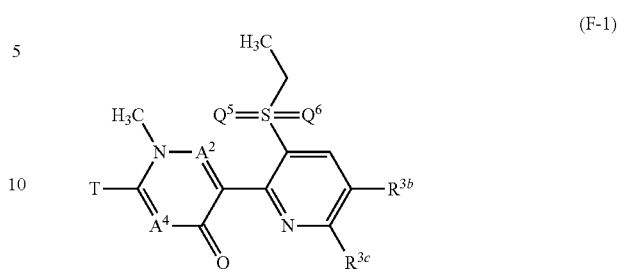

wherein the combination of T, A$^2$, A$^4$, Q$^5$, Q$^6$, R$^{3b}$ and R$^{3c}$ represents any combinations indicated in Table 24.

TABLE 24

| Present compound | T | A$^2$ | A$^4$ | Q$^5$ | Q$^6$ | R$^{3b}$ | R$^{3c}$ |
|---|---|---|---|---|---|---|---|
| B-18 | OCH$_2$CF$_2$CF$_3$ | CH | N | — | — | H | H |
| B-19 | OCH$_2$CF$_2$CF$_3$ | CH | N | O | — | H | H |
| B-20 | OCH$_2$CF$_2$CF$_3$ | CH | N | O | O | H | H |
| B-21 | OCH$_2$CF$_2$CF$_3$ | CH | N | O | O | CF$_3$ | H |
| B-22 | OCH$_2$CF$_2$CHF$_2$ | CH | N | O | O | c-Pr | H |
| B-23 | OCH$_2$CF$_2$CF$_3$ | CH | N | O | O | 4-F—Ph | H |
| B-24 | OCH$_2$CF$_2$CF$_3$ | CH | N | O | O | OEt | H |
| B-25 | OCH$_2$CF$_2$CF$_3$ | N | CH | O | O | CF$_3$ | H |
| B-26 | OCH$_2$CF$_2$CF$_3$ | N | CH | O | O | OEt | H |
| B-27 | OCH$_2$CF$_2$CHF$_2$ | N | CH | O | O | H | 4-F—Ph |
| B-28 | OCH$_2$CF$_2$CF$_3$ | N | CH | O | O | H | c-Pr |

Next, the formulation Examples of the Present compound Z is described. The "parts" represents "part by weight" unless otherwise specified.

Formulation Example 1

Into a mixture of 35 parts of xylene and 35 parts of DMF, ten parts of any one of the Present compounds A-1 to A-98, B-1 to B-28, and C-1 to C-10 is added, followed by mixing, and then 14 parts of polyoxyethylene styryl phenyl ether and parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of synthetic hydrated silicon oxide fine powder and 54 parts of diatomaceous earth are mixed, and further 20 parts of any one of the Present compounds A-1 to A-98, B-1 to B-28, and C-1 to C-10 is added, followed by mixing them to obtain each formulation.

Formulation Example 3

To 2 parts of any one of the Present compounds A-1 to A-98, B-1 to B-28, and C-1 to 0-10, 1 part of synthetic hydrated silicon oxide fine powder, 2 parts of calcium lignin sulfonate, 30 parts of bentonite and 65 parts of kaolin clay are added, followed by mixing. Then the mixtures are stirred, granulated with a granulator, and forced-air dried to obtain each formulation.

Formulation Example 4

Into an appropriate amount of acetone, 1 part of any one of the Present compoulds A-1 to A-98, B-1 to B-28, and C-1 to C-10 is added, followed by mixing, and then 5 parts of hydrous silica, 0.3 parts of isopropyl acid phosphate and 93.7 parts of kaolin clay are added, followed by mixing 2) with stirring thoroughly and removal of acetone from the mixtures by evaporation to obtain each formulation.

Formulation Example 5

Thirty five (35) parts of a mixture of polyoxyethylene alkyl ether sulfate ammonium salt and hydrous silica (weight ratio of 1:1), 20 parts of any one of the Present compounds A-1 to A-98, B-1 to B-28, and C-1 to C-10, and 45 parts of water are mixed thoroughly to obtain each formulation.

Formulation Example 6

Into a mixture of 5 parts of xylene and 5 parts of trichloroethane, 0.1 parts of any one of the Present compounds A-1 to A-98, B-1 to B-28, and C-1 to C-10 is added, followed by mixing, and the resulting mixture is then mixed with 89.9 parts of kerosene to obtain each formulation.

Formulation Example 7

Into 0.5 mL of acetone, 10 mg of any one of the Present compounds A-1 to A-98, B-1 to B-28, and C-1 to C-10 is added, followed by mixing, and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example A

Into an aerosol can, 0.1 part of any one of the Present compounds A-1 to A-98, B-1 to B-28, and C-1 to C-10, and 49.9 parts of Neothiozole (Chuo Kasei Co., Ltd.) are placed. After mounting an aerosol valve, 25 parts of dimethyl ether and 25 parts of LPG are filled, followed by shaking and further mounting an actuator to obtain each oily aerosol.

Formulation Example 9

A mixture of 0.6 part of any one of the Present compounds A-1 to A-98, B-1 to B-28, and C-1 to C-10, 0.01 part of BHT (2,6-di-vert-butyl-4-methylphenol), 5 parts of xylene, 3.39 parts of deodorized kerosine and 1 part of an emulsifier {Rheodol MO-60 (registered trademark of Kao Corporation)} and 50 parts of distilled water are filled into an aerosol container, and a valve part is attached. Then, 40 parts of a propellant (LPG) is filled therein through the valve under pressure to obtain each aqueous aerosol.

Formulation Example 10

0.1 parts of any one of the Present compounds A-1 to A-98, B-1 to B-28, and C-1 to C-10 are mixed into 2 mL of propylene glycol, and the resulting solution is impregnated into a ceramic plate having a size of 4.0 cm×4.0 cm and a thickness of 1.2 cm, to obtain each thermal fumigant.

Preparation Example 11

5 parts of any one of the Present compounds A-1 to A-98, B-1 to B-28, and C-1 to C-10, and 95 parts of ethylene-methyl methacrylate copolymer (the ratio of the methyl methacrylate in the copolymer: 10 weight %), Acryft (registered by trademark) WD 301, manufactured by Sumitomo Chemical Co. Ltd.) are melted and kneaded with a closed type pressure kneader (manufactured by Moriyama Manufacturing Co. Ltd.), and the resulting kneaded product is extruded from an extrusion molding machine through a molding die to obtain each rod-shaped molded product having a length of 15 cm and a diameter of 3 mm.

Formulation Example 12

5 parts of any one of the Present compounds A-1 wo A-98, B-1 to B-28, and C-1 to C-10, and 95 parts of plasticized polyvinyl chloride resin are melted and kneaded with a closed type pressure kneader (manufactured by Moriyama Manufacturing Co. Ltd.), and the resulting kneaded product is extruded from an extrusion molding machine through a molding die to obtain each rod-shaped molded product having a length of 15 cm and a diameter of 3 mm.

Formulation Example 13

One hundred (100) mg of any one of the Present compounds A-1 to A-98, B-1 to B-28, and C-1 to C-10, 68.75 mg of lactose, 237.5 mg of corn starch, 43.75 mg of microcrystalline cellulose, 18.75 mg of polyvinylpyrrolidone, 28.75 mg of sodium carbomethyl starch and 2.5 mg of magnesium stearate are mixed, and the resulting mixture was compressed to an appropriate size to obtain each tablet.

Formulation Example 14

Twenty five (25) mg of any one of the Present compounds A-1 to A-98, B-1 to B-28, and C-1 to C-10, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain each capsule.

Formulation Example 15

To 100 mg of any one of the Present compounds A-1 to A-98, B-1 to B-28, and C-1 to C-10, 500 mg of fumaric acid, 2,000 mg of sodium chloride, 150 mg of methyl paraben, 50 mg of propyl paraben, 25,000 mg of granulated sugar, 13,000 mg of sorhitol (70% solution), 100 mg of Veegum K (manufactured by Vanderbilt, 35 mg of perfume and 500 mg of coloring agent, a distilled water is added so that a final volume is set to be 100 mL, followed by mixing them to obtain each suspension for oral administration.

Formulation Example 16

Into a mixture of 5% by weight of an emulsifier, 3% by weight of benzyl alcohol and 30% by ht of propylene glycol, 5% by weight of any one of the Present compounds A-1 to A-98, B-1 to B-28, and C-1 to C-10 is dissolved, and phosphate buffer is added thereto so that a pH of the solution is set to be 6.0 to 6.5, and water is added as the rest parts to obtain each solution for oral administration.

Formulation Example 17

To a mixture of 57% by weight of fractional di tillated palm oil and 3% by weight of polysorbate 85, 5% by weight of aluminum distearate is added, and heated to disperse it.

The resulting mixture is cooled to room temperature, and 25% by weight of saccharin is dispersed in an oil vehicle. Ten (10) % by weight of any one of the Present compounds A-1 to A-98, to B-28, and C-1 to C-10 is divided thereto to obtain each paste for oral administration.

Formulation Example 18

Five (5) % by weight of any one of the Present compounds A-1 to A-98, B-1 to B-28, and C-1 to C-10 is mixed with 95% by weight of limestone filler, followed by a wet granulation of the resulting mixture to obtain each granule for oral administration.

Formulation Example 19

Into 80 parts of diethylene glycol monomethyl ether, 5 parts of any one of the Present compounds A-1 to A-98, B-1 to B-28, and C-1 to C-10 is dissolved, and 15 parts of propylene carbonate is added thereto, and the resulting mixture is mixed to obtain each spot-on solution.

Formulation Example 20

Into 70 parts of diethylene glycol monomethyl ether, 10 parts of any one of the Present compounds A-1 to A-98, B-1 to B-28, and C-1 to C-10 is dissolved, and 20 parts of 2-octyldodecanol is added thereto, and the resulting mixture is mixed to obtain a pour-on solution.

Formulation Example 21

To 0.5 parts of any one of the Present compounds A-2 to A-98, B-1 to B-28, and C-1 to C-10, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain each hydrogenous solution of shampoo formulation.

Formulation Example 22

Zero point one five (0.15)% by weight of any one of the Present compounds A-1 to A-98, B-1 to B-28, and C-1 to C-10, 95% by weight of animal feed, as well as 4.85% by weight of a mixture of dibasic calcium phosphate, diatomaceous earth, aerosol and carbonate (or chalk) are mixed with stirring thoroughly to obtain each premix for animal feed.

Formulation Example 23

Seven point two (7.2) g of any one of the Present compounds A-1 to A-96, B-1 to B-28, and C-1 to C-10, and 92.8 g of Hosco (registered trademark) S-55 (manufactured by Maruishi Pharmaceuticals) are melted and mixed at 100° C., and the resulting mixture was poured into a suppository mold, followed by perforling a cooling solidification to obtain each suppository.

Next, Test Examples are used to show an efficacy of the Present compound Z on controlling harmful arthropods.

The following test examples were carried out at 25° C.

Test Example 1

The test compounds is made to a formulation according to a similar method to that described in the Formulation Example 5, and thereto is added water containing 0.03 v/v % of spreader to prepare a diluted solution containing a prescribed concentration of the test compound.

Cucumber (*Cucurnis sativus*) seedling (on the developmental stage of the second true leaf) is planted in a container and approximately 30 cotton aphids (*Aphis ossypii*) (all stages of life) are released onto the leaves of the cucumber. After 1 day, the diluted solutions are sprayed into the seedling in a ratio of 10 mL/seedling. Further, after 5 days, the number of the surviving insects is examined and the controlling value is calculated by the following equation.

Controlling value (%)={1−($Cb$×$Tai$)/($Cai$×$Tb$)}×100 wherein the symbols in the formula represent the following descriptions.

$Cb$: Number of the test insects in untreated group;
$Cai$: Number of thesurviving insects at the time of the investigation in untreated group;
$Tb$: Number of the test insects in treated group;
$Tai$: Number of the surviving insects at the time of the investigation in treated group;

Here the "untreated group" represents a group where the similar treatment procedure to that of the treated group except not using the test compound is done.

The test was conducted by making the prescribed concentration 500 ppm and using the below-mentioned Present compounds as a test compound according to the test example 1. As a result of the test, the below-mentioned Present compounds showed 90% or greater as the controlling value.

Present compound number: Present compounds A-1, A-3, A-6, A-7, A-8, A-9, A-10, A-11, A-12, A-13, A-14, A-15, A-16, A-17, A-18, A-19, A-21, A-23, A-24, A-25, A-26, A-30, A-31, A-33, A-34, A-35, A-36, A-37, A-38, A-39, A-41, A-48, A-53, A-74, A-75, A-80, A80, A-81, A-82, A-83, B-3, B-8, B-9, B-11, B-13, B-17, C-1 and C-2.

The test was conducted by making the prescribed concentration 200 ppm and using the below-mentioned Present compounds as a test compound according to the test example 1. As a result of the test, the below-mentioned Present compounds showed 90% or greater as the controlling value.

Present compound number: Present compounds A-1, A-2, A-3, A-6, A-7, A-8, A-10, A-11, A-12, A-14, A-15, A-16, A-18, A-19, A-20, A-23, A-24, A-26, A-28, A-29, A-31, A-33, A-34, A-35, A-35, A-37, A-38, A-39, A-40, A-48, A-53, A-54, A-55, A-56, A-57, A-58, A-59, A-60, A-61, A-62, A-66, A-67, A-68, A-69, A-70, A-71, A-72, A-73, A-75, A-79, B-2, 13-3, B-4, B-5, B-6, B-8, B-13, B-15, C-1, C-2, C-3, C-4, C-5, and C-6.

Test Example 2

The test compounds are made to a formulation according to a similar method to that described in the Formulation Example 5, and thereto is added water to prepare a diluted solution containing a prescribed concentration of the test compound.

Cucumber seedling (on the developmental stage of the second true leaf) is planted in a container, and the diluted solutions are the ratio on 5 mL/seedling are irrigated into the plant foot. After 7 days, approximately 30 cotton aphids (all stages of life) are inoculated onto the cucumber leaves. Further, after additional 6 days, the number of the surviving insects is examined, and the controlling value is calculated by the following equation.

Controlling value (%)={1−($Cb$×$Tai$)/($Cai$×$Tb$)}×100 wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where the sirrilar treatment procedure to that of the treated group except not using the test compound is done.

The test was conducted by making the prescribed concentration 1,000 ppm and using the below-mentioned Present compounds as a test compound according to the test example 2. As a result of the test, the below-mentioned. Present compounds showed 90% or greater as the controlling value.

Present compound number: Present compounds A-1, A-2, A-3, A-6, A-7, A-8, A-10, A-11, A-14, A-16, A-17, A-18, A-23, A-24, A-26, A-28, A-29, A-31, A-33, A-34, A-35, A-36, A-37, A-38, A-39, A-40, A-48, A-53, A-54, A-55, A-56, A-57, A-58, A-59, A-60, A-61, A-62, A-67, A-68, A-69, A-70, A-71, A-72, A-73, A-75, A-79, B-2, B-3, B-4, B-13, C-1, C-2, C-3, and C-5.

Test Example 3

The test compounds are made to a formulation according to a similar method to that described in the Formulation Example 5, and thereto is added water containing 0.03 v/v % of a spreader to prepare a diluted solution containing a prescribed concentration of the test compound.

Rice (*Oryza sativa*) seedling (on the developmental age of the second true leaf) is planted in a container, and the diluted solutions are sprayed into the seedling in a ratio of 10 mL/seedling. Thereafter, 20 3rd instar larvae of brown planthoppers (*Nilaparvata lugens*) are released onto the rice leaves. After 6 days, the morality is calculated by the following equation.

Morality (%)={1−the number of the surviving insects/20}×100

The test was conducted by making the prescribed concentration 500 ppm and using the below-mentioned Present compounds as a test compound according to the test example 3. As a result of the test, the below-mentioned Present compounds showed 90% or greater as the morality.

Present compound number: Present compounds A-1, A-2, A-3, A-6, A-11, A-12, A-18, A-23, A-26, A-31, A-33, A-34, A-39, A-83, B-3, B-17, C-1, and C-2.

Test Example 4

The test compounds are made to a formulation according to a similar method to that described in the Formulation Example 5, and thereto is added water to prepare a diluted solution containing a prescribed concentration of the test compound.

Five (5) mL of the diluted solutions described above are added to a container, and therein is installed Rice seedling (on the developmental stage of the second true leaf) that is planted in a container having a hole in the bottom. After 7 days, 20 3rd instar larvae of brown planthoppe res (*Nalaparvata lugens*) are released. After 6 days, the number of the surviving insects is examined, and the morality is calculated by the following equation.

Morality (%)={1−the number of the surviving insects/20}×100

The test was conducted by making the prescribed concentration 1,000 ppm and using the below-mentioned Present compounds as a test compound according to the test Example 4. As a result of the test, the below-mentioned Present compounds showed 90% or greater as the morality.

Present compound number: Present compounds A-1, A-2, A-3, A-6, A-7, A-8, A-11, A-12, A-14, A-16, A-17, A-18, A-19, A-20, A-23, A-24, A-28, A-29, A-31, A-33, A-34, A-35, A-36, A-37, A-38, A-39, A-40, A-54, A-55, A-56, A-57, A-58, A-59, A-60, A-66, A-67, A-68, A-69, A-70, A-71, A-72, A-79, B-2, B-3, C-1, C-2, and C-5.

Test Example 5

The test compounds are made to a formulation according to a similar method to that described in the Formulation Example 5, and thereto is added water containing 0.03 v/v % of a spreader to prepare a diluted solution containing a prescribed concentration of the test compound.

The diluted solutions are sprayed into the cabbage (*Brassicae oleracea*) seedling (on the developmental stage of the second to third true leaf) that is planted in a container in a ratio of 20 mL/seedling. Thereafter, the stem and leaf thereof is cut out and then is installed into the container that is covered with the filter paper. Five cabbage moths (*Plutella xylostella*) at the second instar larval stages are released into the cup. After 5 days, the surviving insects are counted, and the mortality of insects is calculated by the following equation.

Morality (%)={1−the number of the surviving insects/5}×100

The test was conducted by making the prescribed concentration 500 ppm and using the below-mentioned Present compounds as a test compound according to the test example 5 As a result of the test, the below-mentioned Present compounds showed 80% or greater as the morality.

Present compound number: Present compounds A-1, A-2, A-3, A-6, A-7, A-8, A-9, A-10, A-11, A-12, A-13, A-14, A-15, A-16, A-17, A-18, A-19, A-21, A-22, A-23, A-24, A-25, A-26, A-27, A-30, A-31, A-33, A-34, A-35, A-36, A-37, A-38, A-39, A-41, A-53, A-63, A-75, A-80, A-81, B-3, B-8, B-9, B-11, and B-13.

Test Example 6

The test compounds are made to a formulation according to a similar method to that described in the Formulation Example 5, and thereto is added water containing 0.03 v/v % of a spreader to prepare a diluted solution containing a prescribed concentration of the test compound.

The diluted solutions are sprayed into the cucumber seedling (on the developmental stage of the third to fourth true leaf) that is planted in a container in a ratio of 20 mL/seedling. Thereafter, 10 cabbage moths (*Plutella xylostella*) at the third instar larval stages are released into the container. After 5 days, the surviving insects are counted, and the mortality of insects is calculated by the following equation.

Morality (%)={1−the number of the surviving insects/10}×100

The test was conducted by making the prescribed concentration 200 ppm and using the below-mentioned Present compounds as a test compound according to the Test Example 6. As a result of the test, the below-mentioned Present compounds showed 90% or greater as the morality.

Present compound number: Present compounds A-1, A-2, A-3, A-7, A-8, A-9, A-12, A-13, A-18, A-19, A-20, A-21, A-22, A-23, A-24, A-25, A-26, A-27, A-28, A-29, A-31, A-33, A-34, A-35, A-36, A-37, A-38, A-39, A-40, A-41, A-53, A-54, A-56, A-57, A-58, A-59, A-60, A-61, A-66, A-67, A-68, A-69, A-75, A-79, B-2, B-3, B-13, C-2, C-3, and C-4.

Test Example 7

The test compounds are dissolved into a mixed solution of polyoxyethylene sorbitan mono-cocoate and acetone (acetone and polyoxyethylene sorbitan mono-cocoate=5:95 (v/v ratio)) in a ratio of 50 μL of the mixed solution per 1 mg of the test compound. Thereto is added water containing 0.03% by volume of a spreader to prepare a diluted solution containing a prescribed concentration of the test compound.

The young seedling Corns (*Zea mays*) are immersed into the diluted solution for 30 seconds. Thereafter, two grains of the seedling are installed in a plastic petri dish (90 mm radiue), and 10 western corn rootworms (*Diabrotica virgifera virgifera*) at the second instar larval stages are released onto the container. After 5 days, the number of the died insects are counted and the mortality of insects is calculated by the following equation, Morality (%)=(the number of the died insects/10)×100

The test was conducted by making the prescribed concentration 500 ppm and using the below-mentioned Present compounds as a test compound according to the Test Example 7. As a result of the test, the below-mentioned Present compounds showed 80% or greater as the morality.

Present compound number: Present compounds A-1, A-3, A-5, A-7, A-8, A-11, A-13, A-18, A-19, A-20, A-22, A-23, A-26 A-31, A-33, A-34, A-38, A-39, A-40, A-66, and B-3

Test Example 8

The test compounds are made to a formulation according to a similar method to that described in the Formulation Example 5, and thereto is added water containing 0.03 v/v % of a spreader to prepare a diluted solution containing a prescribed concentration of the test compound.

Silverleaf whiteflies (*Bemisia tabaci*) are released on tomato (*Lycopersicon esculentum*) seedling that is planted in the container, and then spawn for about 24 hours. The seedling are stored for 8 days, and the larvae of cilverleaf whiteflies are hatched from the laid eggs. The diluted solutions are sprayed into the seedling in a ratio of 10 mL/seedling. After 7 days, the number of the surviving insects is examined, and the controlling value is calculated by the following equation.

Controlling value (%)={1−(*Cb*×*Tai*)/(*Cai*×*Tb*)}×100 wherein the symbols in the formula represent the following descriptions.

Cb: Number of the insects shortly before the treatment in untreated group;

Cai: Number of the surviving insects at the time of the investigation in untreated group;

Tb: Number of the insects shortly before the treatment in treated group;

Tai: Number of the surviving insects at the time of the investigation in treated group;

Here the "untreated group" represents a group where the similar treatment procedure to that of the treated group except not using the test compound is done.

The test was conducted by making the prescribed concentration 200 ppm and using the below-mentioned Present compounds as a test compound according to the test example 8. As a result of the test, the below-mentioned Present compounds showed 90% or greater as the morality.

Present compound number: Present compounds A-1, A-2, A-7, A-11, A-12, A-18, A-20, A-23, A-26, A-31, A-33, A-34, A-39, A-54, A-55, A-56, A-59, A-61, A-66, A-67, A-69, and A-79.

Test Example 9

The test compounds are made to a formulation according to a similar method to that described in the Formulation Example 5, and thereto is added water containing 0.03 v/v % of a spreader to prepare a diluted solution containing a prescribed concentration of the test compound.

The diluted solutions are sprayed into the cabbage (*Brassicae oleracea*) seedling (on the developmental stage of the second to third true leaf) that is planted in a container in a ratio of 20 mLf seedling. Thereafter, the stem and leaf thereof is cut out and then is ins ailed into the container that is covered with the filter paper. Five oriental leaf worm moths (*Spodoptera litura*) at the second instar larval stages are released into the cup. After 5 days, the surviving insects are counted, and the mortality of insects is calculated by the following equation.

Morality (%)={1−the number of the surviving insects/5}×100

The test was conducted by making the prescribed concentration 500 ppm and using the below-mentioned Present compounds as test compound according to the test example 9. As a result of the test, the below-mentioned Present compounds showed 80% or greater as the morality.

Present compound number: Present compounds A-12, A-13, A-18, A-23, A-26, A-31, A-33, A-34, A-35, A-36, A-37, A-38, A-39, A-81,ᵥ B-9, B-11, and B-13.

Test Example 10

The present compounds are dissolved into a mixed solution of xylene, DMF and surfactants (xylene, DMF and surfactants=4:4:1 (v/v ratio)) in a ratio of 10 μL of the mixed solution per 1 mg of the present compound. The mixture is diluted with water containing 0.03% by volume of a spreader to prepare a diluted solution A containing a prescribed concentration the present compound.

The present ingredients are dissolved into a mixed solution of xylene, DMF and surfactants (xylene, DMF and surfactants=4:4:1 (v/v ratio)) in a ratio of 10 μL of the mixed solution per 1 mg of the present compound. The mixture is diluted with water containing 0.03% by volume of a spreader to prepare a diluted solution B containing a prescribed concentration of the present ingredient.

The diluted solution A is mixed with the diluted solution B to prepare diluted solution C.

Leaf discs of Cucumber (Cucumber *sativus*) cotyledon (length 1.5 cm) are placed in each well of 24-well microplate. Two (2) apterous adults and 8 larvae of cotton aphids (*Aphis gossypii*) per one well are released and the diluted solution C is sprayed at 20 μL per one well. The group is defined as "treated group". A well that is sprayed with 20 μL of water containing 0.02% by volume of a spreader instead of the diluted solution C is defined as "untreated group".

After drying the diluted solution C, the upper microplate is covered with a film sheet. After 5 days, the number of the surviving insects in each well is examined.

The controlling value is calculated by the following equation.

Controlling value (%)={1−(Tai)/(Cai)}×100 wherein the symbols in the equation represent the following descriptions.

Cai: Number of the surviving insects at the time of the examination in untreated group;

Tai: Number of the surviving insects at the time of the examination in treated group.

Specific examples of the diluted solution C whose efficacies can be confirmed by Test Example 11 include the followings) to 5).

1) A diluted solution C comprising any combinations described in the List. A wherein the concentration of the present compound is 200 ppm, and the concentration of the present ingredient is 2,000 ppm. Here in the List A, "Comp X" represents a compound selected from any one of the present compounds A-1 to, A-98, B-1 to B28, and C-1 to C-10, List A:
Comp X+Clot hianidin; Comp X+Thiamethoxam; Comp X+Imidacloprid; Comp X+Thiacloprid; Comp X+Furupirajituron; Comp X+Sulfoxaflor; Comp X+Triflumezopyrim; Comp X+Dicloromezotiaz; Comp X+Beta-cyfluthrin; Comp X+Tefluthrin; Comp X+Fipronil; Comp X+Chlorantraniliprole; Comp X+Cyantraniliprole; Comp X+Tetraniliprole; Comp X+Thiodicarb; Comp X+Carbofuran; Comp X+Fluxametamide; Comp X+Afoxolaner; Comp X+Fluralaner; Comp X+Broflanilide; Comp X+Avermectin; Comp X+Fluopyram; Comp X+Fluensulfone; Comp X+Fluazaindolizine; Comp X+Tioxazafen; Comp X+Flupyrimin; Comp X+Mycorrhizal fungi; Comp X+*Bradyrhizobium japonicum* TA-11; Comp X+*Bacillus firmus*; Comp X+*Bacillus firmus* 1-1582; Comp X+*Bacillus amyloliquefaciens*; Comp X+*Bacillus amyloliquefaciens* FZE42; COMP X+*Pasteuria nishizawae*; Comp X+*Pasteuria nishizawae* Pn1; Comp X+*Pasteuria penetrans*; Comp X+Tebuconazole; Comp X+Prothioconazole; Comp X+Metconazole; Comp X+Ipconazole; Comp X+Triticonazole; Comp X+Difenoconazole; Comp X+Imazalil; Comp X+Triadimenol; Comp X+Tetraconazole; Comp X+Flutriafol; Comp X+Mandestrobin; Comp X+Azoxystrobin; Comp X+Pyraclostrobin; Comp X+Trifloxystrobin; Comp X+Fluoxastrobin; Comp X+Picoxystrobin; Comp X+Fenamidone; Comp X+Comp X+Metalaxyl-M; Comp X+Fludioxonil; Comp X+Sedaxa e; Comp X+Penflufen; Comp X+Fluxapyroxad; Comp X+Benzovindiflupyr; Comp X+Boscalid; Comp X+Carboxin; Comp X+Penthiopyrad; Comp X+Flutolanil; Comp X+Captan; Comp X+thiram; Comp X+Tolclofos-methyl; Comp X+Thiabendazole; Comp X+Ethaboxam; Comp X+Mancozeb; Comp X+Picarbutrazox; Comp X+Oxathiapiprolin; Comp X+Silthiofam; Comp X+Inpyrfluxam.

2) A diluted solution C comprising any combinations described in the List A wherein the concentration of the present compound is 200 ppm, and the concentration of the present ingredient is 200 ppm.

3) A diluted solution C comprising any combinations described in the List A wherein the concentration of the present compound is 500 ppm, and the concentration of the present ingredient is 50 ppm.

4) A diluted solution C comprising any combinations described in the List A wherein the concentration of the present compound is 500 pm, and theconcentration of the present ingredient is 5 ppm.

5) A diluted solution C comprising any combinations described in the List A wherein the concentration of the present compound is 500 ppm, and the concentration of the present ingredient is 0.5 ppm.

INDUSTRIAL APPLICABILITY

The present compound Z shows an excellent control effect against a harmful arthropod.

The invention claimed is:

1. A compound represented by formula (I):

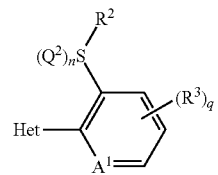

wherein,
$R^2$ represents a C1-C6 alkyl group,
n is 0, 1 or 2,
$R^3$ represents a C1-C6 chain hydrocarbon group optionally having one or more substituents selected from Group B, a C3-C7 cycloalkyl group optionally having one or more substituents selected from group E, $OR^{12}$, $NR^{11}R^{12}$, $NR^{11}C(O)R^{13}$, $NR^{11}C(O)OR^{14}$, a cyano group, or a halogen atom,
q is 0 or 1,
Het represents a group represented by the following formula Het 1:

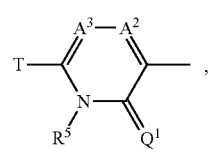

$A^1$ represents a nitrogen atom,
$A^2$ represents $CR^{4a}$,
$A^3$ represents a nitrogen atom or $CR^{4b}$,
$Q^1$ represents an oxygen atom,
$Q^2$ represents an oxygen atom,
$R^5$ represents a C1-C6 chain hydrocarbon group optionally having one or more substituents selected from group F, or a C3-C6 cycloalkyl group
$R^{4a}$ and $R^{4b}$ represents a hydrogen atom,
T represents a C1-C10 chain hydrocarbon group, wherein the C1-C10 chain hydrocarbon group has one or more halogen atoms, or $OR^1$
$R^1$ represents a C1-C10 chain hydrocarbon group, wherein the C1-C10 chain hydrocarbon group has one or more substituents selected from the group consisting of a cyano group and a halogen atom, a (C3-C7 cycloalkyl)C1-C3 alkyl group, or a C3-C7 cycloalkyl group, wherein the (C3-C7 cycloalkyl) C1-C3 alkyl group and the C3-C7 cycloalkyl group each independently have one or more substituents selected from the group consisting of a cyano group, a halogen atom and a C1-C6 haloalkyl group, R$^{11}$ represents a C1-C6 chain hydrocarbon group optionally having one or more halogen atoms, or a hydrogen atom, R$^{12}$ represents a C1-C6 chain hydrocarbon group optionally having one or more substituents selected from Group F, a phenyl group, a six membered heterocyclic group, wherein the phenyl group, and the six membered heterocyclic group each independently may optionally have one or more substituents selected from Group D, or a hydrogen atom, R$^{13}$ represents a hydrogen atom, a C1-C6 chain hydrocarbon group optionally having one or more halogen atoms or a C3-C7 cycloalkyl group optionally having one or more halogen atoms, R$^{14}$ represents a C1-C6 chain hydrocarbon group optionally having one or more halogen atoms, or a C3-C7 cycloalkyl group optionally having one or more halogen atoms, Group B: a group consisting of a C1-C6 alkoxy group optionally having one or more halogen atoms, a C3-C6 cycloalkyl group optionally having one or more halogen atoms, a cyano group, a hydroxy group, and a halogen atom, Group D: a group consisting of a cyano group and a halogen atom, Group E: a group consisting of a C1-C6 chain hydrocarbon group optionally having one or more halogen atoms, a halogen atom, and a cyano group;

Group F: a group consisting of a C3-C6 cycloalkyl group optionally having one or more halogen atoms, a phenyl group or a six membered aromatic heterocyclic group, wherein the phenyl group and the six membered aromatic heterocyclic group each independently may optionally have one or more substituents selected from Group D, a halogen atom, and a cyano group.

2. The compound according to claim 1 wherein R$^1$ represents a C1-C10 chain hydrocarbon group having one or more halogen atoms, a (C3-C7 cycloalkyl)C1-C3 alkyl group having one or more substituents selected from the group consisting of a cyano group, a halogen atom and a C1-C6 haloalkyl group, or a C3-C7 cycloalkyl group having one or more substituents selected from Group G the group consisting of a cyano group, a halogen atom and a C1-C6 haloalkyl group.

3. The compound according to claim 1, wherein A$^3$ represents CR$^{4b}$.

4. The compound according to claim 1, wherein T represents a C1-O5 chain hydrocarbon group having one or more halogen atoms, or OR$^1$.

5. The compound according to claim 1, wherein T represents a C1-O5 chain hydrocarbon group having one or more halogen atoms, or OR$^1$, and R$^1$ represents a C1-O5 chain hydrocarbon group having one or more halogen atoms.

6. The compound according to claim 1, wherein R$^3$ represents a C1-C6 alkyl group optionally having one or more substituents selected from Group B, a C3-C7 cycloalkyl group optionally having one or more substituents selected from Group E, NR$^{11}$R$^{12}$, NR$^{11}$C(O)OR$^{14}$, OR$^{12}$, or a halogen atom.

7. The compound according to claim 1 wherein R$^2$ represents an ethyl group.

8. A composition for controlling harmful arthropod comprising the compound according to claim 1 and an inert carrier.

9. A method for controlling harmful arthropod which comprises applying an effective amount of the compound according to claim 1 to a harmful arthropod or a habitat where a harmful arthropod lives.

10. A method for controlling harmful arthropod which comprises applying an effective amount of the compound according to claim 1 to a plant or a soil where a plant grows.

11. A method for controlling harmful arthropod which comprises applying an effective amount of the compound according to claim 1 to a seed or a bulb.

12. A composition comprising the compound according to claim 1 and one or more ingredients selected from:
Group (a): insecticidal ingredients, miticidal ingredients, and nematicidal ingredients;
Group (b): fungicidal ingredients;
Group (c): plant growth modulating ingredients;
Group (d): phytotoxicity-reducing ingredients; and
Group (e): synergist ingredients.

13. A composition for controlling pest comprising the composition according to claim 12 and an inert carrier.

14. A method for controlling pest which comprises applying an effective amount of the composition according to claim 12 to a pest or a habitat where a pest lives.

15. A method for controlling pest which comprises applying an effective amount of the composition according to claim 12 to a plant or a soil where a plant grows.

16. A method for controlling pest which comprises applying an effective amount of the compound according to claim 12 to a seed or a bulb.

17. A seed or bulb carrying an effective amount of the compound according to claim 1.

18. A compound represented by formula (II):

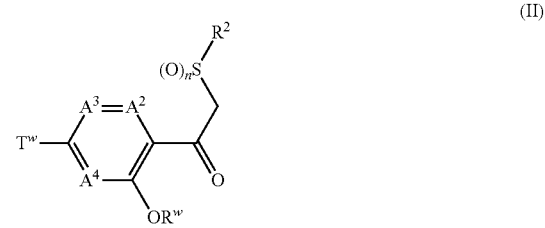

wherein,
R$^2$ represents a C1-C6 alkyl group,
n is 0, 1 or 2,
A$^2$ represents CR$^{4a}$,
a combination of A$^3$ and A$^4$ represents a combination where A$^3$ represents a nitrogen atom, A$^4$ represents a nitrogen atom, or a combination where A$^3$ represents CR$^{4b}$, and A$^4$ represents a nitrogen atom,
R$^{4a}$ and R$^{4b}$ represent a hydrogen atom,
R$^w$ represents a C1-C6 chain hydrocarbon group optionally having one or more halogen atoms, a benzyl group optionally having one or more substituents selected from Group A, a C2-C7 alkylcarbonyl group, a (C1-C3 alkoxy)methyl group, or a hydrogen atom,
T$^w$ represents a C1-C10 chain hydrocarbon group, wherein the C1-C10 chain hydrocarbon group has one or more halogen atoms, OR$^1$, a halogen atom, a C1-C6 alkylsulfanyl group, a C1-C6 alkylsulfinyl group, a C1-C6 alkylsulfonyl group, wherein the C1-C6 alkylsulfanyl group, the C1-C6 alkylsulfinyl group, and the C1-C6 alkylsulfonyl group each may optionally have a C3-C6 cycloalkyl group, a C3-C6 cycloalkylsulfanyl group, a C3-C6 cycloalkylsulfinyl group, a C3-C6 cycloalkylsulfonyl group, a benzyloxy group optionally having one or more substituents selected from Group A, a C2-C7 alkylcarbonyloxy group optionally having one or more halogen atoms, a (C1-C3 alkoxy)methoxy group, or a hydroxy group, r¹ represents a C1-C10 chain hydrocarbon group, wherein the C1-C10 chain hydrocarbon group has one or more substituents selected from the group consisting of a cyano group and a halogen atom, a (C3-C7 cycloalkyl)C1-C3 alkyl group, or a C3-C7 cycloalkyl group, wherein the (C3-C7 cycloalkyl) C1-C3 alkyl group and the C3-C7 cycloalkyl group each independently have one or more substituents selected from the group consisting of a cyano group, a halogen atom and a C1-C6 haloalkyl group, Group A: a group consisting of a C1-C6 alkyl group optionally having one or more halogen atoms, a C1-C6 alkoxy group optionally having one or more halogen atoms, a halogen atom, a cyano group and a nitro group.

19. A compound represented by formula (III):

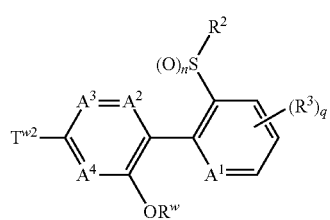

wherein,
R² represents a C1-C6 alkyl group,
n is 0, 1 or 2,
A¹ represents a nitrogen atom,
A² represents CR⁴a,
a combination of A³ and A⁴ represents a combination where A³ represents a nitrogen atom, A⁴ represents a nitrogen atom or CR⁴c, or a combination where A³ represents CR⁴b, and A⁴ represents a nitrogen atom,
R⁴ᵃ, R⁴ᵇ and R⁴ᶜ represents a hydrogen atom,
Rʷ represents a C1-C6 chain hydrocarbon group optionally having one or more halogen atoms, a benzyl group optionally having one or more substituents selected from Group A, a C2-C7 alkylcarbonyl group, a (C1-C3 alkoxy)methyl group, or a hydrogen atom,
Tʷ² represents a C1-C10 chain hydrocarbon group, wherein the the C1-C10 chain hydrocarbon group has one or more halogen atoms, OR¹, a halogen atom, a C1-C6 alkoxy group, a C1-C6 alkylsulfanyl group, a C1-C6 alkylsulfinyl group, a C1-C6 alkylsulfonyl group, wherein the C1-C6 alkylsulfanyl group, the C1-C6 alkylsulfinyl group, and the C1-C6 alkylsulfonyl group each independently may optionally have a C3-C6 cycloalkyl group, a C3-C6 cycloalkylsulfanyl group, a C3-C6 cycloalkylsulfinyl group, a C3-C6 cycloalkylsulfonyl group, a benzyloxy group optionally having one or more substituents selected from Group A, a C2-C7 alkyl-carbonyloxy group optionally having one or more halogen atoms, a (C1-C3 alkoxy)methoxy group, or a hydroxy group, R¹ represents a C1-C10 chain hydrocarbon group, wherein the C1-C10 chain hydrocarbon group has one or more substituents selected from the group consisting of a cyano group and a halogen atom, a (C3-C7 cycloalkyl)C1-C3 alkyl group, or a C3-C7 cycloalkyl group, wherein the (C3-C7 cycloalkyl) C1-C3 alkyl group and the C3-C7 cycloalkyl group each independently have one or more substituents selected from the group consisting of a cyano group, a halogen atom and a C1-C6 haloalkyl group, R³ represents a C1-C6 chain hydrocarbon group optionally having one or more substituents selected from Group B, a C3-C7 cycloalkyl group optionally having one or more substituents selected from group E, OR¹², NR¹¹R¹², NR¹¹C(O)R¹³, NR¹¹C(O)OR¹⁴, a cyano group, or a halogen atom, q is 0 or 1, R¹¹ represents a C1-C6 chain hydrocarbon group optionally having one or more halogen atoms, or a hydrogen atom, R¹² represents a C1-C6 chain hydrocarbon group optionally having one or more substituents selected from Group F, a phenyl group, a six membered heterocyclic group, wherein the phenyl group and the six membered heterocyclic group each independently may optionally have one or more substituents selected from Group D or a hydrogen atom R¹³ represents a hydrogen atom, a C1-C6 chain hydrocarbon group optionally having one or more halogen atoms or a C3-C7 cycloalkyl group optionally having one or more halogen atoms, R¹⁴ represents a C1-C6 chain hydrocarbon group optionally having one or more halogen atoms or a C3-C7 cycloalkyl group optionally having one or more halogen atoms, Group A: a group consisting of a C1-C6 alkyl group optionally having one or more halogen atoms, a C1-C6 alkoxy group optionally having one or more halogen atoms, a halogen atom, a cyano group and a nitro group, Group B: a group consisting of a C1-C6 alkoxy group optionally having one or more halogen atoms, a C3-C6 cycloalkyl group optionally having one or more halogen atoms, a cyano group, a hydroxy group, and a halogen atom, Group D: a group consisting of a cyano group and a halogen atom, Group E: a group consisting of a C1-C6 chain hydrocarbon group optionally having one or more halogen atoms, a halogen atom, and a cyano group;

Group F: a group consisting of a C3-C6 cycloalkyl group optionally having one or more halogen atoms, a phenyl group or a six membered aromatic heterocyclic group, wherein the phenyl group and the six membered aromatic heterocyclic group each independently may optionally have one or more substituents selected from Group D, a halogen atom, and a cyano group.

20. A compound represented by formula (IV):

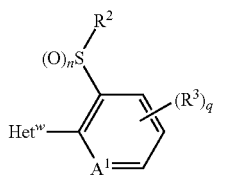

(IV)

wherein,
R² represents a C1-C6 alkyl group,
n is 0, 1 or 2,
R³ represents a C1-C6 chain hydrocarbon group optionally having one or more substituents selected from Group B, a C3-C7 cycloalkyl group optionally having one or more substituents selected from group E, $OR^{12}$, $NR^{11}R^{12}$, $NR^{11}C(O)OR^{14}$, a cyano group, or a halogen atom,
q is 0 or 1,
$Het^W$ represents a group represented by the following formula Het 3:

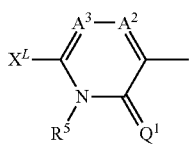

Het3

A¹ represents a nitrogen atom,
A² represents $CR^{4a}$,
A³ represents a nitrogen atom or $CR^{4b}$,
Q¹ represents an oxygen atom,
R⁵ represents a C1-C6 chain hydrocarbon group optionally having one or more substituents selected from group F, or a C3-C6 cycloalkyl group
$R^{4a}$ and $R^{4b}$ represent a hydrogen atom,
$X^L$ represents a halogen atom, a C1-C6 alkoxy group, a C1-C6 alkylsulfanyl group, a C1-C6 alkylsulfinyl group, a C1-C6 alkylsulfonyl group, wherein the C1-C6 alkylsulfanyl group, the C1-C6 alkylsulfinyl group, and the C1-C6 alkylsulfonyl group each independently may optionally have a C3-C6 cycloalkyl group, a C3-C6 cycloalkylsulfanyl group, a C3-C6 cycloalkylsulfinyl group, a C3-C6 cycloalkylsulfonyl group, a benzyloxy group optionally having one or more substituents selected from Group A, a C2-C7 alkylcarbonyloxy group optionally having one or more halogen atoms, a (C1-C3 alkoxy)methoxy group, or a hydroxy group,
R¹¹ represents a C1-C6 chain hydrocarbon group optionally one or more halogen atoms, or a hydrogen atom,
R¹² represents a C1-C6 chain hydrocarbon group optionally having one or more substituents selected from Group F, a phenyl group, or six membered heterocyclic group, wherein the phenyl group, and the six membered heterocyclic group each independently may have optionally one or more substituents selected from Group D or a hydrogen atom,
R¹³ represents a hydrogen atom, a C1-C6 chain hydrocarbon group optionally having one or more halogen atoms or a C3-C7 cycloalkyl group optionally having one or more halogen atoms,
R¹⁴ represents a C1-C6 chain hydrocarbon group optionally having one or more halogen atoms, or a C3-C7 cycloalkyl group optionally having one or more halogen atoms,
Group A: a group consisting of a C1-C6 alkyl group optionally having one or more halogen atoms, a C1-C6 alkoxy group optionally having one or more halogen atoms, a halogen atom, a cyano group and a nitro group,
Group B: a group consisting of a C1-C6 alkoxy group optionally having one or more halogen atoms, a C3-C6 cycloalkyl group optionally having one or more halogen atoms, a cyano group, a hydroxy group, and a halogen atom,
Group D: a group consisting of a cyano group and a halogen atom,
Group E: a group consisting of a C1-C6 chain hydrocarbon group optionally having one or more halogen atoms, a halogen atom, and a cyano group;
Group F: a group consisting of a C3-C6 cycloalkyl group optionally having one or more halogen atoms, a phenyl group or a six membered aromatic heterocyclic group, wherein the phenyl group and the six membered aromatic heterocyclic group each independently may optionally have one or more substituents selected from Group D, a halogen atom, and a cyano group.

* * * * *